United States Patent
King et al.

(10) Patent No.: US 8,367,693 B1
(45) Date of Patent: Feb. 5, 2013

(54) OPIOID SALTS AND FORMULATIONS EXHIBITING ANTI-ABUSE ANTI-DOSE DUMPING PROPERTIES

(75) Inventors: Clifford Riley King, Hendersonville, NC (US); Stephen G. D'Ambrosio, Etowah, NC (US); David W. Bristol, Mills River, NC (US); Michael L. English, Cashiers, NC (US)

(73) Assignee: Pisgah Laboratories, Inc., Pisgah Forest, NC (US)

( * ) Notice: Subject to any disclaimer, the term of this patent is extended or adjusted under 35 U.S.C. 154(b) by 0 days.

(21) Appl. No.: 13/339,456

(22) Filed: Dec. 29, 2011

Related U.S. Application Data

(60) Division of application No. 13/211,718, filed on Aug. 17, 2011, which is a division of application No. 12/423,641, filed on Apr. 14, 2009, now Pat. No. 8,211,905, which is a continuation-in-part of application No. 11/805,225, filed on May 22, 2007, now abandoned, and a continuation-in-part of application No. 11/973,252, filed on Oct. 5, 2007, and a continuation-in-part of application No. 12/080,514, filed on Apr. 3, 2008, and a continuation-in-part of application No. 12/080,513, filed on Apr. 3, 2008, and a continuation-in-part of application No. 12/080,531, filed on Apr. 3, 2008.

(51) Int. Cl.
*A61K 31/44* (2006.01)
*C07D 489/00* (2006.01)

(52) U.S. Cl. .................................. 514/282; 546/44
(58) Field of Classification Search .................. 514/282; 546/44
See application file for complete search history.

(56) References Cited

U.S. PATENT DOCUMENTS

| | | | |
|---|---|---|---|
| 2,925,417 A | 2/1960 | Elslager et al. | 260/240 |
| 3,502,661 A | 3/1970 | Kasubick et al. | 260/240 |
| 4,622,244 A | 11/1986 | Lapka et al. | 427/213.32 |
| 5,225,205 A | 7/1993 | Orsolini | 424/489 |
| 5,232,919 A | 8/1993 | Scheffler et al. | 514/212 |
| 5,271,946 A | 12/1993 | Hettche | 424/490 |
| 5,439,688 A | 8/1995 | Orsolini et al. | 424/489 |
| 5,445,832 A | 8/1995 | Orsolini et al. | 424/491 |
| 5,776,885 A | 7/1998 | Orsolini et al. | 514/2 |
| 6,203,813 B1 | 3/2001 | Gooberman | 424/422 |
| 7,105,486 B2 | 9/2006 | Mickie | 514/12 |
| 2004/0058946 A1 | 3/2004 | Buchwald et al. | 514/282 |
| 2004/0131552 A1 | 7/2004 | Boehm | 424/10.1 |
| 2005/0158382 A1 | 7/2005 | Cruz et al. | 424/468 |
| 2005/0266070 A1 | 12/2005 | Mickle | 424/451 |
| 2006/0051298 A1 | 3/2006 | Groenewoud | 424/10.2 |
| 2006/0104909 A1 | 5/2006 | Vaghefi et al. | 424/10.2 |

FOREIGN PATENT DOCUMENTS

| | | |
|---|---|---|
| EP | 0137600 | 7/1984 |
| GB | 295 656 | 11/1929 |

OTHER PUBLICATIONS

Hamlin, William E., Northam, Jack I., and Wagner, John G., Relationship Between in Vitro Dissolution Rates and Solubilities of Numerous Compounds Representative of Various Chemical Species, Mar. 31, 1965.
Berge SM, Bighley LD and Monkhouse DC, "Pharamceutical Salts" Journal of Pharmaceutical Sciences, Jan. 1977, 66(1), 1-19.
Morissette SL, Almarsson O, Peterson ML, Remenar JG, Read MJ, Lemmo AC, Ellis S, Cima MJ, Gardner CR, "High Throughput Crystallization: Polymorphs, Salts, C-Crystals and Solvates of Pharmaceutical Solids", Adv. Drug Deliv Rev., Feb. 2004.

*Primary Examiner* — Paul Zarek
(74) *Attorney, Agent, or Firm* — Joseph T. Guy; Nexsen Pruet, LLC

(57) ABSTRACT

A drug substance with a pharmaceutically acceptable organic acid addition salt of an opioid wherein said organic acid is selected from Structure A:

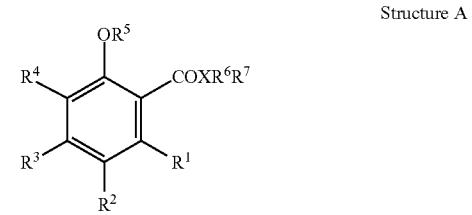

Structure A wherein $R^1$-$R^4$ are independently selected from H, alkyl or substituted alkyl of 1-6 carbons, adjacent groups may be taken together to form a cyclic alkyl, cyclic alkyl-aryl, or cyclic aryl moiety;
$R^5$ is selected from H, or an alkali earth cation;
$R^6$ and $R^7$ are independently selected from H, alkyl of 1-6 carbons, an alkali earth cation, and aryl of 6 to 12 carbons, in a number sufficient to complete the valence bonding of X, and
wherein X is selected from nitrogen, oxygen or sulfur; and
wherein the drug substance has a morphology selected from amorphous and crystalline.

132 Claims, 105 Drawing Sheets

Figure 19,

OPIOID SALTS AND FORMULATIONS EXHIBITING ANTI-ABUSE ANTI-DOSE DUMPING PROPERTIES

CROSS REFERENCE TO RELATED APPLICATIONS

This application is divisional application of pending U.S. patent application Ser. No. 13/211,718 filed Aug. 17, 2011 which is a divisional application of U.S. patent application Ser. No. 12/423,641 filed Apr. 14, 2009 now U.S. Pat. No. 8,211,905 which is a continuation-in-part application of U.S. patent application Ser. Nos. 11/805,225 filed May 22, 2007 now abandoned; 11/973,252 filed Oct. 5, 2007; 12/080,514 filed Apr. 3, 2008; 12/080,513 filed Apr. 3, 2008 and 12/080,531 filed Apr. 3, 2008 all of which are incorporated herein by reference. The present application is related to U.S. patent application Ser. Nos. 11/595,379 filed Nov. 10, 2006 now U.S. Pat. No. 7,718,649; 11/843,690 filed Aug. 23, 2007 now U.S. Pat. No. 8,039,461; 11/928,592 filed Oct. 30, 2007 and 11/932,336 filed Oct. 31, 2007 now U.S. Pat. No. 7,858,663 each of which is incorporated herein by reference.

BACKGROUND OF THE INVENTION

The abuse of controlled substances in the United States and other parts of the world has reached epidemic proportions. To address this human tragedy significant administrative and technical resources are currently being expended to identify and implement technologies which deter, inhibit or prevent the unintentional, illicit, illegal and/or recreational use of controlled substances. Within the context of this discussion controlled substances are those identified by the US Drug Enforcement Administration (DEA) and as context of discussion herein may dictate, the controlled substance may either be the active pharmaceutical ingredient (as its free base or salt) or the formulated drug product. Further, the controlled substances of interest to this invention are the opioid narcotics—that is, the alkaloids derived from opium either by isolation from natural sources, semi-synthetic derivatives prepared by transformation of the natural isolates, synthetic acquisition and combinations thereof. A useful overview is "Opium and Its Alkaloids" found in the American Journal of Pharmaceutical Education, Vol. 66, Summer 2002, pp. 186-194.

The detrimental practice of drug abuse, particularly of oxycodone, the active ingredient in OxyContin®, is well recognized. Indeed, in December 2003 the General Accounting Office (GAO) issued a report to Congressional requesters entitled "Prescription Drugs, OxyContin Abuse and Diversion and Efforts to Address the Problem". The document contains a statistical assessment indicating the severity of the abuse problem, the employment of marketing practices contrary to FDA regulations, the actions taken by Purdue Pharma, Federal and State Agencies tasked to prevent abuse and diversion of Oxycontin® while recognizing the legitimate medical necessity of the opioid narcotics to treat pain. Like many governmental reports, the GAO's assessment was thorough and presented a factual basis to the problem of Oxycontin® abuse. However, the report contained a "Recommendation for Executive Action" which essentially returned the problem to the FDA as indicated by the following excerpted paragraph.

"To improve the efforts to prevent or identify the abuse and diversion of schedule II controlled substances, we recommend that the Commissioner of Food and Drugs ensure that FDA's risk management plan guidance encourages pharmaceutical manufactures that submit new drug application for these substances to include plans that contain a strategy for monitoring the use of these drugs and identifying potential abuses and diversion problems."

Indeed, the FDA has several "Guidance for Industry" documents, namely: 1) Development and Use of Risk Minimization Action Plans, 2) Pre-marketing Risk Assessment, and e) Good Pharmacovigilance Practices and Pharmacoepidemiologic Assessment. In the first cited Guidance the following excerpt is particularly poignant to this discussion:

"Opiate drug products have important benefits in alleviating pain but are associated with significant risk of overdose, abuse, and addiction. The Agency recommends that sponsors of Schedule II controlled substances, including Schedule II extended release or high concentration opiate drug products, consider developing RiskMAPS for these products." [Note: RiskMAPS=risk minimization action plans.]

These Guidances, while well intended, employ administrative measures in an attempt to prevent drug abuse. As an example, the FDA recommends the RiskMAP to be designed according to the following criteria: 1) compatible with current technology, 2) applicable to both outpatient and inpatient use, 3) accessible to patients in diverse locales, including non-urban settings, and 4) consistent with existing tools and programs, or systems that have been shown to be effective with similar products, indications, or risks.

Again, the abuse of controlled substances in the United States has reached epidemic proportions which has yielded a significant economic burden on society and has seriously impacted the general health condition of the nation's society. While the origin of the abuse may be accredited to the irresponsible behavior of the abuser, the detrimental effects to society remain. For more than twenty-five years, the actions by the federal and state governments have had no apparent impact on the drug abuse crisis and the problem has escalated faster than the population's growth rate. Similarly, educational programs and intervention by the medical community have had limited effect. Indeed, those individuals who on their own initiative or through the assistance of family or friends who have sought help through drug addiction treatment programs have also responded poorly. In fact, the behavioral and/or physiological change needed to eliminate their abuse/dependence on controlled substances is usually only temporary. This is especially evident when you consider the rising epidemic in methadone abuse with the frequent occurrence of such abuse leading to death of the "patient"; i.e. even the treatment is leading to death.

In the context of public health, controlled substances fulfill medical necessities and will be required to treat legitimate ailments in both controlled environments (clinics, hospitals, alternate care sites) as well as in unmonitored circumstances (drug administration by the patient). Medical professionals, alert to the potential for drug abuse and diversion, attempt to restrict the use of various drugs particularly pain relief medications such as Oxycontin®. Unfortunately, this approach is inconsistent and may deny relief to patients truly suffering from pain. To the medical practitioner, the decision to prescribe, or not to prescribe, pain medication is agonizing and may be accompanied by legal liability. In regard to non-prescription drug products, the "decision" to restrict availability of pseudoephedrine containing products by requiring the pharmacy to stock and track these products from "behind-the-counter" also impedes the legitimate use of these products and places an undue burden on the pharmacist and the consumer. Of course, this action was taken in an effort to stem the trade of these products for their use in illicit methamphetamine production.

An additional burden is placed on the medical practitioner as drug abuse continues to escalate and is not limited to the abuse of "traditional" illegal/recreational drugs of previous generations but abuse practices have now broadened to include legitimate prescription drugs. A full-page advertisement was sponsored by eleven professional medical organizations in the Feb. 10, 2008 edition of The New York Times page A7 indicating that "teens abuse prescription drugs more than any illicit street drug except marijuana". The advertisement further extols "prescription drugs are the drugs of choice for 12 and 13 year olds" and that "every day, 2500 kids age 12 to 17 try a painkiller for the first time". Simply stated, teens are raiding the family medicine cabinet to get high. In fact, The Wall Street Journal Online of Mar. 25, 2008 reported in an article by Elizabeth Bernstein entitled "New Addiction on Campus: Raiding the Medicine Cabinet", the increased prevalence of 18-25 years olds abusing prescription narcotics primarily due to their ready availability. In January 2008, the Office of National Drug Control Policy, under the authority of the Executive Office of the President, published "Prescription for Danger, A Report on the Troubling Trend of Prescription and Over-the-Counter Drug Abuse Among the Nation's Teens". This report summarizes the crisis well and adds additional insight to the problem. For instance, "teens are abusing prescription drugs because many believe the myth that these drugs provide a "safe" high and they are easily available". Statistically, it would appear parenting skills are ineffective and may only have limited influence on preventing a teen from abusing drugs.

Government initiatives to curb drug abuse, the heightened awareness among medical professionals for observing symptoms of drug abuse or for recognizing the potential for such abuse, and parental guidance have all apparently remained ineffective.

Within the last few years, the pharmaceutical industry has responded to this difficult problem in an attempt to provide controlled substance drug products possessing anti-abuse features. There are essentially three "classical" technical approaches to imparting abuse resistant properties to controlled substances: 1) through a prodrug, 2) via an intractable matrix formulation technique, and 3) by antagonist incorporation into the product formulation. Each approach has been shown to have significant limitations for universal application to a broad range of products. The intent is to impart anti-abuse properties to a drug product via formulation mechanisms which modulate the physical and/or chemical properties of the drug dosage product. This approach may employ admixtures of various excipients, drug antagonists, or utilize production techniques, and combinations thereof to achieve some level of anti-abuse product feature. To date this approach has been relatively ineffective. For instance, Purdue Pharma recently (May 2008) was subject to a regulatory submission review by a panel of FDA experts regarding New Drug Application 22-272 Reformulated Oxycontin®. Panelists' expressed displeasure about the lack of abuse-prevention data and the "poor scientific rigor" as reported in the Wall Street Journal. Purdue's intention was to prepare a tamper-resistant form of the product employing a polymeric excipient which prevented manipulation to an abusable, injectable form.

In contrast to these formulation techniques, anti-abuse properties may be addressed through the drug substance, also known as the active pharmaceutical ingredient (API). At the API level, the physical and/or chemical properties necessary to impart anti-abuse features to the formulated drug product are introduced while maintaining the desired therapeutic value of the drug substance. Two broad categories to this approach have been utilized: 1) the preparation of prodrugs, and 2) the selection of novel salts of the API which exhibit anti-abuse features.

In regard to the prodrug approach, the most celebrated example is the FDA approved product Vyvanse™. Vyvanse™ is a formulated product for solid oral dose administration and employs a prodrug of amphetamine. The FDA's Orange Book refers to two patents covering this technology; U.S. Pat. No. 7,105,486 and U.S. Pat. No. 7,223,735. The anti-abuse feature of Vyvanse™ arises from the drug substance being released only after ingestion and subsequent hydrolysis by enzymes located in the epithelial cells of the intestine. Attempts to abuse the drug by other means are prevented because of the absence of the enzyme.

In co-pending U.S. patent application Ser. No. 11/805,225 [Bristol, et al.] entitled "Salts of Physiologically Active and Psychoactive Alkaloids and Amines Simultaneously Exhibiting Bioavailability and Abuse Resistance", incorporated herein in its entirety, a number of "classical" formulation and prodrug approaches are referenced which allegedly impart anti-abuse properties to drug substances and to drug products. However, Bristol teaches how the careful selection of organic acid addition salts of amine-containing controlled substances can be prepared which exhibit anti-abuse properties; one factor of several for this desired feature results from the salt's lack of solubility in the mucosal membranes of humans (or animals). In contrast, the salts when subjected to the gastro-intestinal tract were transformed and bio-available. The co-pending application describes a platform approach to introducing anti-abuse properties to controlled substances.

Further, in co-pending U.S. patent application Ser. No. 11/928,592 [King, et al.] entitled "Drug Release Properties of Polymorphic Pharmaceutical Substances", incorporated herein in its entirety, the dissolution profiles associated with various organic acid salts of amine-containing controlled substances is disclosed. In conjunction with the salts lacking solubility in the mucosal membranes, the in vitro dissolution testing of these salts indicated polymorphic behaviors suitable for controlled and targeted release. Consequently, the selection of an organic acid addition salt and of a particular polymorph associated with that salt, provide a means to impart substantial anti-abuse properties into controlled substance drug products.

Drug abuse, in particular controlled substance abuse, is a difficult problem to curtail. There are behavioral aspects to the abuse which may not surrender to any reasonably available solution. For instance, an individual's choice to deliberately swallow multiple doses of a legitimately prescribed oral dosage is nearly impossible to control. The controlled release product approach has had limited effect in mitigating this occurrence. Alternatively, there are proposed product formulations which contain low amounts of an emetic such that when used in the intended dosing regimen the individual is unaffected by the emetic. However, with an intentional oral overdose, the cumulative amounts of emetic from multiple doses results in emesis (and supposedly the extirpation by vomiting of the controlled substance). Consequently, drug abuse while retaining the definition employed above, may also be considered that activity wherein the controlled substance is employed in a route of administration other than by which the product was designed or intended.

It is clear that administrative efforts and chemical technologies will be needed and employed in combination to impede the practice of drug abuse. In co-pending U.S. patent application Ser. No. 11/973,252 filed on Oct. 5, 2007[King et al.], incorporated herein by reference in its entirety, a process is disclosed which employs anti-abuse properties of selected organic acid salts of amine-containing controlled substances and which provides track and trace capabilities through computer databases. The invention provides enablement to the FDA's initiative to develop a new guidance for a similar to, but the chemically comparable topic of, anti-counterfeiting. The FDA's proposed guidance, entitled "Incorporation of Physical-Chemical Identifiers (PCID) into Solid Oral Dosage Form Drug Products for Anti-counterfeiting" is also applicable to the cradle-to-grave administrative monitoring of controlled substances. Indeed, California has instituted such a tracking requirement pursuant to Cal. Bus. & Prof. Code §4034(d), and stating a "pedigree shall track each dangerous drug at the smallest package or immediate container distributed by the manufacturer, received and distributed by the wholesaler, and received by the pharmacy or another person furnishing, administering, or dispensing the dangerous drug". Also, in a news report found in Generics Bulletin, 2 May 2008 page 7 entitled, "US Aims for Federal Track-and-Trace Route", legislation has been proposed (HR5839 Safeguarding America's Pharmaceuticals Act) which "will require pedigrees on all prescription medicines sold in the US". The Act, if enacted, "will require manufacturers, distributors and pharmacies to put in place systems and technologies that will electronically track and trace individual prescription medicines".

European Patent Application 137600 [Stuart et al.; filed Jul. 19, 1984; now withdrawn], which is incorporated herein by reference, entitled "Pharmaceutically Active Salts of Morphine" asserts the preparation of morphine pamoate salts as the mono-morphine salt and the dimorphine salt trihydrate. The authors further performed pharmacological tests in rats and humans to compare the effect of morphine pamoate versus morphine sulfate (human tests) or morphine hydrochloride (rats). Within the context of the application, morphine pamoate employed in the pharmacological testing was dimorphine pamoate trihydrate, the preparation of which was described in applicants' Example 1. In addition, a reference was cited during the initial examination of the application to "morphine pamoate" found in the article "Relationship Between In Vitro Dissolution Rates and Solubilities of Numerous Compounds Representative of Various Chemical Species" published in the Journal of Pharmaceutical Sciences, Volume 54, No. 11, November 1965, pp. 1651-53. Incidentally, in this article, no reference was made to the type of morphine pamoate salt evaluated (mono- or di-morphine salt, or of any polymorphic considerations).

In U.S. Pat. No. 7,201,920 B2 [Kumar et al.], entitled "Method and Composition for Deterring Abuse of Opioid Containing Dosage Forms" the inventors disclose a formulation containing an analgesic and a gel forming polyethylene oxide component and is incorporated herein in its entirety. The matrix resulting from this and other non-active ingredients (excipients) is intended to result in an abuse resistant formulation.

In U.S. Pat. No. 7,153,966 B2 [Casner et al.], the disclosure of which is incorporated herein in its entirety, a process is identified for the preparation of oxycodone possessing very low impurities of 14-hydroxycodeinone. Similarly, in US Patent Application Publication US 2006/0173029 A1 [Chapman et al.], the disclosure of which is incorporated herein in its entirety, a method is disclosed for preparing oxycodone hydrochloride having less than 25 ppm of 14-hydroxycodeinone.

The control of impurity levels in medicinal opiates continues to receive significant inventive attention due to the oversight the US Food and Drug Administration applies to impurities during the drug approval process. US Patent Application Publication US 2008/0132703 A1 [Cox et al.] describes a process for reducing impurities in oxycodone base. In U.S. Pat. No. 6,589,960 B2 [Harclerode et al.] the inventors assert the preparation of hydromorphone and hydrocodone compositions having novel impurity profiles. Similarly, in United States Patent Application Publication US 2007/0293676 A1 [Antoninin] describes a method for the separation and purification of hydrocodone by preparative chromatography. A process for the purification of levorphanol, a morphinan, is described in United States Patent Application Publication US 2008/0146805 A1 [Haar et al.] And in U.S. Pat. No. 5,981,751 [Mudryk et al.], the inventors describe a process for the removal of residual organic solvents from various opiate based compounds.

In addition to the impurities contained within a given medicinal product, the FDA scrutinizes the polymorphic content of a drug substance and drug product before market approval is granted. Perhaps as a consequence of this scrutiny, a series of relevant United States Patent Application Publications describe various opiate polymorphs, principally those polymorphs observed as the mineral acid salt. United States Patent Application Publication US 2007/0197572 A1 [Calderon et al.] describes nine novel polymorphic forms of oxycodone hydrochloride. United States Patent Application Publication US 2006/0235039 A1 [Lorimer et al.] describes four novel polymorphic forms of hydromorphone hydrochloride. United States Patent Application Publication US 2007/0072889 A1 [Hagen et al.] describes ten novel forms of hydrocodone bitartrate Related to the assessment of the polymorphic content of drug substances, the preparation, characterization and utility of pharmaceutical co-crystals is emerging as a new approach to imparting unique physical and chemical properties to drug substances. In an article, "Diversity in Single- and Multiple-Component Crystals; The Search for and Prevalence of Polymorphs and Cocrystals, published in Crystal Growth & Design, Volume 7, Number 6, 2007, pp. 1007-1026, the author, G. Patrick Stahly, provides an excellent overview of techniques used in polymorph and co-crystal screening. The investigation of cocrystals is well exemplified in United States Patent Application Publication US 2008/016772 A1 [Zaworotko et al.] wherein the solid-sate synthesis of imides and imines using cocrystals is described.

In a Mar. 29, 2005 report by Dr. William K. Schmidt of Renovis, Inc. the author provides an excellent summation of the approaches employed to impart abuse resistance to controlled substances. This often cited report can be found at http://www.thci.org/opioid/mar05docs/schmidt.pdf or at http://www.thci.orp/opioid/documents/schmidt.pdf. Four approach categories were identified along with the companies pursuing a technical implementation strategy for that approach. These four categories and the associated companies are listed below. Additional companies have been added to the original Schmidt report to represent the current contributions and understandings within the industry.

Category 1 Approach: Modified release to resist crushing/extraction Companies: Collegium, Pain Therapeutics (Durect and King Pharmaceuticals), Roxane (Boehringer Ingelheim), TheraQuest, Acura Pharmaceuticals, Intellipharmaceutics Corporation Category 2 Approach: Prodrugs
Company: New River Pharmaceuticals (purchased by Shire Pharmaceuticals)

Category 3 Approach: Agonist and antagonist combinations
Companies: Elite, Endo, Purdue Pharma (Euro-Celtique), and 3M Category 4 Approach: Nasal gel
Company: Ionex Pharmaceuticals (purchased by Vernalis)

With the exception of the prodrug approach, the remaining three categories rely upon a formulation technique to impart anti-abuse features to the drug product and consequently, the four categories cited are essentially equivalent to the three classical approaches described in the Background of the Invention. Therefore, to fully recognize the scope and benefit of the present invention it is useful to contrast and compare the prior art generated by the above listed companies to the inventive disclosure herein.

For clarification, each category above is described briefly for the benefit of those unfamiliar with the techniques used by persons abusing drug products. First, the GAO report cited herein describes the crushing/extraction mechanism used by people intent on abusing drugs. Crushing the final dose product can allow for the "liberation" of the controlled substance and defeat any controlled release benefit the formulated drug product may have provided. Without the controlled release property, the full effect of the active ingredient may be felt by the abuser. Similarly, dissolving the formulated drug product in an appropriate solvent and isolating the active ingredient allows for the anti-abuse property to be circumvented. Hence, methods which defeat crushing or extraction impart an anti-abuse property to the drug product.

Indeed, formulation techniques in conjunction with final dose manufacturing technologies have been the mainstay for the production of anti-abuse opioid containing drug products. The approach was to employ ingredients and coatings technologies to modify the behavior of the opioid API, usually available as it's highly water soluble, mineral acid salt or as its small organic acid salt yielding similar solubility properties. Such approaches to anti-abuse formulations are well documented in U.S. Pat. No. 6,103,261 [Chasin et al.] assigned to Purdue Pharma and entitled "Opioid Formulations Having Extended Controlled Release", the disclosure of which is incorporated herein in its entirety. The literature cited within the '261 patent also provides a significant foundation to the formulation approach to extended and controlled release formulations. The inventors claim a solid oral dosage form of an analgesic compound contained in a controlled release matrix and assert its kinetic release as a function of pH and time as measured by a specific method. In a similar vein, U.S. Pat. No. 6,245,357 B1 [Edgren et al.], incorporated herein by reference in its entirety, describes a sustained release dosage form comprising a drug surrounded by an interior and an exterior wall with an exit for administering the drug to a patient. The pH independent release of drug products consistent with the compartmentalization principles of medicinal chemistry led to U.S. Pat. No. 6,150,410 [Eng et al.] entitled "pH Independent Extended Release Pharmaceutical Formulation", the disclosure of which is incorporated herein by reference in its entirety, wherein water swellable and acid-soluble polymers in conjunction with pre-tablet granulation methodologies provide unit dosage forms with the titled properties. Besides controlling the extraction and/or release properties of the drug substance from a dosage form by employing extended release properties, dose dumping has also been addressed using formulation techniques. For purposes herein, dose dumping is defined as the, intentional or unintentional, ethanol accelerated phenomenon in which the active pharmaceutical ingredient may be more rapidly released from the dosage form than intended and thereby creating a safety risk and/or the enablement of drug abuse. US Patent Application Publication 2007/0212414 A1 [Baichal et al.] entitled "Ethanol Resistant Sustained Release Formulations", describes sustained release delivery systems employing hetero- and homo-polysaccharide gums, said systems inhibiting dose dumping of a selected opioid. Finally, in relation to formulation and manufacturing technologies, U.S. Pat. No. 6,419,960 [Krishnamurthy et al.] entitled "Controlled Release Formulation Having Rapid Onset and Rapid Decline of Effective Plasma Drug Concentrations", the disclosure of which is incorporated herein in its entirety, describes a formulation simultaneously exhibiting immediate release and controlled release properties and employing enteric coating manufacturing technology to achieve same.

In regard to the prodrug approach, release is dependent on biochemical in situ enzymatic cleavage of a covalently bound protecting group or in general, an enzymatic transformation of the prodrug is required in order to produce the pharmaceutically active compound (or subsequently, a metabolite) that exhibits the desired biological activity. The prodrug concept as an anti-abuse mechanism is predicated on the belief that the "protected" pharmaceutical active ingredient is otherwise unavailable for abuse (i.e. in vitro manipulation to yield the active ingredient). The in vivo results from prodrug approaches demonstrate limitations as well. For instance the drug product, Vyvanse™, containing the prodrug lisdexamphetamine dimesylate, exhibits incomplete in vivo removal of the protecting group as indicated by lisdexamphetamine found in the urine, as reported in the FDA's Drug Approval Package, Clinical Pharmacology assessment for Vyvanse™ found at the following website: (http://www.fda.gov.cder/foi/nda/2007/021977s000TOC.htm).

The agonist/antagonist approach is constructed around the ability to sequester an antagonist within an agonist product formulation. In the event that the product formulation is employed in a manner inconsistent with it's intended route of administration, the antagonist is released defeating the anticipated effect from the agonist. With the nasal gel listed in Schmidt's report, the analgesic buprenorphine is formulated for fast effective delivery of the opioid so an anti-abuse product feature is absent perhaps explaining the observation that only sublingual product presentations have been approved in the US in conjunction with Vernalis' partner, Reckitt Benckiser.

In regard to Collegium's effort to impart anti-abuse properties to controlled substances, an abuse-deterrent pharmaceutical composition is described in United States Patent Application Publication Number US 2004/0052731 A1 [Hirsh et al.], the disclosure of which is incorporated herein in its entirety. The publication indicates the intention to alter the lipophilicity of an opioid drug substance by complexation with oleophilic metal salts such as zinc stearate. It is suggested that the "likelihood of improper administration of drugs, especially drugs such as opioids" would be due to the increase in lipophilicity imparted to the opioid by the complexation.

Another version of the modified release approach to resist crushing/extraction and to impart abuse deterrence to a drug formulation is summarized in the following information found on Durect's web site:

"The ORADUR Technology is the basis of Remoxy, a novel long-acting oral formulation of the opioid oxycodone which is targeted to decrease the potential for oxycodone abuse. In December 2007, Remoxy successfully completed a pivotal Phase III study. Pain Therapeutics has stated that it anticipates filing the NDA for Remoxy in the second quarter of 2008. We also have a second ORADUR abuse-resistant opioid product in the Pain Therapeutics alliance, about which Pain Therapeutics has announced positive results from a Phase I clinical trial."

Durect is the assignee of U.S. Pat. No. 7,074,803 B2 [Litmanovitz et al.], the disclosure of which is incorporated herein in its entirety. The inventors describe a means of preparing high concentration opioid formulations suitable for use in gel caps. Interestingly, Pain Therapeutics (mentioned on Durect's website), is the assignee for U.S. Pat. No. 6,765,010, the disclosure of which is incorporated herein in its entirety, describes the use of opioid receptor antagonists in the formulation of tramadol to enhance the analgesic potency of tramadol while mitigating undesired side effects.

Further formulation techniques included those described in United States Patent Application Publication 2003/0118641 A1 [Maloney et al.], which describes a method of combining a therapeutically effective amount of the opioid compound, or a salt thereof, with a matrix-forming polymer and an ionic exchange resin. The inventors assert this combination reduces the abuse potential employing extraction techniques of an oral dosage form of an opioid.

The following information was obtained from TheraQuest's website, http://www.theraguestinc.com/pain/abuse.htm, however no related patents or published patent applications have been identified. TheraQuest describes another formulation technique to impart anti-abuse properties to drug products. Stated therein is:

"TheraQuest's Abuse Deterrent SECUREL™ Technology Toxicity from high blood levels of sustained release opioids and other abusable drugs often occurs when recreational drug users and addicts crush the contents of the tablet or capsule and ingest the drug orally, snort it or inject it intravenously, after extraction and filtration.

TheraQuest has developed a proprietary secure-release (SECUREL™) abuse deterrent sustained release oral drug delivery platform. SECUREL™ operates by resisting crushing, melting and both chemical and physical attempts to extract the abusable drug. SECUREL™ formulations are difficult to tamper with and are designed to form a viscous substance upon contact with a solvent, such that the abusable drug cannot be easily filtered or drawn into a syringe for intravenous drug abuse. They are also resistant to extraction with common solvents, including alcohol. A potential advantage of such a "passive" abuse deterrent system is that it may protect both medical and non-medical users of opioids and other abusable drugs from intentional or unintentional opioid toxicity, without unnecessary harm to either group from the abuse deterrent technology."

In U.S. Pat. No. 7,201,920 B2 [Kumar et al.] assigned to Acura Pharmaceuticals, the disclosure of which is incorporated herein in its entirety, the inventors describe a formulation technique to prepare abuse deterrent dosage forms of opioid analgesics by employing a polyethylene oxide polymer to form a matrix.

In March 2008, Intellipharmaceutics reported the successful completion of a pilot clinical trial for its abuse and alcohol resistant sustained release oxycodone. From their website, www.intellipharmaceuitcs.com, the company reports as excerpted below:

"Mar. 27, 2008—IntelliPharmaCeutics Ltd. (Delaware) is pleased to announce significant results from a recently completed pilot clinical trial for its new abuse-resistant, alcohol-resistant once-a-day oral oxycodone formulation by its operating company IntelliPharmaCeutics Corp. of Toronto ("IntelliPharmaCeutics" or the "Company"). The product is covered by pending patent applications for its novel ReXista™ abuse and alcohol resistant drug delivery technology. It is one of the Company's line of in-house analgesic products in development for the management of moderate to severe chronic and acute pain.

The ReXista™ oxycodone product is a novel dosage form, designed to be resistant to abuse by oral ingestion when crushed or chewed, by injection when combined with solvents, and by nasal application when crushed or powdered. The abuse of this important pain relief drug has been well documented over many years."

Intellipharmaceutics' technology describing the proclaimed attributes through formulation is contained in a series of United States patents, specifically, U.S. Pat. No. 6,676,966 B1 [Odidi et al.], U.S. Pat. No. 6,652,882 B1 [Odidi et al.] and U.S. Pat. No. 6,800,668 B1 [Odidi et al.], each incorporated herein in their entirety.

With respect to the prodrug approach to attaining an anti-abuse formulation, New River's efforts at obtaining FDA approval of Vyvanse™ was well rewarded by Shire Pharmaceutical's purchase of New River for $2.6 billion. New River's patent U.S. Pat. No. 7,105,486 B2 (Mickle et al.) the disclosure of which is totally incorporated herein by reference, describes the covalent attachment of L-lysine to the drug substance, amphetamine, to provide compounds and compositions exhibiting abuse-resistant properties and useful for the treatment of disorders including attention deficit hyperactivity disorder (ADHD), attention deficit disorder (ADD), narcolepsy and obesity.

Similarly, Buchwald, et al. in United States Patent Application Publication (US 2004/0058946 A1), the disclosure of which is totally incorporated herein by reference, identifies modified oxycodone derivatives (prodrug) such that its physiological activity is only observed after the prodrug is converted to the drug in the mammalian gastrointestinal tract. Mickle, et al. in United States Patent Application Publication (US 2005/0266070 A1), the disclosure of which is totally incorporated herein by reference, identifies hydrocodone conjugates that release the drug substance following oral administration yet are resistant to intravenous or intranasal abuse.

Category 3 of Schmidt's report describes the industry's efforts to formulate opioid drug products which also contain an antagonist. The formulation techniques essentially sequester the antagonist so that the drug product produces the desired pharmaceutical effect when used for its intended purpose. However, should the drug product dosage presentation undergo manipulation (i.e. crushing or extraction) the antagonist is released and the potential for drug abuse is thwarted. Several companies have pursued this approach. For example, successful clinical trials were announced by the company Alpharma and reported in FDAnews Drug Pipeline Alert™ (Volume 4, No. 193, Oct. 3, 2006). The capsule formulation consists of an extended-release opioid with a sequestered core of naltrexone, an opioid antagonist. The sequestering subunit enabling this technology is described by Boehm in United States Patent Application Publication US 2004/01341552 A1, and is totally incorporated herein by reference.

Similarly, Elite Pharmaceuticals is reportedly initiating a Phase II clinical trial of its abuse resistant pain drug also employing the antagonist naltrexone hydrochloride. The report found in FDAnews Drug Pipeline Alert™ (Volume 4, No. 179, Sep. 13, 2006) states the previous Phase 1 trial confirmed the technical approach such that when the drug product was taken as intended, no antagonist was measured in the blood stream. However, if the drug product was crushed, the antagonist was released into the blood stream and the euphoria normally experience by oxycodone hydrochloride abusers was reduced.

Not surprisingly, Purdue Pharma (Euro-Celtique) has also pursued the agonist/antagonist combination formulation in an effort to impart anti-abuse properties to opioid analgesics.

In U.S. Pat. No. 7,332,182 B2 [Sackler], the disclosure of which is incorporated herein in its entirety, the inventor includes an irritant in the agonist/antagonist opioid formulation to further discourage use of the drug product for reasons other than its intended purpose. U.S. Pat. No. 6,696,066 [Kaiko et al.], the disclosure of which is incorporated herein in its entirety, describes a sustained release agonist/antagonist formulation capable of producing a mildly negative, "aversive" experience in physically dependent addicts.

Lastly, in regard to the agonist/antagonist approach to abuse resistant products, 3M received U.S. Pat. No. 7,182,955 B2 [Hart et al.], the disclosure of which is incorporated herein in its entirety, the inventors describe an abuse resistant transdermal dosage form (a patch) formulated and assembled to deliver the desired active agent when the product is used in a manner consistent with its intended purpose yet deliver the antagonist if improperly used.

For the Category 4 approach of the Schmidt report regarding use of a nasal gel, Ionix Pharmaceuticals is the assignee of United States Patent Application Publication 2007/0231269 [Birch et al.] describing the nasal delivery of an opioid analgesic or a non-steroidal anti-inflammatory drug in a manner to produce a therapeutic plasma concentration within thirty minutes with a duration of at least two hours.

Despite the administrative efforts to curtail drug abuse via educational materials, medical professional training, patient counseling, law enforcement support, drug abuse treatment programs, drug prescribing protocols, legislative action, public awareness, governmental reporting, medical professional organizations' support of anti-abuse products, and charitable and religious group influence, and all combinations of these and other activities, the statistics indicate drug abuse is growing at a rate faster than the population's growth. It is clear society has recognized and is aware of the consequences of drug abuse and while administrative measures may diminish the problem, the financial gain available to practitioners of the illicit drug trade likely draw an analogy to the government's attempt at alcohol prohibition and enactment of the Eighteenth Amendment. This legislative exercise proved futile and made many willing participants of the illegal trafficking of alcohol wealthy. Ultimately, the Twenty-First Amendment repealed the Volstead Act and Prohibition ended. With its end, the financial incentive was also removed and alcohol taxation returned. Administrative efforts may have little impact on the drug abuse crisis to which the Nation suffers until our borders are secured.

In respect to the technical efforts expended to curtail drug abuse, industry icons and small companies alike have instituted research and development programs at immense expense to identify reliable solutions, through chemistry, to achieve abuse resistant/tamper-proof drug products. Unfortunately, the rational approaches to date have met with limited success and the alternatives require a more extensive and inventive manipulation of the related chemistries—particularly to impart such properties to the opioid family of drug products. Described herein below is such an inventive solution to address the need for a platform approach to introducing anti-abuse properties to controlled substance pharmaceuticals and to other medicinal products which may be abused.

As in the above discussion, administrative and technical measures will be required to effectively curb drug abuse. The technical contributions have primarily centered upon formulation technologies to prevent the physical extraction of the active ingredient from the dosage product. While the formulation approach is valid, it also contains inherent flaws since any pharmaceutical composition relying on physical mixtures and/or the mixture's differential solubilities and/or other physical/mechanical barriers (e.g. a matrix) to impart anti-abuse properties can be overcome employing physical means. Fundamentally, these various formulation techniques would provide excellent second-line defense mechanisms when coupled with a chemical methodology to impart anti-abuse properties to the drug product. By way of example, with the aforementioned prodrug discussion regarding the amphetamine exemplar embodied in New River's Vyvanse™, the drug product delivers an anti-abuse feature through chemical means which would be very difficult to defeat—and only through chemical transformation. Unfortunately, the prodrug approach, in general, requires significant R&D resources to tailor each prodrug to a host of regulatory specifications before market approval can be granted by the FDA. Consequently, the prodrug approach is costly, time-intensive and does not provide a universal, platform solution to imparting anti-abuse properties to the medially necessary amine-containing controlled substances. The invention described herein encompasses a platform approach to imparting anti-abuse properties at the molecular level through unique salt forms of the opioid alkaloids.

In spite of the ongoing, and extensive, efforts there is still and strong, even mandated, desire for an opioid which is less susceptible to purposeful or incidental abuse particularly with regards to dose dumping.

SUMMARY OF THE INVENTION

The present invention provides the ability to modify the dissolution performance features of narcotics, and in particular, opiates by the design and selection of the opiate as an organic acid addition salt. Five design factors are relevant: 1) the hydrophilicity of the opioid, 2) the family of organic acid selected for forming the organic acid addition salt with the amine-containing opiate, 3) the relative stoichiometry available between the amine-containing opiate and the number of salt forming sites on the organic acid component, 4) the selection of an amorphous, polymorphic or combinations thereof of the organic acid addition salt of the amine-containing opiate, and 5) the employment of an additional organic acid (or its non-active ingredient salt) as a functional excipient. For purposes herein, a functional excipient is defined as an otherwise pharmaceutically inert material but when employed with the active pharmaceutical ingredient salts described herein, a synergistic effect is obtained wherein the excipient contributes to the performance features desired which is inhibition of dose dumping. These five factors may be used individually or in combination with one another, and/or employed in concert with existing formulation techniques to provide drug product formulations exhibiting anti-abuse features and/or to provide modified dissolution profiles as compared singularly to the opiate mineral acid salt.

One embodiment of the present invention comprises organic acid addition salts of the amine containing opioid family of narcotic compounds comprising opiates of natural product isolates, natural isolates further processed by synthetic or enzymatic processes, and lastly, those compounds possessing structural characteristics similar to the natural opiates yet obtained completely from synthetic processes, and the processes thereof for their manufacture. The compounds of interest include but are not limited to oxycodone, hydrocodone, morphine, apomorphine, hydromorphone, oxymorphone, codeine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, levorphanol, nalbuphine, nalmefene, naloxone, naltrexone, noscapine, opium, and oripavine. While structurally similar, these compounds represent a range of hydrophilic character predominantly driven by the presence of oxygen-containing functionality (ketone, aryl ether, ring-fused/cyclic aryl-alkyl ether, phenol, primary and secondary alcohol). The hydrophilic character of these opioids and their ability to hydrogen bond with water and alcohols facilitates their ability to be extracted from, and analogously, to be susceptible to dose dumping from a formulated product.

Consequently, it is an object of the present invention to temporarily interrupt the hydrophilic behavior of an opioid or opioids by preparation of its organic acid addition salt such that extraction or dose dumping of the opioid occurs principally in the gastrointestinal tract (human or animal) and in a relevant time frame for therapeutic treatment. Further, the selection of a particular organic acid addition salt for a given opiate is selected based upon the kinetics of dissolution wherein only about 0-80% of the opiate is released from its salt form over a period of about 60-90 minutes while in the presence of about 0-40% alcohol.

It is an object of the present invention to provide organic acid addition salts of opioid amine-containing compounds which exhibit anti-abuse properties providing for bio-availability of the drug substance when the drug product is used in a manner consistent with its intended route of administration, but which is otherwise bio-unavailable if used by an unintended route of administration.

It is an object of the present invention to impart unique anti-dose dumping properties to alkaloids by preparation of their amorphous and polymorphic organic acid addition salts and formulations therewith.

It is an object of this invention to engineer into, or tailor, the dissolution profiles of the organic acid addition salts of opioid amine-containing compounds by employing at least one of the following factors: a) selection of an organic acid family selected from the group of pamoates, xinafoates or salicylates, b) selection of an available stoichiometric relationship between the amine and the organic acid family, c) selection of a particular polymorph, or combinations or polymorphs, each with or without amorphous content and each with or without solvent inclusion such as hydrates or solvates, and d) formulation of the organic acid salt of the opioid with additional quantities of an organic acid or its non-API salt such as formulation with pamoic acid, disodium pamoate, beta-hydroxynaphthoic acid its isomers and inorganic salts.

It is an object of the present invention to provide organic acid addition salts of opioid compounds which are resistant to and inhibit dose dumping.

It is an object of the present invention to provide formulations comprising an organic acid or its non-API salt such as formulation with pamoic acid, disodium pamoate, beta-hydroxynaphthoic acid its isomers and inorganic salts to impart an anti-dose-dumping feature to a drug product formulation.

It is an object of the present invention to provide organic acid addition salts of opioid compounds similar in structure to the following substituted morphinans and to opiates in general, for example but not limited to that of morphine:

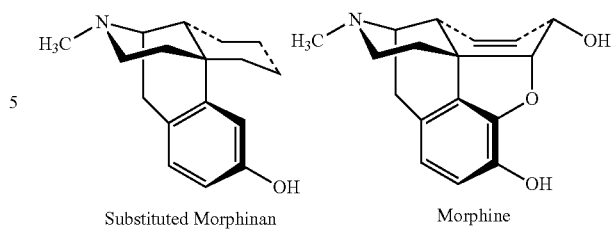

Substituted Morphinan        Morphine

It is an object of the present invention to provide organic acid addition salts of opioid compounds selected from the group consisting of but not limited to oxycodone, hydrocodone, morphine, apomorphine, hydromorphone, oxymorphone, codeine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, levorphanol, nalbuphine, nalmefene, naloxone, naltrexone, noscapine, opium, and oripavine, their (bio)-synthetic intermediates and synthetic derivatives.

It is an object of the present invention to provide organic acid addition salts of opioid compounds wherein the organic acid component defined as Structure A further herein.

It is a feature of the present invention that the organic acid addition salts of the opioid family of alkaloids are available in amorphous and polymorphic forms, said amorphous and polymorphic forms having unexpectedly low phase transitions for the amorphous form and significantly high phase transitions for the polymorphic form.

It is a feature of the present invention that the amorphous and polymorphic forms of the organic acid addition salts of the opioid family of alkaloids exhibit unexpectedly high enthalpies of phase transition.

A particular feature of the present invention is that the amorphous and polymorphic forms of the organic acid addition salts of the opioid family of alkaloids exhibit essentially identical dissolution rates.

A feature of the present invention is robust and stable drug product formulations prepared from the organic acid addition salts of the opioid family of alkaloids.

It is yet another feature of the present invention to provide tamper resistant and/or tamper proof drug product formulations employing the organic acid addition salts of the opioid family of alkaloids.

It is another feature of the present invention to provide organic acid addition salts of the opioid family of alkaloids which when employed with an anti-Page abuse formulation technique impart at least two anti-abuse mechanisms into the drug product.

It is a feature of the present invention to employ physical and chemical means to prepare anti-abuse controlled substance formulations.

Another feature of the invention described herein is the synergistic effect observed for reducing dose dumping when formulating opioid organic acid addition salts with an excess of the specific acid component or selected from the group of organic acids imparting anti-abuse properties and whereas in the acid component or those of the group may be employed as their alkali metal salt.

These and other advantages, as will be realized, are provided in a drug substance with a pharmaceutically acceptable organic acid addition salt of an opioid wherein said organic acid is selected from Structure A:

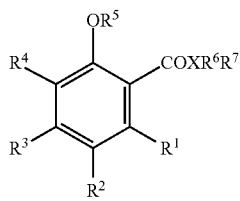

Structure A wherein $R^1$-$R^4$ are independently selected from H, alkyl or substituted alkyl of 1-6 carbons, adjacent groups may be taken together to form a cyclic alkyl, cyclic alkyl-aryl, or cyclic aryl moiety;
$R^5$ is selected from H, or an alkali earth cation;
$R^6$ and $R^7$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur; and wherein the drug substance has a morphology selected from amorphous and crystalline.

Another embodiment is provided in a method for mitigating dose dumping comprising providing a drug product comprising a drug substance wherein the drug substance comprises an opioid wherein the opioid has a wt % released at 30 minutes in 0.1 N hydrochloric acid comprising ethanol which is no higher than in 0.1 N hydrochloric acid without ethanol.

Yet another embodiment is provided in a drug product which is not susceptible to dose dumping wherein the drug product comprises a drug substance comprising an opioid wherein the opioid has a wt % released at 30 minutes in 0.1 N hydrochloric acid comprising ethanol which is no higher than in 0.1 N hydrochloric acid not comprising ethanol.

Yet another embodiment is provided in a drug product comprising a drug substance comprising a pharmaceutically acceptable organic acid addition salt of an opioid wherein the organic acid is selected from Structure A:

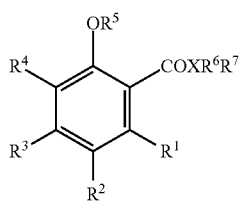

Structure A wherein $R^1$-$R^4$ are independently selected from H, alkyl or substituted alkyl of 1-6 carbons, adjacent groups may be taken together to form a cyclic alkyl, cyclic alkyl-aryl, or cyclic aryl moiety;
$R^5$ is selected from H, or an alkali earth cation;
$R^6$ and $R^7$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur and wherein less than 85 wt % of said opioid is released at a biological pH in 1 hour.

Yet another embodiment is provided in a drug product which is not susceptible to dose dumping comprising a pharmaceutically acceptable organic acid addition salt of an opioid wherein said organic acid is selected from Structure A:

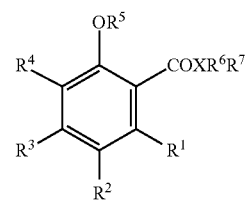

Structure A wherein $R^1$-$R^4$ are independently selected from H, alkyl or substituted alkyl of 1-6 carbons, adjacent groups may be taken together to form a cyclic alkyl, cyclic alkyl-aryl, or cyclic aryl moiety;
$R^5$ is selected from H, or an alkali earth cation;
$R^6$ and $R^7$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur; and a material defined by Structure H:

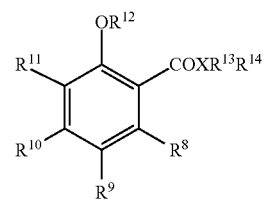

Structure H wherein $R^8$-$R^9$ are independently selected from H, alkyl or substituted alkyl of 1-6 carbons, adjacent groups may be taken together to form a cyclic alkyl, cyclic alkyl-aryl, or cyclic aryl moiety;
$R^{12}$ is selected from H, or an alkali earth cation;
$R^{13}$ and $R^{14}$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur and wherein said opioid has a wt % released at 30 minutes in 0.1 N hydrochloric acid comprising ethanol which is no higher than in 0.1 N hydrochloric acid not comprising ethanol.

Yet another embodiment is provided in a method of administering an active pharmaceutical comprising providing an opioid containing pharmaceutically active compound in a dose suitable for achieving a therapeutic dose of said opioid in a predetermined time wherein said therapeutic dose is not exceeded by ingestion of alcohol at biological pH.

A solid, controlled release, oral dose form of an active pharmaceutical wherein said dose form comprises an analgesically effective amount of an opioid salt wherein at least 12.5 wt % to no more than 42.5 wt % of said opioid is bioavailable at 1 hour at a biological pH and wherein said opioid bioavailability is not increased in the presence of ingested alcohol.

DETAILED DESCRIPTION OF THE INVENTION

Figure 1:
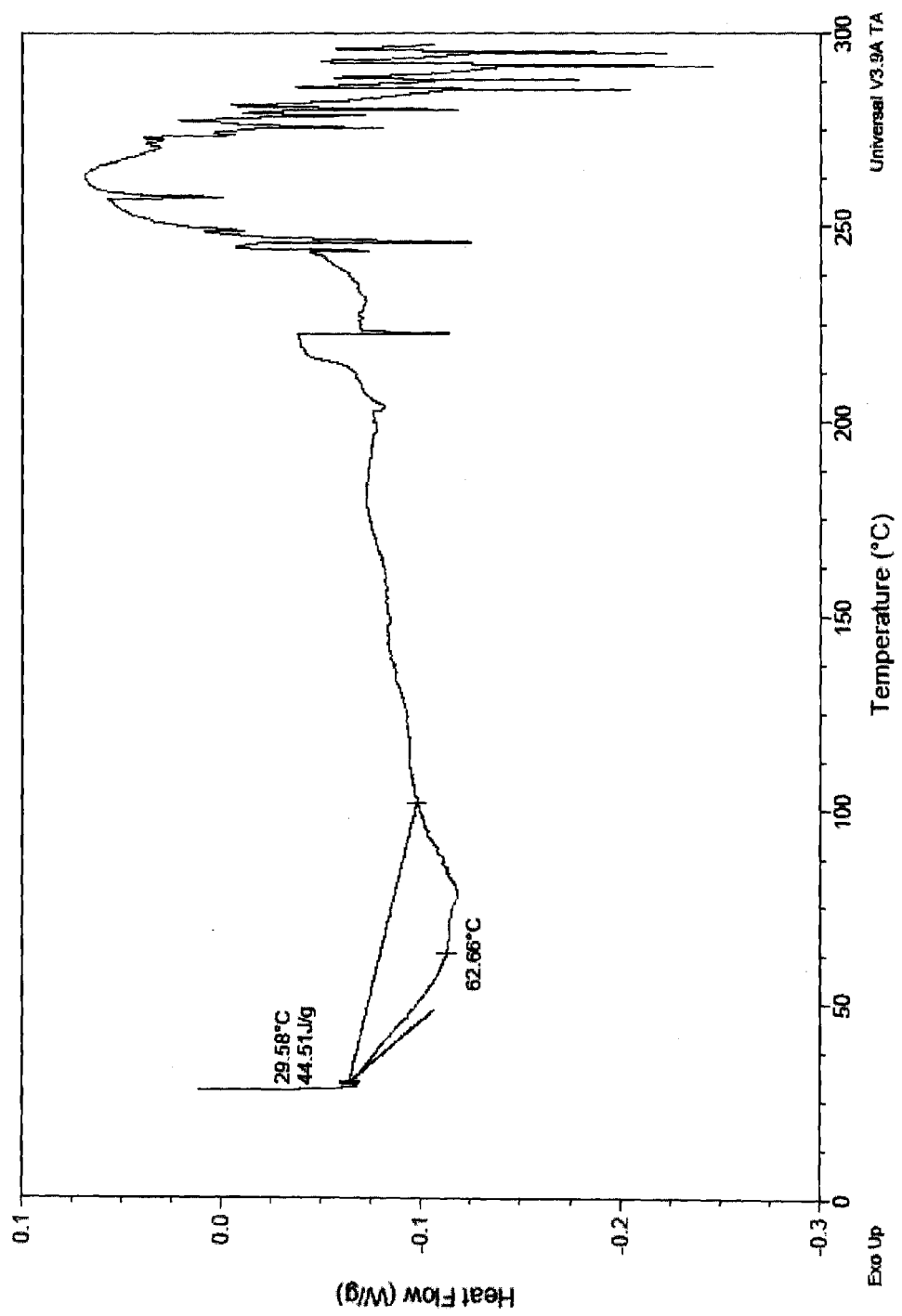
FIG. 1 is the differential scanning calorimetry (DSC) thermogram of amorphous oxycodone pamoate.

A pharmaceutical formulation is provided which is particularly advantageous with regards to patient safety is described herein. The formulation comprises a salt of an opioid wherein the salt prohibits the opioid from being susceptible to abuse particularly with regards to dose dumping.

Particularly preferred for the present application are morphinans, synonymous herein with the term opioids, with hydrocodone, oxycodone, hydromorphone and morphine being most preferred. Together these opioids represent a range of potential chemical and physical phenomena pertaining to opioid hydrophilicity as a class. Indeed, each of these opioids as their hydrochloride salt exhibit good solubility in water as expected. However, to demonstrate the depth and breadth of the present invention, the degree of hydrophilicity as determined by hydroxyl moieties on the opioid, was considered as a demonstrative factor for the general applicability of the processes and performance features described herein. Specifically, hydrocodone does not contain a hydroxyl group; oxycodone contains one hydroxyl moiety as a tertiary cyclo-alkyl alcohol; hydromorphone contains one phenolic hydroxyl whereas morphine contains one phenolic hydroxyl and one secondary cyclo-alkyl alcohol. The formation of organic acid addition salts with these compounds was shown to have a significant impact on their properties such that the type of salt formed, i.e. of the pamoate or xinafoate families, when compared with the mineral acid or small organic acid salt such as tartrate. Indeed, the hydrophilic nature of the opioids by the presence of hydroxyl groups would need to be overcome in order to obtain performance differentiation between the mineral acid salts versus the salts of the present invention.

In an embodiment of the present invention, the controlled substance is an amine-containing organic salt which does not release in the pH window of about 4 to about 9. At a pH of less than about 4, the subject organic salts become protonated with the concomitant precipitation of organic acid. At pH greater than about 9, the addition salt is soluble yet it is quite difficult to distinguish between the organic acid component and the active amine by organic solvent extraction.

The organic acids of the present invention are those forming salts with amine-containing active pharmaceutical ingredients which preferably do not release in an aqueous solution within a pH window of about 4 to about 9 and which interfere with the direct isolation of the API outside of the central pH window.

The organic acid is defined by the following Structures A through G wherein Structure A represents the general family of Markush compounds embodied within the invention. Structure B represents the subset of salicylic acid and its derivatives conceived as a component of this invention. Structures C, D and E are regio-isomeric variations on Compound A wherein two adjacent substituents on Compound A form a fused aryl ring (i.e. $R^1+R^2$; $R^2+R^3$; and $R^3+R^4$). Structures F and G represent a further sub-category of dimer-like compounds derived from Structure A. In Structure F, dimerization has occurred through $R^4$ of two Structure A compounds with both possessing fused-aryl ring systems formed via $R^2+R^3$. In Structure G, dimerization has again occurred through $R^4$ of two Structure A compounds however both Structure A residues possess fused-aryl ring systems formed via $R^1+R^2$.

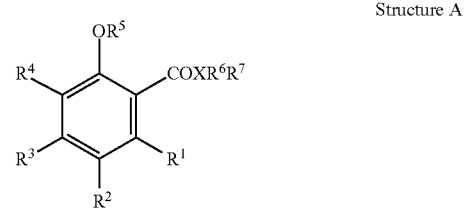

Structure A

Wherein $R^1$-$R^4$ are independently selected from H, alkyl or substituted alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6+R^7$ may represent an alkali earth cation, ammonium or together form a heterocyclic moiety;

Particularly preferred organic acids include Structures B through E.

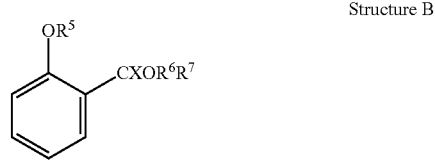

Structure B wherein $R^5$, $R^6$, $R^7$ and X remain as defined above for Structure A;

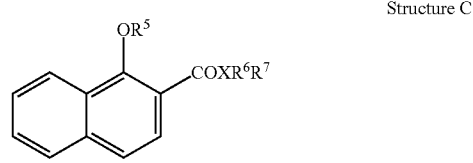

Structure C wherein X, $R^5$, $R^6$ and $R^7$ remain as defined above for Structure A and more preferably X is O;

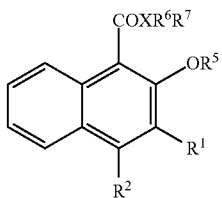

Structure D wherein X, $R^1$, $R^2$, $R^5$, $R^6$ and $R^7$ remain as defined above for Structure A and more preferably X is O; $R^1$ and $R^2$ are hydrogen;

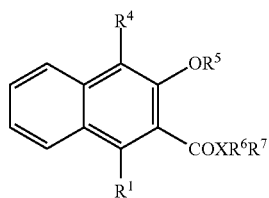

Structure E wherein X, $R^1$, $R^4$, $R^5$, $R^6$ and $R^7$ remain as defined above for Structure A and more preferably X is O, $R^1$ and $R^4$ are hydrogen;

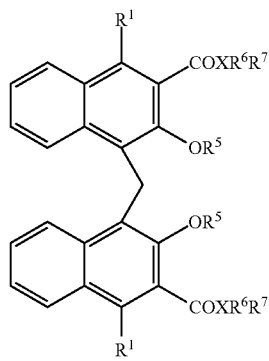

Structure F wherein X, $R^1$, $R^5$, $R^6$ and $R^7$ are independently defined as above for Structure A and more preferably at least one X is O and at least one $R^1$ is hydrogen; and

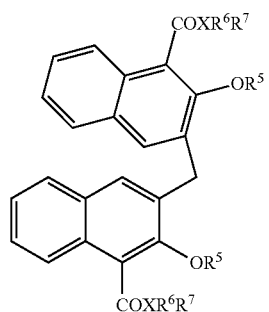

Structure G wherein X, $R^5$, $R^6$ and $R^7$ are independently defined as above for Structure A and more preferably X is O and $R^5$ is hydrogen.

Pamoic acid, or a synthetic equivalent of pamoic acid, is the preferred embodiment. Pamoic acid has a formula corresponding to Structure F wherein X is O; $R^5$, $R^6$ and $R^7$ are hydrogen.

A synthetic equivalent of pamoic acid is a material that provides the structural moiety independent of its particular salt, ester, or amide form and that upon pH adjustment yields pamoate functionality suitable for reaction, optionally with one or two equivalents of an amine-containing active pharmaceutical ingredient to form a pamoate salt. Examples of synthetic equivalents of pamoic acid capable of manipulation to produce pamoate salts include but are not limited to, disodium pamoate, mono-alkali pamoate, di-ammonium pamoate, di-potassium pamoate, lower molecular weight di-alkyl and/or di-aryl amine pamoate, lower molecular weight di-alkyl and/or di-aryl esters of pamoic acid, and lower molecular weight di-alkylacyl and/or di-arylacyl O-esters of pamoic acid, i.e. those alkylacyl and arylacyl esters formed using the hydroxyl moiety of pamoic acid and not the carboxylic acid functional group. The descriptor phrase "lower molecular weight" used above means the indicated moiety has a molecular mass contribution within the pamoate derivative of less than about 200 amu.

For clarity, the use of lower molecular weight di-alkyl or di-aryl amine pamoate allows for the exchange of higher molecular weight amines, or drug free bases, to be exchanged for the lower molecular weight amine component during the salt formation reaction. Similarly, the use of lower molecular weight di-alkylacyl and/or di-arylacyl pamoates allow for their conversion through ester hydrolysis to the pamoic/pamoate moiety followed by reaction with the desired drug free base.

In a preferred embodiment of the invention, at least one equivalent of the amine containing drug substance is reacted per mole of disodium pamoate to yield the drug substance pamoic acid salt. Preferably, 2:1, 1:1, or mixtures thereof, equivalents of amine per mole pamoic acid moiety or related organic acids are prepared. Typically, an aqueous acidic solution of the amine containing drug substance is combined with a basic solution of pamoic acid or disodium pamoate. The acid/base reaction ensues and the insoluble organic acid salt precipitates from the aqueous solution. Optionally, the salt can be purified, dried and milled to obtain a drug substance ready for formulation into the desired delivery format. The drug product formulated with the drug substances then possesses the targeted delivery characteristics of the drug substance and the potential for abuse of either the drug substance and/or drug product is eliminated or greatly reduced when abuse is attempted via the mucosal surfaces or by injection.

Another feature of the invention is the preparation of pamoate salts for legitimate active pharmaceutical ingredients wherein the active pharmaceutical ingredient is otherwise used as a synthetic raw material in the illegal or illicit production of dangerous drugs.

For the purposes of the present invention an API of a drug product is not directly isolable if it can not be isolated by solubilizing the drug product to form a solubilized drug substance and filtering the solubilized drug substance without further chemical processing.

A useful and unexpected observation was made while preparing the selected organic acid addition salts of these compounds. Bristol et al. (cited above) describes processes for preparing the pamoate, xinafoate and salicylate families of amine-containing controlled substances. Further, and in particular during preparation of the pamoate salts, the salt precipitated from the reaction mixture and exhibited poor solubility characteristics in the primarily aqueous reaction medium. As the pamoate salts of various controlled substances were isolated, they were subjected to a host of manipulations to obtain different polymorphic forms of the salt. In King et al., also cited above, these different pamoate polymorphic forms of the same active ingredient were demonstrated to behave significantly differently than expectation. In general, the findings reported herein for the opioid active ingredients do not follow the observed processing trends or dissolution features found for other organic acid addition salt compounds. The amorphous and polymorphic forms were shown to have essentially identical dissolution profiles. There appears to be a unique feature to the salt formed between the opiate moiety and the organic acid components of the present invention. Formation of the salt within an aqueous medium affords a precipitate, however, with unforeseen characteristics. The "solids" formed are very gummy or taffy-like in nature, and exhibit very poor handling qualities well beyond the normally expected wetcakes isolated from pamoate salt-forming reaction mixtures. The gummy solids proved very difficult to manipulate for analytical testing or product formulation purposes and careful processing conditions were required to isolate the amorphous and polymorphic forms of the compounds reported herein.

It is reasoned that the careful isolation conditions are required to defeat the hydrophilic character of the opioids, even as their pamoate salts, and to remove excess amounts of water from the compounds. As amorphous and polymorphic opiate salts were isolated, analytical characterization confirmed the presence of water from about 0 to 6 percent. Despite this water content, the taffy, or gummy-like nature of the original isolates was no longer observed.

Amorphous materials of other, non-opioid, pamoate salts have been reported in the literature. In U.S. Pat. No. 4,076,942 (Smith et al.) entitled "Crystalline Dipilocarpinium Pamoate", the inventors describe the amorphous form of this compound as presenting "a drawback in not being readily and easily handleable, in being difficult to formulate in an appropriate ocular delivery system and in being difficult to generate stoichiometrically". The inventors ultimately prepared solvated forms of the title compounds which, through a de-solvating process yielded crystalline dipilocarpinium pamoate.

The intractable nature of the pamoate salts isolated was a very unexpected result and required further investigation and assessment at a molecular level. Experiments were conducted to assess the fundamental characteristics of the gums for comparison to other pamoate, xinafoate and salicylate salt families of amine-containing active pharmaceutical ingredients. The differential scanning calorimetry (DSC) thermograms of the gums indicated amorphous behavior with low phase transition temperatures, generally below 100° C., but with large heats of fusion, generally higher than 100 Joules per gram. Typically for the non-opioid pamoate salts, the amorphous materials had phase transitions greater than 100° C. and low heats of fusion, less than 50 Joules per gram. Clearly, the opioid component of the salt was contributing to the paradoxical thermal analysis results.

Without holding to any particular theory or mechanism, it was postulated that the abundance of oxygen atom constituents, that is, oxygen atom containing substituents or functionality commonly found grouped to one face/side of the opioid structure may possess sufficient hydrophilicity to entrap or bind water to the molecule. Since the pamoate moiety (or other suitable organic acid component to the salt) would bind to the opioid on the molecule's face containing the nitrogen functionality, the oxygen-atom rich face would be exposed and capable of binding water through strong hydrogen bonding mechanisms. The high heats of fusion and amorphous appearance of the isolated salts along with the poor tactile properties of the salt support the complexation of water with the salt. These gummy solids were also readily soluble in ethanol, ethyl acetate, tetrahydrofuran and the like, which is a totally unexpected characteristic of pamoate salts. Without additional processing, it is unlikely these salts would have been identified as possessing beneficial anti-abuse properties, e.g. as gummy solids they exhibit ethanol solubility whereas when isolated as free flowing amorphous or crystalline powders, ethanol solubility is substantially reduced.

Besides the complexation of water to the salt causing the observed behaviors, it was unknown if the opioids would exist as both the 1:1 and 2:1 (amine:pamoate) salts, or if both were available but one thermodynamically preferred. Two fundamental experiments were conducted to attempt to delineate this possibility. The first was to extend the salt forming reaction for longer times under higher temperature with the intent to "cure" the salt into a polymorphic form. Further, the reaction conditions were established with the intent of preparing the 2:1 salt. As a control experiment to this approach, the stoichiometry of the reaction was altered to determine if the opioids preferred a 1:1 salt form. Secondly, the preparation of the xinafoate salts were attempted which are by structural restriction limited to yielding only the 1:1 (amine:xinafoate) salt. In all cases, gummy, tacky solids were initially isolated. Ultimately, the pamoate series exhibited only the 2:1 amine:pamoate stoichiometric relationship.

In Bristol et al. pamoate, xinafoate and salicylate families of amine-containing controlled substances were disclosed which yielded active pharmaceutical ingredient salts exhibiting anti-abuse properties. In King et al. it was further demonstrated that these salts may exhibit polymorphism and in conjunction with the salt's stoichiometric composition a dissolution profile could be obtained which provides controlled release and optionally targeted release of the active ingredient. The fundamental structure of the opioids, which contains the morphine-type ring system and the nearly stereofacial arrangement of an oxygen-rich region of these molecules led to very unexpected findings with respect to dose dumping. To illustrate this stereofacial arrangement of oxygen atoms, the structure of morphine below represents this general arrangement within the opiates.

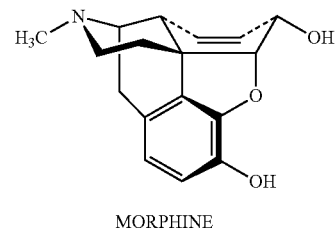

MORPHINE

Figure 102:
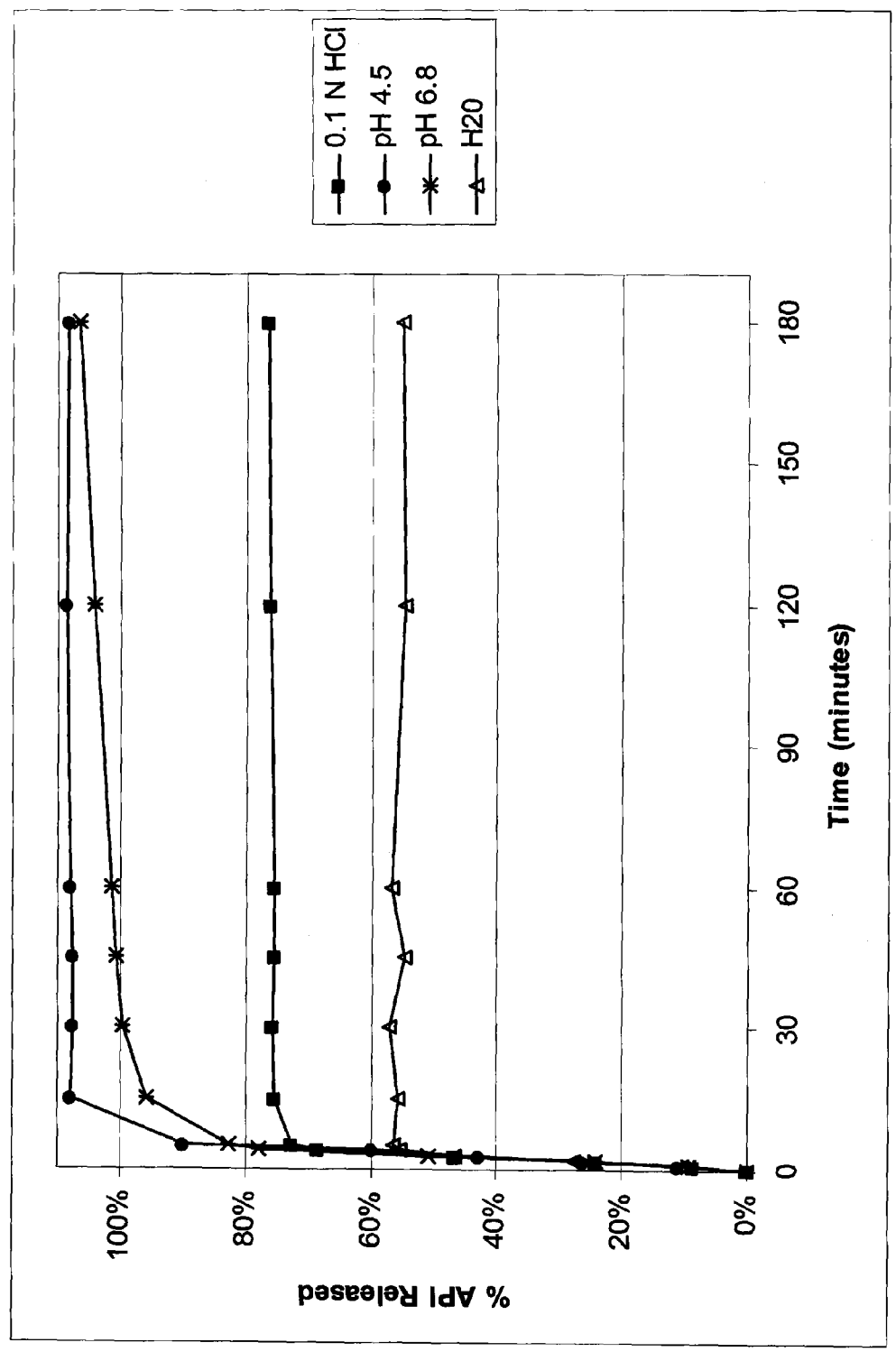
FIG. 102 is the graphical representation of the dissolution profiles of imipramine hydrochloride as a function of pH.
Figure 103:
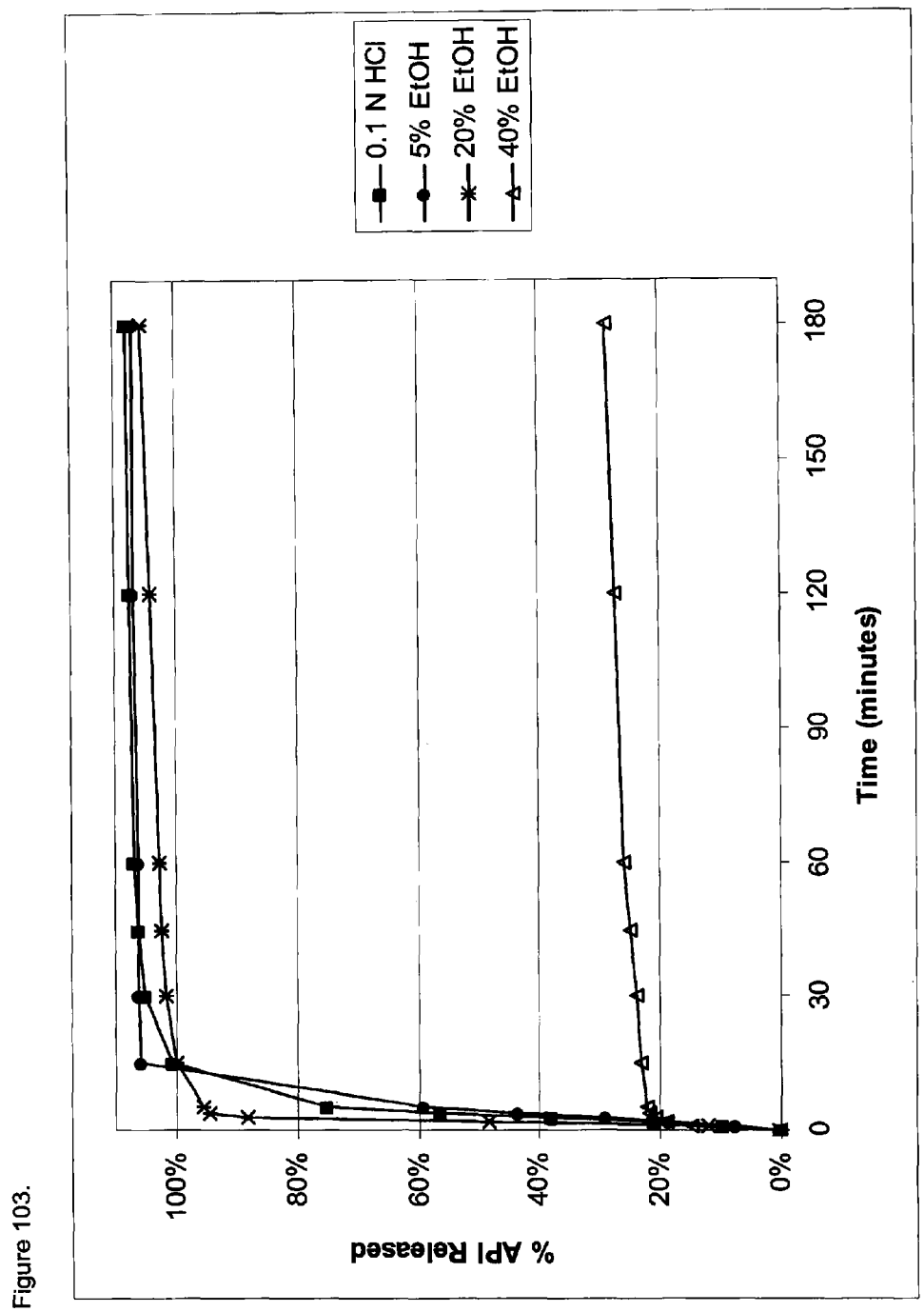
FIG. 103 is the graphical representation of the dissolution profiles of imipramine hydrochloride in acidic media as a function of ethanol concentration.
Figure 104:
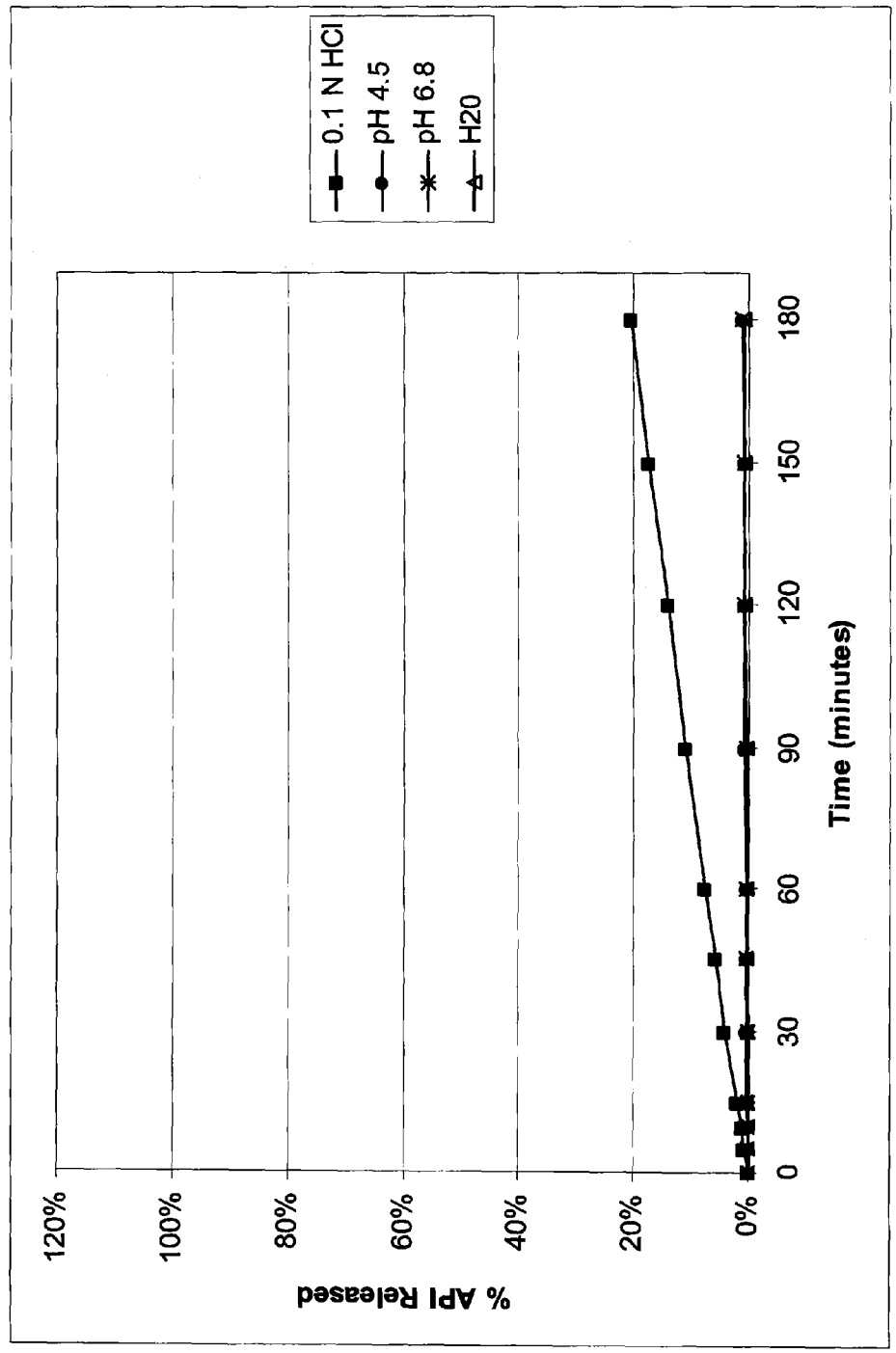
FIG. 104 is the graphical representation of the dissolution profiles of imipramine pamoate as a function of pH.
Figure 105:
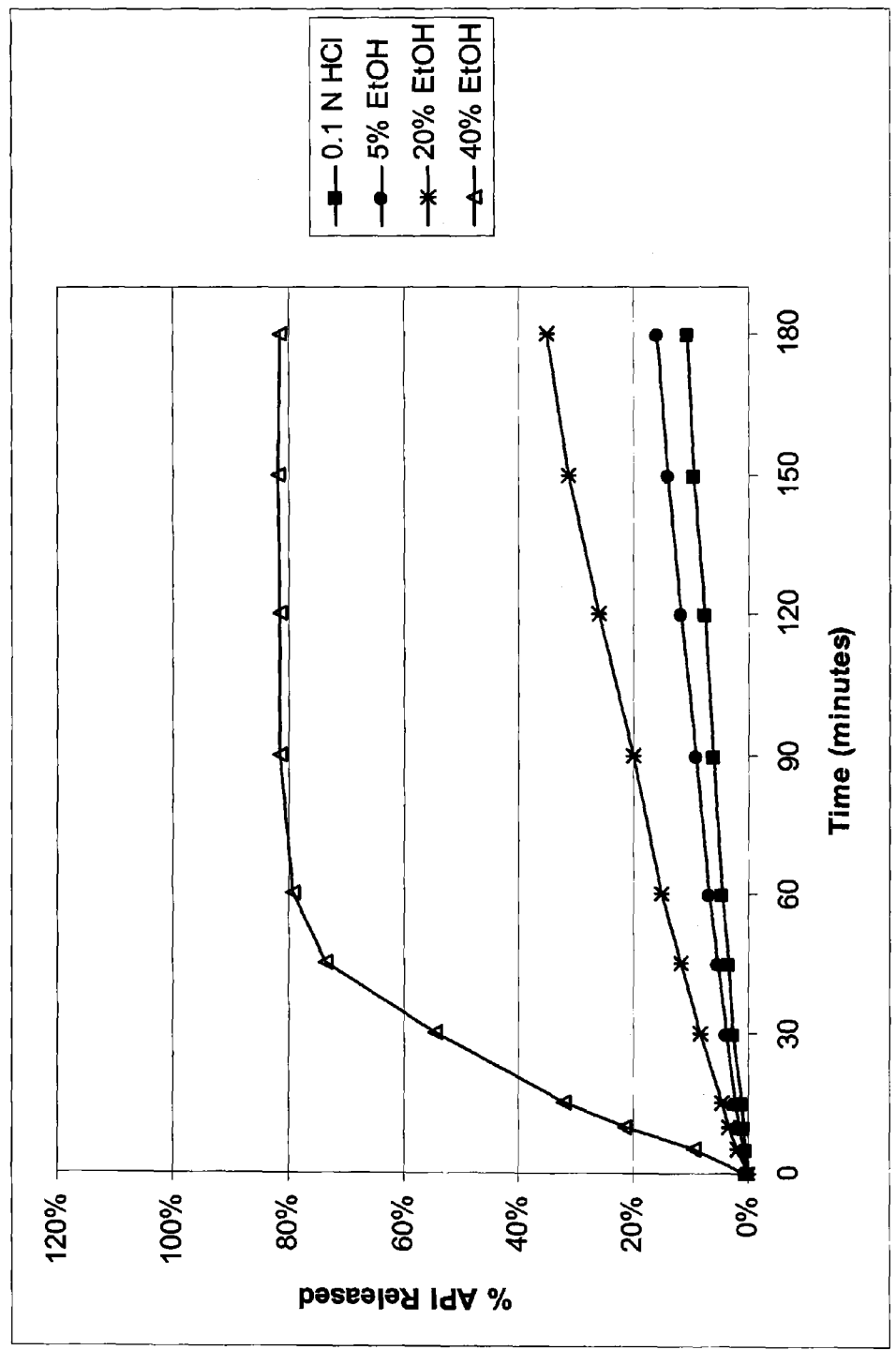
FIG. 105 is the graphical representation of the dissolution profiles of imipramine pamoate in acidic media as a function of ethanol concentration.

The dose dumping experiments performed were based on a United States Food and Drug Administration Guidance developed to evaluate dose dumping on the opiate, oxymorphone. When applied to the opiate salts of the present invention, it was observed that dose dumping could be controlled and prevented at the API level, that is, in an unformulated dosage form. This observation is a unique, unexpected, feature of the opiate salts reported herein and was confirmed by conducting a set of dissolution experiments on imipramine hydrochloride and imipramine pamoate as a mixture of amorphous and polymorphic forms. The pH dissolution profiles of these compounds, FIGS. 102 and 104 (hydrochloride and pamoate, respectively), provided results consistent with expectations. However, the dose dumping results were very unexpected: imipramine pamoate exhibited dose dumping properties (FIG. 105) at the three levels of alcohol content (5, 20 and 40%) tested. Hence, it is reasoned that the pamoate moiety when employed as a salt forming component with an opiate alters the hydrophilic/lipophilic balance of the opiate sufficiently to impair and compete with hydrogen bonding with the alcoholic solution in acidic media. In contrast, the pamoate salt of imipramine cannot overcome the lipophilic, oily nature of imipramine which is readily solubilized in an alcoholic, acidic medium. The unexpected behavior in dose dumping performance between pamoate salts of imipramine and of the opiates was further confirmation of the herein described technology's effective application to the opiates. It is acknowledged in the opiate literature ("Opiates", by George R. Lenz, Suzanne M. Evans, D. Eric Walters, and A. J. Hopfinger, Academic Press, Inc., ©1986, p. 177 and reference cited therein: Med. Res. Rev., 2, 355 (1982), P. R. Andrews and E. J. Lloyd) that many of the pharmacophores of central nervous system (CNS) drugs (including for example imipramine and morphine) possess "rings and nitrogens [which] occupy equivalent spatial locations". The authors' assertion is demonstrated by the remarkable superposition of the crystal structures of eight diverse CNS drugs.

As is discussed herein, a number of organic acid addition salts of these four opioids were prepared and evaluated against dissolution and dose-dumping parameters as compared with the current commercial offerings of these alkaloids as other salt forms. To provide an organizational framework for the observed discoveries, essentially five factors contribute to understanding the invention herein. These are:
1) the hydrophilicity of the opioid;
2) the organic acid family used to prepare the organic acid addition salt, most preferably a pamoate or xinafoate;
3) the stoichiometry observed from preparation of the organic acid addition salt;
4) the amorphous versus polymorphic form of the opioid organic acid addition salt; and
5) the effect of (a) additional organic acid or its conjugate base formulated with the opioid organic acid addition salt, and/or (b) the effect of a different organic acid or its conjugate base formulated with the opioid organic acid addition salt, and/or the effect of the stoichiometric ratio within the formulation between the so named ingredients within (a) and/or (b).

The hydrophilicity of the selected opioids has been discussed vide supra, and it is well known in the industry that careful processing is required to remove water from opioids and their salts. Indeed, the propensity of these opioids to retain water impaired the preparation and isolation of their organic acid addition salts until processes could be identified which would yield the desired compounds. No doubt, the ability of the opioids to retain water impacts their in-vitro and in-vivo dissolution behavior, which to impart an anti-abuse feature to such compounds, must be addressed by an alternative mechanism or mechanisms. The following discussion demonstrates how the five factors listed above were employed to yield a platform technology exhibiting features with the express purpose of curtailing the abuse of the medically important opioids.

FIGS. 1 through 36 and FIGS. 98 through 101 contain the characterization data for the organic acid addition salts of the selected opioids. Amorphous and polymorphic forms of each opioid were prepared as their pamoate salt, and in the case of oxycodone, two pamoate polymorphs were isolated. For each opioid, the pamoate salt isolated was analyzed as the 2:1 (opioid:pamoate moiety) compound. The pamoate polymorphs of oxycodone did not exhibit inclusion of solvent into the isolated crystalline material; however, hydrocodone, hydromorphone and morphine pamoates contained approximately one equivalent of acetone within the compound. Most interestingly, the acetone adducts, while isolated from acetone, were not soluble in acetone. Further the compounds (amorphous and/or polymorphic) have poor aqueous and alcohol (iso-propanol) solubility. This solubility property is further elucidated in a subsequent section wherein the anti-dose dumping feature of these salts was explored in depth as a function of ethanol concentration in acidic media. Each of the opioid xinafoate salts was isolated as a crystalline compound and characterized.

The general (in)solubility features of the cited salts are one aspect of imparting anti-abuse features to opioid drug substances. The active ingredient, as the free base or a mineral acid salt is often extracted from the dosage presentation by employing a readily available organic solvent such as iso-propanol (IPA), acetone, toluene, xylenes or a petroleum fuel. The poor solubility of the organic acid addition salts in these media exacerbate the attempts to isolate the active from the dosage form for purposes of abuse.

Figure 37:
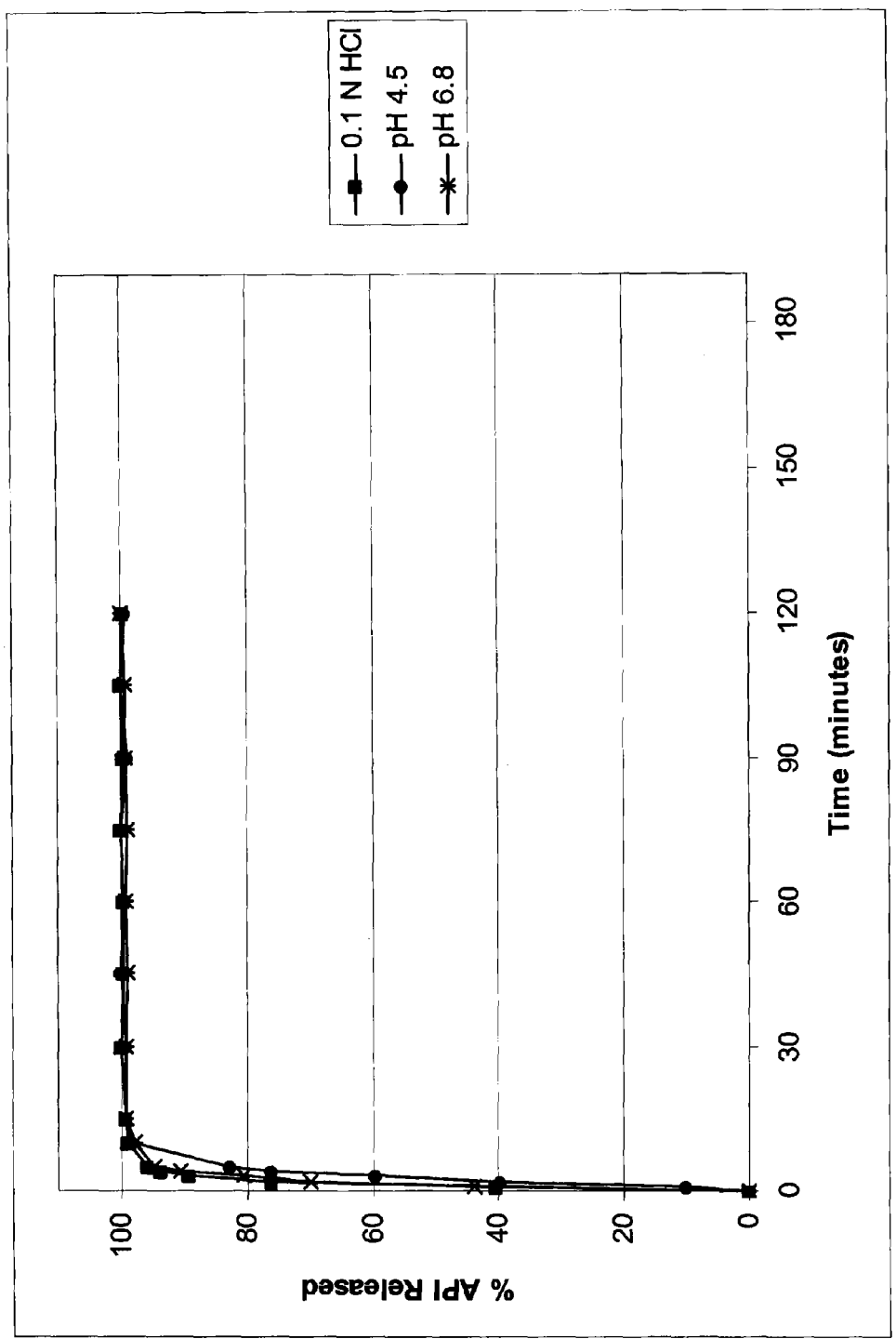
FIG. 37 is the graphical representation of the dissolution profiles for oxycodone hydrochloride as a function of pH.
Figure 97:
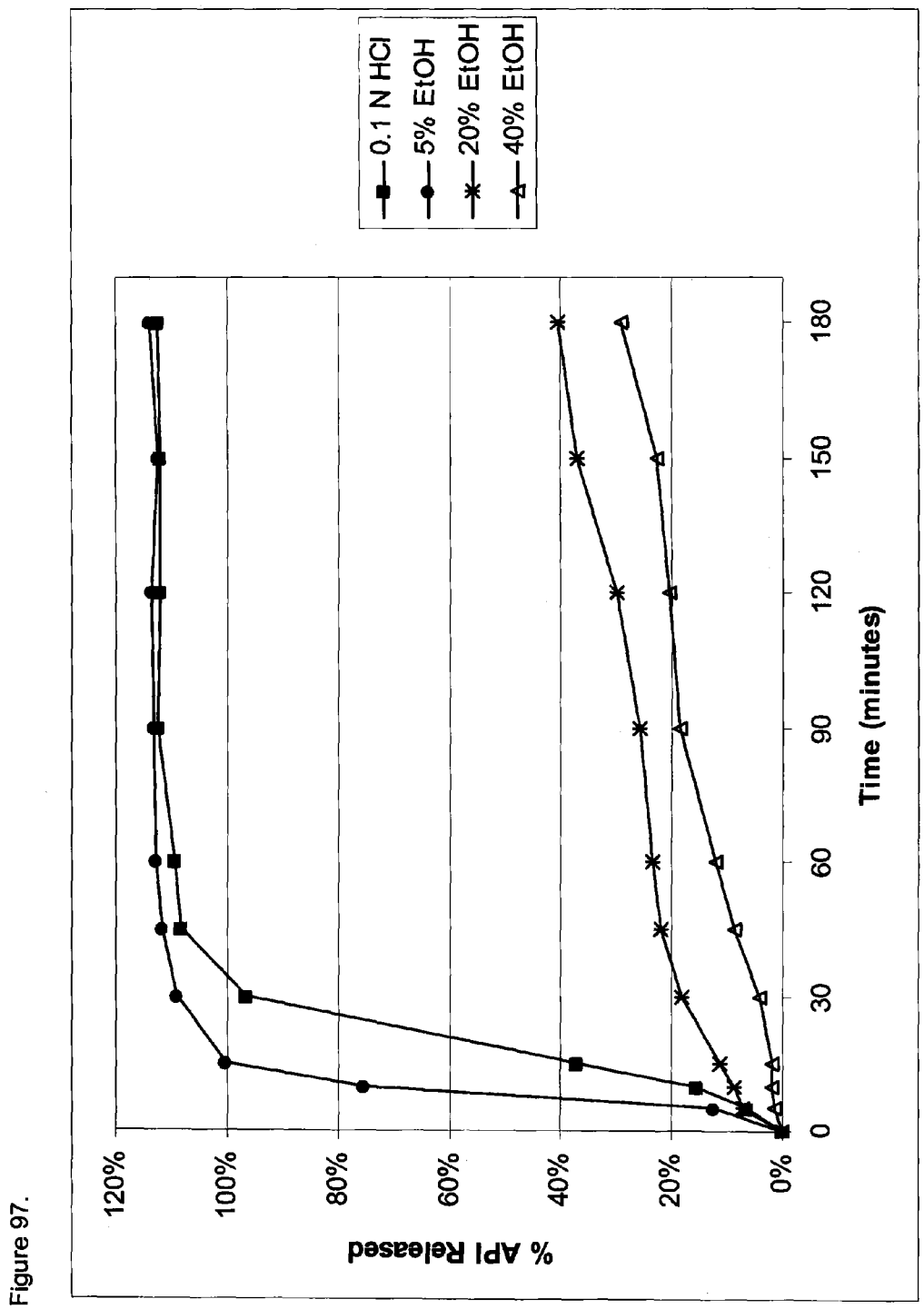
FIG. 97 is a graphical representation of the dissolution profiles of oxycodone pamoate in a $2^{nd}$ polymorphic form in acidic media as a function of ethanol concentration.
Figure 98:
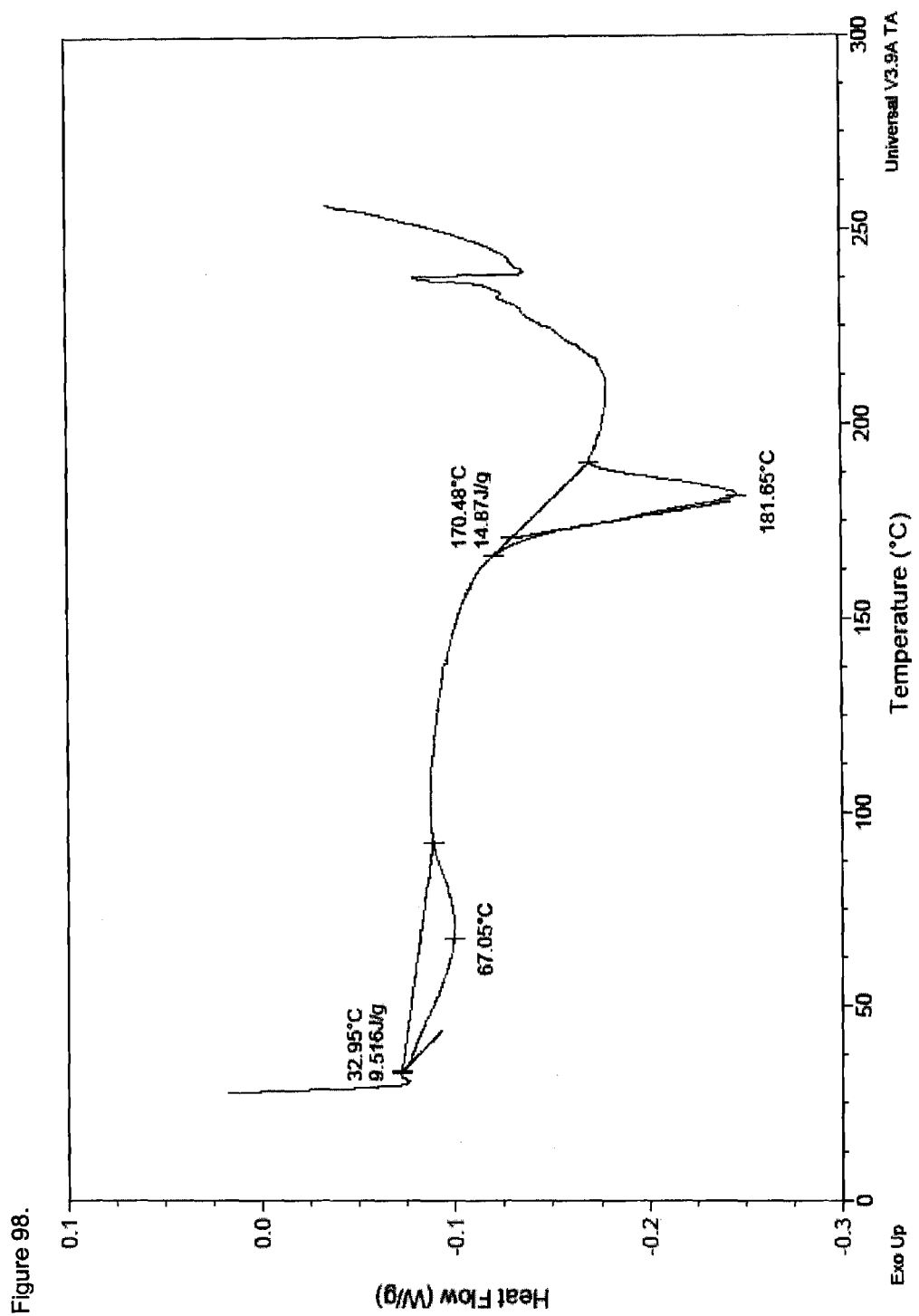
FIG. 98 is the differential scanning calorimetry (DSC) thermogram of oxycodone pamoate in a $2^{nd}$ polymorphic form.
Figure 99:
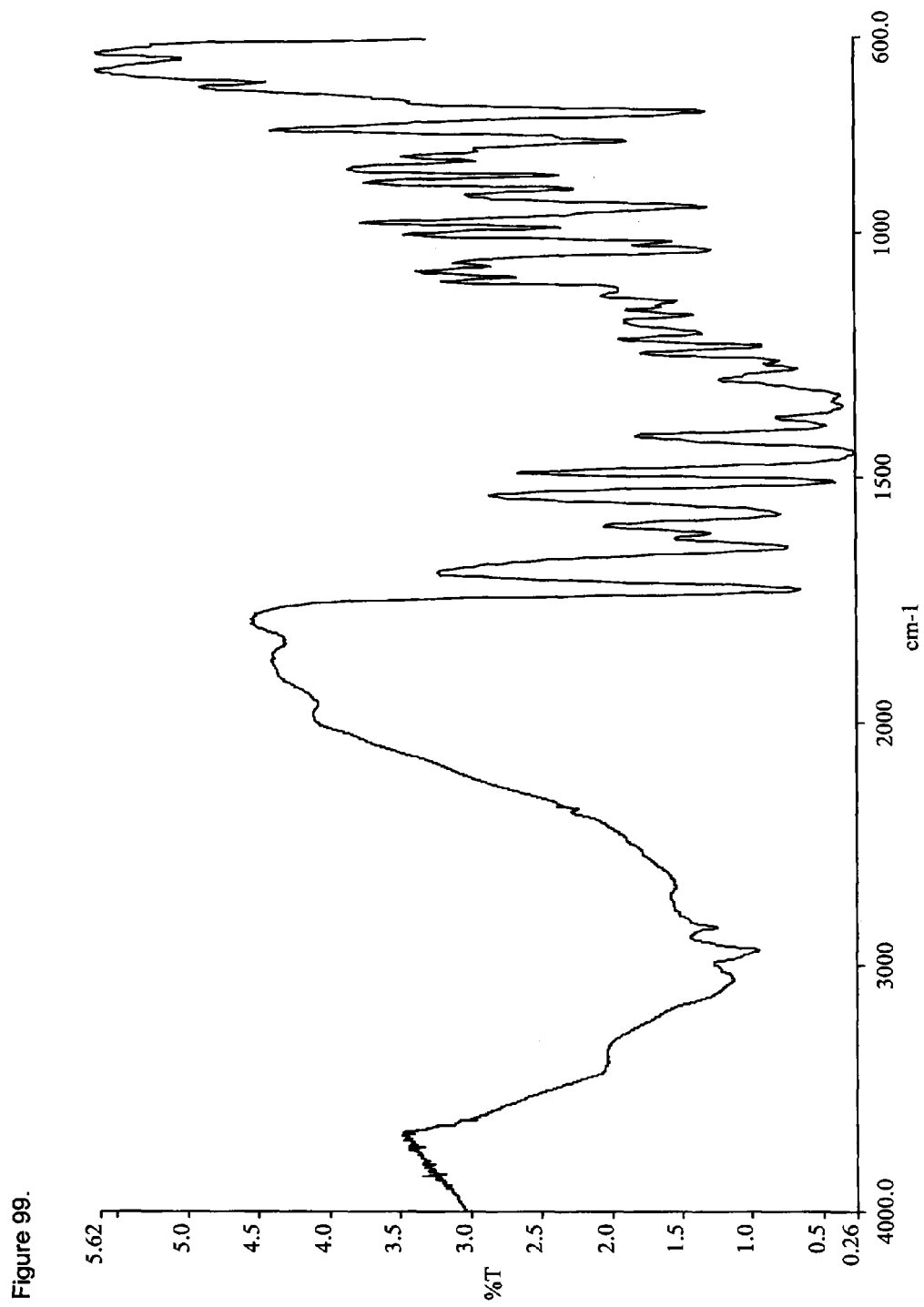
FIG. 99 is the Fourier Transform Infrared (FTIR) spectrum of oxycodone pamoate in a $2^{nd}$ polymorphic form.
Figure 100:
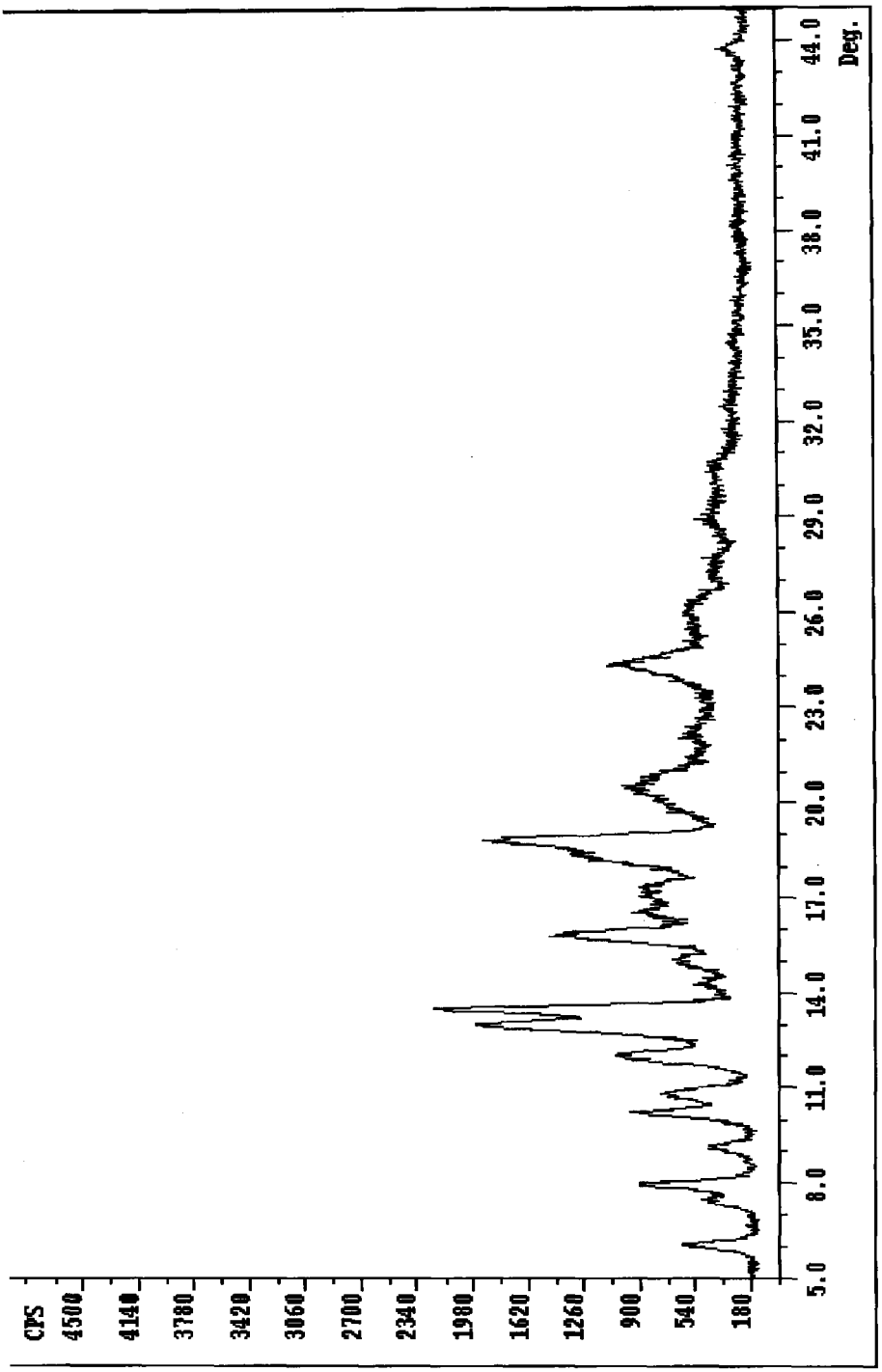
FIG. 100 is the Powder X-Ray Diffraction (PXRD) diffractogram of oxycodone pamoate in a $2^{nd}$ polymorphic form.

FIGS. 37 through 97, inclusive, are the graphical representations of the dissolution profiles of the selected opioid salts comparing the commercial offerings (mineral acid and tartrate salts) with those of the present invention. Two types of dissolution profiles are presented: 1) the dissolution profile of the compound as a function of pH, and 2) the dissolution profile of the compound as a function of ethanol concentration in acidic media which mimics dose dumping. Not surprisingly, the "traditional" opioid salts currently employed in commerce exhibit pH dissolution and dose dumping profiles substantiating the serious abuse potential observed in society. As can be seen in FIGS. 37 (oxycodone hydrochloride), 78 (hydrocodone bitartrate), 90 (hydromorphone hydrochloride) and 94 (morphine sulfate), each has a pH dissolution profile exhibiting immediate release (IR) characteristics. Indeed, formulation activities by companies offering dosage forms of these compounds often yield extended release (ER) dissolution properties; yet these measures are quickly defeated by those intent on abusing the active ingredient.

Figure 38:
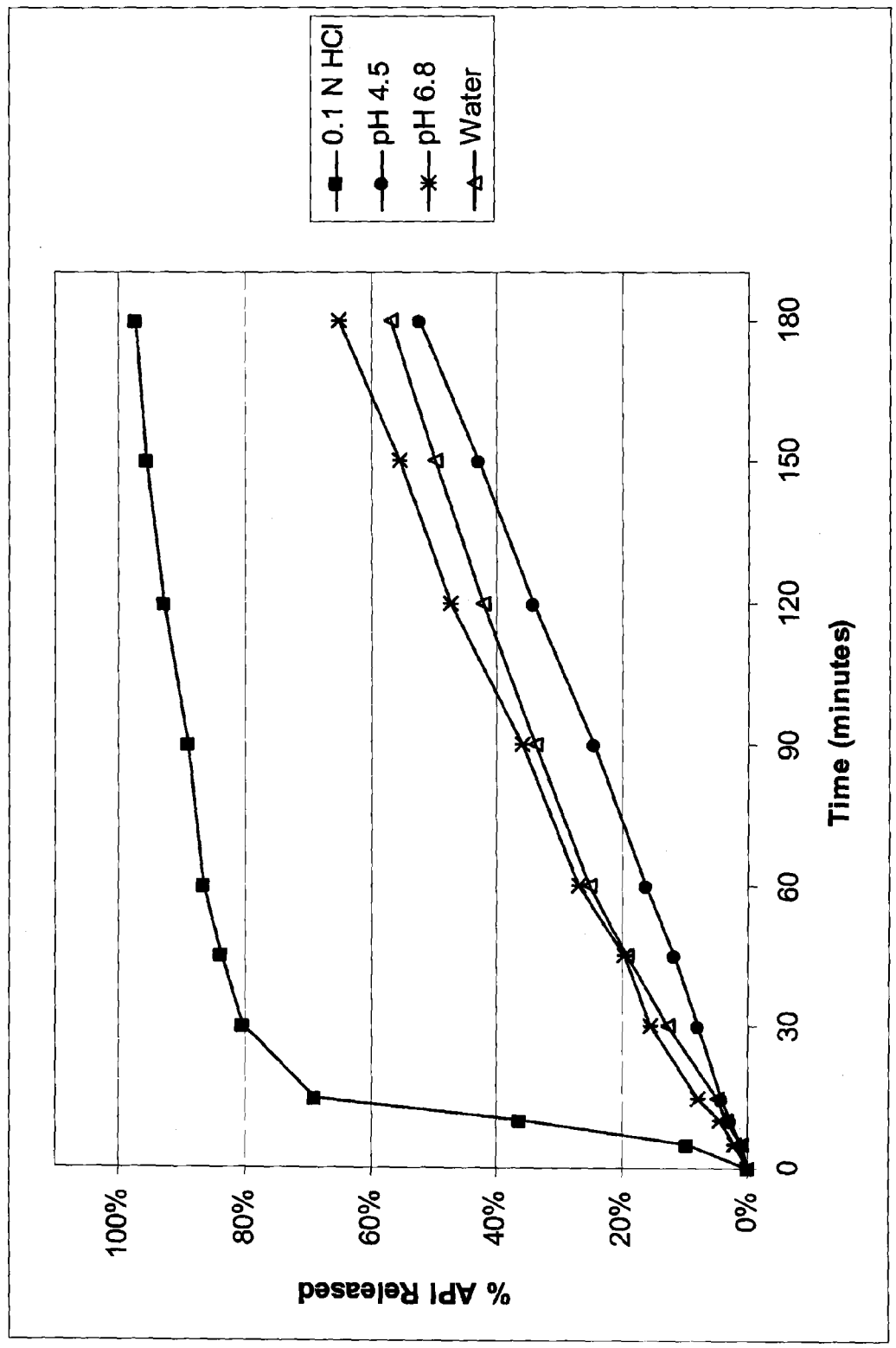
FIG. 38 is the graphical representation of the dissolution profiles for amorphous oxycodone pamoate as a function of pH.
Figure 39:
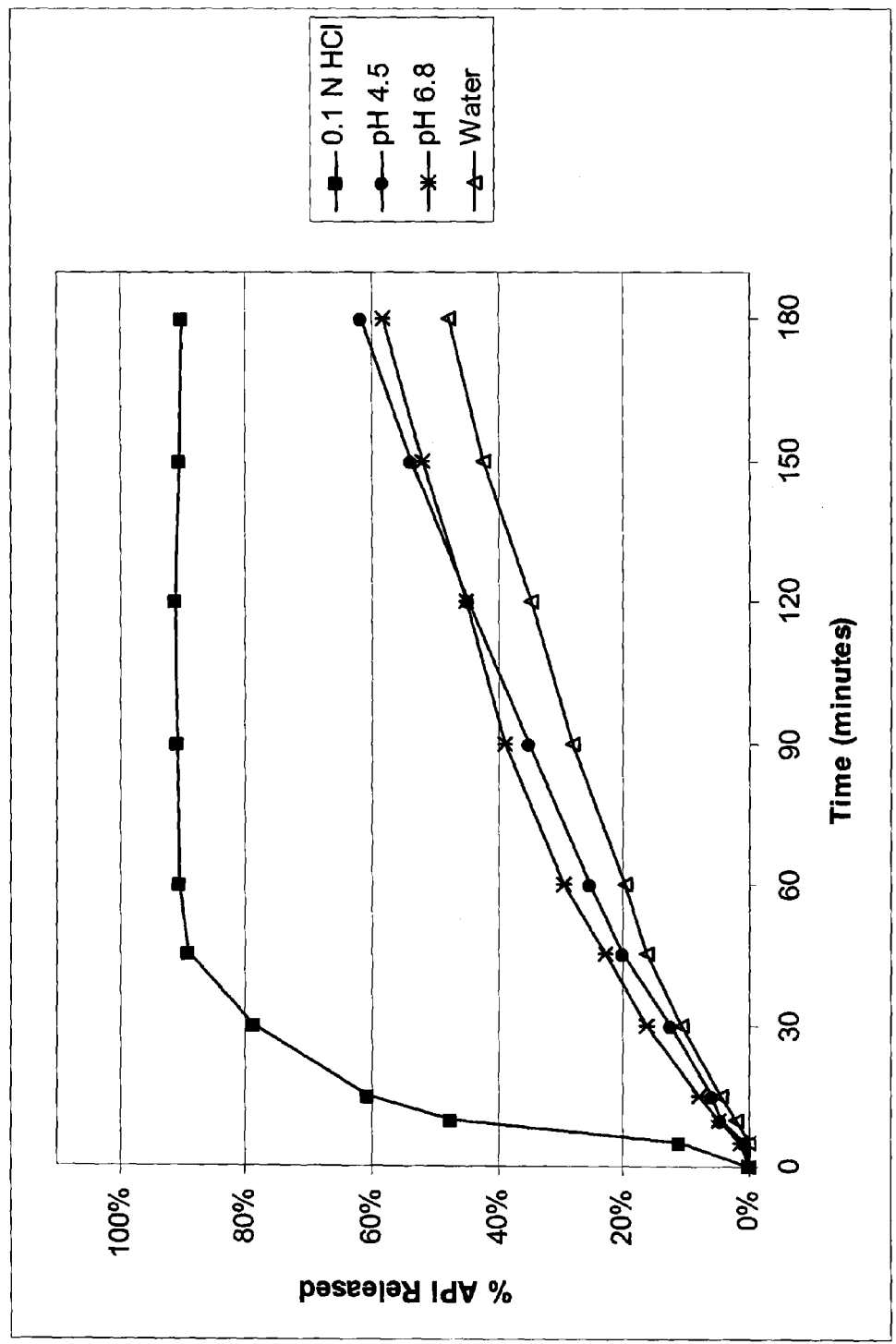
FIG. 39 is the graphical representation of the dissolution profiles for polymorphic oxycodone pamoate as a function of pH.
Figure 49:
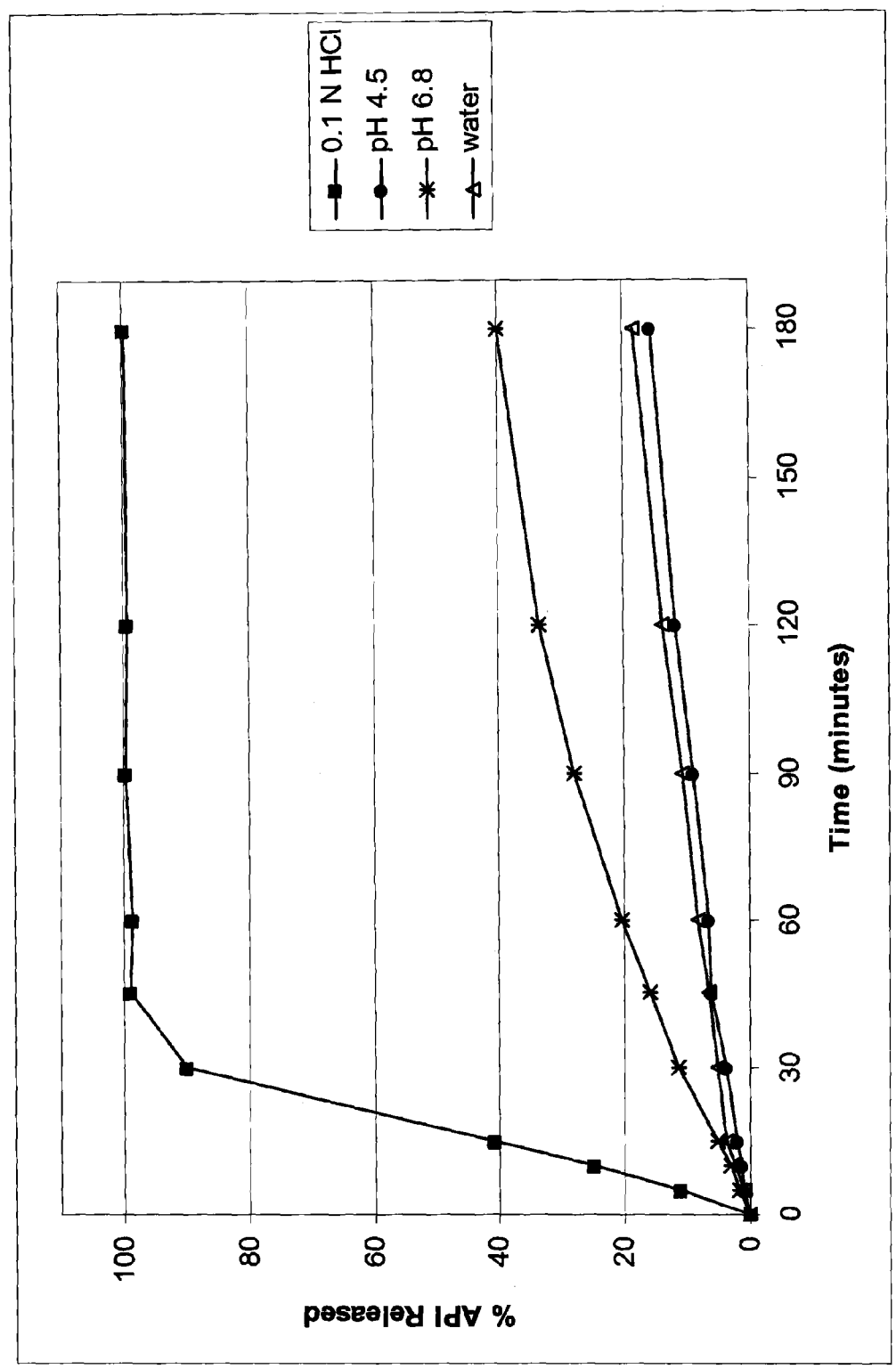
FIG. 49 is the graphical representation of the dissolution profiles for amorphous hydrocodone pamoate as a function of pH.
Figure 50:
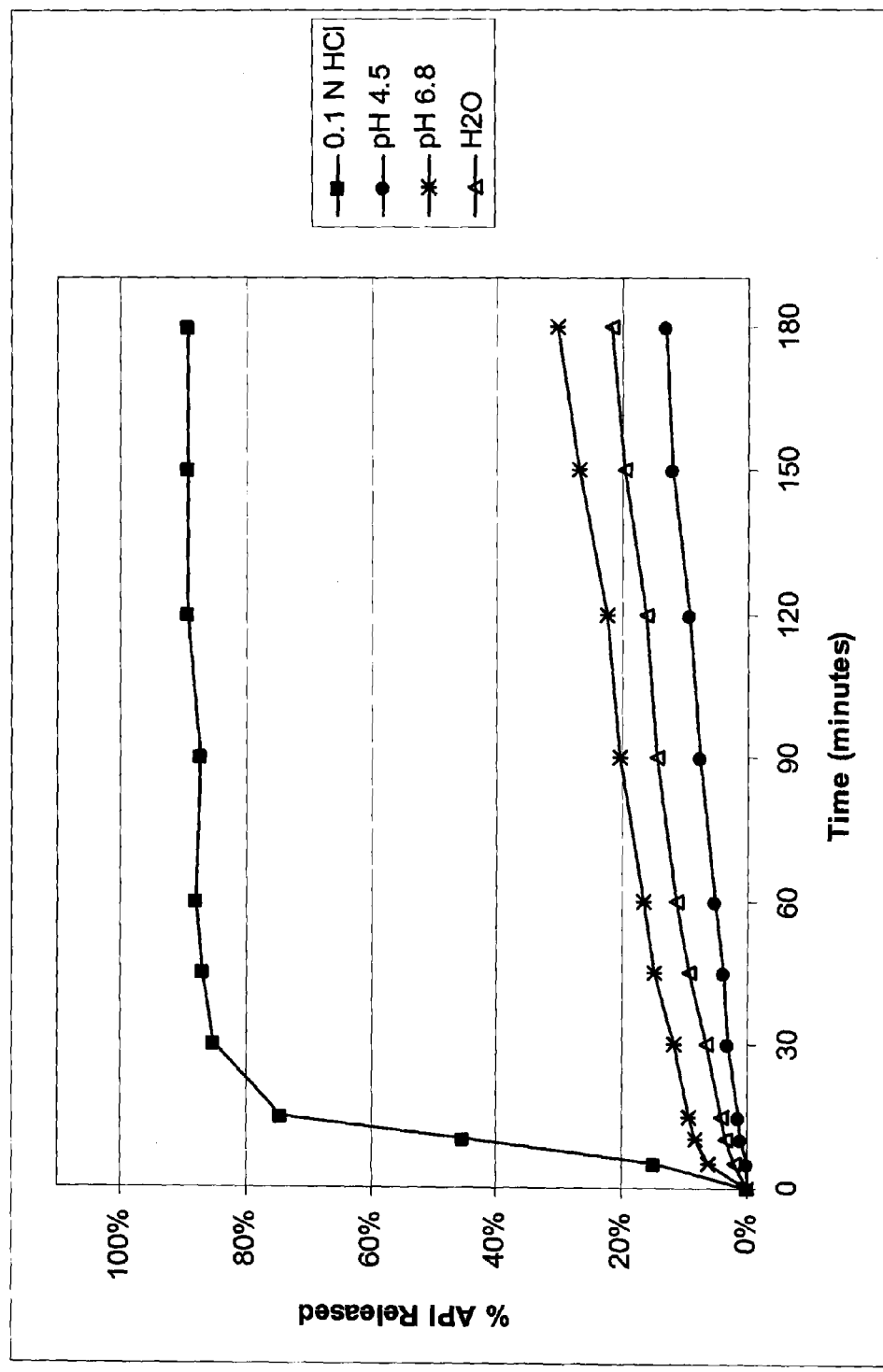
FIG. 50 is the graphical representation of the dissolution profiles for polymorphic hydrocodone pamoate as a function of pH.
Figure 52:
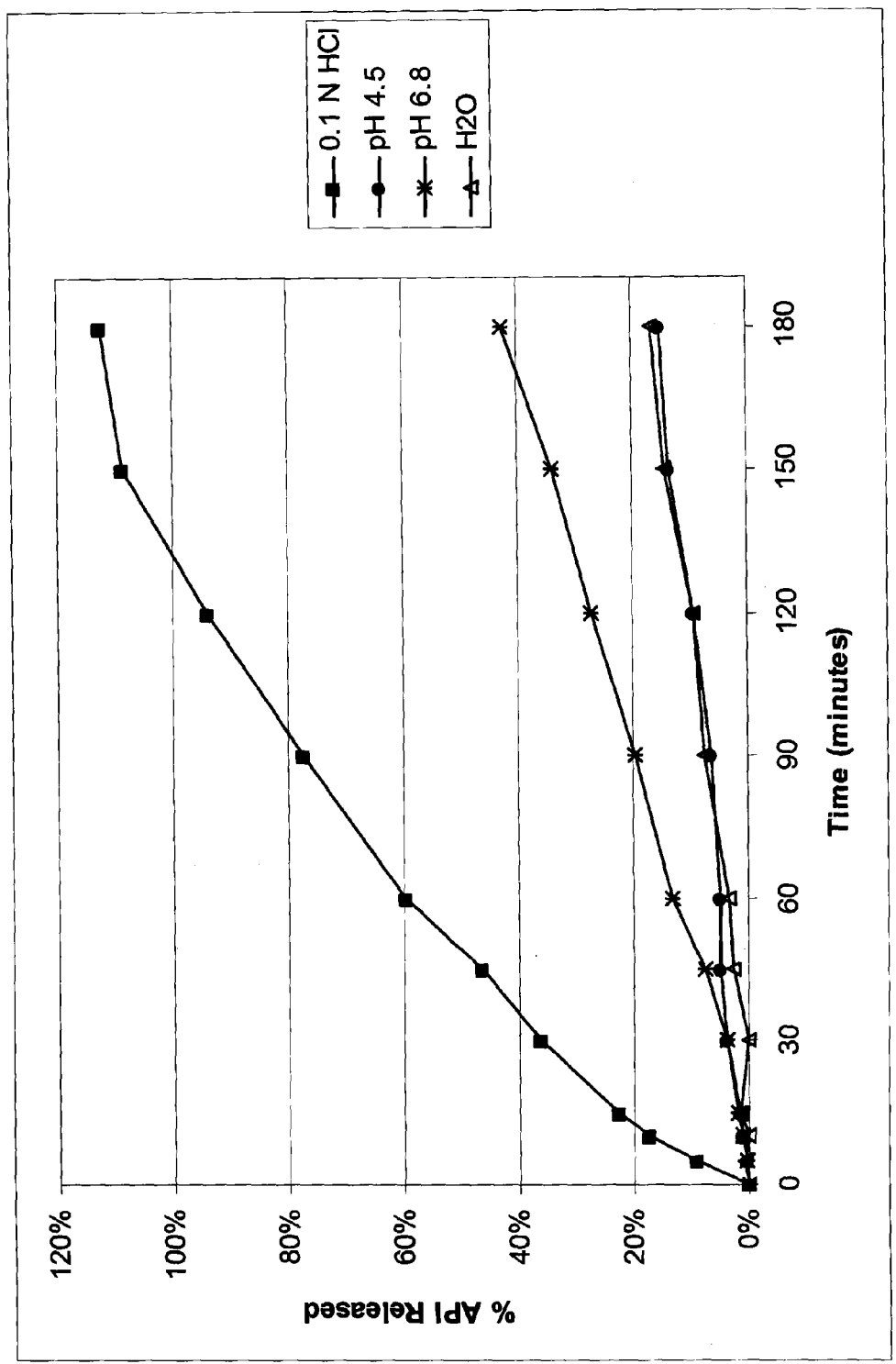
FIG. 52 is the graphical representation of the dissolution profiles for amorphous hydromorphone pamoate as a function of pH.
Figure 53:
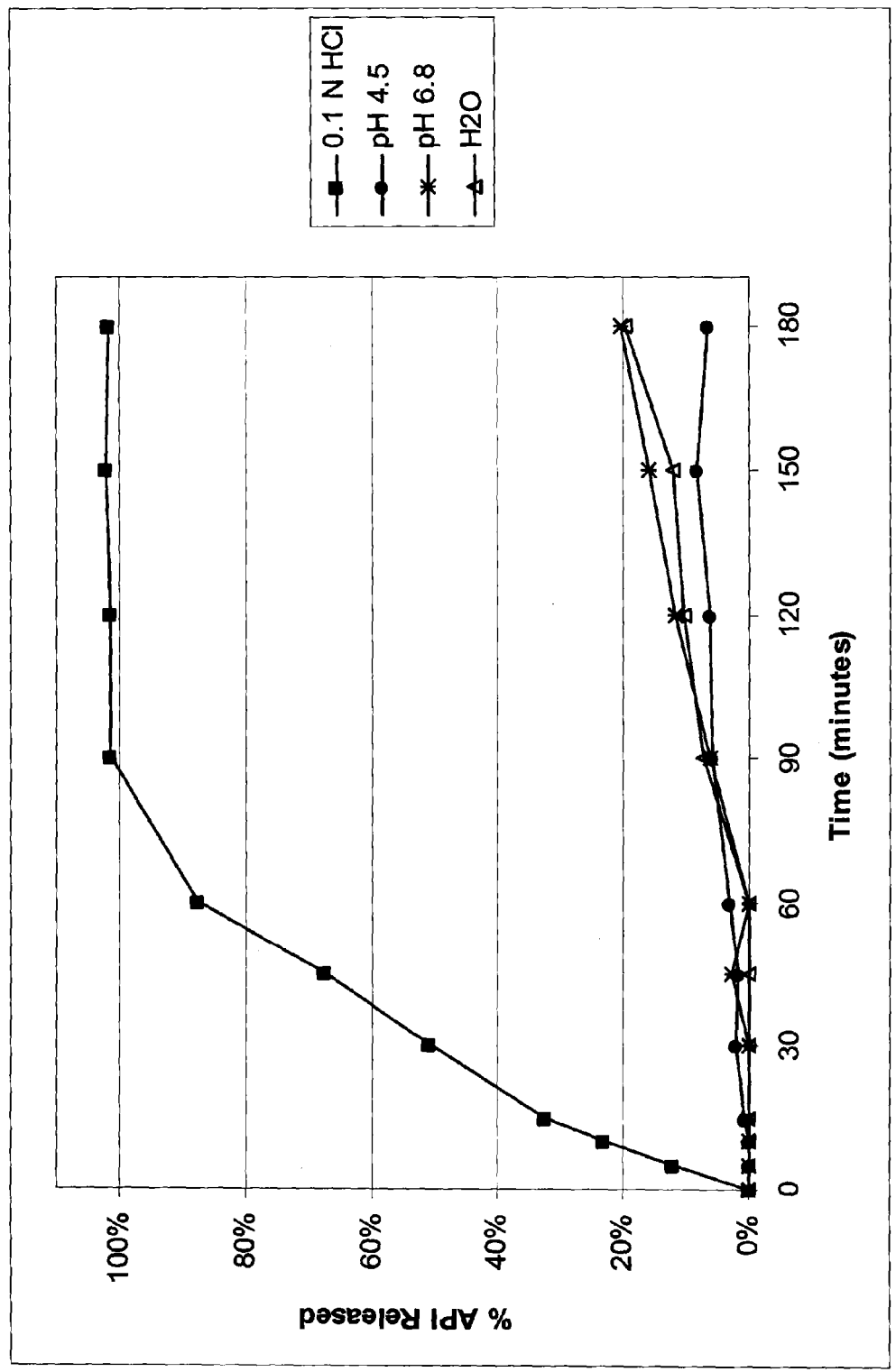
FIG. 53 is the graphical representation of the dissolution profiles for polymorphic hydromorphone pamoate acetone solvate as a function of pH.
Figure 55:
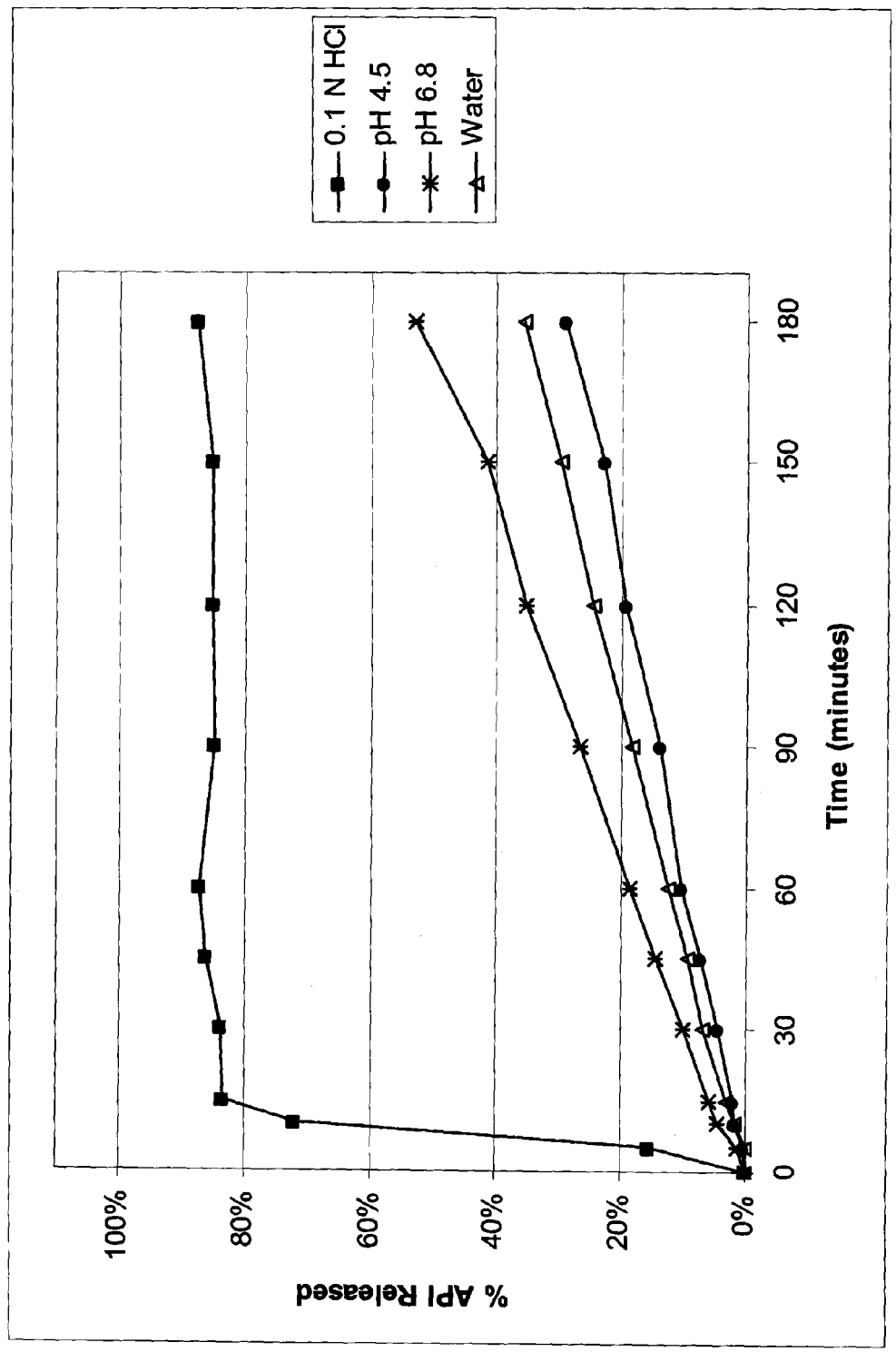
FIG. 55 is the graphical representation of the dissolution profiles for amorphous morphine pamoate as a function of pH.
Figure 56:
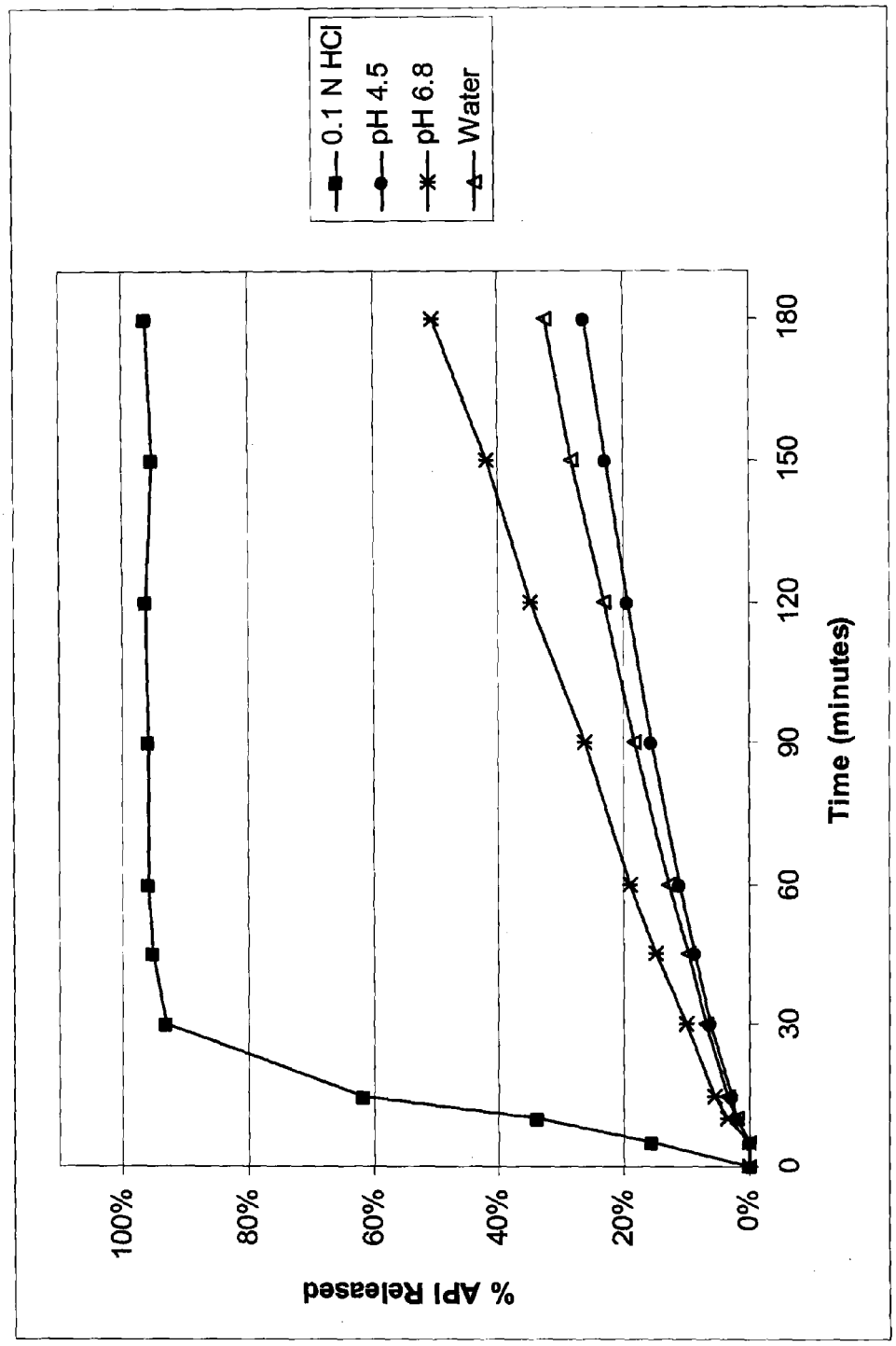
FIG. 56 is the graphical representation of the dissolution profiles for polymorphic morphine pamoate acetone solvate as a function of pH.
Figure 96:
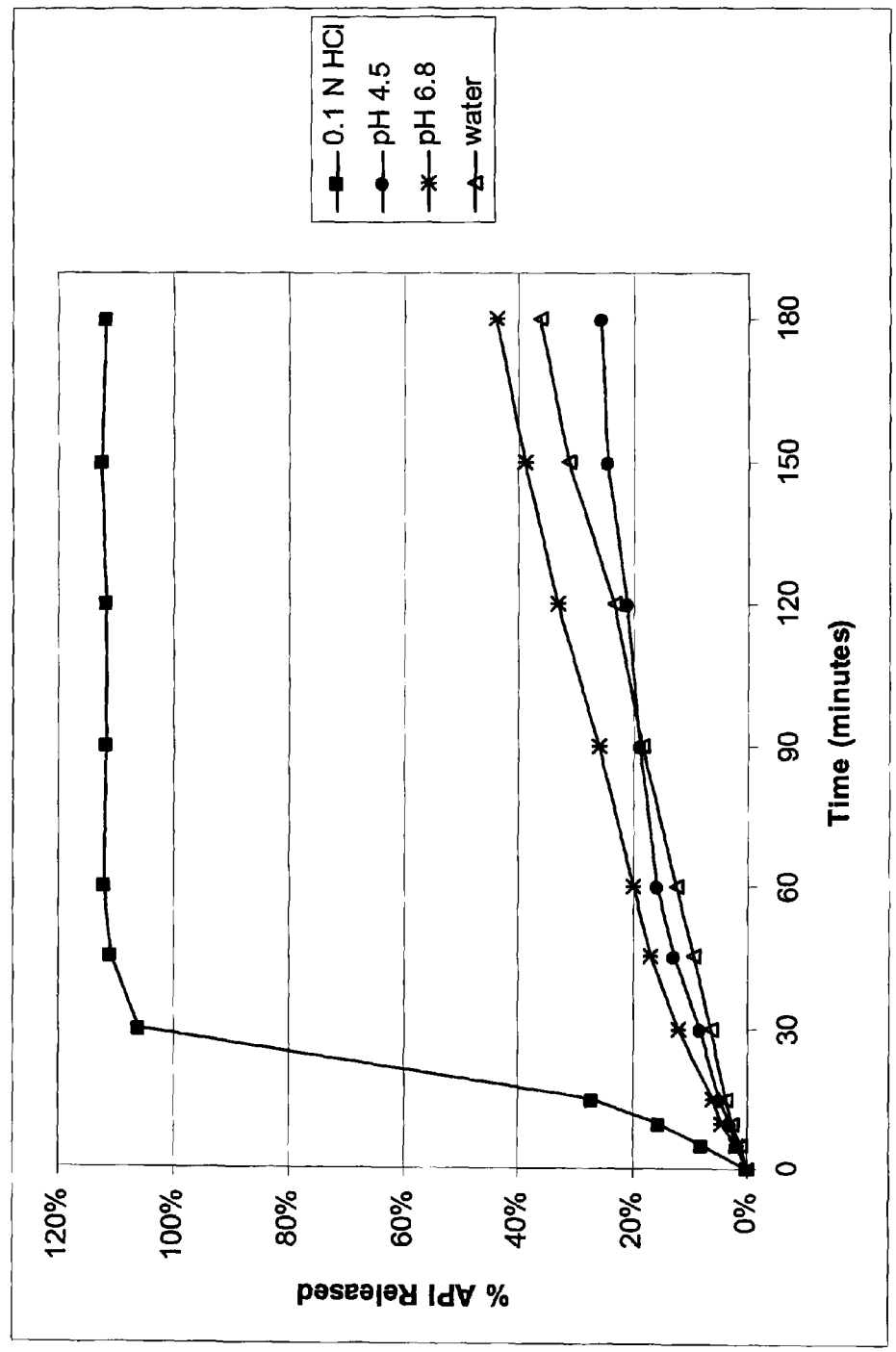
FIG. 96 is a graphical representation of the dissolution profiles of oxycodone pamoate in a $2^{nd}$ polymorphic form as a function of pH.

In contrast to the traditional APIs, the dissolution profiles of the comparable pamoate salts are found in FIG. 38 for amorphous oxycodone pamoate, FIG. 39 for polymorphic oxycodone pamoate, FIG. 96 for oxycodone pamoate in a $2^{nd}$ polymorphic form, FIG. 49 for amorphous hydrocodone pamoate, FIG. 50 for polymorphic hydrocodone pamoate acetone solvate, FIG. 52 for amorphous hydromorphone pamoate, FIG. 53 for polymorphic hydromorphone pamoate acetone solvate, FIG. 55 for amorphous morphine pamoate and FIG. 56 for polymorphic morphine pamoate acetone solvate. Several features are notable by comparison of these dissolution profiles with those of the traditional salts. First, the pamoate salts attenuate the immediate release characteristic inherent to the mineral acid/tartrate salts. Indeed, the traditional salts exhibit an immediate release profile under all pH conditions. At equivalent concentration of opioid (i.e. correcting for the molecular weight difference between the opioid pamoate versus its mineral acid salt), the pamoates exhibited an attenuated release profile to the extent an extended release dosage presentation could be considered wherein this attribute is due to the API and not to a formulation technique. Further, it was a highly unexpected observation counter to pharmaceutical science teaching and to the invention described in [King, et al.], that there does not appear to be a difference in dissolution profiles between amorphous and polymorphic forms of the opioid pamoate salts. In addition, the inclusion of acetone as part of the polymorphic form of the opioid solvate appeared to have no effect on the dissolution profile as compared to the non-solvated amorphous forms.

Opioid pamoates are available with or without a solvate. If prepared in DMF and precipitated by addition of isopropanol alcohol the non-solvated product is obtained which can then be formed as an acetone solvate by taking up in acetone. Oxycodone was not isolated as the acetone solvate. An aqueous solvate is prepared by precipitation in aqueous solution. Without adequate treatment the degree of solvation is difficult to define. For the purposes of the present invention treatment of aqueous formed salts are treated by vacuum oven to achieve a lower degree of hydration. For the purposes of the present invention treatment of aqueous formed salts are subjected to vacuum oven drying to achieve a lower degree of hydration. With regards to morphine pamoate vacuum drying provides a morphine pamoate with less than 3 waters of hydration, whereas dessicant drying at atmospheric pressure provides at least 3 waters of hydration.

It is often a concern for the traditional pharmaceutical formulation scientist to formulate with an API which exhibits pH independent release such as that observed for the mineral acid, tartrate and similar salts. Initially, the opioid pamoate dissolution profiles were interpreted to have the "undesirable" pH dependence yet this characteristic confers an additional inventive contribution to the present invention. For instance, the dissolution profiles are substantially attenuated for the higher pH conditions and less so for the pH 1 (0.1 N HCl) and pH 4.5 conditions. This circumstance is not a hindrance to the commercial development of formulated product offering but represents a desired feature. The dissolution at the pH 1 condition is easily manipulated in a proposed dosage by enterically coating the tablet or capsule. The coating allows for the tablet to pass from the low pH stomach to the higher pH intestines where the API is released. Further, the dissolution profile for the pH 4.5 condition represents that intermediate range between the low pH of the stomach and the progressively higher pH range encountered in the intestines. In all cases, the pamoate exhibits an extended release profile when compared to the traditional salts and the minor pH dependencies are actually advantageous to producing anti-abuse opioid products. For instance, at pH near 4.5, the pamoates would not be soluble in the body's mucosal membranes.

Figure 51:
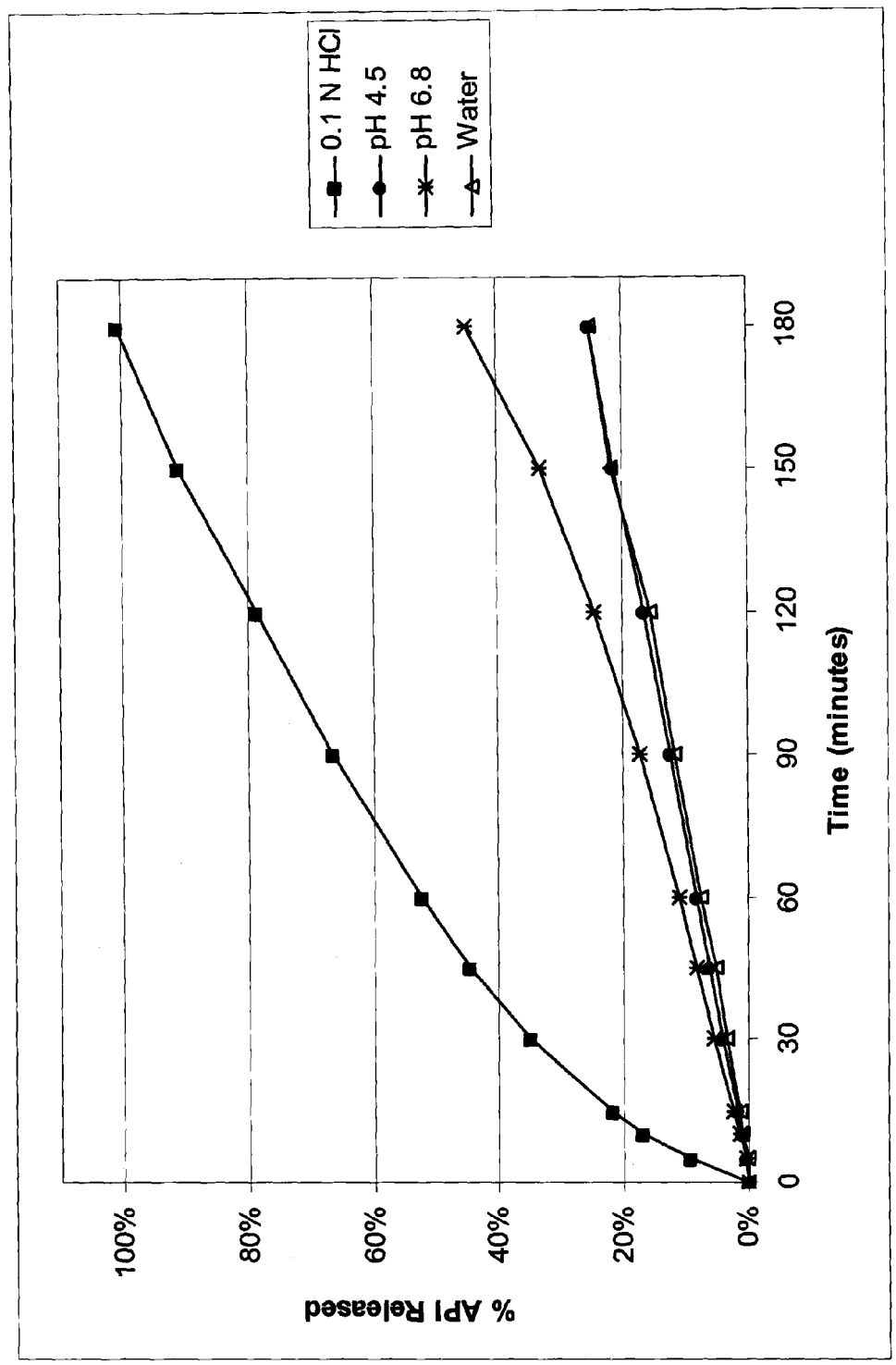
FIG. 51 is the graphical representation of the dissolution profiles for hydrocodone xinafoate as a function of pH.
Figure 54:
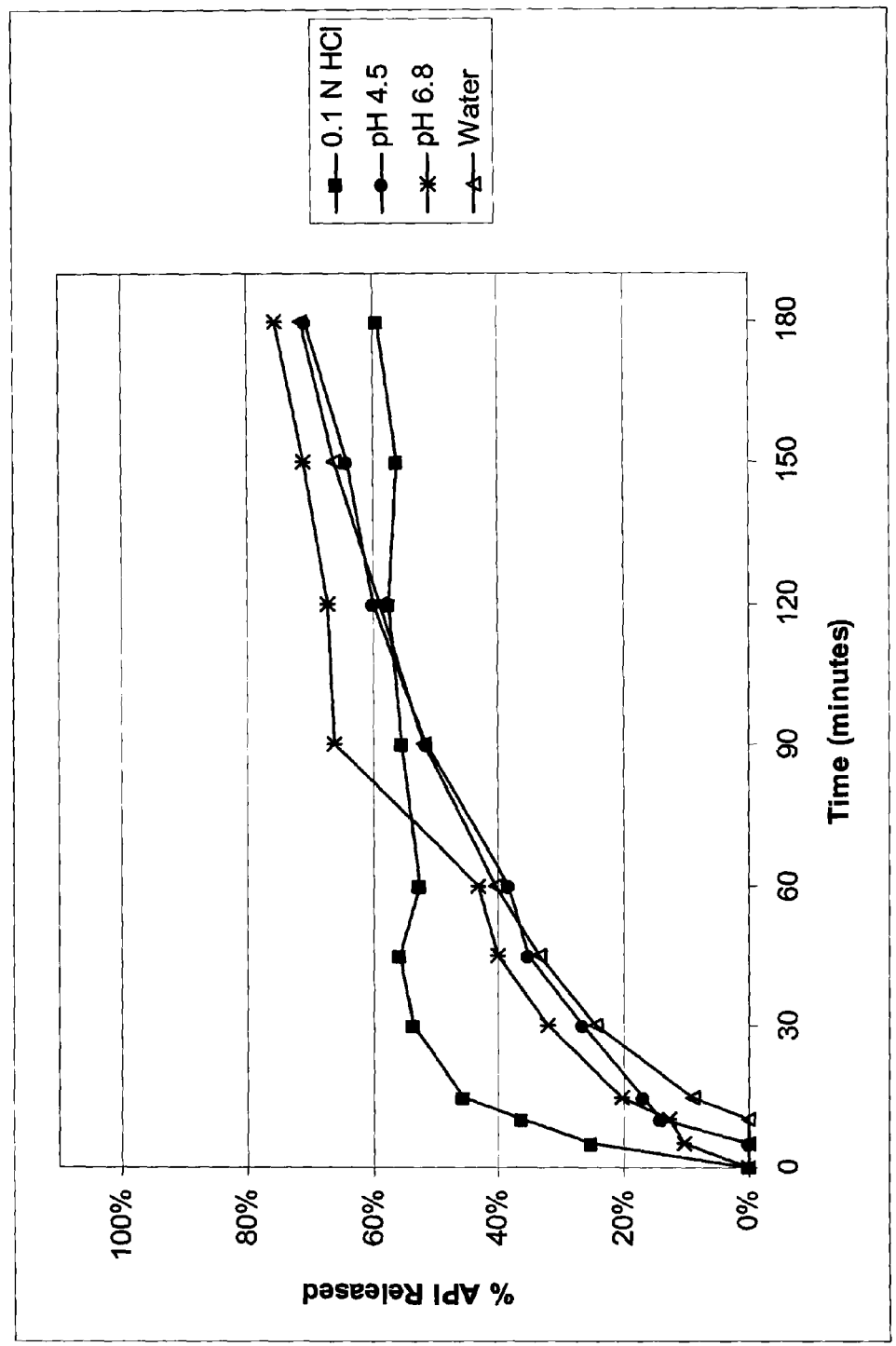
FIG. 54 is the graphical representation of the dissolution profiles for hydromorphone xinafoate as a function of pH.
Figure 57:
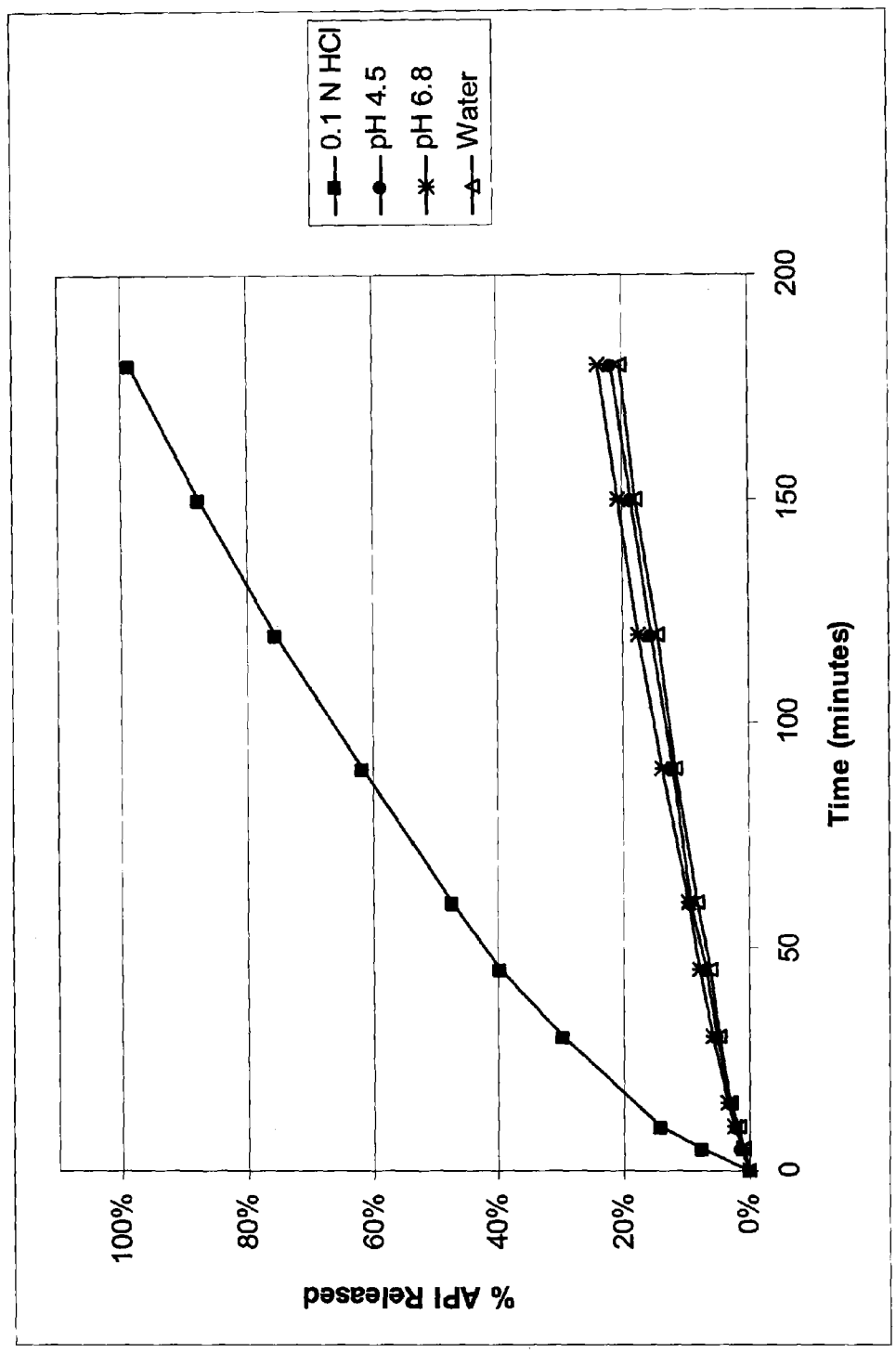
FIG. 57 is the graphical representation of the dissolution profiles for morphine xinafoate as a function of pH.
Figure 68:
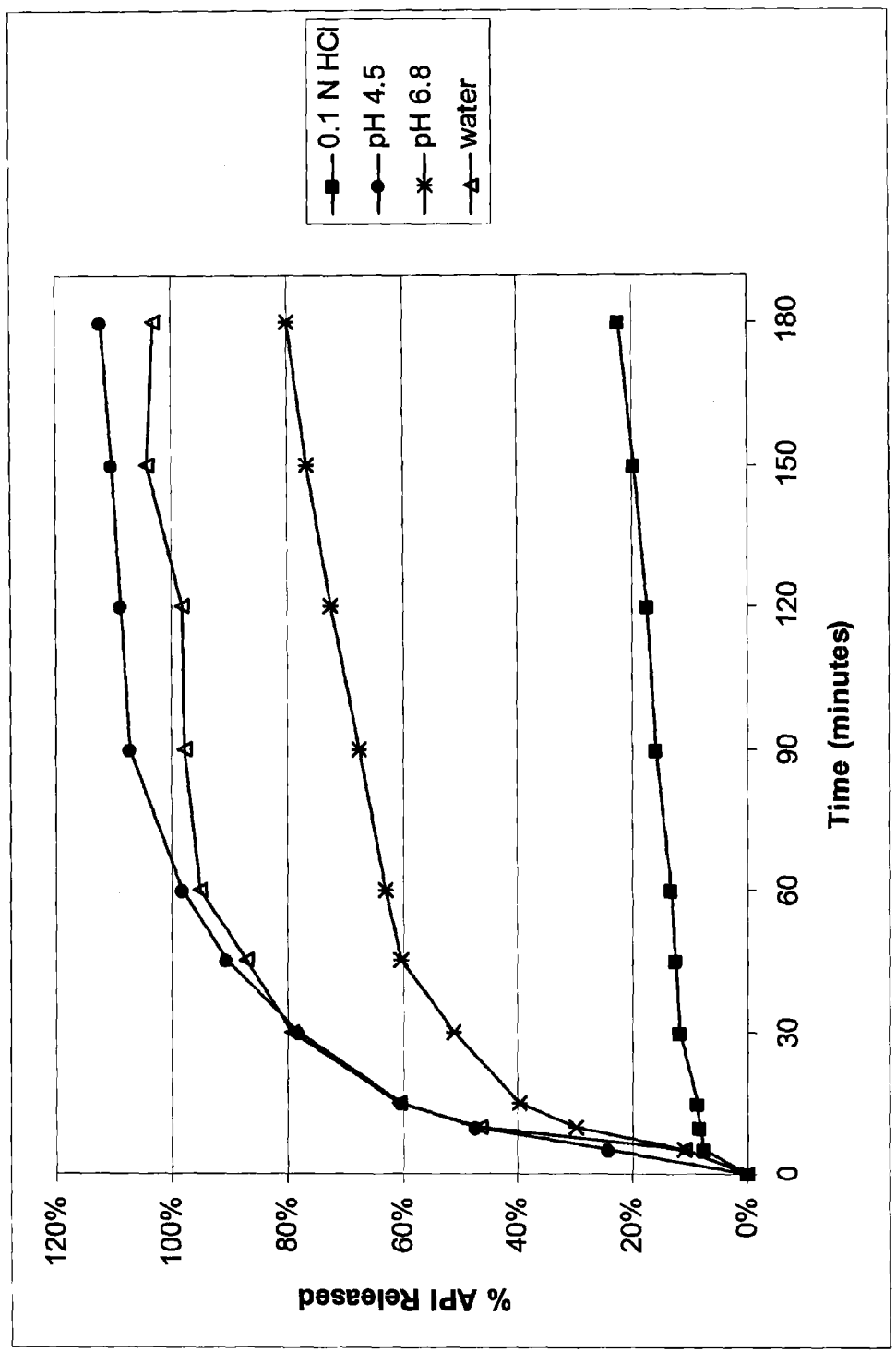
FIG. 68 is the graphical representation of the dissolution profiles oxycodone xinafoate as a function of pH.

In regard to the opioid xinafoate salts, the comparable dissolution profiles are found in the following figures: FIG. 68 for oxycodone xinafoate, FIG. 51 for hydrocodone xinafoate, FIG. 54 for hydromorphone xinafoate and FIG. 57 for morphine xinafoate. The xinafoate moiety represents about half of the structural components of the pamoate group and only the 1:1 opioid:xinafoate moiety salt is available. However, the xinafoate's contribution to the opioid organic acid addition salt is still quite noticeable in the cited dissolution profiles. Oxycodone xinafoate exhibits a poor dissolution profile at pH 1 with a gradual release as the pH increases. This phenomena clearly makes the xinafoate salt a candidate for an enteric coated, extended release final dosage presentation. Similarly, hydrocodone xinafoate and morphine xinafoate exhibit similar release properties such that each salt exhibits an extended release at pH 1, and independent release as the pH increases. As with the pamoates, these properties are impediments to attempts to free base the active ingredient for purposes of abuse. Hydromorphone xinafoate generally exhibits a pH independent release profile and as with each opioid xinafoate, the release properties are substantially attenuated compared with the traditional, commercial salts.

The pH dissolution profiles for opioid pamoates and xinafoates, independent of amorphous or polymorphic considerations, or the inclusion of an organic solvent (e.g. acetone) in the crystalline structure each represent a significant improvement over the traditional mineral acid and/or tartrate salts of these opioids. Further, the pamoates or xinafoates can be directly processed to yield an extended release, pH independent drug product dissolution profile. Of significant concern was how the additional organic character of these salts would contribute to the opioids' ability to dose-dump and a more in-depth discussion herein is warranted.

The US FDA has issued a draft guidance found at http://www.fda.gov/cder/guidance/bioequivalence/recommendations/Oxymorphon e_HCl_ERtab_21610_RC11-07.pdf concerning oxymorphone hydrochloride and has requested specific dissolution tests be performed to demonstrate alcohol (ethanol) does not promote dose dumping. A general overview of this concern may be found at http://www.fda.gov/ohrms/dockets/AC/05/slides/2005-4187S2_02_Hussain.ppt. This Oct. 26, 2005 overview presentation by the deputy director OPS/CDER of the FDA and entitled "Preventing Alcohol Induced Dose Dumping is a Desired Product Design Feature" describes the dose-dumping phenomenon. Dose dumping can be employed by those with the deliberate intention of abusing the drug, but may also occur during the normal/moderate consumption of alcohol while taking a prescribed medication. Simply, dose dumping is that condition "in which the complete dose may be more rapidly released from the dosage form than intended, creating a potential safety risk". Clearly, with the opioid narcotics, dose dumping for the intention of experiencing the "high" or rush, may have severe, even deadly consequences. The presentation further categorizes the results from dose dumping testing as either vulnerable, rugged or uncertain. If the dissolution profile in the presence of alcohol accelerates the release of the active ingredient, the product is classified as vulnerable and would likely not receive FDA market approval. In contrast, a rugged product design is achieved when the dissolution profile of the drug substance, again in the presence of alcohol, is identical to or is available to a lesser extent as compared to the control. The testing regimen recommended within the FDA's draft guidance includes determining the dissolution profile in 0.1 N HCl solutions wherein the sample is tested in the medium and at increasing levels of ethanol, specifically at 5, 20 and 40% alcohol. The current invention demonstrates the ability to formulate anti-dose-dumping pharmaceutical products specifically for those compounds often the subject of abuse, e.g. oxycodone, hydrocodone, and the like.

The dose dumping phenomenon was evaluated with respect to oxycodone hydrochloride as the standard for comparison since the hydrochloride salt is most often found in commercial/FDA approved product formulations.

Figure 58:
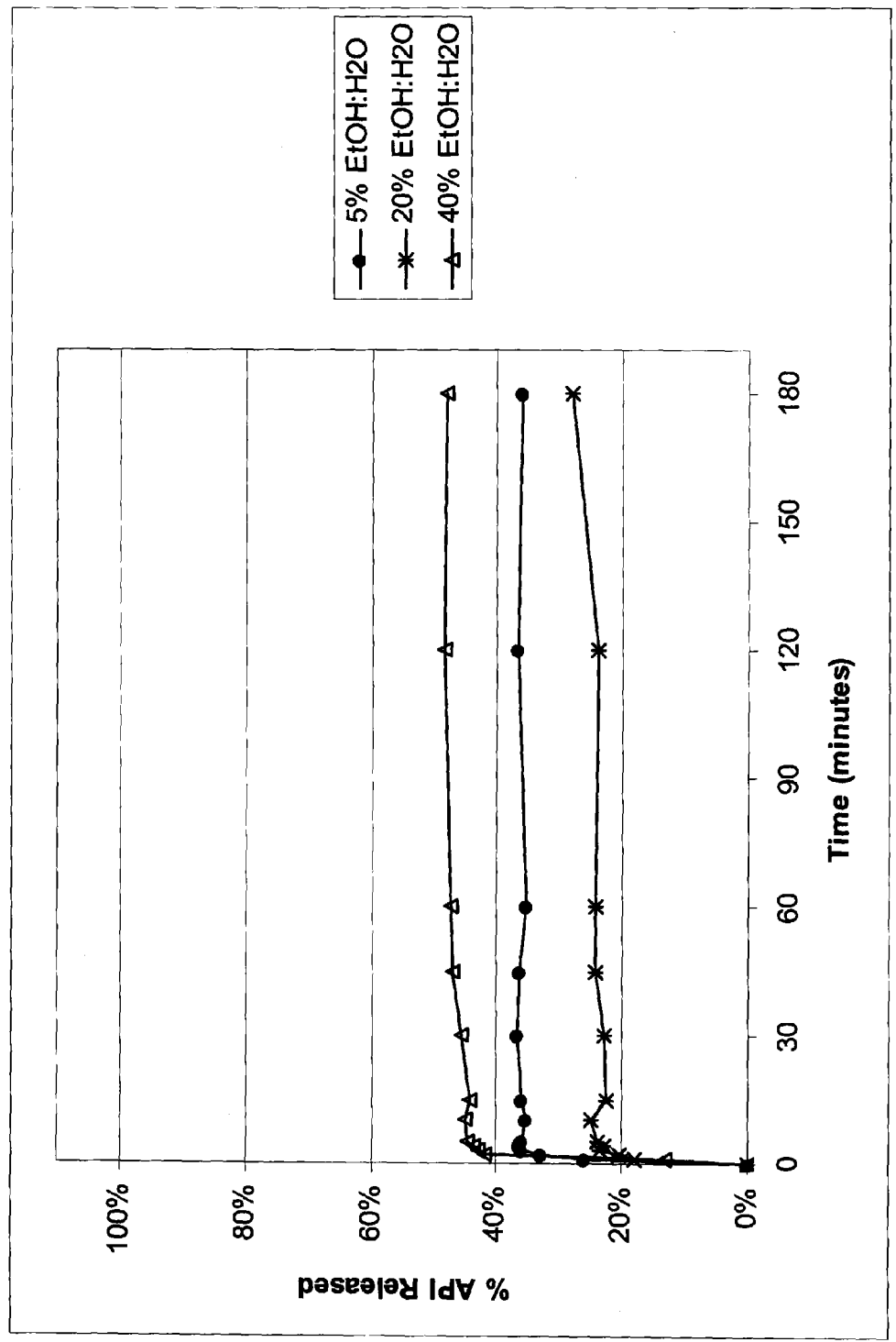
FIG. 58 is the graphical representation of the dissolution profiles for oxycodone hydrochloride as a function of ethanol concentration.
Figure 59:
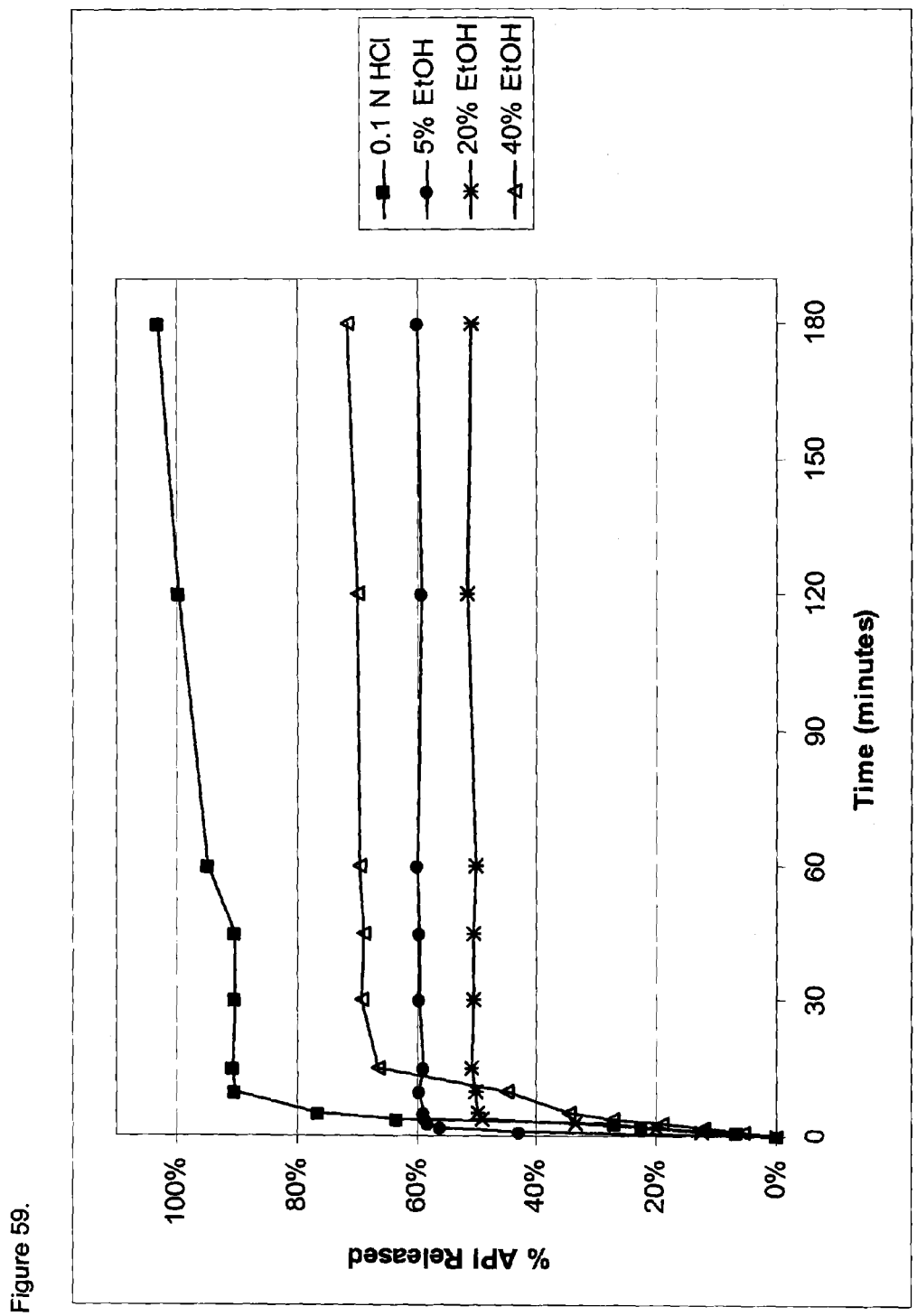
FIG. 59 is the graphical representation of the dissolution profiles for oxycodone hydrochloride in acidic media as a function of ethanol concentration.
Figure 79:
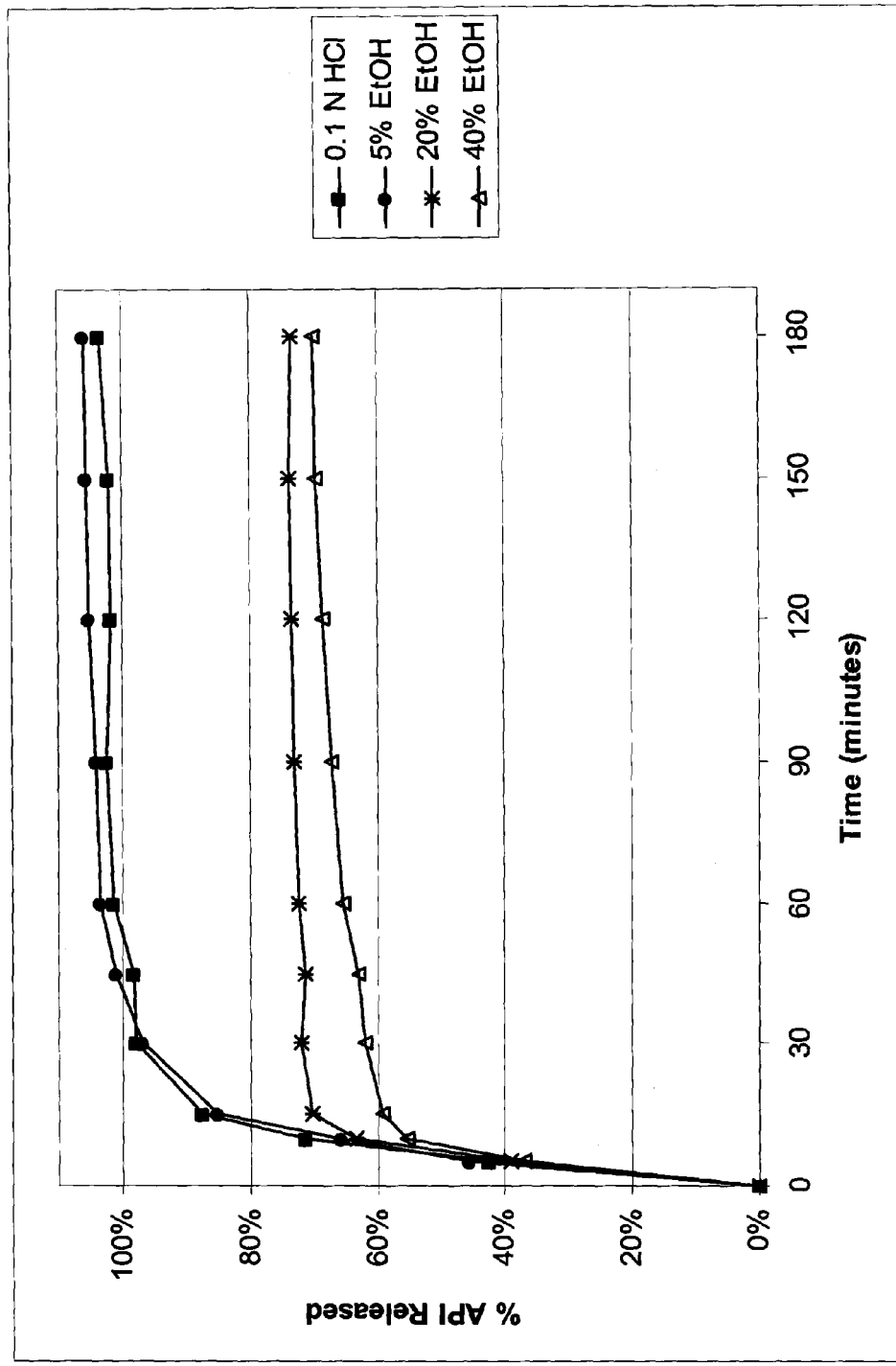
FIG. 79 is the graphical representation of the dissolution profiles of hydrocodone bitartrate in acidic media as a function of ethanol concentration.
Figure 91:
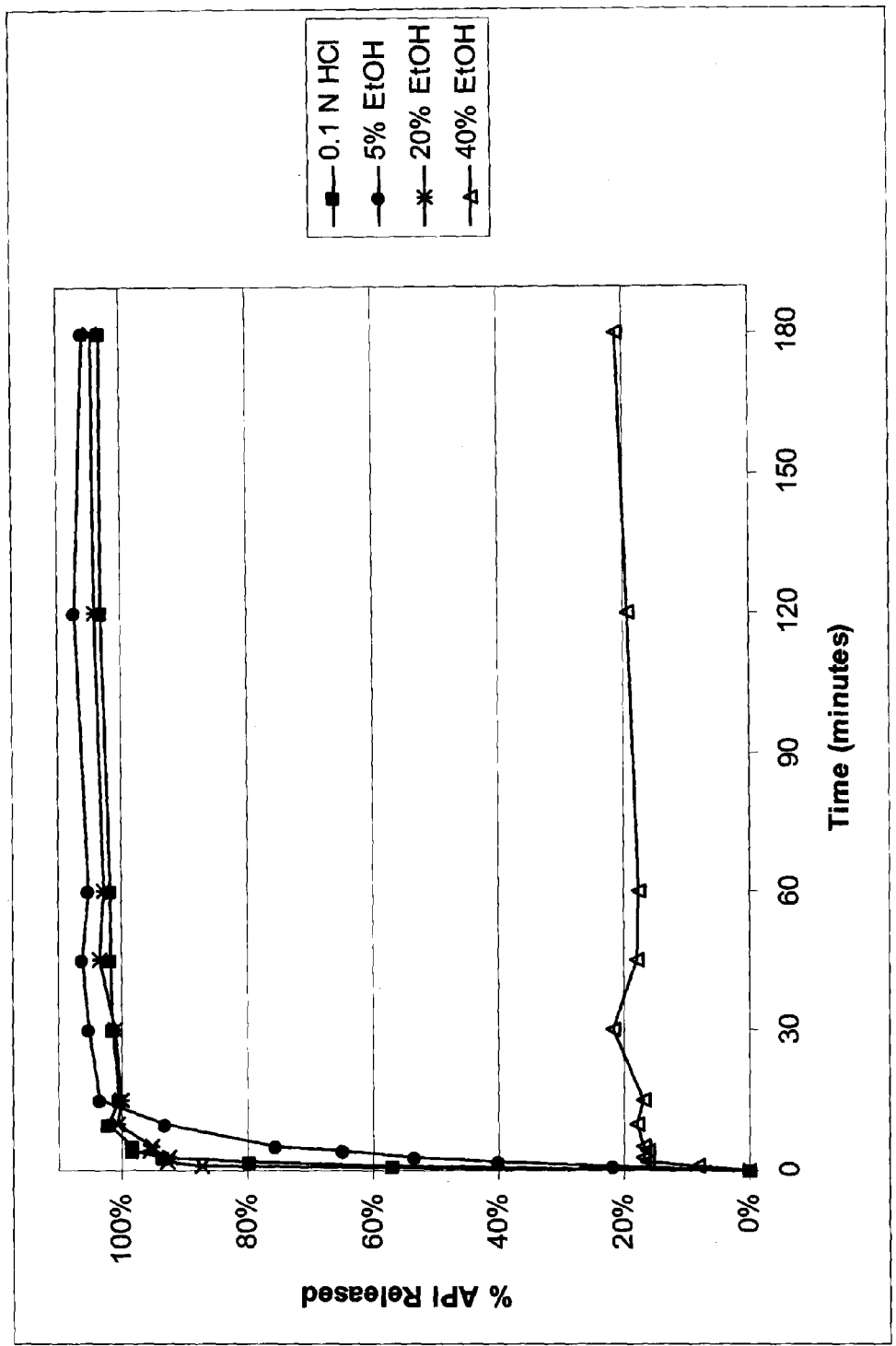
FIG. 91 is the graphical representation of the dissolution profiles of hydromorphone hydrochloride in acidic media as a function of ethanol concentration.

For the initial discussion and to demonstrate the dose dumping phenomenon, it is useful to consider the following figures: FIG. 58 (oxycodone hydrochloride EtOH:water), FIG. 59 (oxycodone hydrochloride), FIG. 79 (hydrocodone bitartrate), and FIG. 91 (hydromorphone hydrochloride). Three dose dumping experiments were conducted on oxycodone hydrochloride. The first experiment employed a modified procedure of the aforementioned standard dose dumping protocol. In this case, oxycodone HCl was tested under four conditions: 1) in 0.1 N HCl containing 20% EtOH, 2) in 5% EtOH, 3) 20% EtOH, and in 40% EtOH. The subtlety in this experiment demonstrates the dose dumping characteristics in 5, 20 and 40% ethanol and in the absence of the acidic, 0.1 N HCl media; the results are graphically represented in FIG. 58. The experiment provided an indication of the quantity of oxycodone extracted by ethanolic solutions and demonstrated a dissolution profile resembling equilibrium solubility was obtained with each of the four conditions, albeit at different percentages of API released. Equilibrium solubility is a fixed quantity at a constant temperature and pressure that is given as the amount of solute contained in the saturated solution in a unit amount of the solvent or solution. A maximum amount of oxycodone extraction capability of about 50% could be predicted if a potential abuser used 40% EtOH, (i.e. about 80 proof alcohol). Further the efficiency of the extraction would be highly dependent upon the concentration of the alcohol employed and if attention was given to the pH of the extraction solution.

In contrast, the experiment was repeated with adherence to the FDA's dose dumping protocol wherein, a volume of the 0.1 N HCl dissolution media was progressively replaced with 5, 20 and 40% concentrations of EtOH. The results of this experiment are captured in FIG. 59. Here too, dissolution profiles resembling equilibrium solubility were obtained quickly, i.e. apparent solution equilibrium was obtained within minutes. Not surprisingly, the control condition using 0.1 N HCl without EtOH exhibited complete dissolution within minutes. By contrast, the progressive replacement of the dissolution media with the specified increasing amounts of EtOH led to diminished API release. Clearly, the presence of the acidic media, independent of the ethanol concentration enhances the release profile of oxycodone hydrochloride by more than 20% (absolute) at each ethanol level as can be seen by comparing FIGS. 58 and 59. However, the test condition absent EtOH provided the highest concentration of the opiate in a very short time. As an aside, current commercial forms of oxycodone HCl, such as Oxycontin®, employ an extended release formulation technique to prevent the immediate release of the API which can have serious and highly detrimental health effects to a patient. Hence, the time dependent, extended release property of the drug is deliberately defeated by individuals intent on abusing the drug by using alcohol to release the API from its formulated matrix while in the presence of stomach acid; immediate release is predictable and with the associated consequences. An inspection of FIGS. 79 and 91 indicate hydrocodone bitartrate and hydromorphone hydrochloride, respectively, exhibit dose dumping propensities. It should become clear that formulation mechanisms relying on differential solubilities of the traditional API salts as a function of pH and solvent concentration to yield a drug product presentation exhibiting 1) pH independent extended release when used in the body and 2) impart anti-dose dumping properties (whether for intended abuse or just to a non-compliant patient) is a nearly impossible task when employing traditional API salts.

Figure 63:
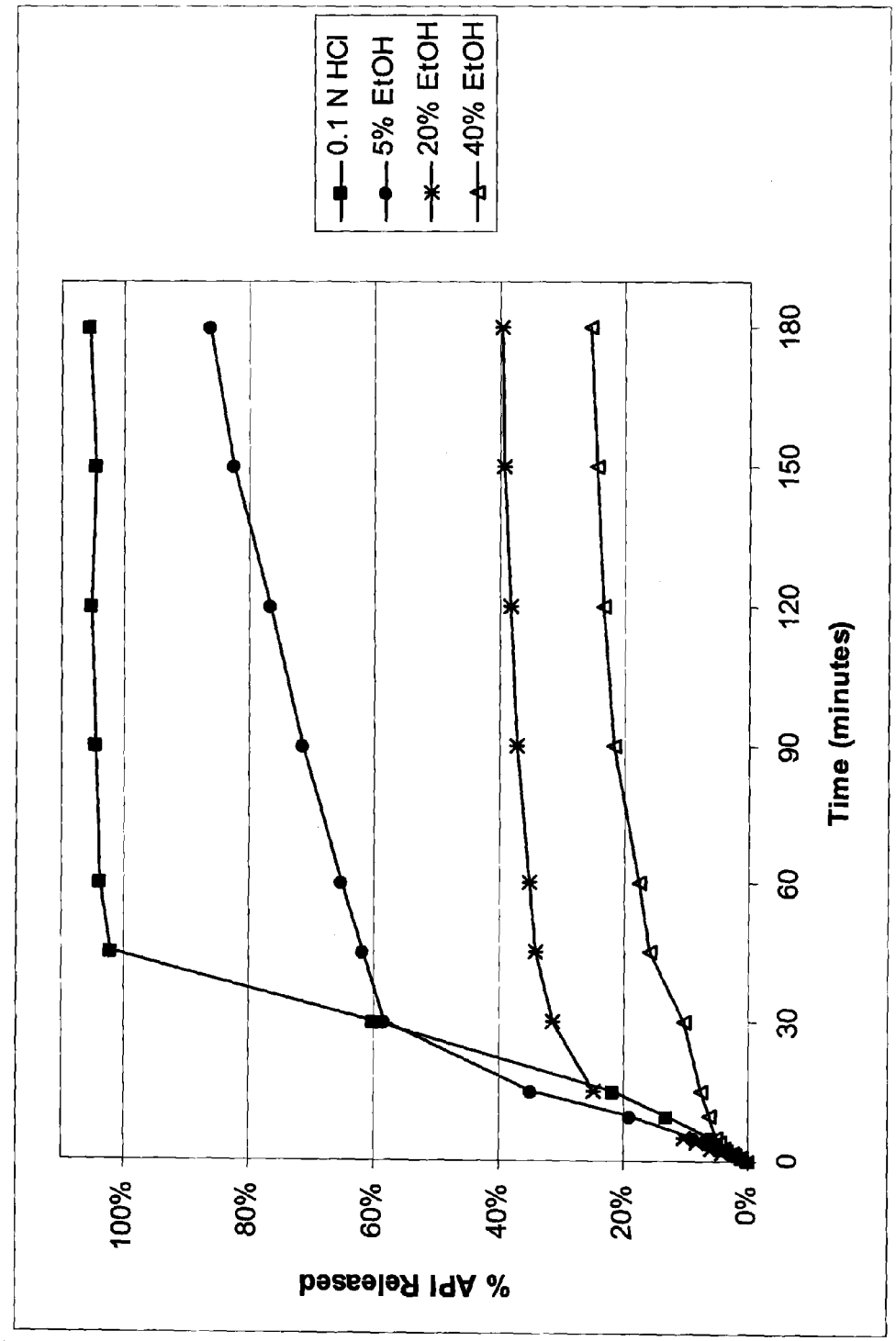
FIG. 63 is the graphical representation of the dissolution profiles for amorphous oxycodone pamoate in acidic media as a function of ethanol concentration.
Figure 67:
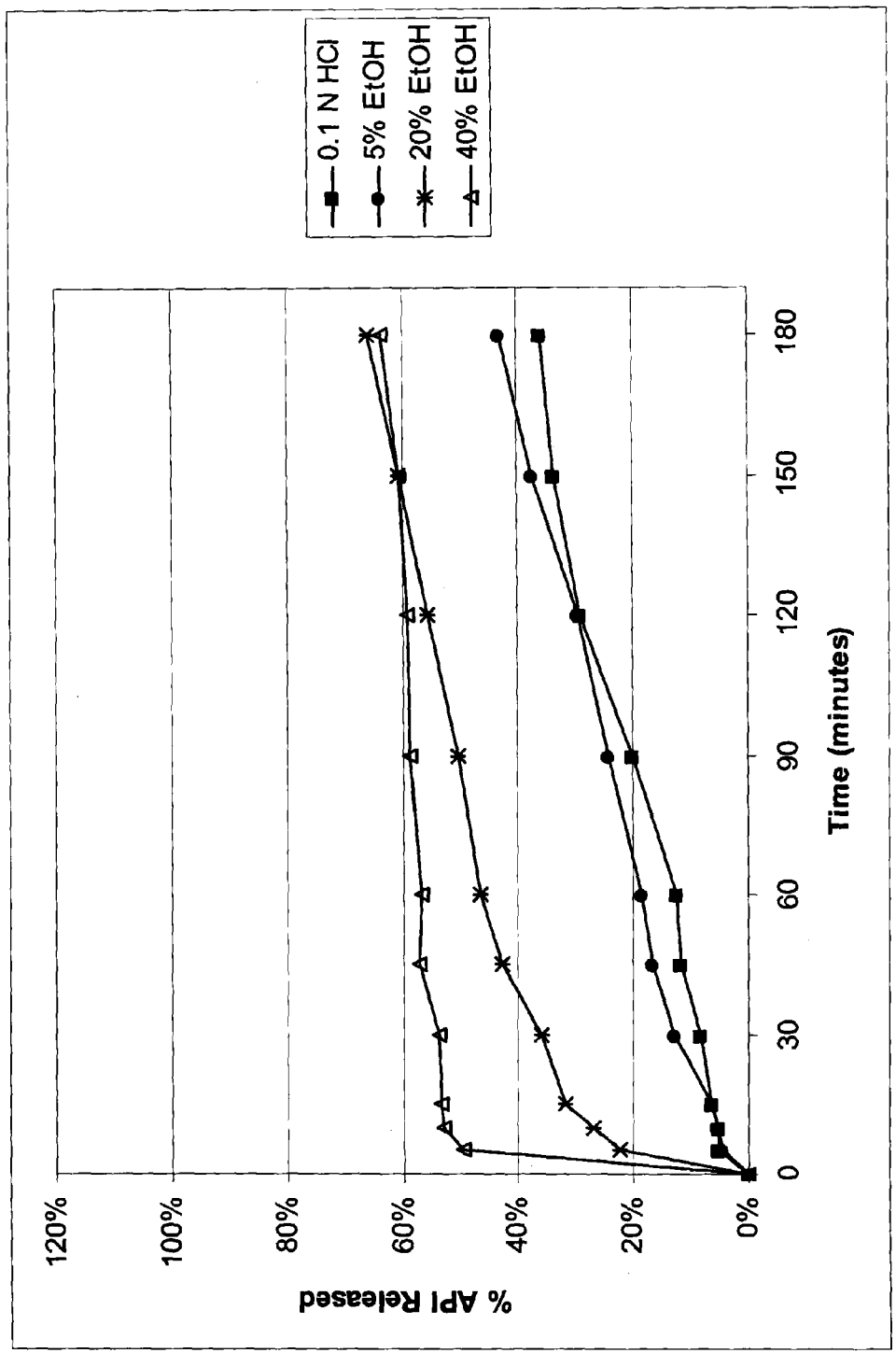
FIG. 67 is the graphical representation of the dissolution profiles for oxycodone xinafoate in acidic media as a function of ethanol concentration.
Figure 82:
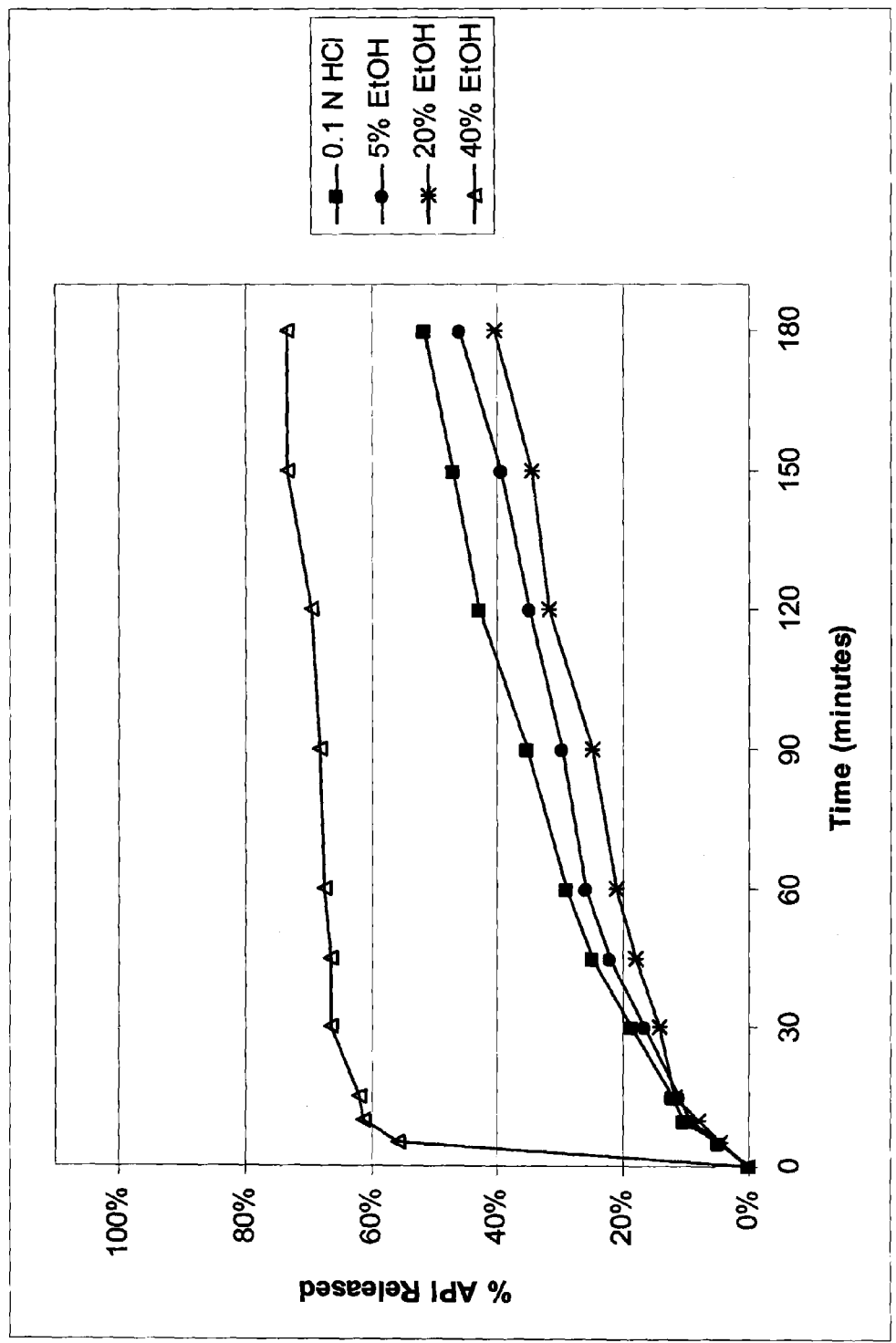
FIG. 82 is a graphical representation of the dissolution profiles of hydrocodone xinafoate in acidic media as a function of ethanol concentration.
Figure 87:
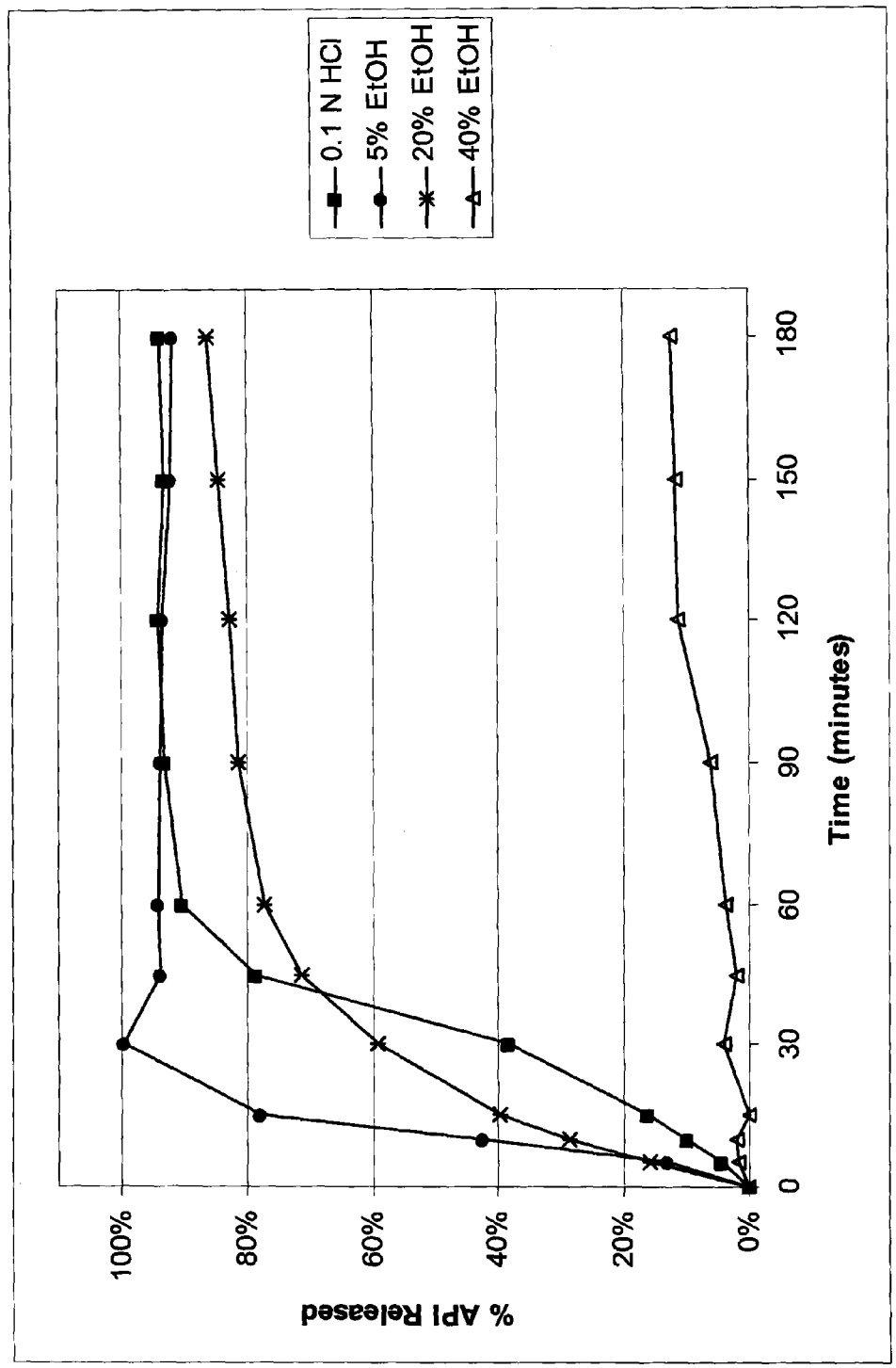
FIG. 87 is a graphical representation of the dissolution profiles of amorphous hydrocodone pamoate in acidic media as a function of ethanol concentration.
Figure 88:
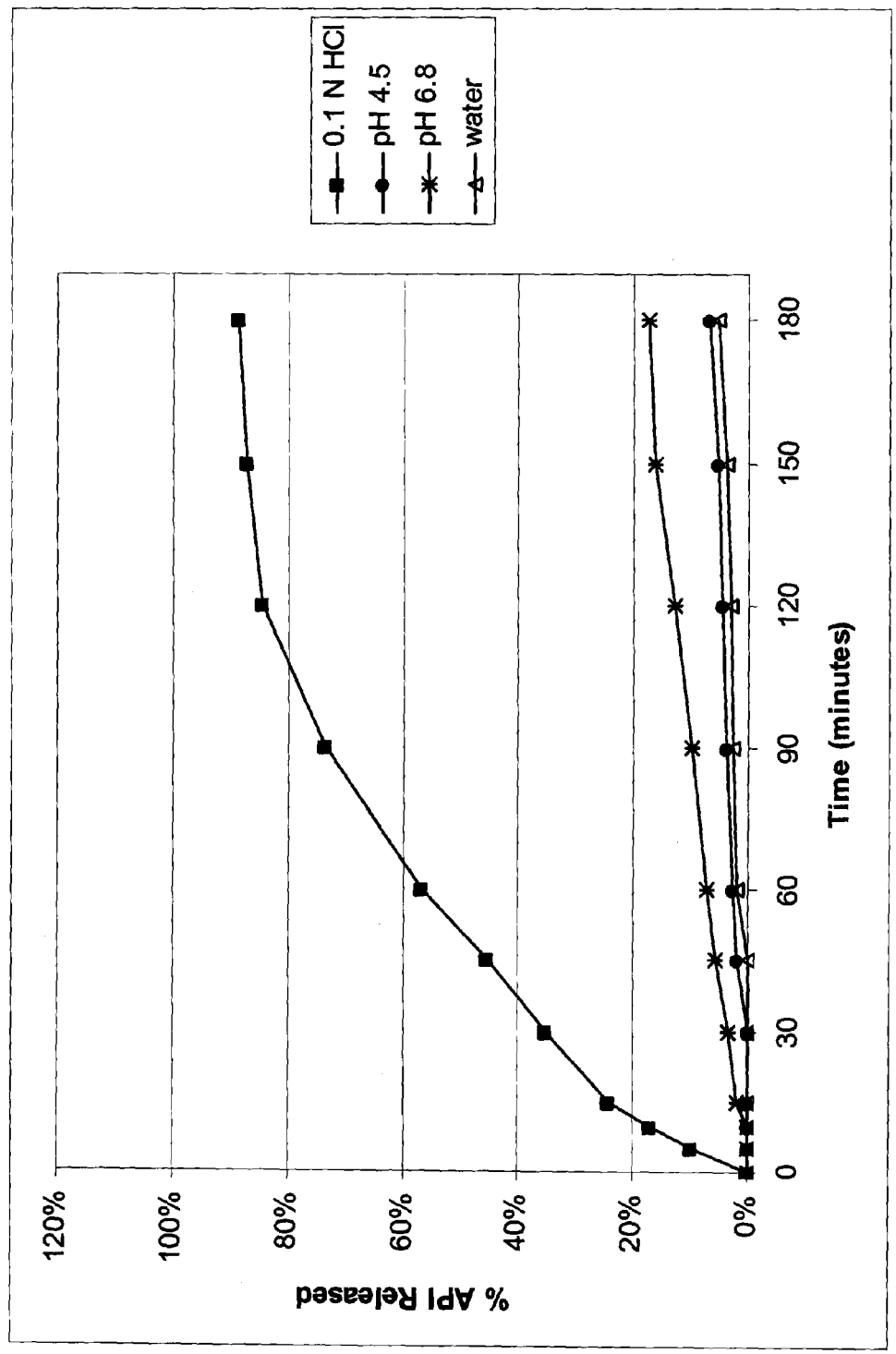
FIG. 88 is a graphical representation of the dissolution profiles of amorphous hydrocodone pamoate acetone solvate as a function of pH.
Figure 89:
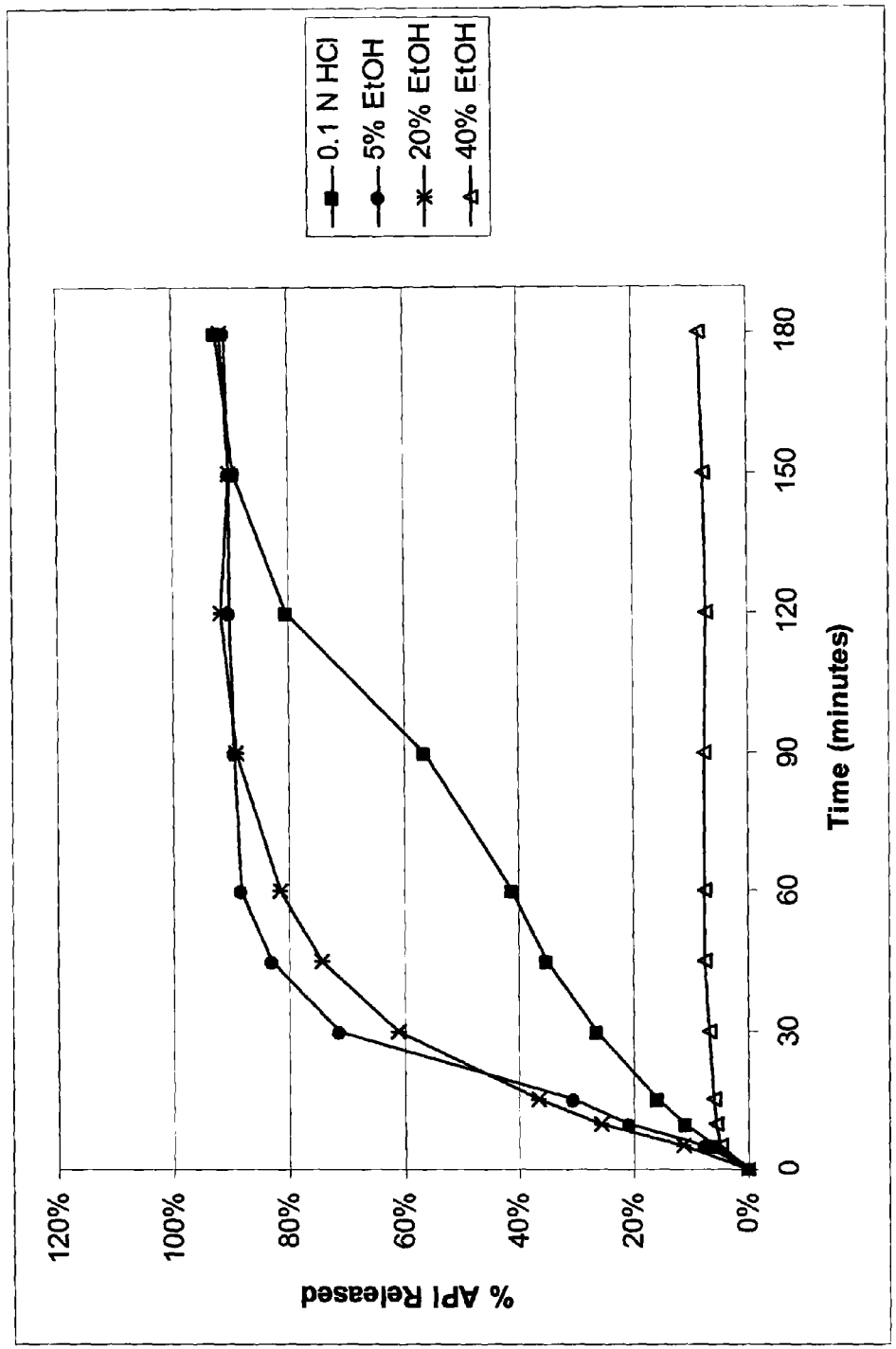
FIG. 89 is a graphical representation of the dissolution profiles of amorphous hydrocodone pamoate acetone solvate in acidic media as a function of ethanol concentration.
Figure 92:
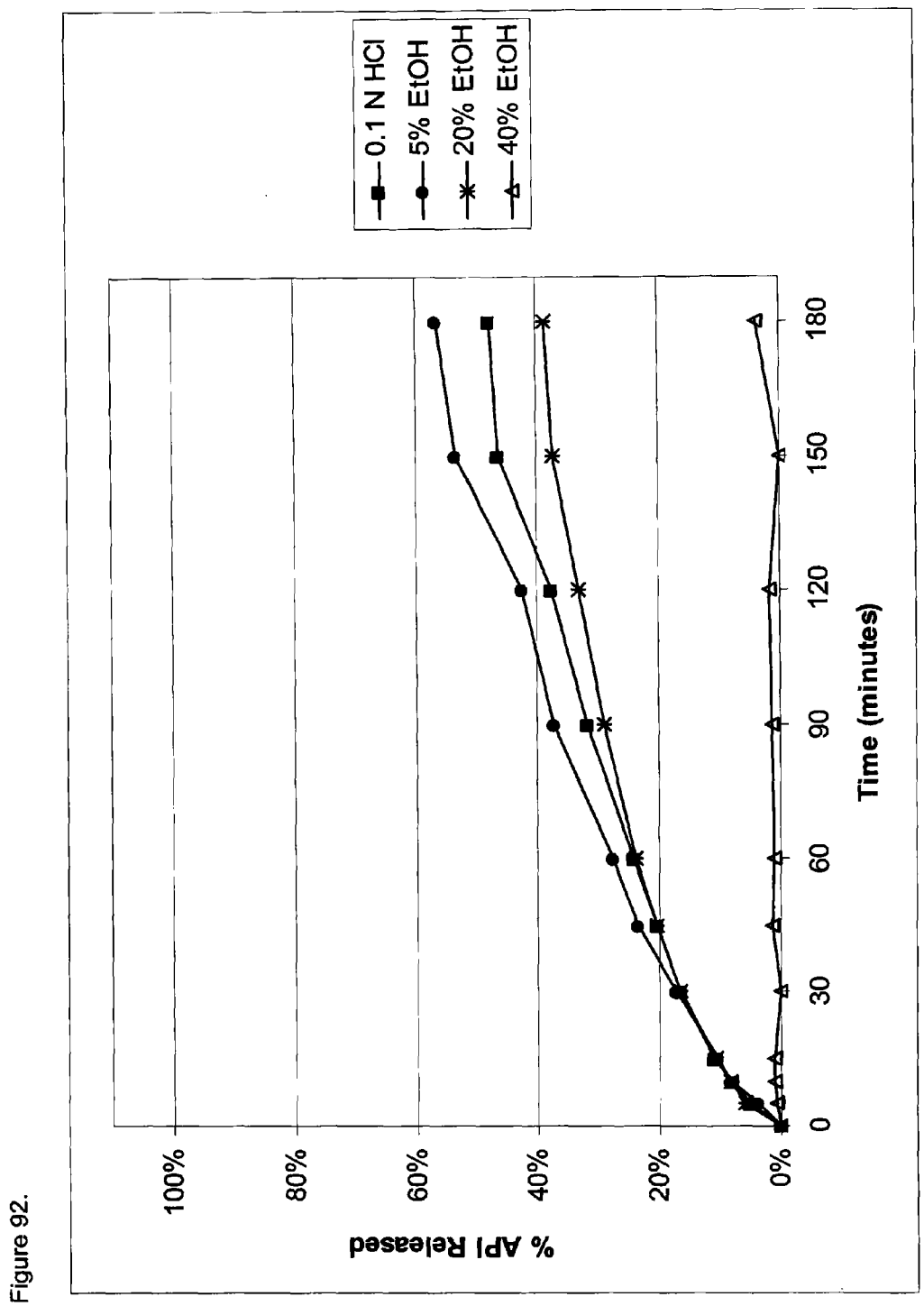
FIG. 92 is a graphical representation of the dissolution profiles of amorphous hydromorphone pamoate in acidic media as a function of ethanol concentration.
Figure 93:
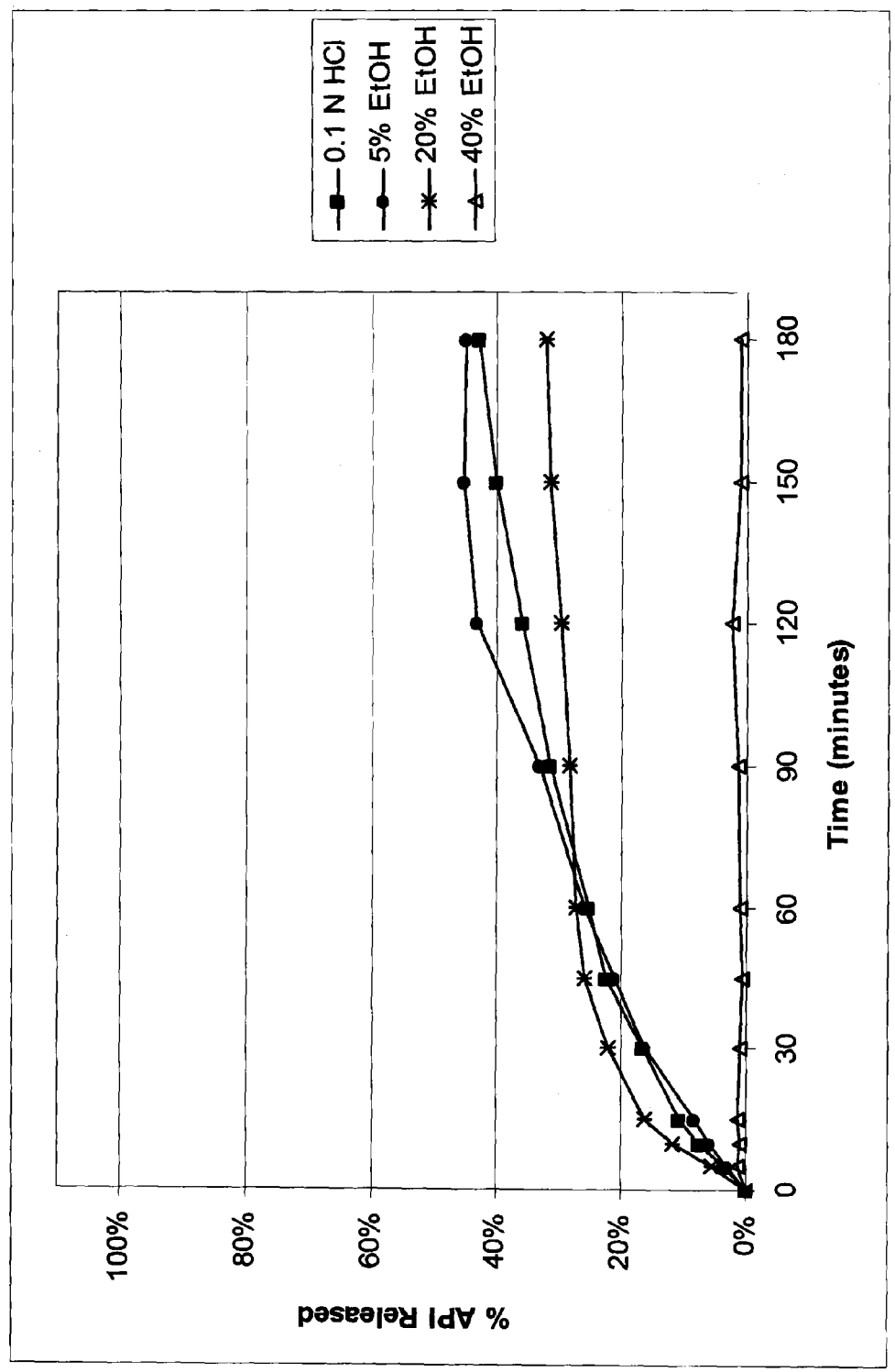
FIG. 93 is a graphical representation of the dissolution profiles of polymorphic hydromorphone pamoate acetone solvate in acidic media as a function of ethanol concentration.
Figure 94:
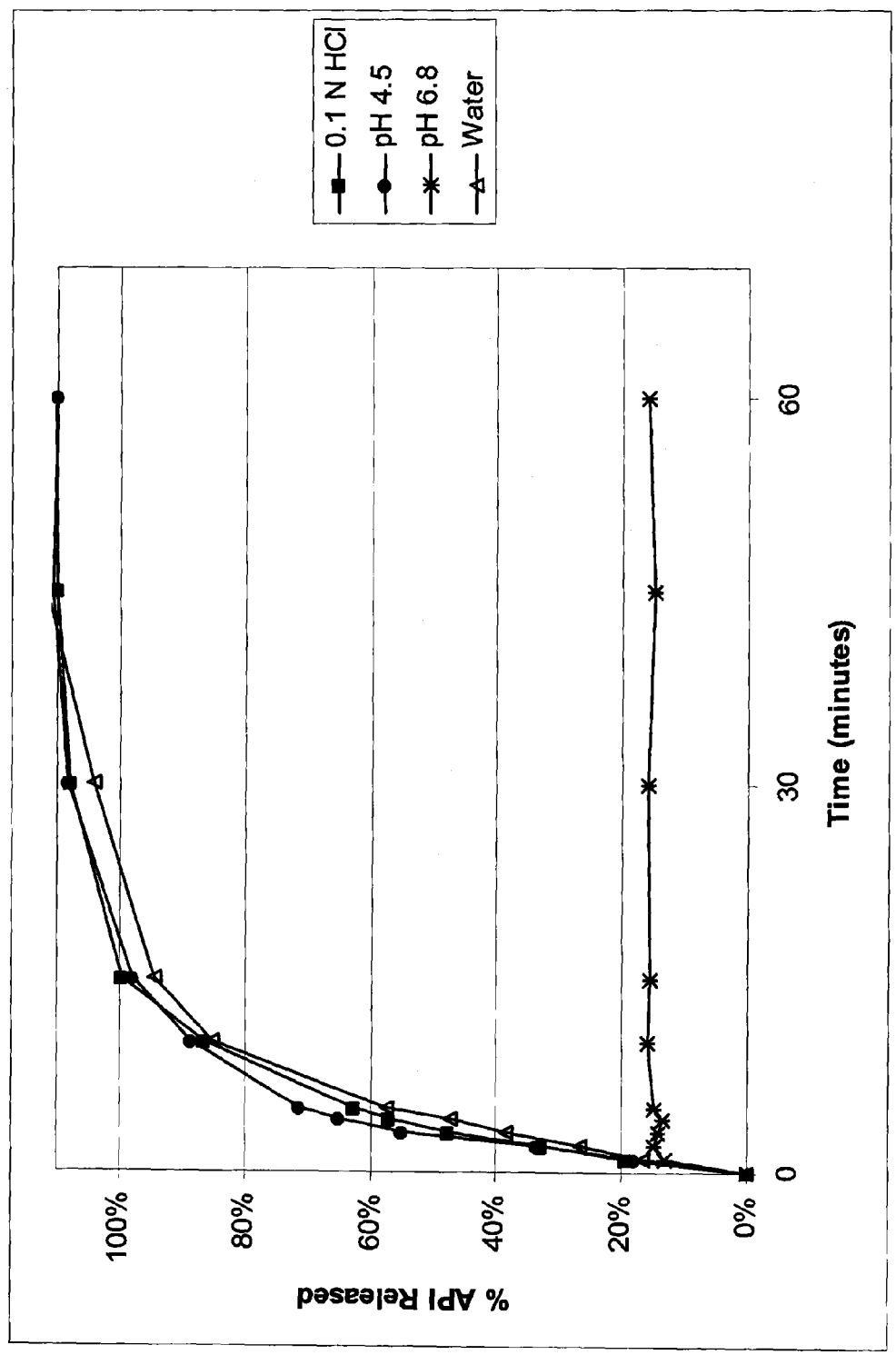
FIG. 94 is a graphical representation of the dissolution profiles of morphine sulfate as a function of pH.
Figure 95:
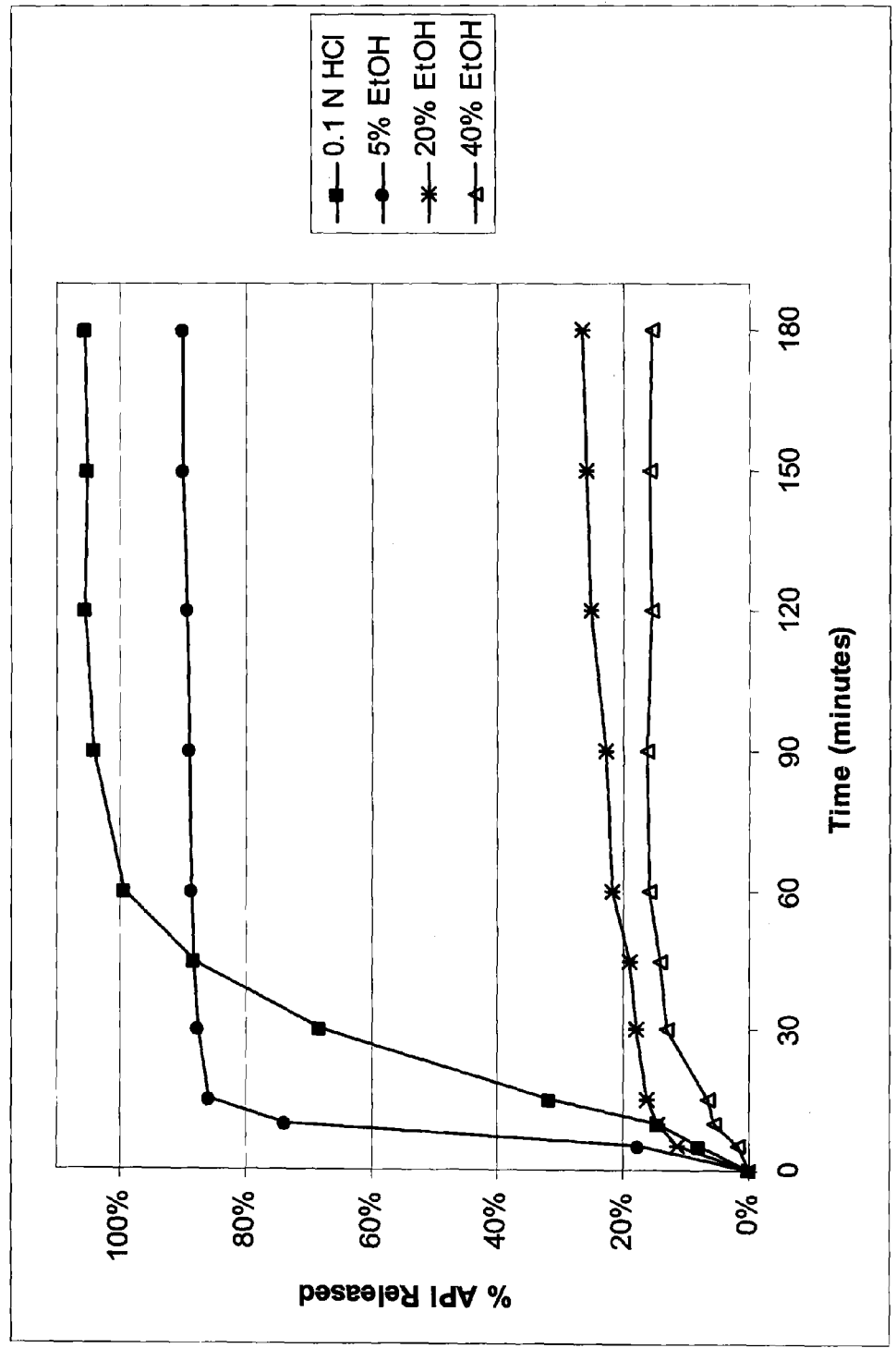
FIG. 95 is a graphical representation of the dissolution profiles of polymorphic morphine pamoate acetone solvate in acidic media as a function of ethanol concentration.

In contrast, the organic acid addition salts of the present invention offer another alternative. The dose dumping characteristic was investigated for the opioid pamoate and xinafoate salts and summarized in the following figures: FIG. 63 for amorphous oxycodone pamoate, FIG. 65 for polymorphic oxycodone pamoate, FIG. 67 for oxycodone xinafoate, FIG. 49 for amorphous hydrocodone pamoate, FIG. 50 for polymorphic hydrocodone pamoate, FIG. 87 for amorphous hydrocodone pamoate acetone solvate, FIG. 88 for polymorphic hydrocodone pamoate acetone solvate, FIG. 82 for hydrocodone xinafoate, FIG. 92 for amorphous hydromorphone pamoate, FIG. 93 for polymorphic hydromorphone pamoate acetone solvate, and FIG. 95 for polymorphic morphine pamoate acetone solvate. In each case, the dose dumping response was dramatically improved as compared to the comparable API as its mineral acid or tartrate salt. Surprisingly, the unexpected result was the increased organic nature of the opioid pamoate or xinafoate salts did not increase the solubility of the material in acidic media containing increased amounts of ethanol (i.e. 5-40% ethanol).

Figure 61:
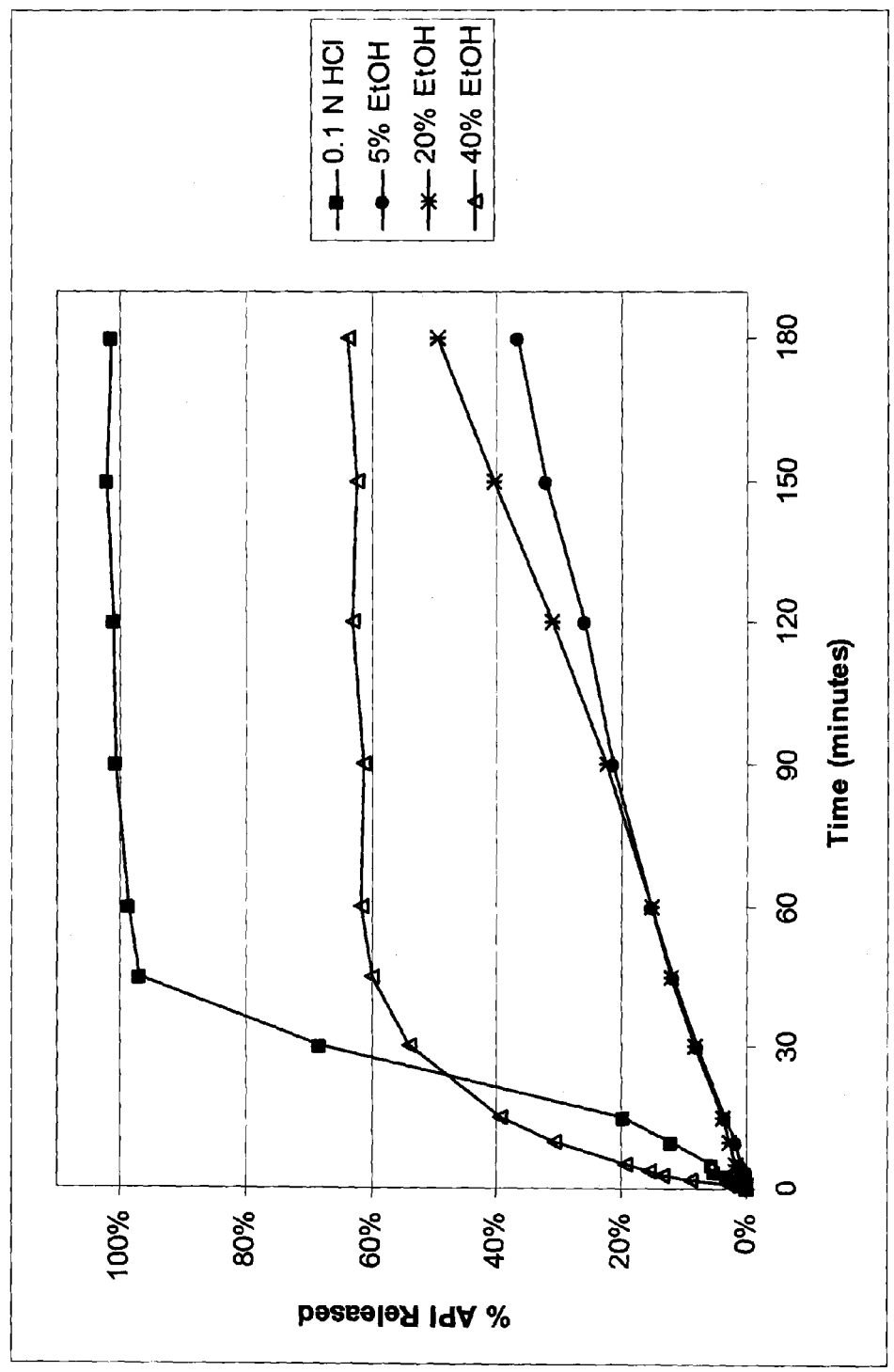
FIG. 61 is the graphical representation of the dissolution profiles of amorphous oxycodone pamoate as a function of ethanol concentration.
Figure 62:
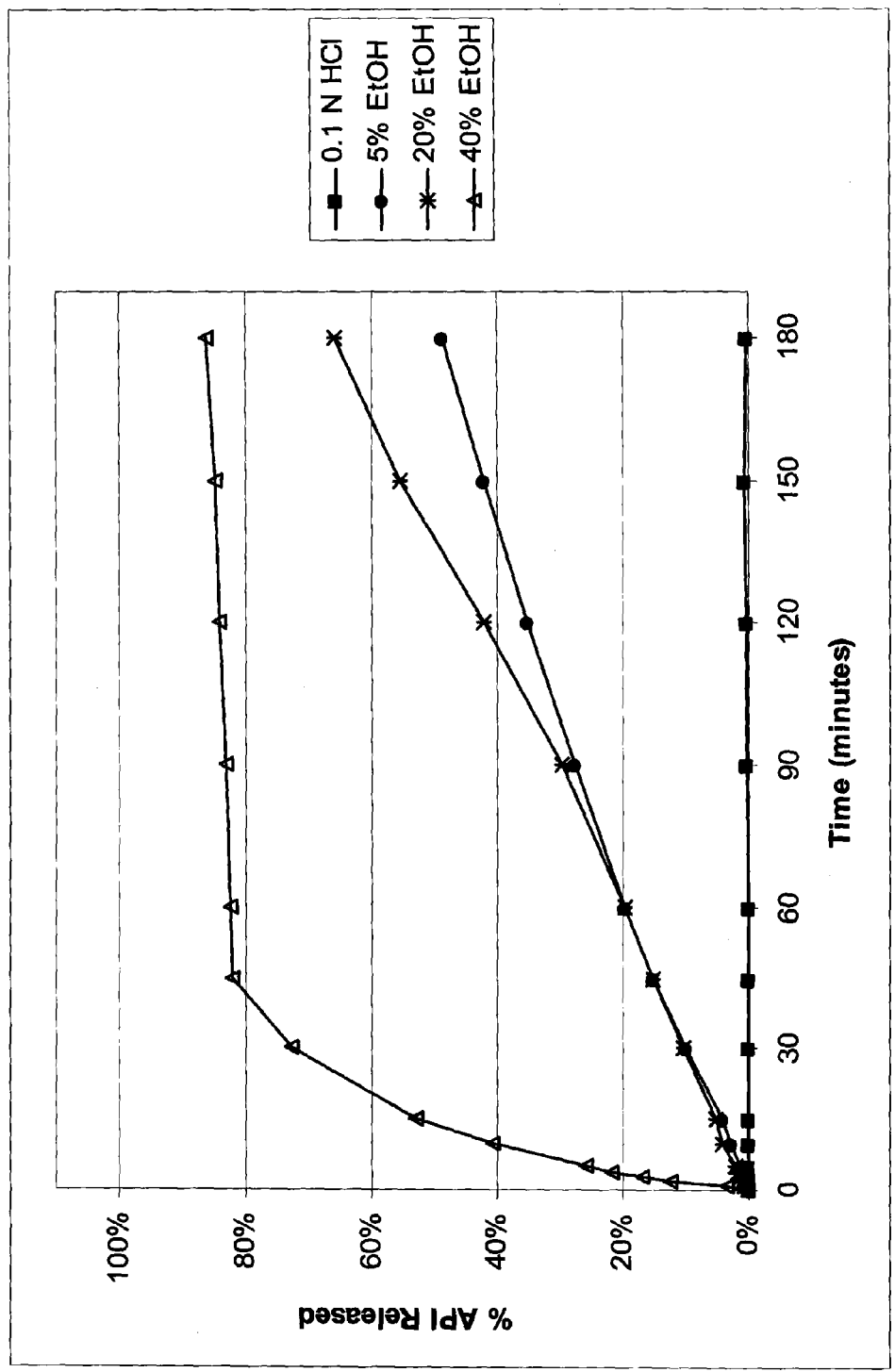
FIG. 62 is the graphical representation of the dissolution profiles for amorphous oxycodone pamoate in acidic media as a function of ethanol concentration.

A similar set of experiments was conducted on oxycodone pamoate with additional dose dumping dissolution profiles obtained to distinguish between the amorphous and polymorphic forms of oxycodone pamoate. To first address the amorphous oxycodone pamoate dose dumping experiments, the results obtained from the modified dose dumping protocol (analogous to the method used for obtaining those results in FIG. 58) are summarized in FIG. 61. It should be noted that the HPLC analyses of the organic acid addition salts of the present invention exhibit detection peaks for both the freebase opioid and for the particular organic acid family employed (pamoate and/or xinafoate and their derivatives). FIG. 62 corresponds to FIG. 63 except that the pamoate concentration was plotted as a function of time instead of the release of the opiate. A number of observations were made from these FIGS. 62 and 63. First, the opiate when delivered as the pamoate salt to the 0.1 N HCl media does not exhibit an immediate release profile; release is complete at times approaching one hour. Certainly, this release profile is not what is sought by one attempting to abuse the drug. When 40% EtOH is employed to enhance dose dumping, the amount of opiate released was time dependent but reaches an apparent equilibrium solubility concentration greater than the same condition observed for oxycodone HCl in 40% EtOH. This increase from about 50% opiate immediately released for the hydrochloride salt versus the approximately 60% released opiate over about one hour when delivered as the pamoate represents a significant decrease to dose dumping potential. Additionally, it required about ninety minutes before appreciable amounts of the opiate were released from the pamoate under the 5 and 20% EtOH conditions. As such, dose dumping would not be a preferred route of abuse administration if oxycodone pamoate was employed in a formulated product. This conclusion was further supported by the results summarized in FIG. 62 particularly when the pamoate concentration was determined for the 40% ethanol condition. The time dependent release of the pamoate moiety, in FIG. 62, was observed and corresponded well to the release of the opiate in FIG. 61 for 40% EtOH. The apparent pamoate equilibrium solubility was achieved after approximately 45 minutes, to yield about 85% of the pamoate released. A superficial analysis of these data may lead one to conclude the opiate could be effectively extracted from a dissolution media of 80 proof alcohol and to easily separate the pamoate moiety form the oxycodone. However, the opiate and the pamoate are present in the dissolution medium and removal of the solvent by evaporation will only lead to the reformation and precipitation of oxycodone pamoate. Consequently, there is no benefit by a potential abuser to attempt dose dumping with 40% ethanol. In addition, by inspection of either FIG. 61 or 62, dose dumping at 5 and 20% is a slow linear process.

Figure 65:
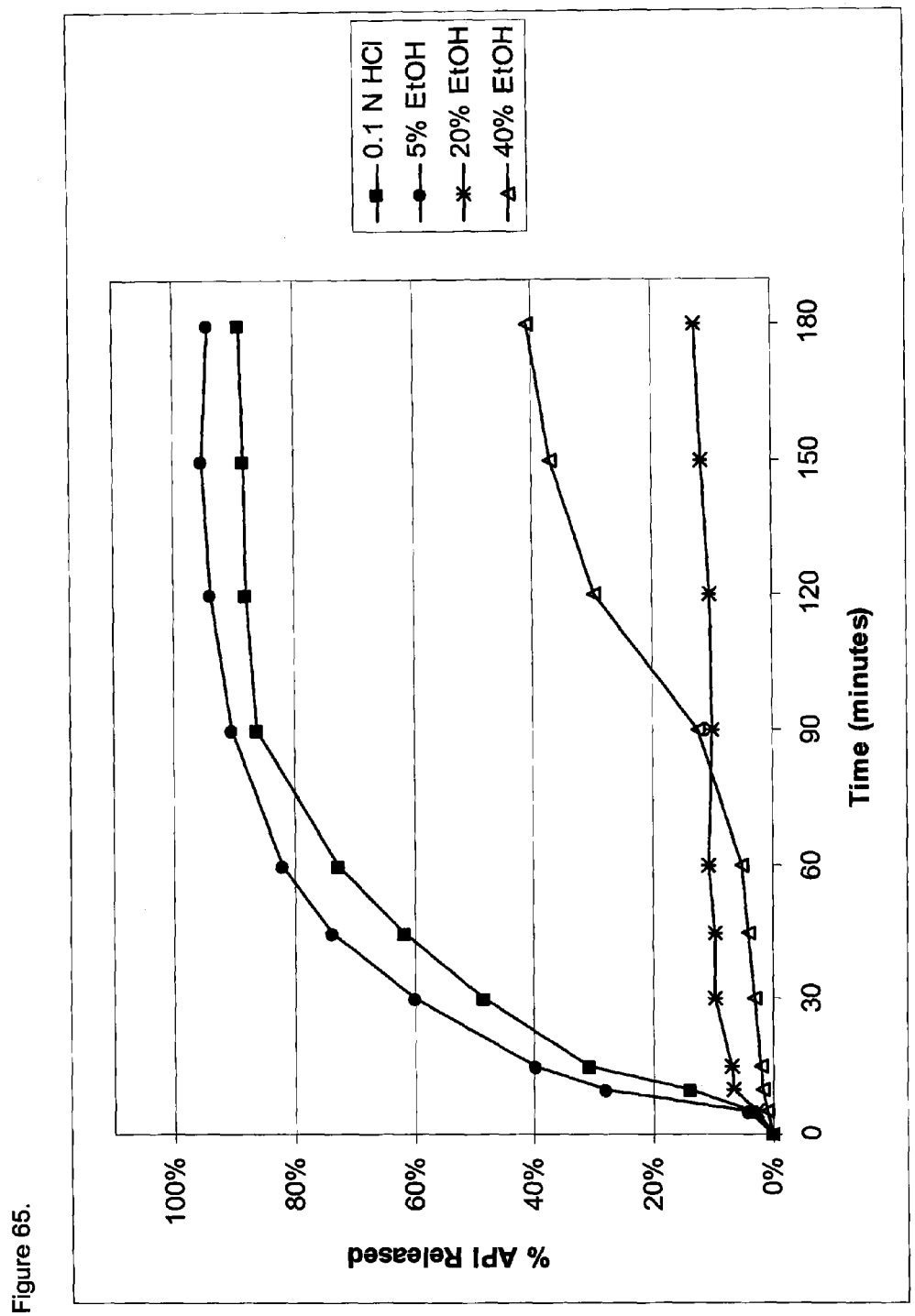
FIG. 65 is the graphical representation of the dissolution profiles of polymorphic oxycodone pamoate in acidic media as a function of ethanol concentration.

These experiments were repeated using the FDA's dose dumping protocol wherein present in the various ethanol concentrations was 0.1 N HCl. Results from these experiments are summarized in FIG. 63. The amorphous oxycodone pamoate exhibits a modified release profile in 0.1 N HCl with full release occurring after about one hour. The presence of alcohol significantly impacts the release of the opiate and in this case with acid present, no dose dumping benefit would be obtained by a drug abuser by drinking a bottle of 80 proof alcohol to accelerate release of the opiate. In fact, drinking beer (nominally 5% EtOH) would diminish release of the opiate. Further FIG. 65 summarizes the results from the dose dumping experiment conducted on a polymorphic form of oxycodone pamoate. The polymorphic form which had exhibited an essentially identical pH dissolution profile as the amorphous form, exhibited an unexpected and modified release profile under the FDA's dose dumping protocol. The dissolution profiles for the 0.1 N HCl and that containing 5% EtOH exhibited an extended release profile wherein about 70% of the active was released in approximately sixty minutes. Overall, the dissolution profiles for these two conditions were quite similar. In contrast, the 20% EtOH profile reached approximately a 10% equilibrium solubility in about 30 minutes. The 40% EtOH condition exhibited a delayed release profile with approximately a 10% release after about 80 minutes with a gradual rise to approximately 40% release after 3 hours. These results indicate essentially no dose dumping effects, or extraction capabilities are available to the oxycodone pamoates present as either the amorphous, polymorphic or combinations of both forms. Like the pH dependent dissolution profiles for oxycodone pamoate (FIG. 38) amorphous and FIG. 39 (polymorphic), the dose dumping profiles for the amorphous polymorphic pair did not significantly distinguish between these forms of the drug substance yet both attenuated dose dumping as compared to oxycodone hydrochloride.

Figure 90:
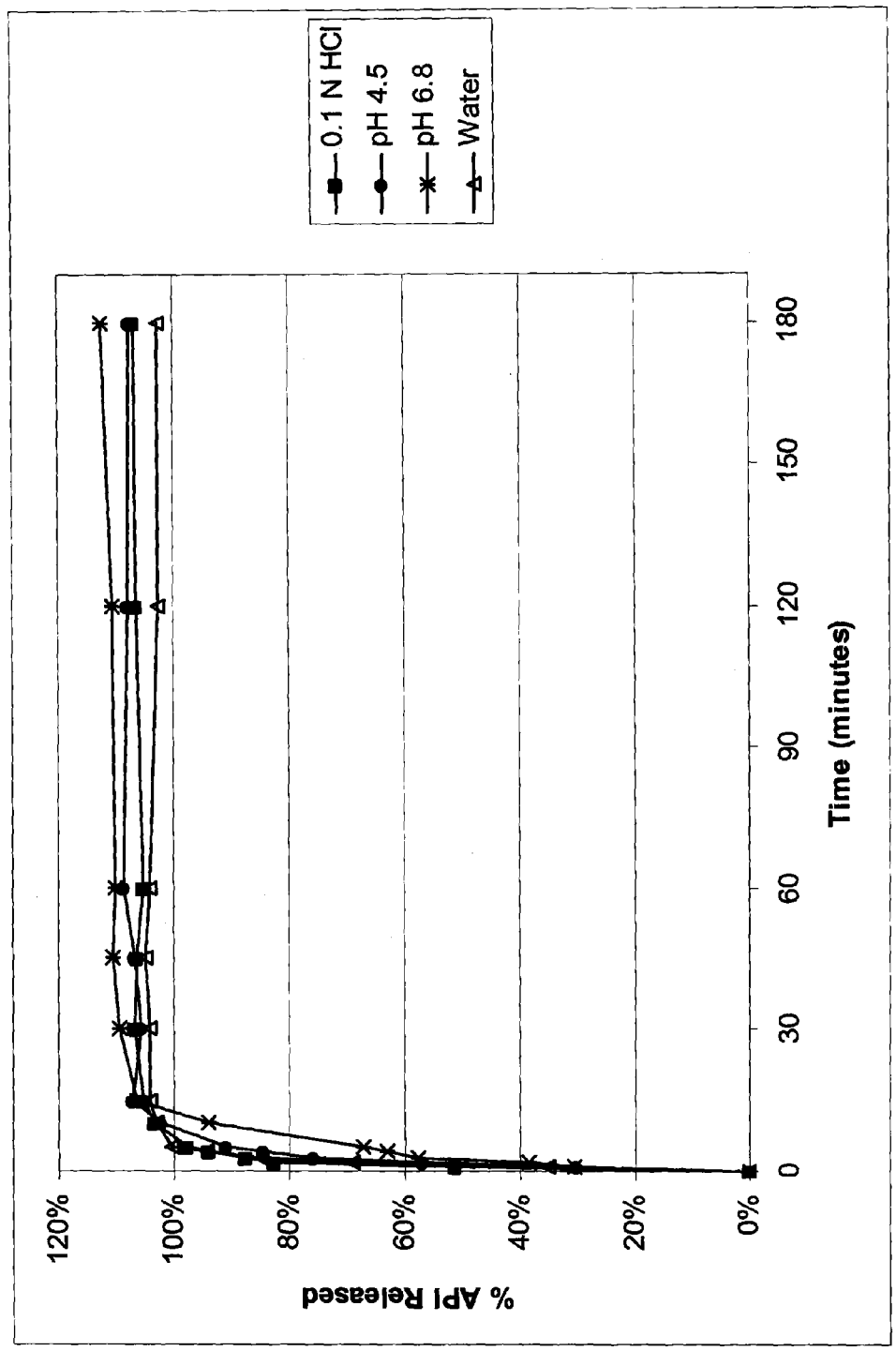
FIG. 90 is a graphical representation of the dissolution profiles of hydromorphone hydrochloride as a function of pH.

While much of the attention herein has been placed on oxycodone pamoate as a means to elucidate and identify the extended release and anti-dose dumping mechanisms, the findings are applicable to the family of opioid compounds. The pamoate salts appear to be the most generally applicable; however experiments with the xinafoate salts have also proved fruitful. The xinafoate salts of oxycodone, hydrocodone, hydromorphone and morphine each demonstrated some level of extended release property at various pH values and could accommodate formulations designed to obtain a pH independent release. These properties are easily observed as presented in FIG. 54 (hydromorphone xinafoate) as compared with FIG. 90 (hydromorphone hydrochloride). Clearly however, the xinafoate salts do not have the dominating role in interrupting dose dumping as well as the pamoates perform. For instance, comparing FIG. 63 (amorphous oxycodone pamoate) vs. FIG. 67 (oxycodone xinafoate); the xinafoate salt dose dumps immediately at the higher EtOH concentrations. Interestingly however, the xinafoate salt has a significantly attenuated dose dumping profile when compared with the comparable hydrochloride salt.

Many, many comparisons such as these are possible from the extensive data set, which may overshadow some fundamental conclusions:
1) the hydrochloride and bitartrate salts exhibit immediate release profile and are highly susceptible to dose dumping;
2) the pamoate and xinafoate salts attenuate the pH dissolution profiles of the opioids and impart a level of extended release directly to the active substance;
3) the pamoate and xinafoate salts are suitable for providing pH independent release drug product formulations;
4) the expected differences between the amorphous and polymorphic opioid pamoate salts were essentially non-existent and consequently contrary to accepted pharmaceutical teachings;
5) the solvated forms of the amorphous and/or polymorphic forms of the opioid pamoate salts had little impact on their dissolution profiles or dose dumping properties; and
6) the pamoate salts are a dominating factor in preventing dose dumping and are independent of the opioid.

Analogous to the traditional dissolution tests discussed herein, formulation experiments were conducted to determine the effect of an excess stoichiometric amount of the pamoate and/or xinafoate moiety on both the pH dependent dissolution tests and dose dumping protocol. Experiments were conducted with disodium pamoate (dispam), pamoic acid and 3-hydroxy-2-naphthoic acid (BON Acid) in various ratios expressed as a molar ratio between the particular opioid salt evaluated (e.g. oxycodone pamoate) and the additional organic acid component (perhaps as its alkali metal salt). Control experiments were performed on the simple hydrochloride, sulfate and bitartrate opioid salts as a basis for comparison to the opioid pamoate and xinafoate salts when formulated with additional organic acid component.

This investigation generated a large data set with striking conclusions. The addition of excess amounts of the pamoate or xinafoate moieties to an opioid pamoate or xinafoate salt, i.e. a formulation, provided markedly attenuated pH dissolution profiles and significantly inhibited dose dumping. A review of the oxycodone series of experiments illustrates this conclusion well and was demonstrated to be applicable to the family of opioids in general. The stoichiometry range investigated for dispam was 2:1 to 1:2 opioid salt to dispam and included the 1:1 mid-range condition. Screening experiments indicated the desired effects were less pronounced when employing BON Acid or pamoic acid, however, specific experiments were conducted at similar stoichiometric ratios as those performed employing dispam and included the "cross" experiments. The "cross" experiments include those conditions wherein more than one organic acid component was added and wherein the additional organic acid component was different from the counter-ion employed to produce the opioid salt.

Figure 40:
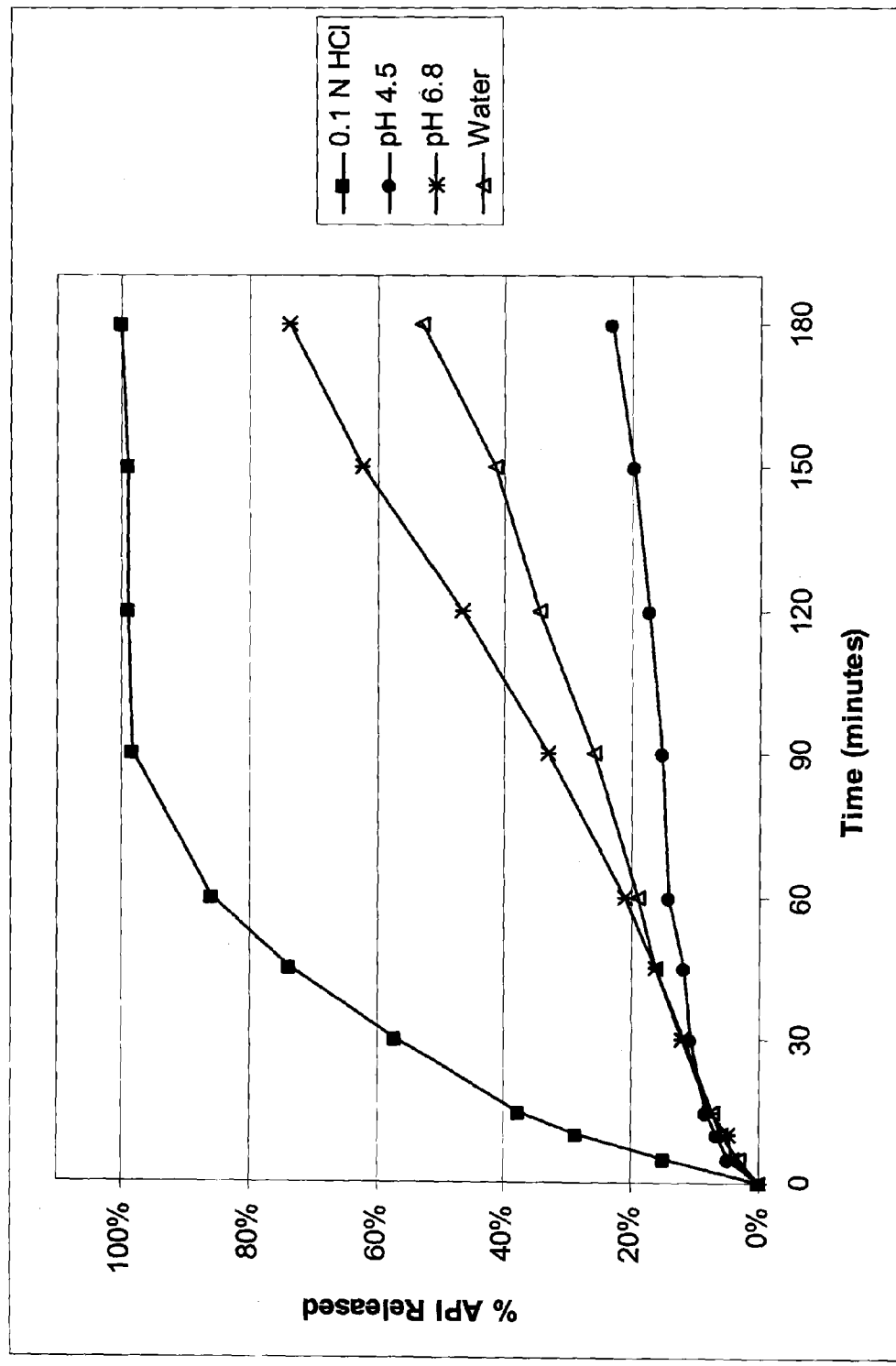
FIG. 40 is the graphical representation of the dissolution profiles for a formulation (2:1 molar) of oxycodone hydrochloride and disodium pamoate as a function of pH.
Figure 44:
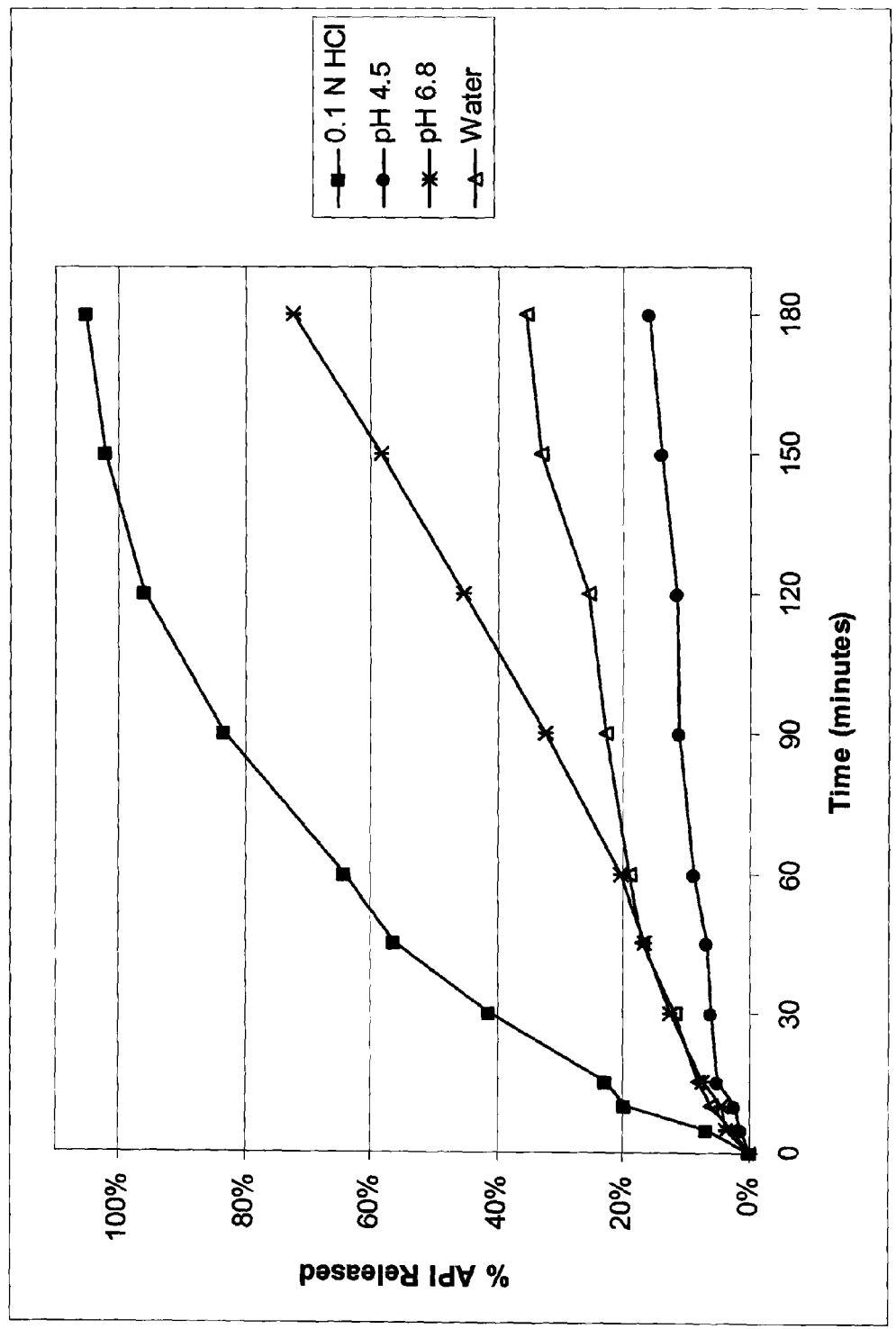
FIG. 44 is the graphical representation of the dissolution profiles for a formulation (1:1:1 molar) of oxycodone hydrochloride, disodium pamoate and pamoic acid as a function of pH.
Figure 77:
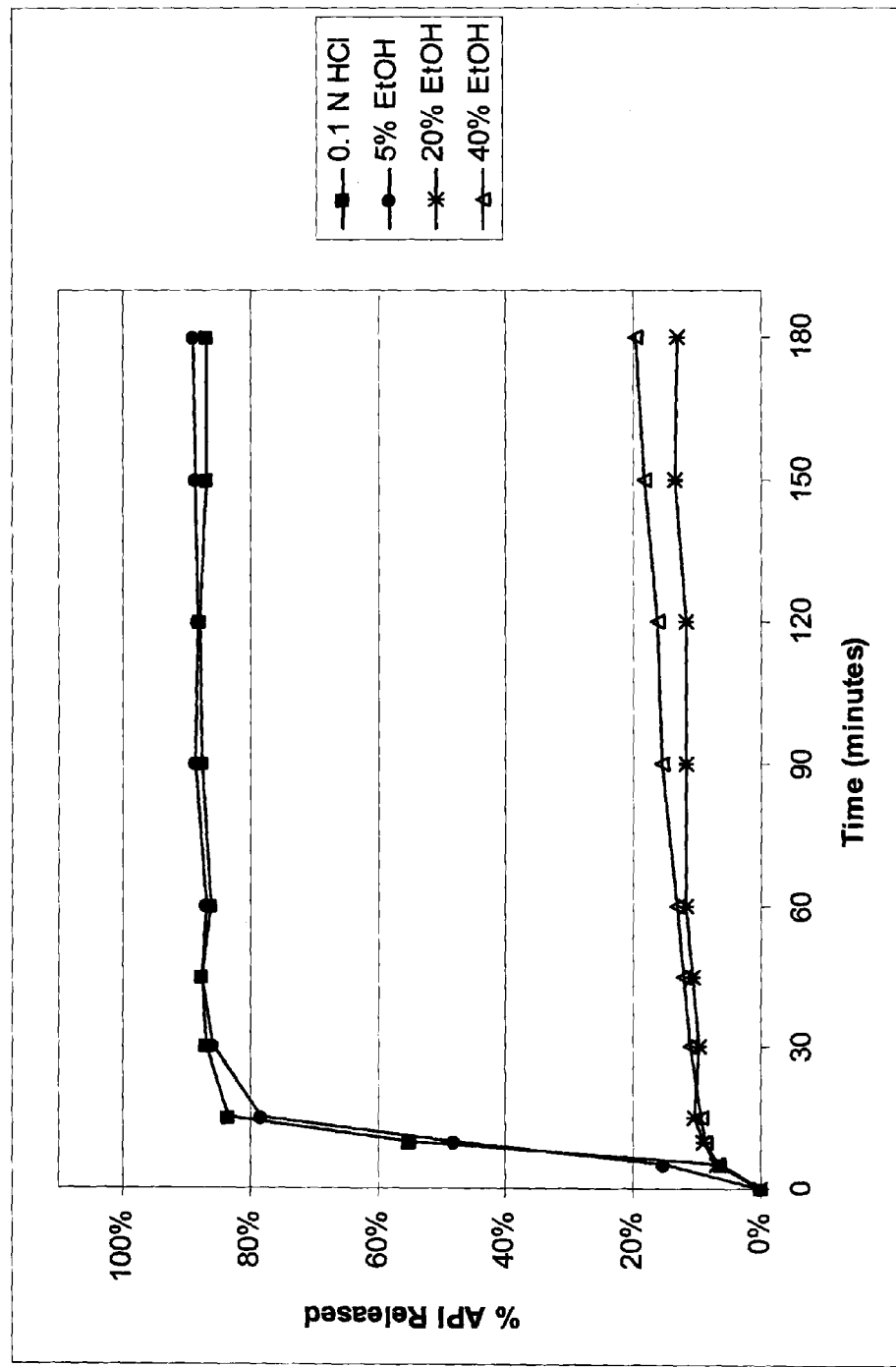
FIG. 77 is the graphical representation of the dissolution profiles of a formulation (1:2 molar) of polymorphic oxycodone pamoate with 3-hydroxy-2-naphthoic acid (BON acid) in acidic media as a function of ethanol concentration.
Figure 78:
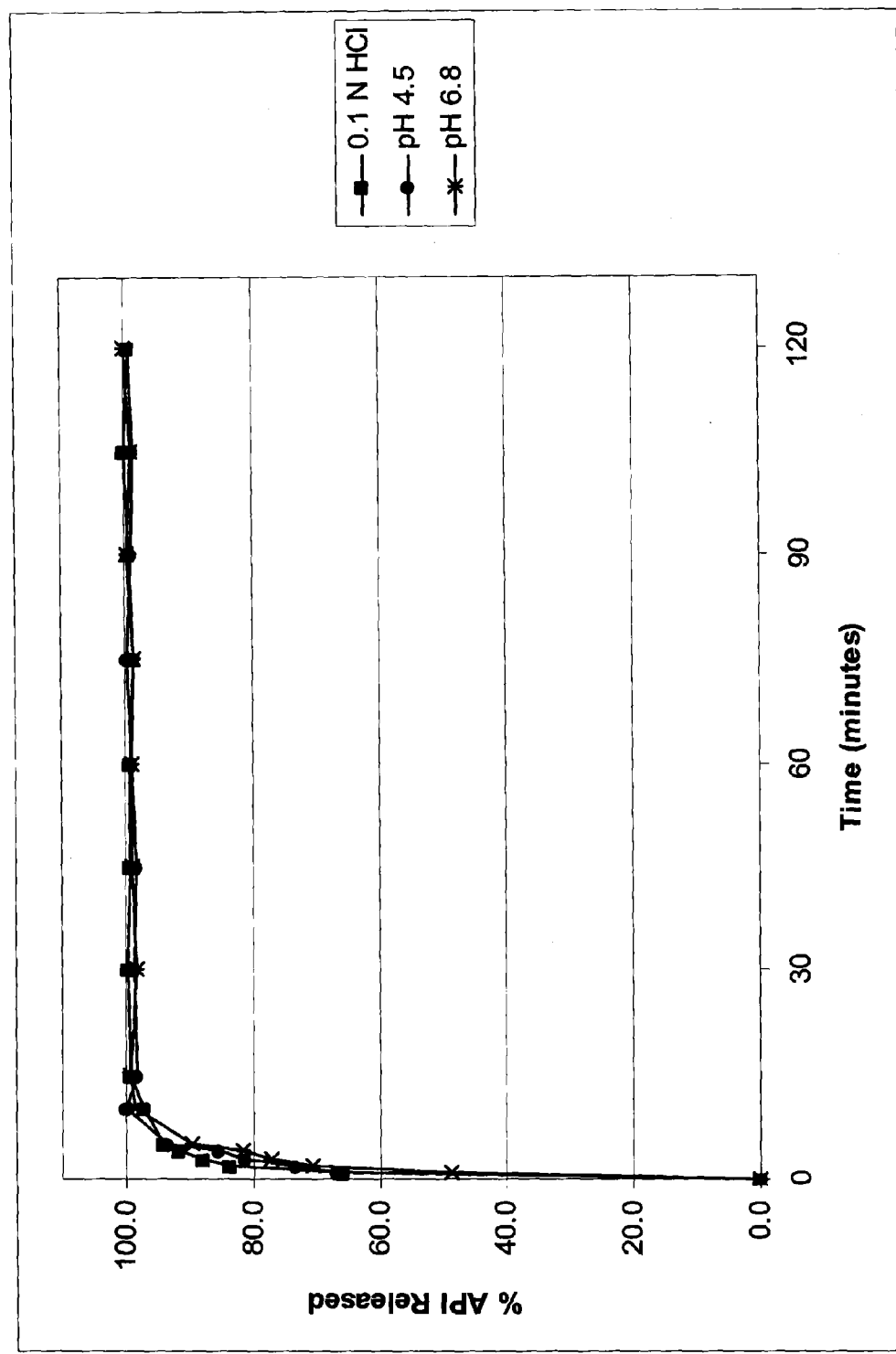
FIG. 78 is the graphical representation of the dissolution profiles of hydrocodone bitartrate as a function of pH.

Pertinent to the discussion regarding formulation experiments and by way of example regarding the nomenclature identifying each experiment, consider FIG. 40 (oxycodone hydrochloride 2:1 dispam). The parenthetical descriptor indicates the API was oxycodone hydrochloride which was formulated in a 2:1 stoichiometric ratio with disodium pamoate. Similarly, FIG. 44 (oxycodone hydrochloride 1:1:1 dispam: pamoic) indicates oxycodone was formulated in a 1:1:1 ratio with dispam and pamoic acid. For completeness and in context of the present invention, another example of the nomenclature employed is represented by FIG. 77 (oxycodone pamoate polymorph 1:2 BON Acid) symbolizing the evaluation of a polymorphic form of oxycodone pamoate was formulated with a stoichiometric excess of BON Acid in a ratio of 1 mole of the API and 2 moles of BON Acid.

Figure 41:
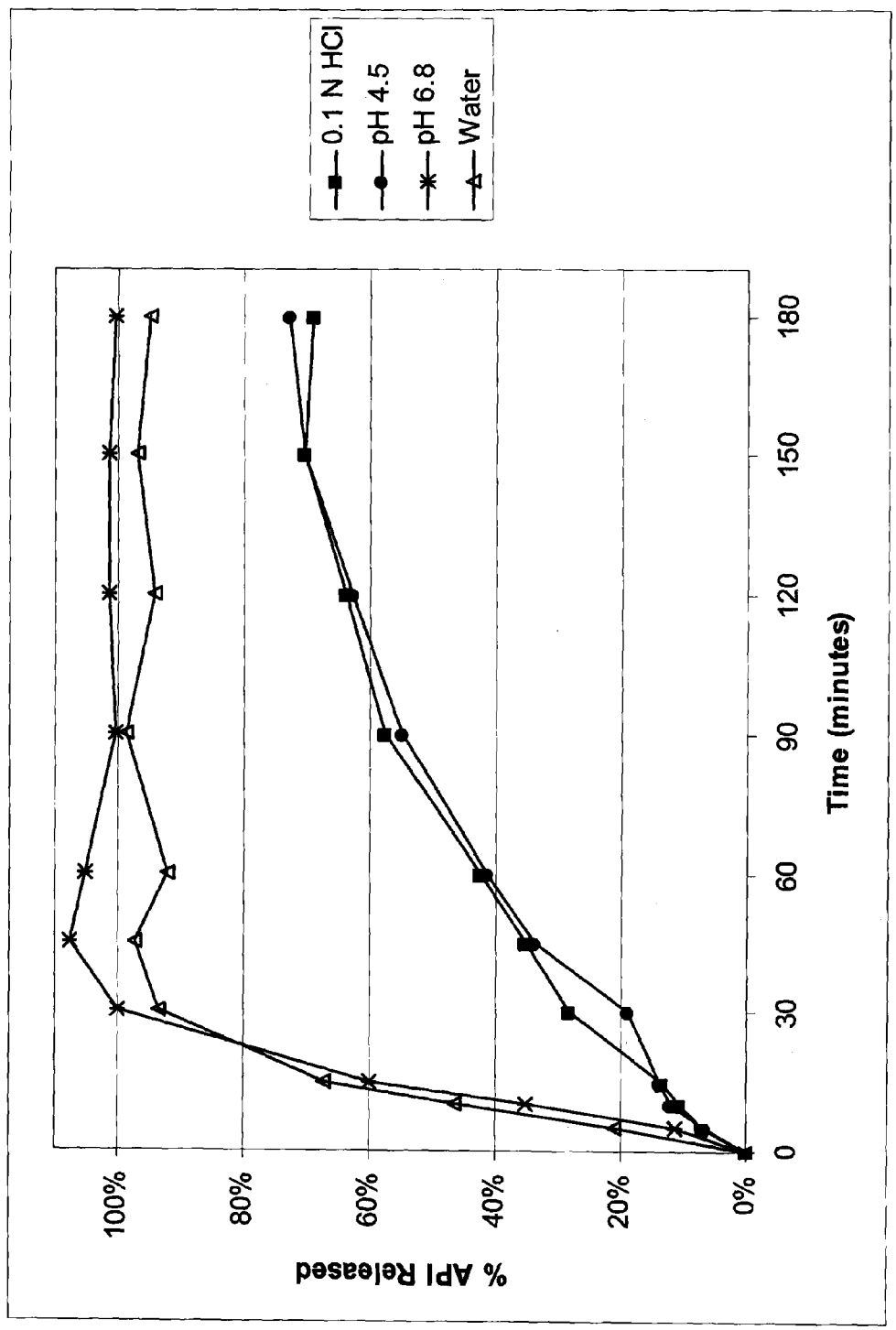
FIG. 41 is the graphical representation of the dissolution profiles for a formulation (1:2 molar) of oxycodone hydrochloride and disodium pamoate as a function of pH.
Figure 42:
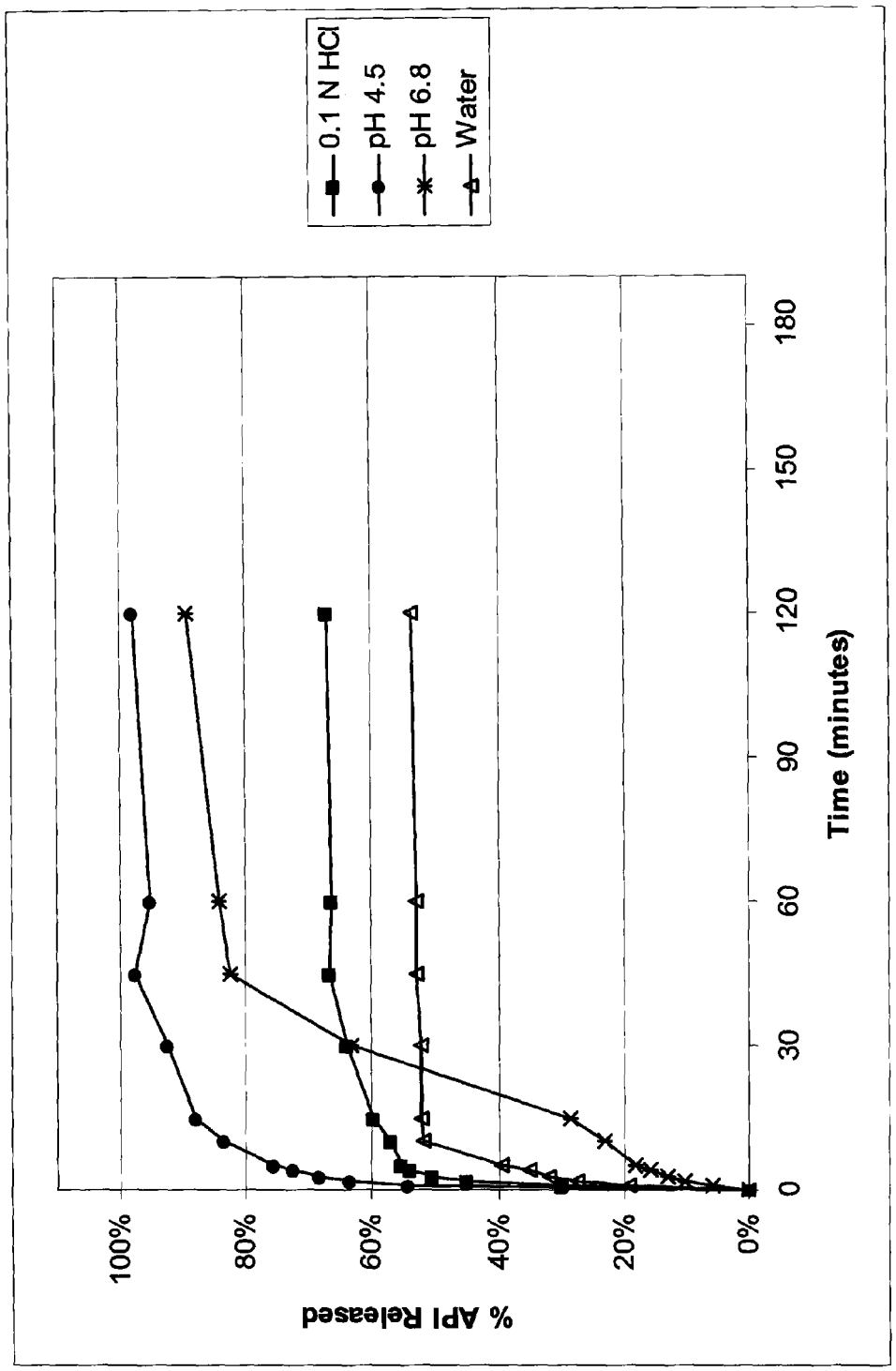
FIG. 42 is the graphical representation of the dissolution profiles for a formulation (2:1 molar) of oxycodone hydrochloride and pamoic acid as a function of pH.
Figure 43:
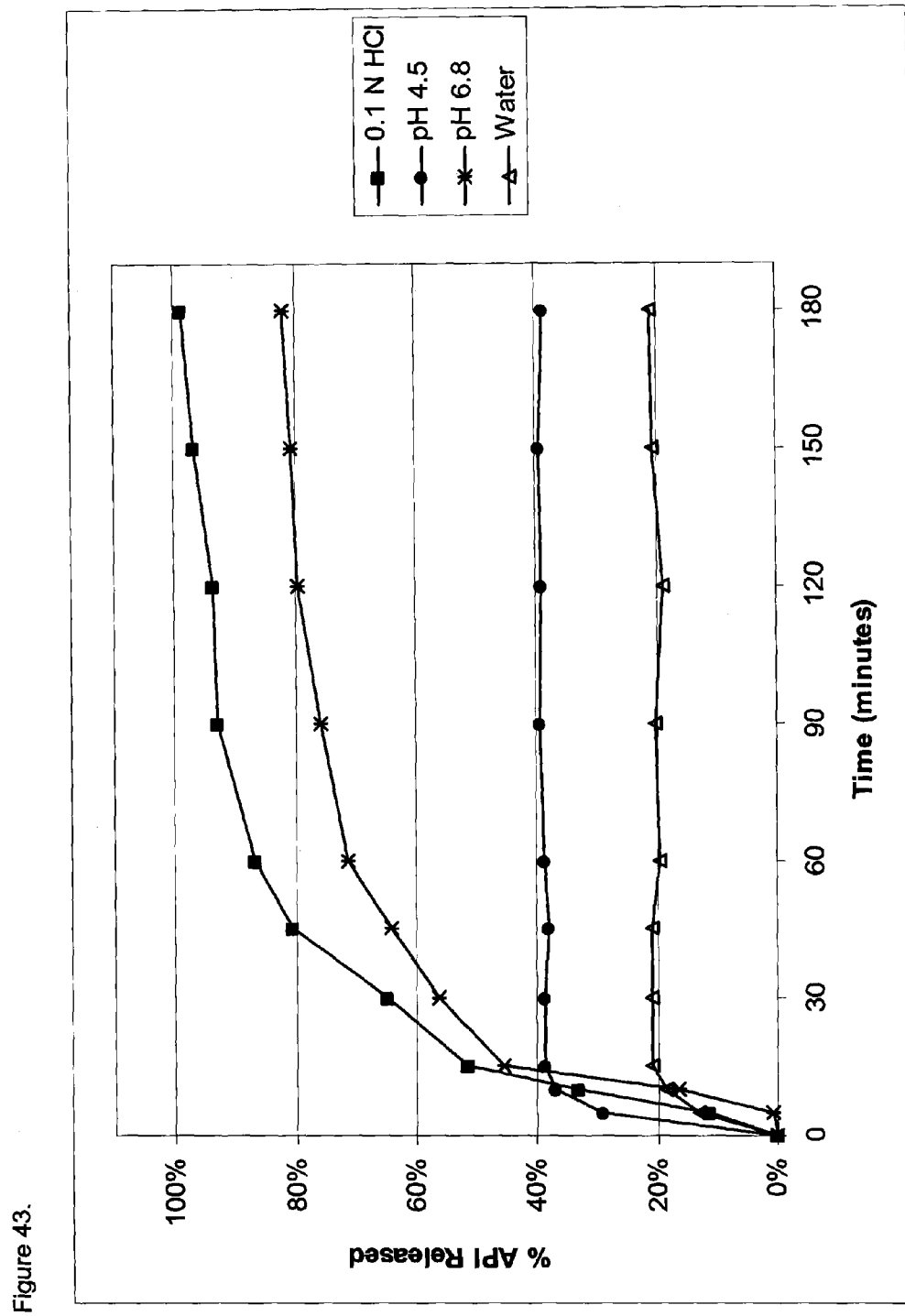
FIG. 43 is the graphical representation of the dissolution profiles for a formulation (1:2 molar) of oxycodone hydrochloride and pamoic acid as a function of pH.
Figure 45:
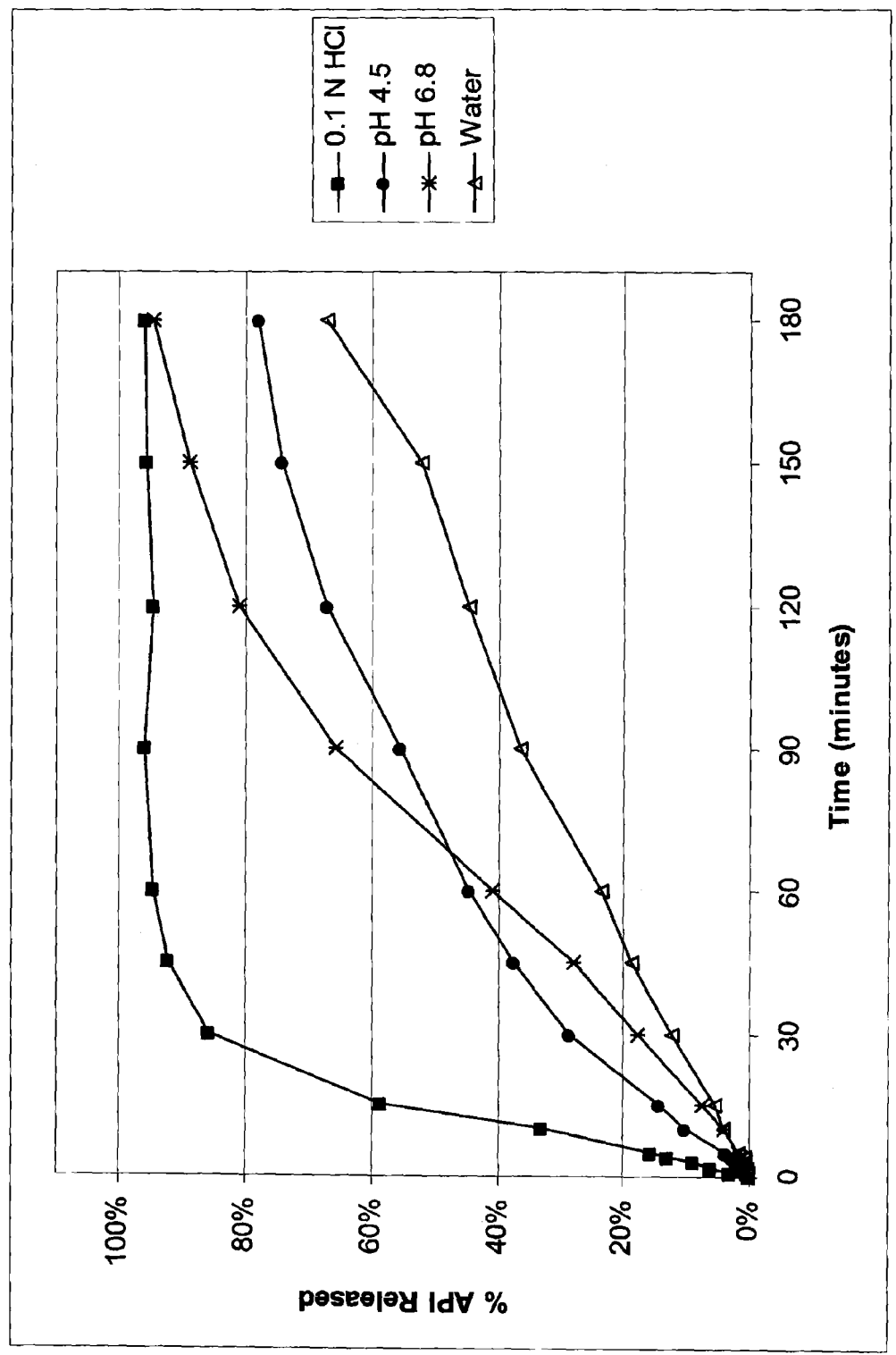
FIG. 45 is the graphical representation of the dissolution profiles for a formulation (2:1 molar) of oxycodone free base and pamoic acid as a function of pH.
Figure 60:
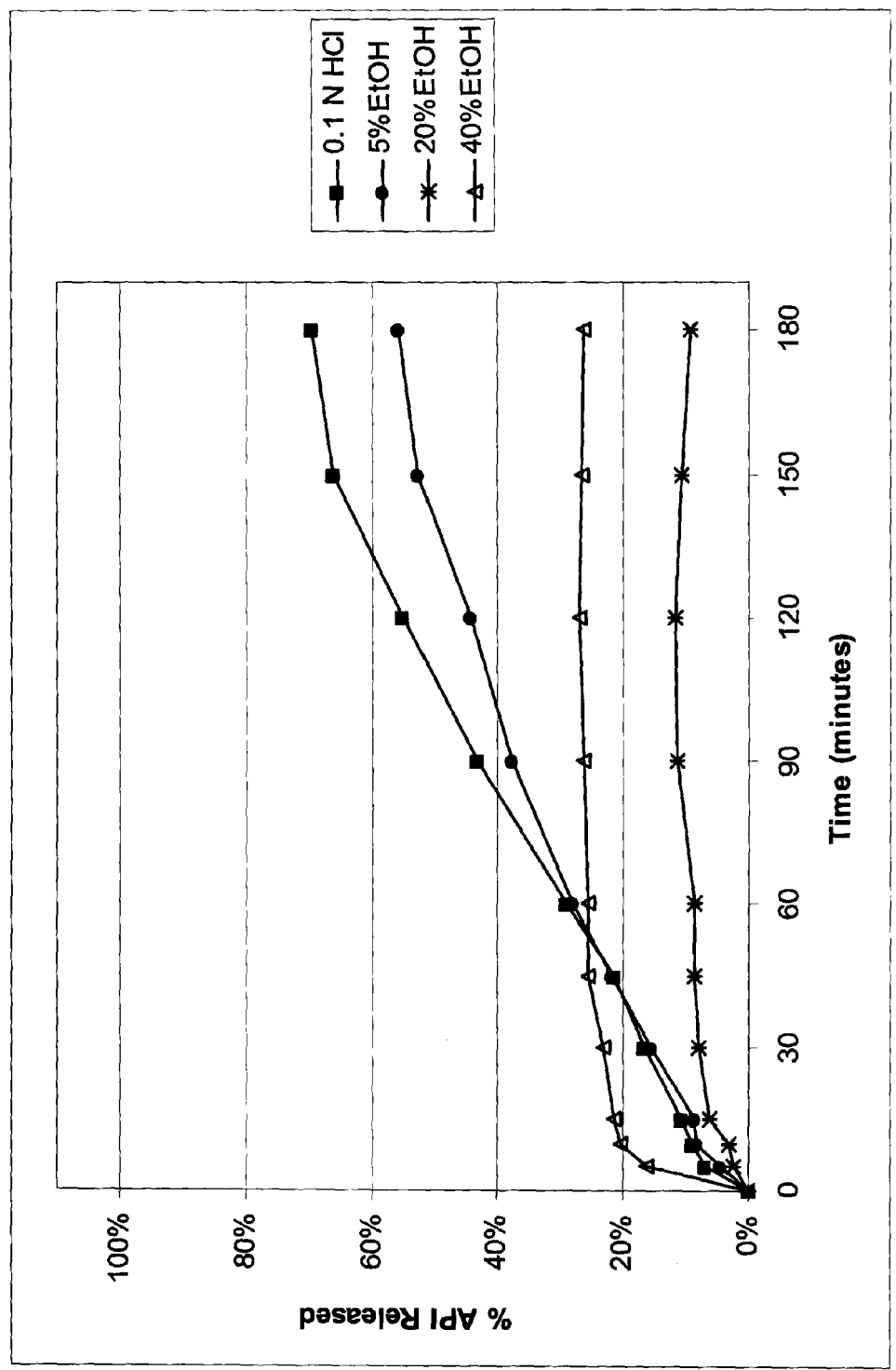
FIG. 60 is the graphical representation of the dissolution profiles for a formulation (1:1 molar) of oxycodone hydrochloride and disodium pamoate in acidic media as a function of ethanol concentration.
Figure 69:
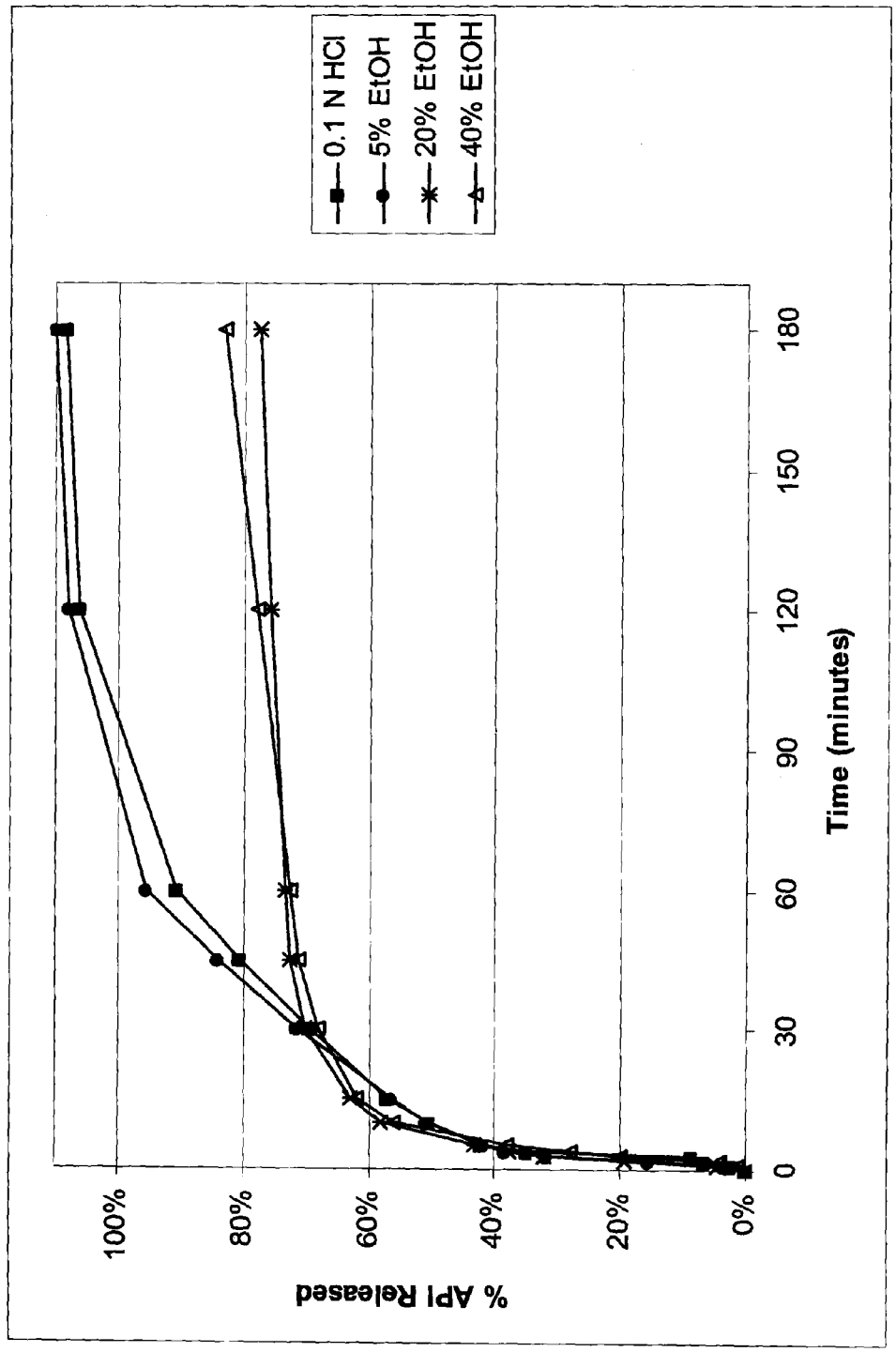
FIG. 69 is the graphical representation of the dissolution profiles for a formulation (2:1 molar) of oxycodone hydrochloride and disodium pamoate in acidic media as a function of ethanol concentration.
Figure 71:
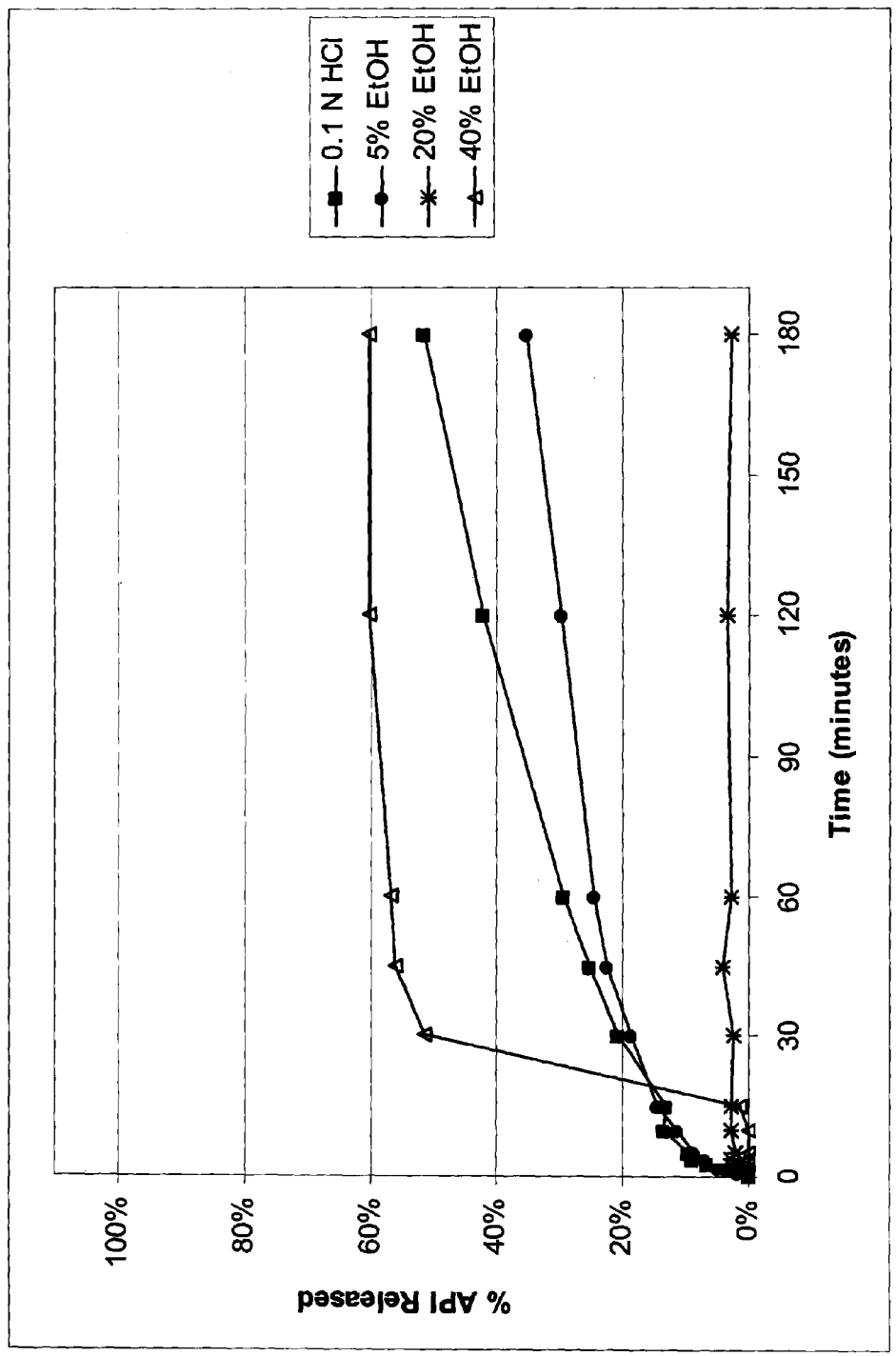
FIG. 71 is the graphical representation of the dissolution profiles for a formulation (1:2 molar) of oxycodone hydrochloride and disodium pamoate in acidic media as a function of ethanol concentration.
Figure 72:
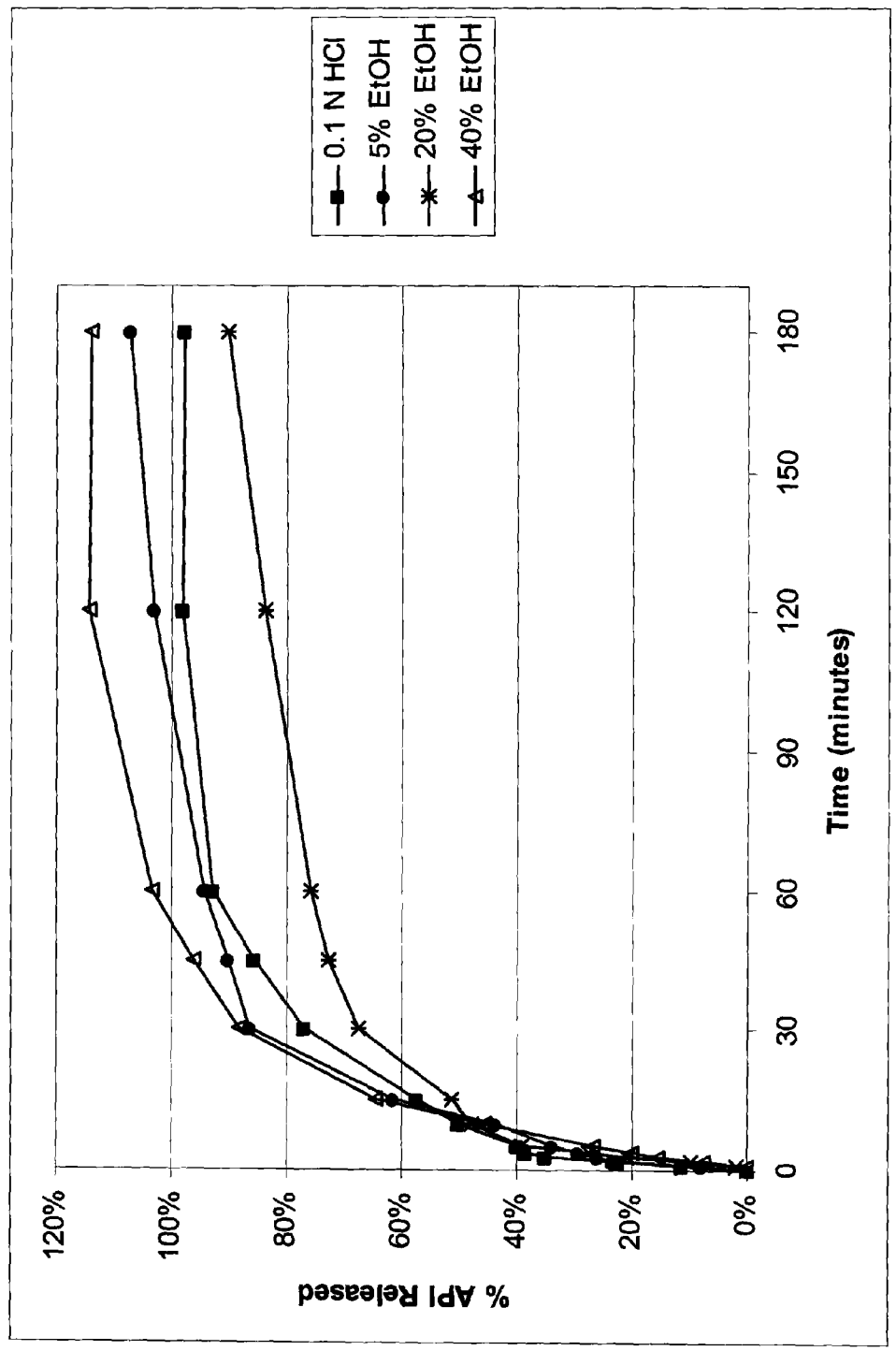
FIG. 72 is the graphical representation of the dissolution profiles for a formulation (1:2 molar) of oxycodone hydrochloride and pamoic acid in acidic media as a function of ethanol concentration.

The following figures represent the control experiments related to oxycodone hydrochloride for pH and dose dumping dissolution profiles: FIG. 40 (oxycodone hydrochloride 2:1 dispam), FIG. 41 (oxycodone hydrochloride 1:2 dispam), FIG. 42 (oxycodone hydrochloride 2:1 pamoic acid), FIG. 44 (oxycodone hydrochloride 1:1:1 dispam:pamoic acid), FIG. 42 (oxycodone hydrochloride 2:1 pamoic acid), FIG. 45 (oxycodone base 2:1 pamoic acid), FIG. 70 (oxycodone hydrochloride 1:1 dispam), FIG. 60 (oxycodone hydrochloride 1:1 dispam), FIG. 69 (oxycodone 2:1 dispam), FIG. 71 (oxycodone hydrochloride 1:2 dispam) and FIG. 72 (oxycodone hydrochloride 1:2 pamoic acid).

Figure 70:
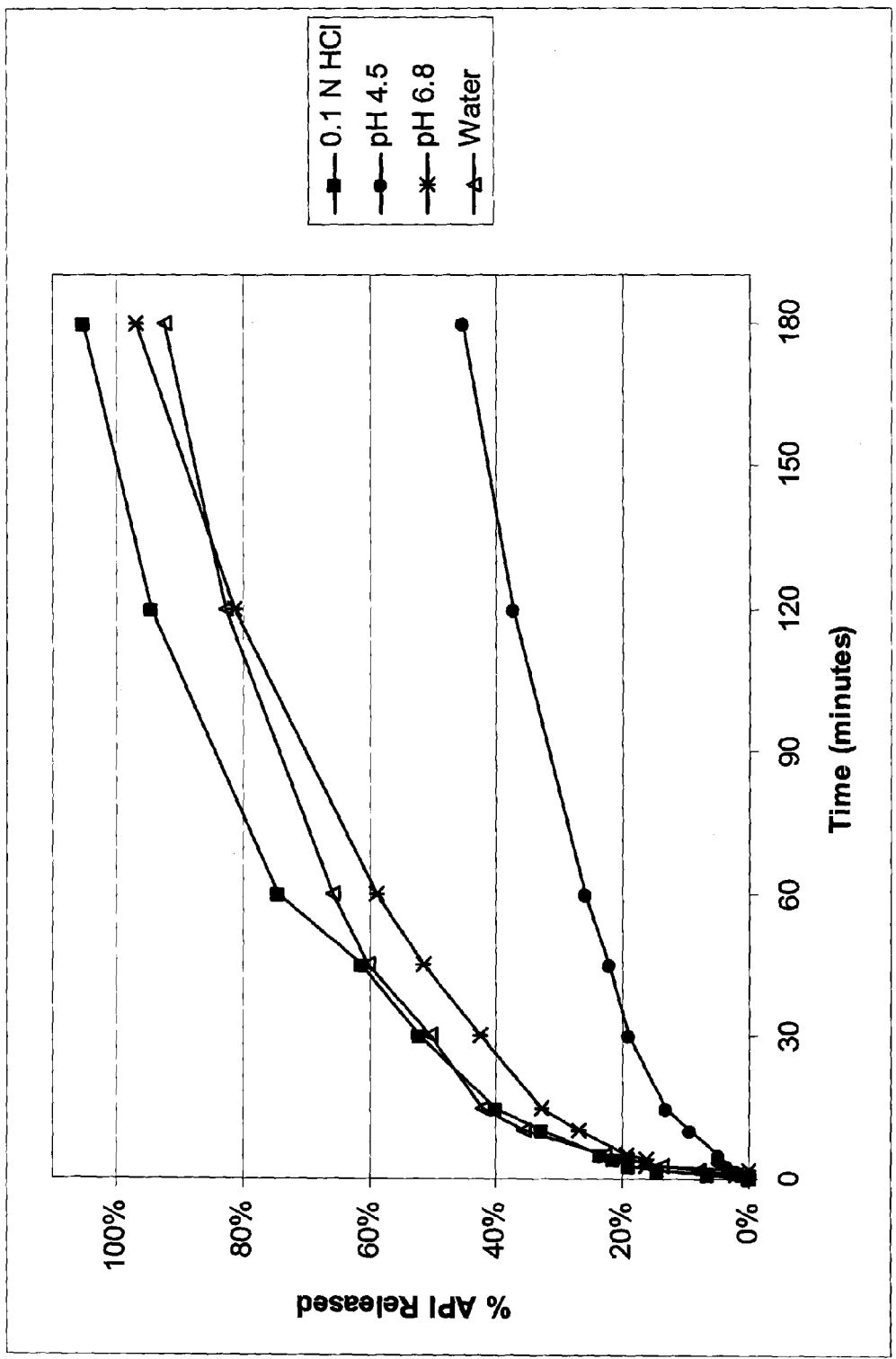
FIG. 70 is the graphical representation of the dissolution profiles of a formulation (1:1 molar) of oxycodone hydrochloride and disodium pamoate as a function of pH.

Several valuable conclusions can be drawn from the oxycodone hydrochloride formulation series when compared with the API hydrochloride alone. The comparison between the pH dissolution profile results contained in FIG. 37 (oxycodone hydrochloride) compared the comparable formulation experiment summarized in FIG. 70 (oxycodone hydrochloride 1:1 dispam) is most instructive. FIG. 37 illustrates the immediate release nature of the hydrochloride salt; FIG. 70 demonstrates the ability to provide an extended release profile independent of pH except for the pH 4.5 condition as an outlier. The pH 4.5 condition is representative of a desirable design feature of the invention such that the combination of oxycodone hydrochloride and dispam provides a material exhibiting limited solubility in the pH range associated with the physiological pH of the mucosal membranes. Consequently, formulation of the active ingredient with dispam incorporates one line of defense toward the abuse of the drug. It is well noted that the physical admixture of the solid active ingredient hydrochloride with solid disodium pamoate did not produce any sign of salt formation as evidenced by analytical methods (FTIR, PXRD, DSC). The dose dumping criteria investigated as well as the results are summarized in FIG. 60 (oxycodone hydrochloride 1:1 dispam) and can be compared with the control experiment, FIG. 59 (oxycodone hydrochloride). For oxycodone hydrochloride alone, equilibrium concentrations are reached reasonably quickly and are an indication that the active would be susceptible to extraction by alcohol. Conversely, the formulation of the active opiate with dispam shuts down its propensity to dose dump with only small amounts of active available after more than an hour. Clearly, an individual intent on abusing a drug formulated with dispam would not be willing to wait up to ninety (90) minutes for only about half the drug to become available while employing alcohol to accelerate the release of the drug. Lastly, for oxycodone hydrochloride, FIG. 69 (oxycodone hydrochloride 2:1 dispam) and FIG. 72 (oxycodone hydrochloride 1:2 pamoic acid) demonstrate other aspects of the invention. The combination of 2:1 active to dispam indicates that level of dispam is insufficient to totally quell dose dumping, while the use of pamoic acid provides a tight spread in the dose dumping response; it too would not be the best choice for inhibiting dose dumping. Consequently a preferred embodiment of the invention constitutes the admixture of oxycodone hydrochloride in a 1:1 molar ratio with dispam.

Figure 46:
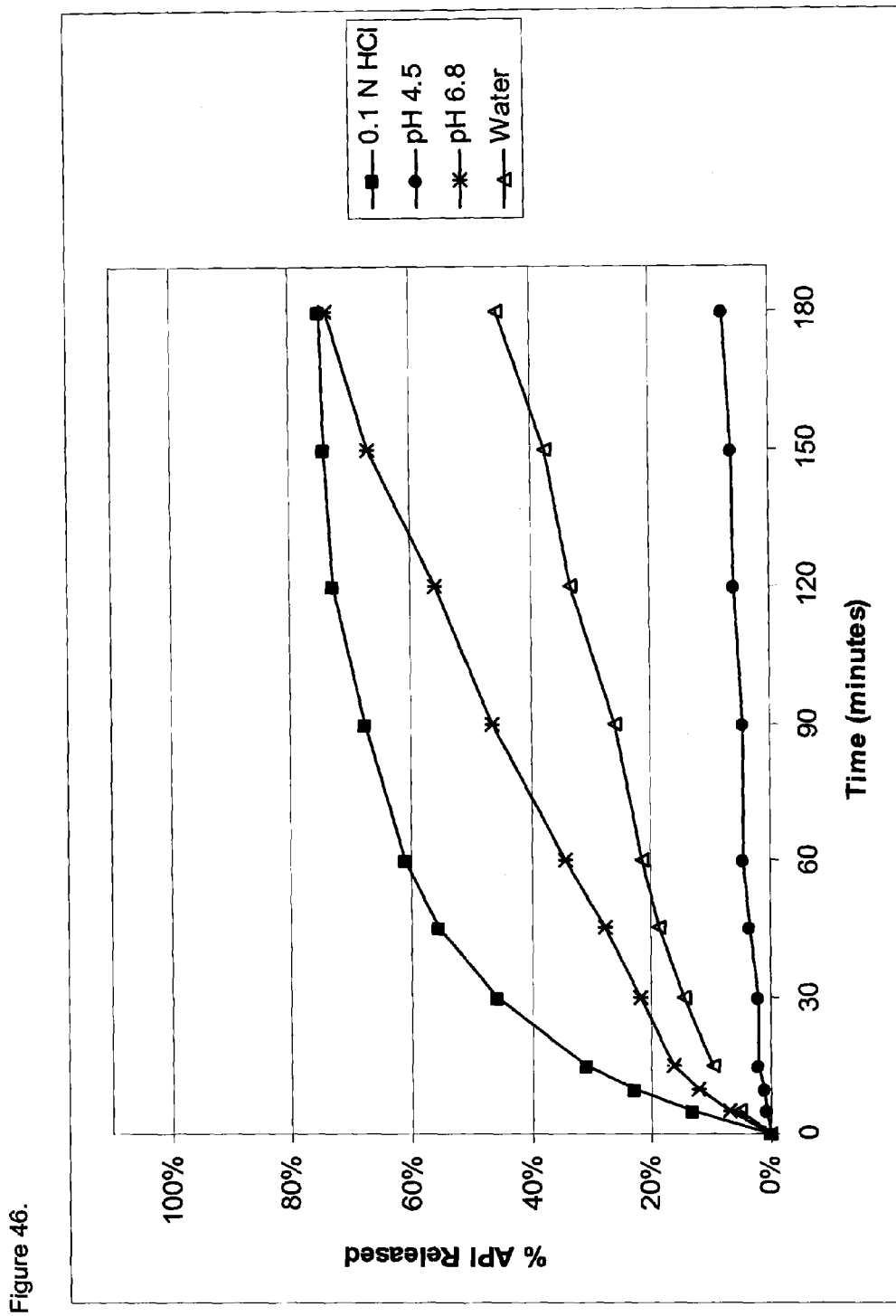
FIG. 46 is the graphical representation of the dissolution profiles for a formulation (1:1 molar) of amorphous oxycodone pamoate and disodium pamoate as a function of pH.
Figure 47:
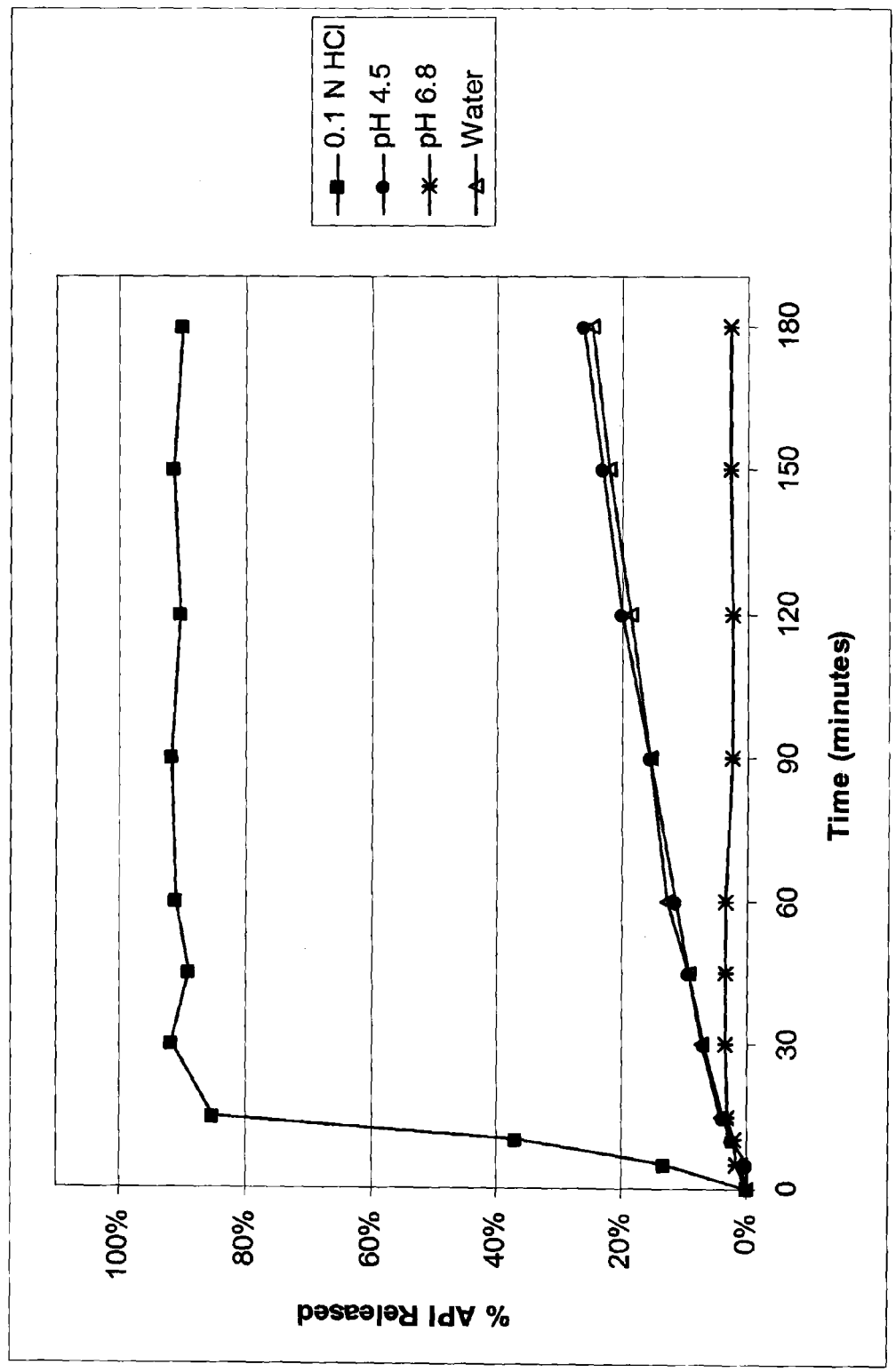
FIG. 47 is the graphical representation of the dissolution profiles for a formulation (1:1 molar) of amorphous oxycodone pamoate and pamoic acid as a function of pH.
Figure 64:
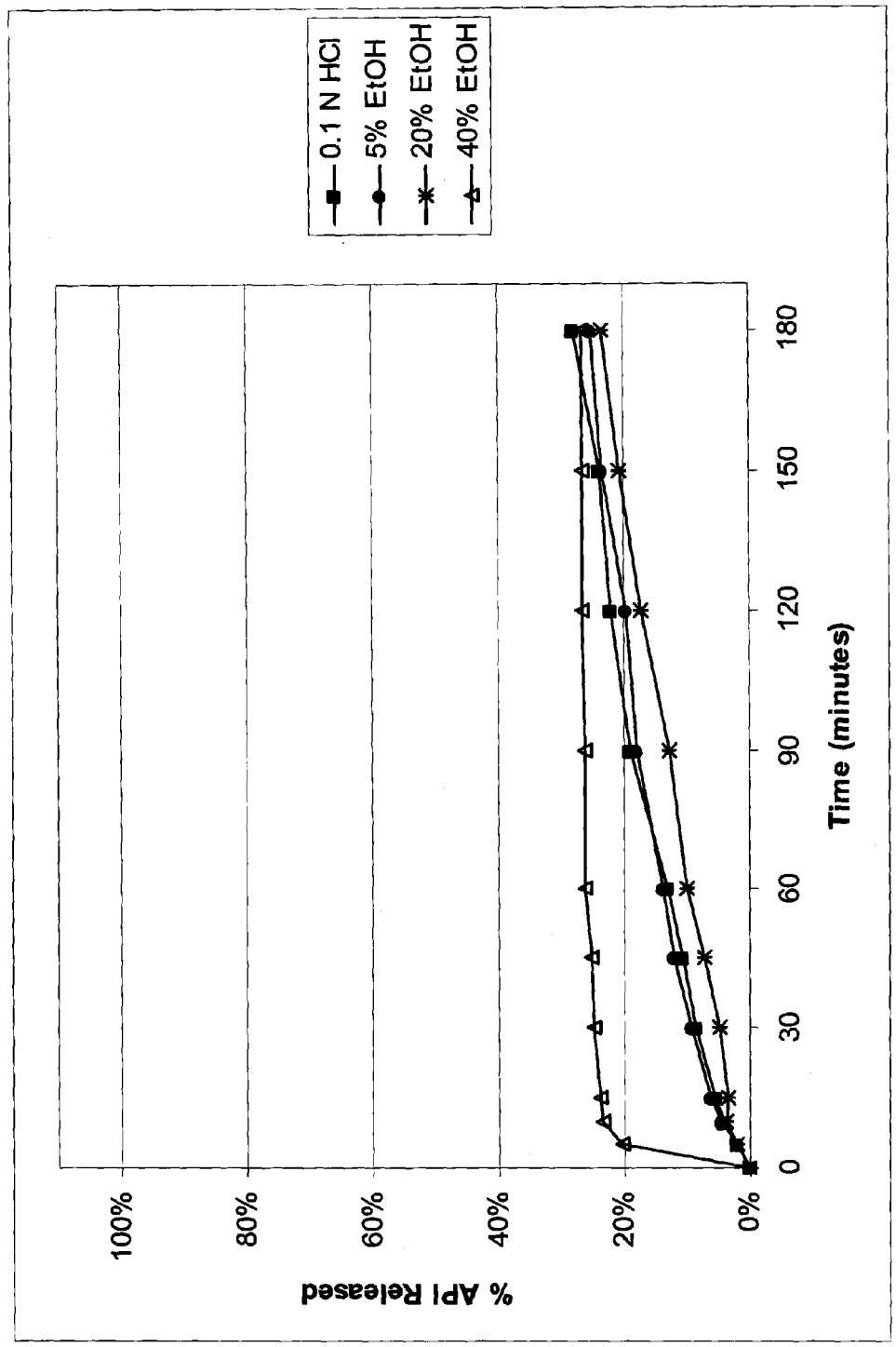
FIG. 64 is the graphical representation of the dissolution profiles for a formulation (1:1 molar) of amorphous oxycodone pamoate and disodium pamoate in acidic media as a function of ethanol concentration.
Figure 73:
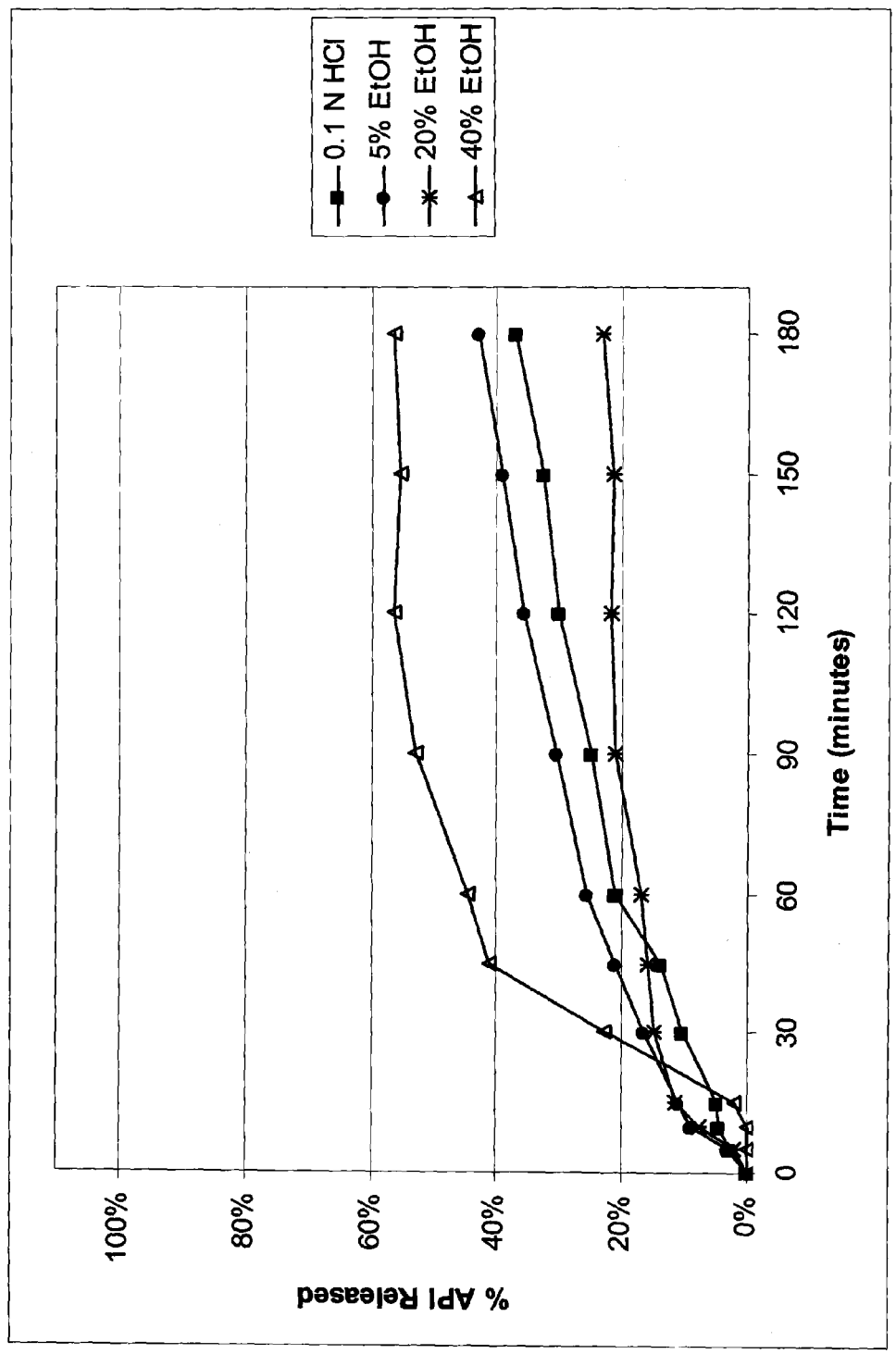
FIG. 73 is the graphical representation of the dissolution profiles for a formulation (1:2 molar) of amorphous oxycodone pamoate and disodium pamoate in acidic media as a function of ethanol concentration.
Figure 74:
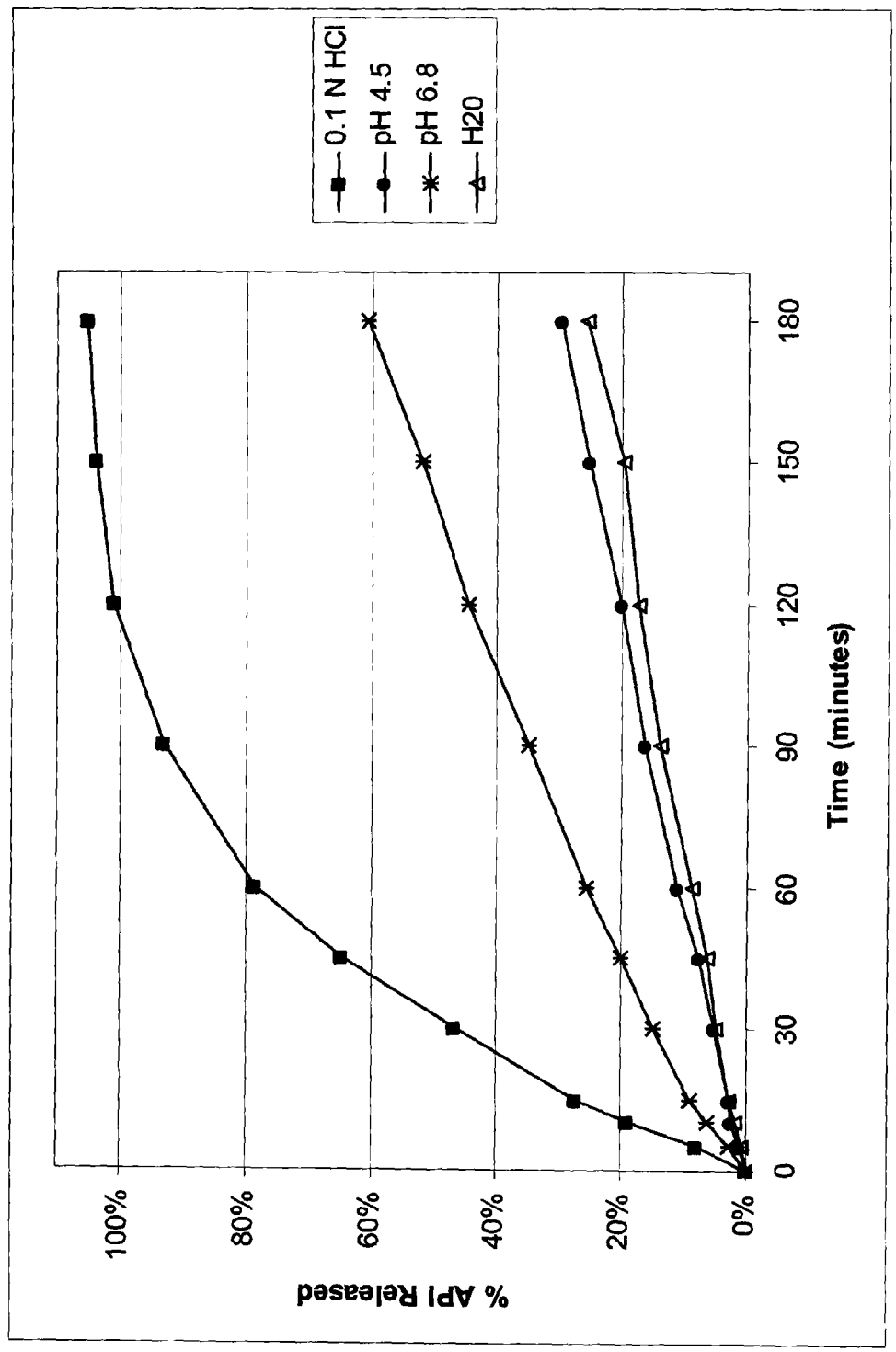
FIG. 74 is the graphical representation of the dissolution profiles for a formulation (1:2) molar of amorphous oxycodone pamoate and 3-hydroxy-2-naphthoic acid (BON Acid) as a function of pH.

Continuing with the oxycodone series with respect to formulation, oxycodone pamoate provides a further refinement of the invention. For the amorphous series of oxycodone pamoate, the following paired figures (pH and dose dumping dissolution profiles respectively) are useful to consider: FIG. 46 (oxycodone pamoate 1:1 dispam) and FIG. 64 (oxycodone pamoate 1:1 dispam, and FIG. 38 (oxycodone pamoate) and FIG. 63 (oxycodone pamoate). The analysis of FIG. 73 (oxycodone pamoate 1:2 dispam) and FIG. 74 (oxycodone pamoate 1:2 BON Acid) also contributes to the following conclusions:

1) oxycodone pamoate (amorphous or polymorphic) exhibits an extended release pH dissolution profile and significantly reduces dose dumping;
2) formulation of oxycodone pamoate with dispam further imparts an anti-abuse feature and restricts dose dumping;
3) additional dispam (2 molar equivalents) does not provide additional quelling of the dose dumping phenomenon; and
4) the addition of BON Acid demonstrated its ability to decrease dose dumping.

Figure 48:
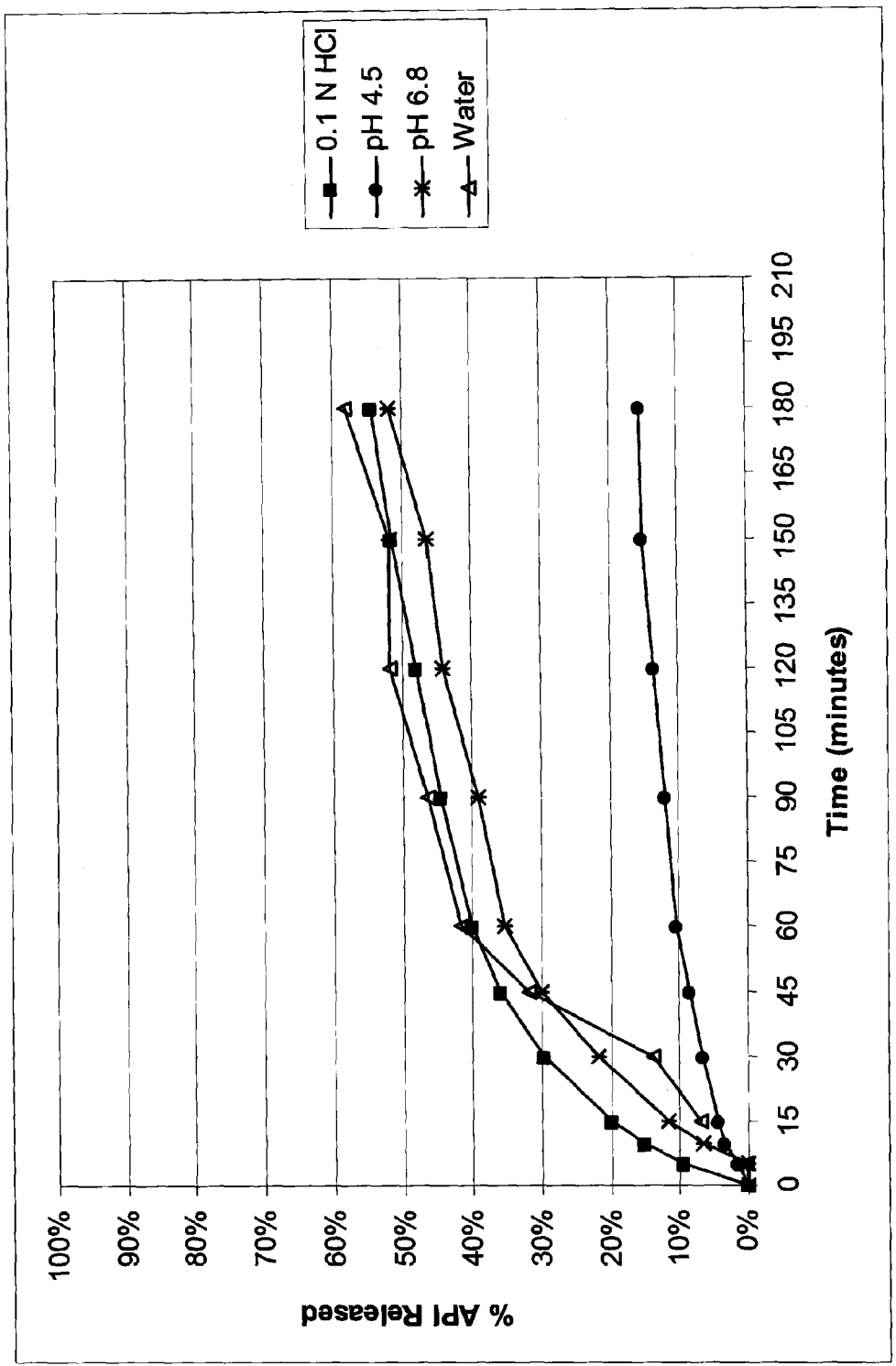
FIG. 48 is the graphical representation of the dissolution profiles for a formulation (1:1 molar) of polymorphic oxycodone pamoate and disodium pamoate as a function of pH.
Figure 66:
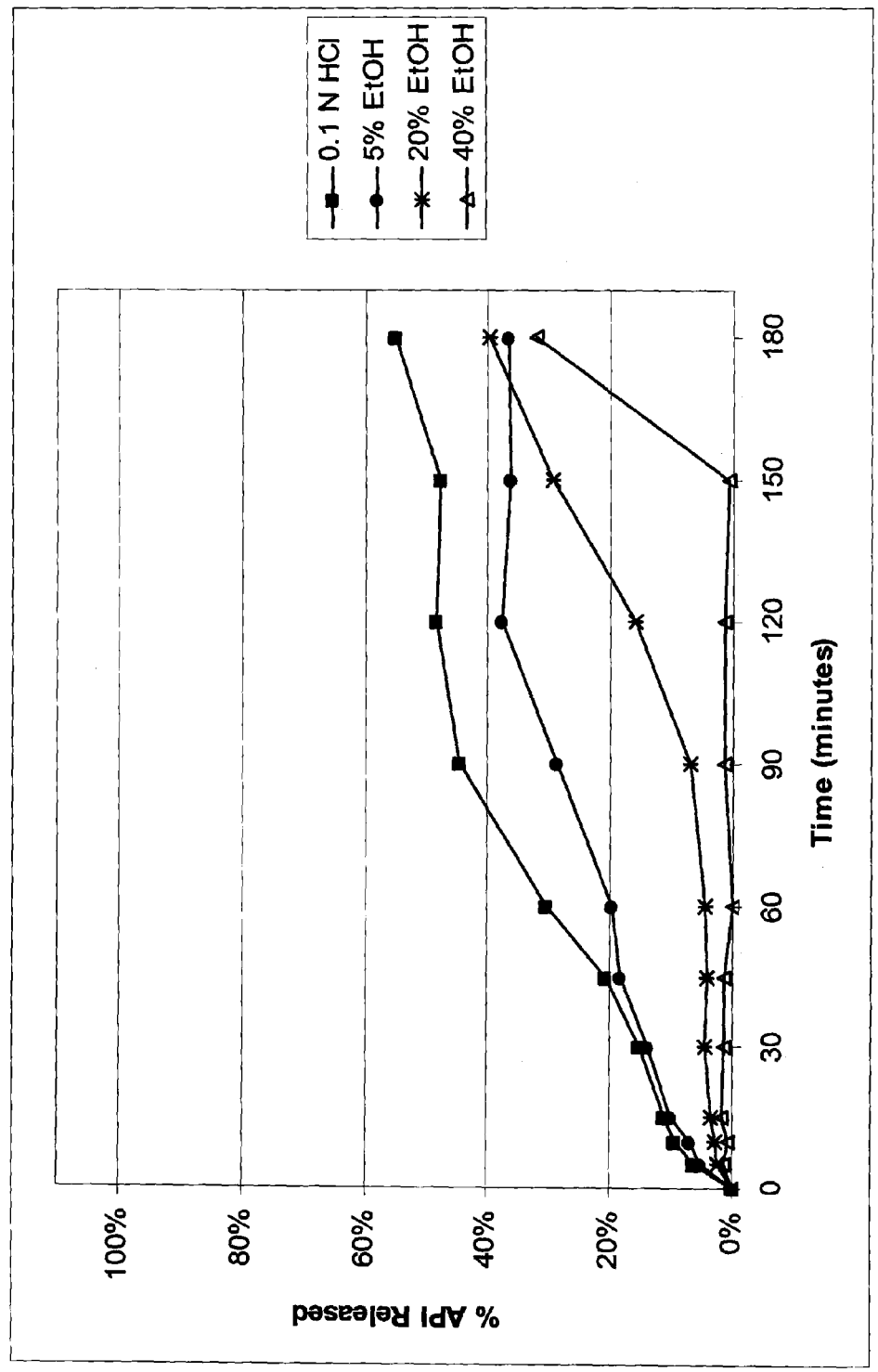
FIG. 66 is the graphical representation of the dissolution profiles for a formulation (1:1 molar) of polymorphic oxycodone pamoate and disodium pamoate in acidic media as a function of ethanol concentration.

The oxycodone pamoate polymorphic series supported these conclusions as well as seen in the paired figures (pH and dose dumping dissolution profiles respectively), FIG. 48 (oxycodone pamoate polymorph 1:1 dispam) and FIG. 66 (oxycodone pamoate polymorph 1:1 dispam). This pair of figures, FIGS. 48 and 66 represent an excellent embodiment of the invention to ultimately yield an extended release product that is not susceptible to dose dumping.

Figure 75:
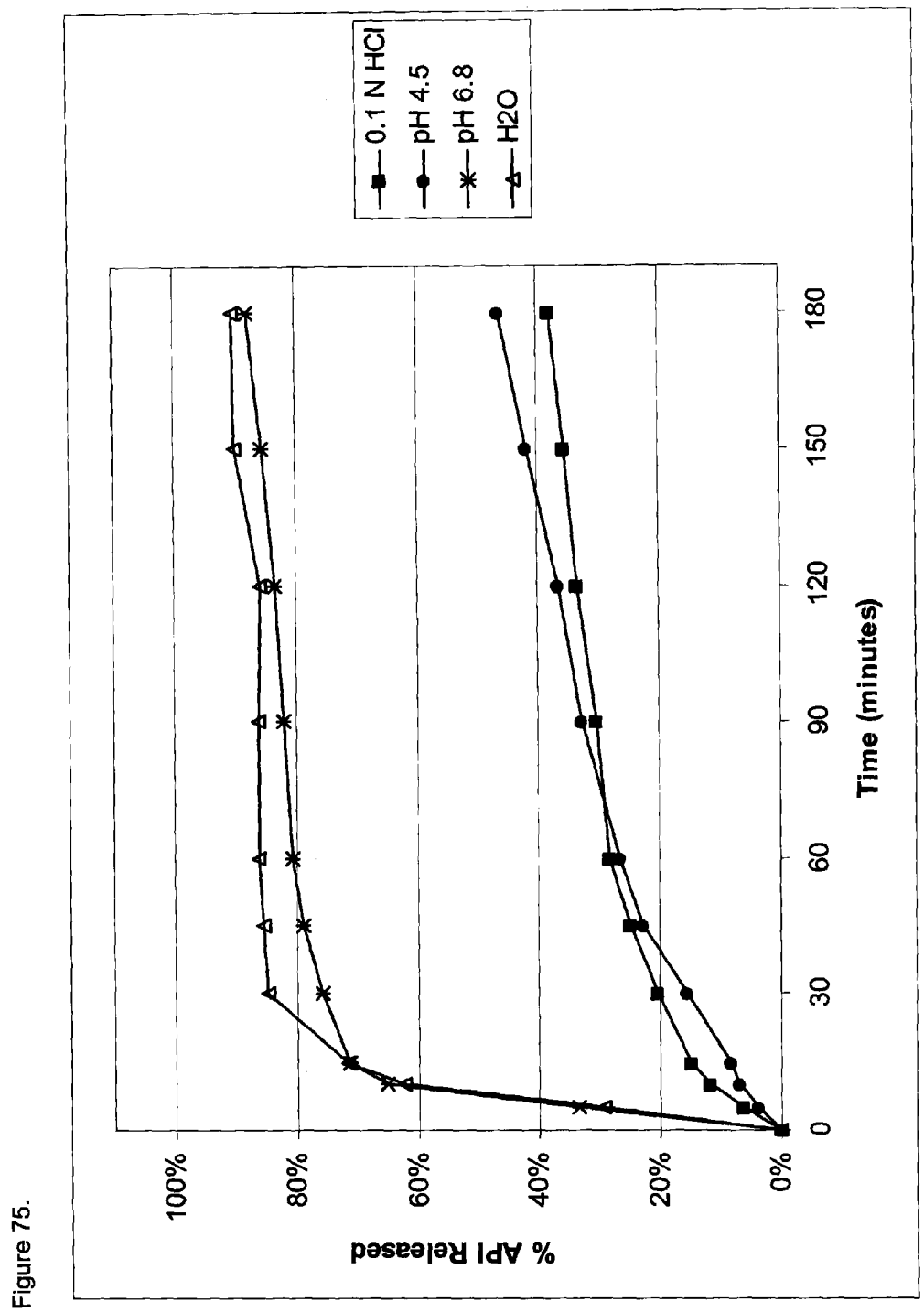
FIG. 75 is the graphical representation of the dissolution profiles for a formulation (1:2 molar) of polymorphic oxycodone pamoate and disodium pamoate as a function of pH.
Figure 76:
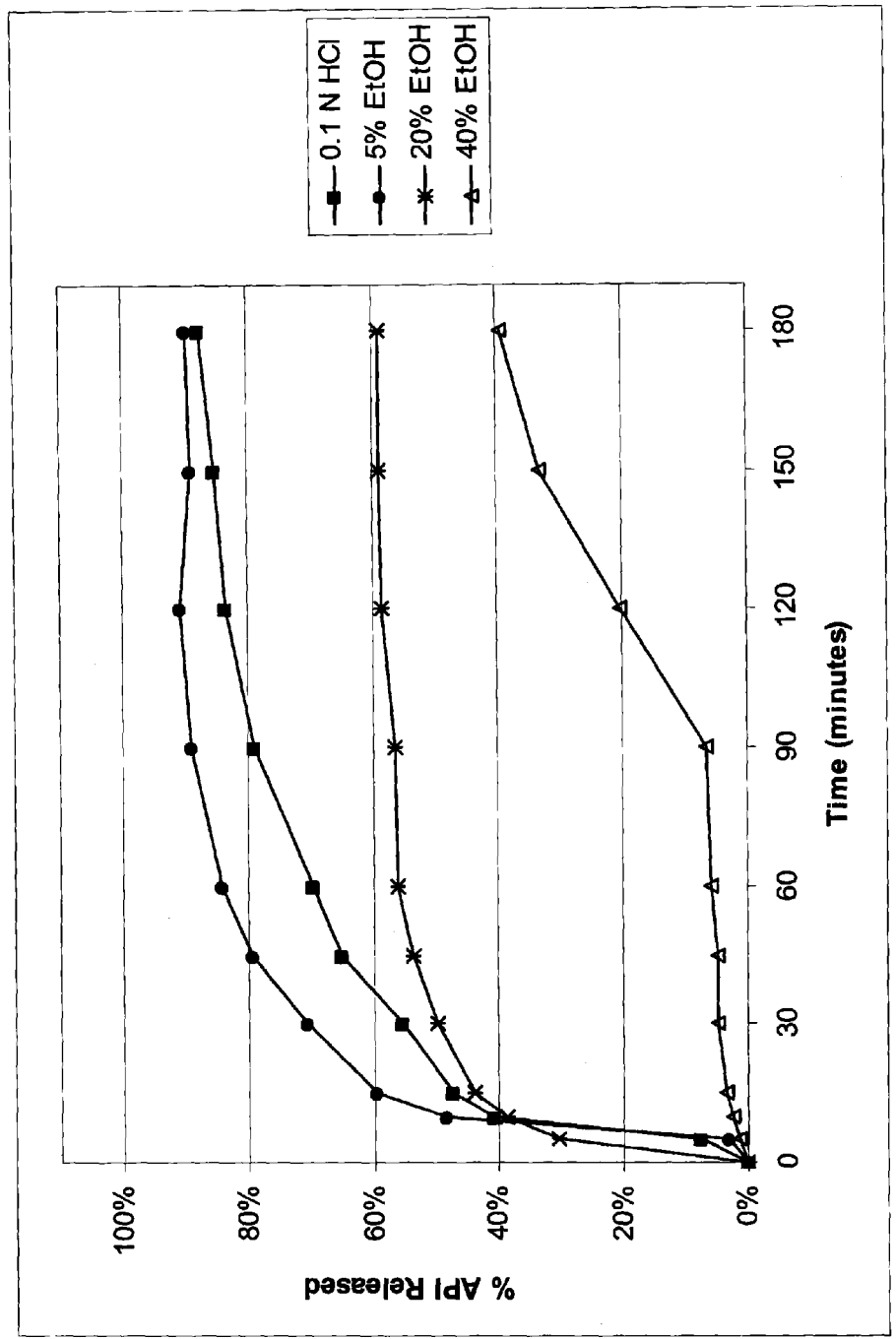
FIG. 76 is the graphical representation of the dissolution profiles for a formulation (1:1 molar) of polymorphic oxycodone pamoate with pamoic acid in acidic media as a function of ethanol concentration.

The results in FIG. 75 (oxycodone pamoate polymorph 1:2 dispam) represents a unique opportunity arising from these specialized organic acid addition salts formulated with additional acid component for targeted release directly to the bowel. The mixture exhibits a slow release of active opiate at both pH 1 and pH 4.5 but a faster release at the higher pH. The presence of dispam also inhibits dose dumping (in the stomach by consumption of alcohol).

Figure 80:
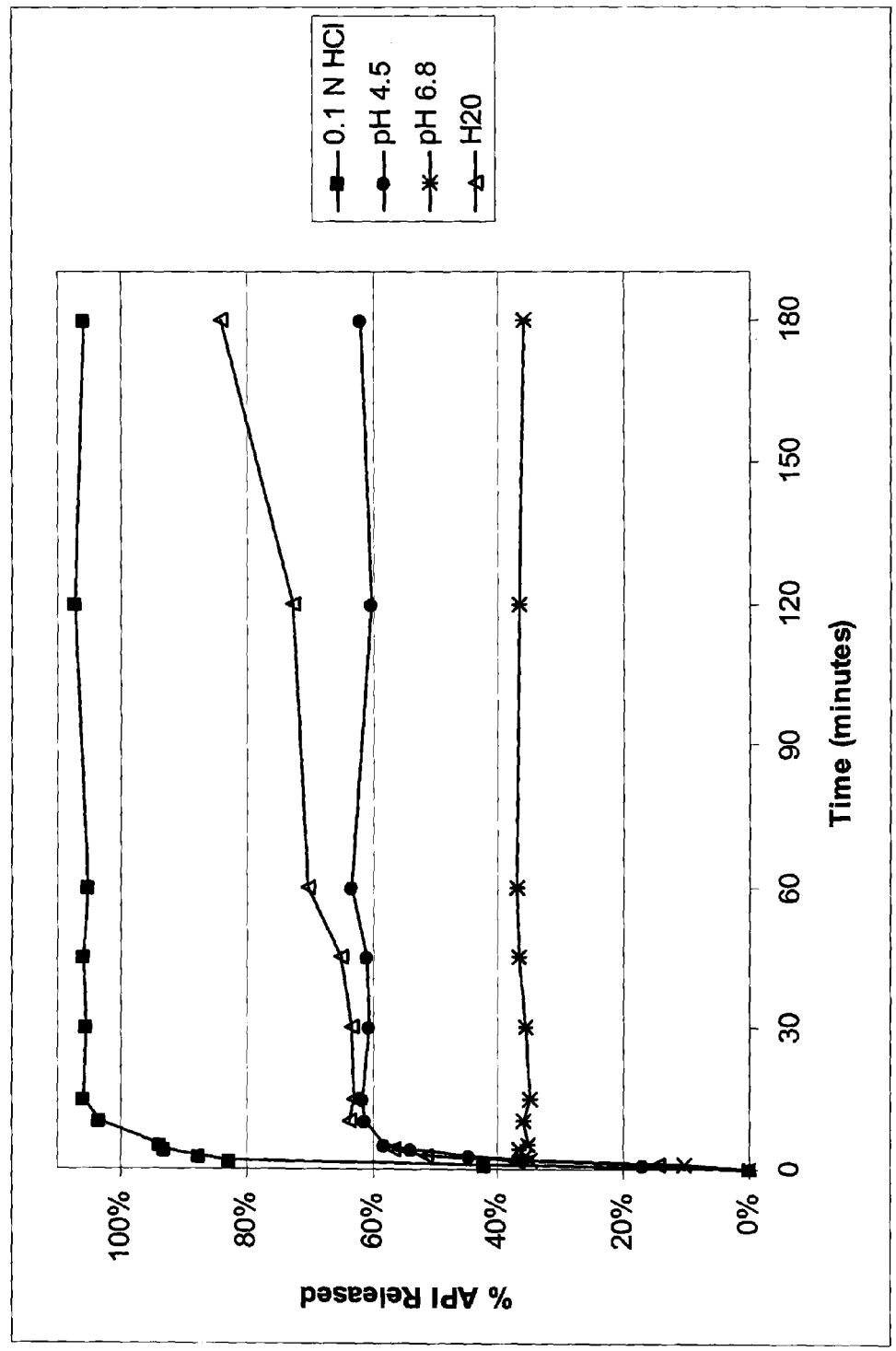
FIG. 80 is the graphical representation of the dissolution profiles of a formulation (1:2) molar of hydrocodone bitartrate and 3-hydroxy-2-naphthoic acid (BON Acid) as a function of pH.
Figure 81:
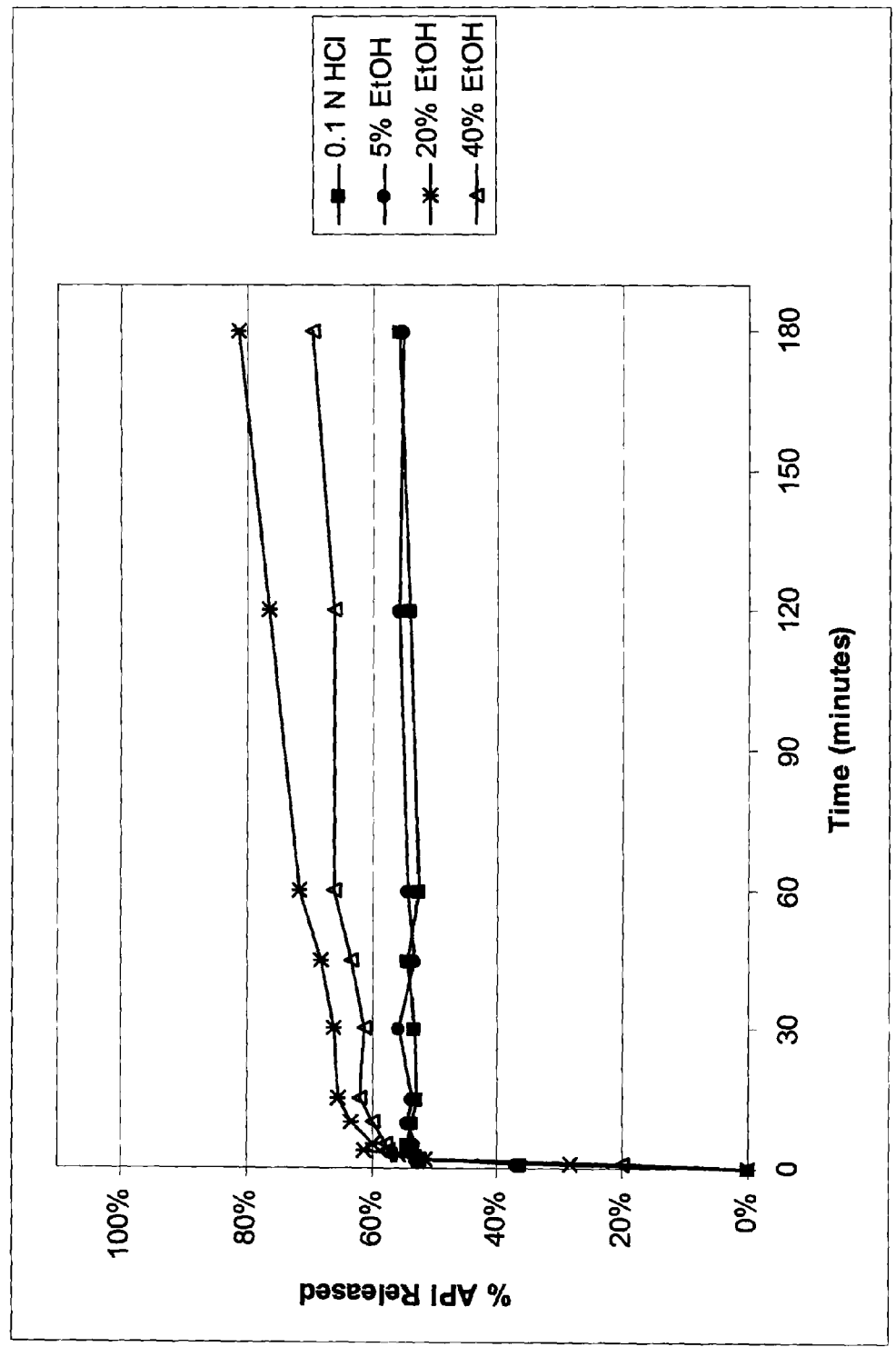
FIG. 81 is the graphical representation of the dissolution profiles of a formulation (1:2 molar) of hydrocodone bitartrate and 3-hydroxy-2-naphthoic acid (BON Acid) in acidic media as a function of ethanol concentration.
Figure 83:
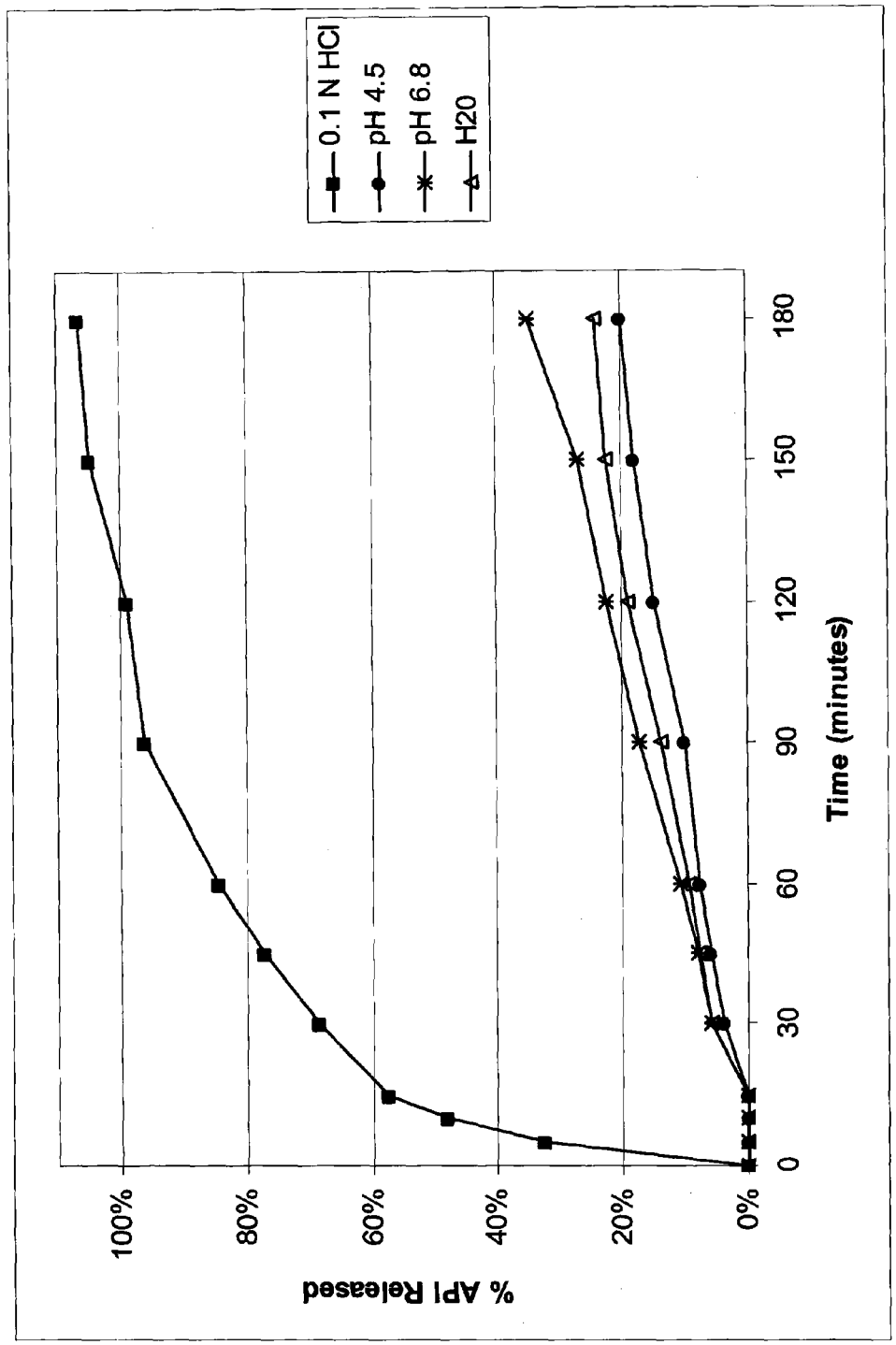
FIG. 83 is a graphical representation of the dissolution profiles of a formulation (1:2 molar) of hydrocodone xinafoate and 3-hydroxy-2-naphthoic acid (BON acid) as a function of pH.
Figure 84:
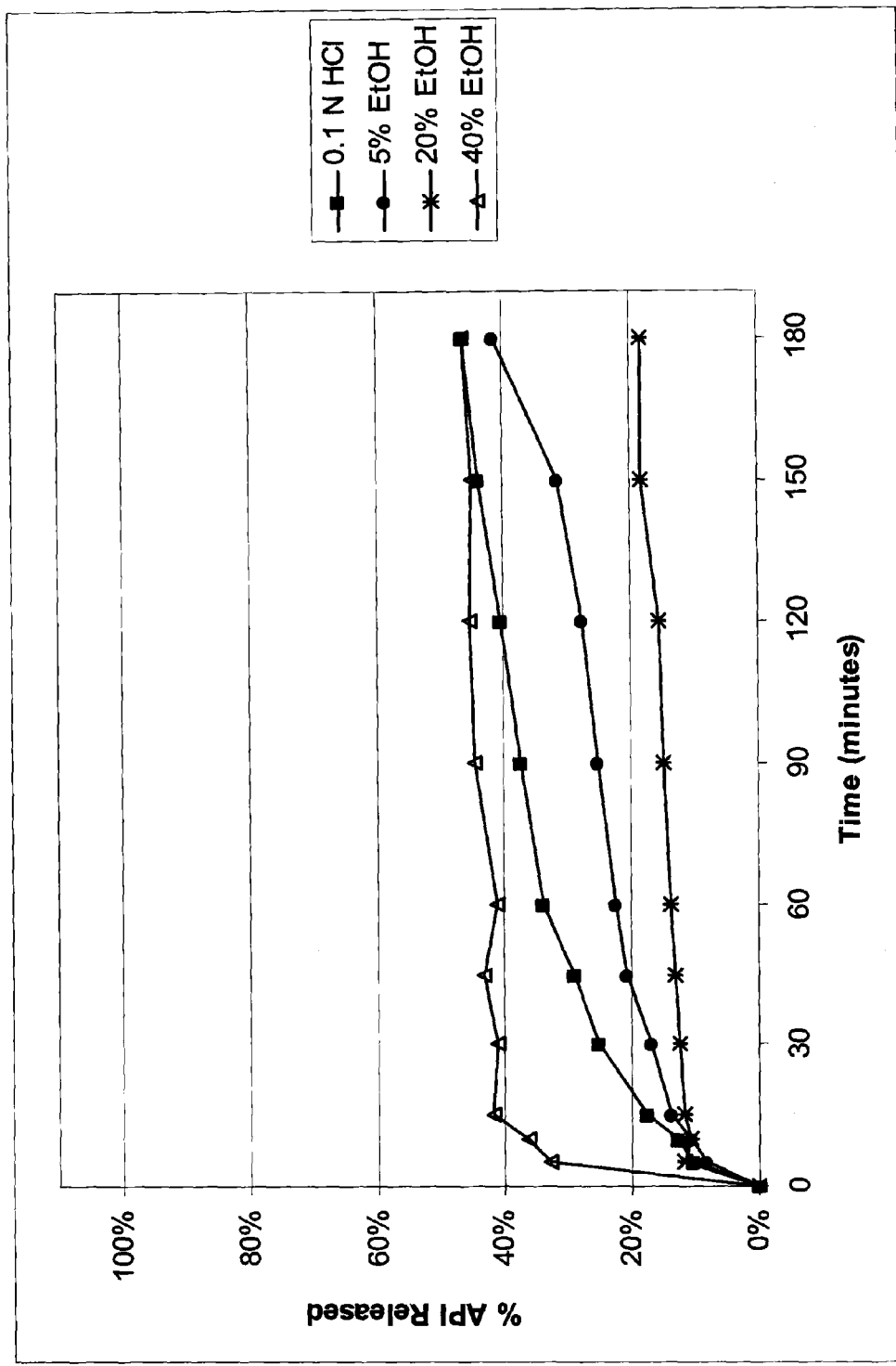
FIG. 84 is a graphical representation of the dissolution profiles of a formulation (1:2 molar) of hydrocodone xinafoate and 3-hydroxy-2-naphthoic acid (BON acid) in acidic media as a function of ethanol concentration.
Figure 85:
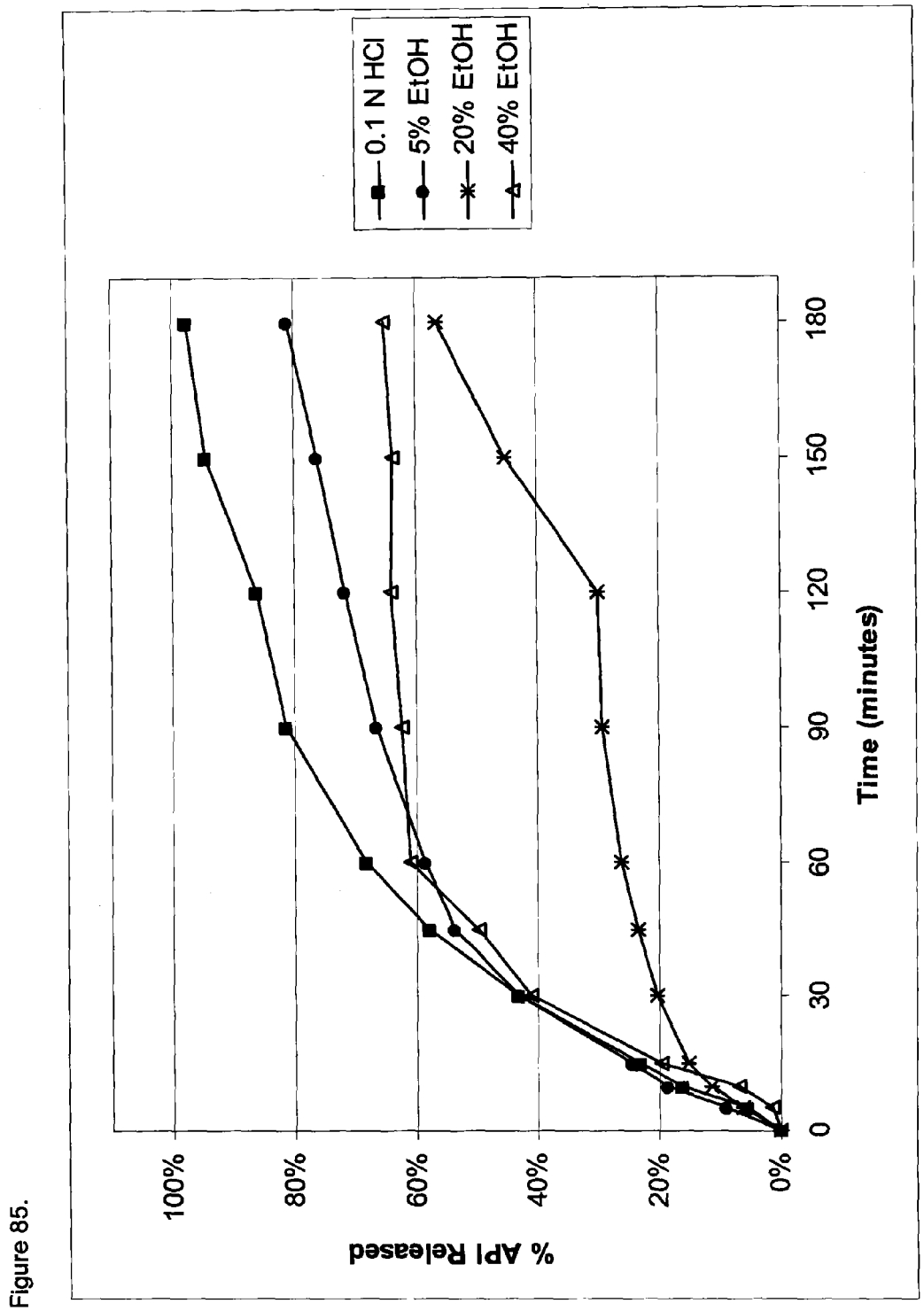
FIG. 85 is a graphical representation of the dissolution profiles of a formulation (2:1 molar) of amorphous oxycodone pamoate and disodium pamoate in acidic media as a function of ethanol concentration.
Figure 86:
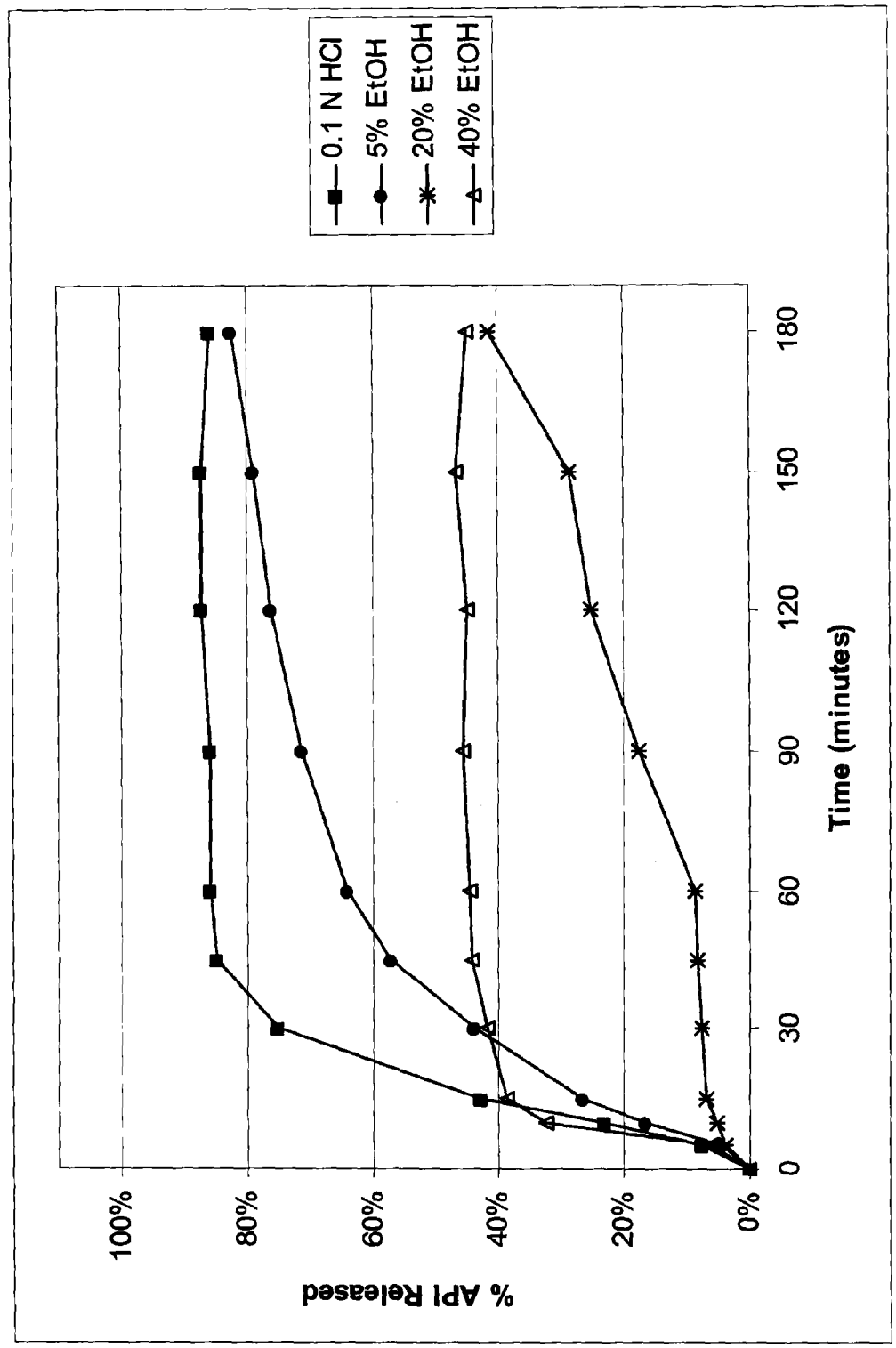
FIG. 86 is a graphical representation of the dissolution profiles of a formulation (2:1) molar of polymorphic oxycodone pamoate and disodium pamoate in acidic media as a function of ethanol concentration.

In order to ascertain the depth and breadth of the discoveries associated with oxycodone, a similar approach based on a truncated series of experiments was implemented to investigate the response and receptiveness of other opioid salts to formulation techniques. A few exemplars are noteworthy. For the control experiments regarding hydrocodone bitartrate, the following paired figures (pH and dose dumping dissolution profiles respectively) should be considered: FIGS. 80 and 81 (hydrocodone bitartrate 1:2 BON Acid). The addition of BON Acid to the formulation has a significant effect, particularly at attenuating the pH dissolution profile. However, while BON Acid impacts the dose dumping propensity of the bitartrate, it is not completely adequate at eliminating this phenomenon. Conversely, when BON Acid was employed with hydrocodone xinafoate, excellent results were obtained. The analysis of the paired figures (pH and dose dumping dissolution profiles respectively) for FIG. 83 and FIG. 84 (hydrocodone xinafoate 1:2 BON Acid) indicate, first, a pH independent response is obtained for the pH dissolution profile with the exception of the pH 1 condition which can be addressed by an enteric coating. In other cases it is preferable to not have an enteric coating. Further, the formulation does not does dump since equilibrium solubility is reached quickly at the 40% ethanol condition while only low levels of active ingredient is available at the more reasonable ethanol concentrations.

From these formulation exercises clear conclusions can be reached:

1) the addition of dispam to either the mineral acid or bitartrate opioid salt assists in converting the traditional API release profile to an extended release profile exhibiting some tendency toward a pH independent release except at pH 1;
2) the addition of dispam to opioid organic acid addition salts (e.g. morphine pamoate, hydromorphone xinafoate and the like), creates a synergistic effect greater than the effect seen when mineral acid opioid salts are employed for both the pH and dose dumping dissolution profiles;
3) "cross" salt experiments, e.g. oxycodone pamoate formulated with BON Acid, provide improved performance properties;
4) the preferred selection order of organic acid component additions for providing anti-abuse properties, including but not limited to extended release dissolution profiles and the prevention of dose dumping is: dispam>BON Acid>pamoic acid;
5) the preferred selection order for the addition of excess dispam molar equivalents for imparting anti-abuse properties, including but not limited extended release dissolution profiles and the prevention of dose dumping (API:dispam) is: 1:1>1:2>2:1;

The performance features enabled by the present invention are not limited to the anti-abuse properties imparted by the organic acid addition salts, but also include advances to the manufacture of finished pharmaceutical product dosage presentations. The salts disclosed herein, and the ability to influence their dissolution behavior by formulation via the addition of the organic acid component extends as well to existing drug product formulations exhibiting extended release, controlled release and anti-abuse properties. Indeed, the present invention is compatible with existing drug product formulations which provide extended/controlled release, pH independent release of the active ingredient, and/or anti-dose dumping features and further contributes to the success of these earlier technologies by: 1) reducing the potential variability observed in unit dose manufacturing, and 2) improving the robustness of the manufacturing process.

The hygroscopic nature of the opioids is well known, and as their mineral acid or small organic acid salts, these materials exhibit high solubility in water or organic solvents, especially ethanol. This very solubility hinders formulated dose manufacturing since processes employed to impart anti-abuse features such as wet granulation or particle coating may lead to the opioid salt dissolving instead of agglomerating or being receptive to coating. Consequently, the purpose of the formulation to impart anti-abuse properties (inhibit extraction of the active from dosage form), requires difficult manufacturing procedures using materials essentially incompatible with the manufacturing process required. Of the many consequences to this mismatch of purpose and manufacturing capability is the likelihood of dose uniformity failure, i.e. too much tablet-to-tablet, or capsule-to-capsule dose variation.

In contrast, the opioid salts of the present invention and their formulations disclosed herein improve the capability of commercially existing opioid formulations and provide more manufacturing options for formulation techniques. By way of example, the higher molecular weights of the salts disclosed herein allow for more accurate weighing, dispensing and formulation of the opioid active as compared with the mineral acid salts. Oxycodone hydrochloride has a molecular weight of about 352 grams/mole whereas the pamoate salt has a molecular weight more than two and one-half times larger. To obtain dose uniformity on highly active compounds, such as the opioids, it is much easier to weigh the larger mass required for equal dosing when using the pamoate salt than it is for the hydrochloride salt, or similar low molecular weight salt. As the physiological activity of the opioid increases, this benefit attributable to the molecular weight difference increases dramatically. To a patient who obtains an incorrect dosage administration, the medical consequences can be severe; too low and a therapeutic dosage is not obtained; too high and death may occur. In addition to the molecular weight differences, pre-formulation of the opioid organic acid addition salt with additional organic acid component (same or different to that forming the salt, i.e. cross salts), allows for greater dosage control in the fully formulated drug product. Indeed, this pre-formulated material is suitable for use as the formulated product—in a tablet by direct compression or in a capsule.

The manufacture of a formulated drug product optionally includes, but is not limited to the following steps:
a) wet or dry granulation;
b) direct compression tablet pressing
c) particle coating followed by drying;
d) sieving and/or sizing
e) milling;
f) blending with additional excipients;
g) optionally, additional wet or dry granulation;
h) optionally, sizing and milling
i) blending with additional excipients;
j) tablet pressing or capsule filling;
k) pan or tumbler coating and drying; and
l) packaging.

The traditional opioid salts do not lend themselves well to processing steps requiring wet granulation or particle coating. For instance, opioid salt particle coating employing a fluid bed coater with a liquid spray containing a performance based or functional polymer dissolved in a solvent (typically water or alcohol) with the intention of coating the opioid particle is very difficult. As described, the intention of the polymer coating on the opioid mineral acid salt, or the like, is to prepare a matrix which imparts an anti-abuse property to the otherwise readily available salt. Under the processing conditions described, the traditional opioid salt is prone to dissolve and yield non-uniform agglomerates at best. It is impractical therefore to attempt particle coating as a general procedure to apply anti-abuse coatings to the opioid salt. However, the salts disclosed in the present invention are quite amenable to these coating processes, as well as to wet or dry granulation techniques. Additionally, drug product produced using the organic acid addition salts and cross-salt formulations described herein provide an immediate track and trace capability to prevent diversion, [King, et al.].

An important benefit and comparison enabled herein is the in vitro/in vivo correlation of the existing opioid-based drug products (e.g. Oxycontin® marketed by Purdue Pharmaceutical) with the invention disclosed herein. For instance, U.S. Pat. No. 5,508,042 [Oshlack et al.] discloses a controlled release oxycodone composition and claims ranges of blood plasma concentration as a function of time. The extended release property was achieved singularly through formulation techniques to overcome the widely known release property of oxycodone hydrochloride (as provided herein for reference; see FIG. 37), and indeed the experimental enablement section of the '042 patent uniquely uses oxycodone hydrochloride as the source of active ingredient. Commercially, the extended release feature has been insufficient to defeat attempts at abuse and the formulation is not resistant to dose dumping. Similarly, and not surprisingly, Purdue pulled Palladone®, an extended release capsule product, from the market in 2005 because the active ingredient, hydromorphone hydrochloride, exhibited dose dumping. Clearly, there has remained an on-going need in society and in the marketplace to provide the medical benefits achievable through the use of opioid products. Indeed, their use is considered a medical necessity for relieving pain. However, intentional or unintentional abuse of these products via dose dumping can be eliminated by implementation, in whole or part, of the invention herein. Consequently, the invention provides a means to achieve therapeutic levels of medically prescribed opioid while preventing abuse, including dose dumping. In other words, the invention provides a means for reducing the range in daily dosages required to control pain in human patients, comprising administering an oral controlled release dosage formulation comprising from about 10 to 40 mg oxycodone or a salt thereof which provides a mean maximum plasma concentration of oxycodone from about 6 to about 60 ng/mL from a mean of about 2 to about 4.5 hours after administration and a mean minimum plasma concentration from about 3 to about 30 ng/mL from a mean of about 10 to about 14 hours after repeated administration every 12 hours through steady-state conditions, said concentrations and mean times unaffected by the presence of alcohol imbibed by the patient. The invention also allows for reducing the range in daily dosages required to control pain in substantially all human patients comprising administering an oral solid controlled release dosage formulation comprising from about 10 mg to about 160 mg oxycodone or a salt thereof which provides a mean maximum plasma concentration of oxycodone up to about 240 ng/mL from a mean of up to about 2 to about 4.5 hours after administration and a mean minimum plasma concentration up to about 120 ng/mL from a mean of about 10 to about 14 hours after repeated administration every 12 hours through steady-state conditions, said concentrations and mean times unaffected by the presence of alcohol imbibed by the patient. Further, the invention disclosed herein allows for the therapeutic administration of an opioid at allowable minimum and maximum plasma concentrations sufficient for the relief of pain as extended release formulations dosed at about 12 hour intervals to maintain blood plasma concentrations within the minimum and maximum therapeutic range, said minimum and maximum blood concentrations unaffected by the presence of alcohol imbibed intentionally or otherwise by the patient receiving the therapeutic administration of the opioid.

The present invention is applicable to a variety of drug delivery presentations including solid oral dose, parenteral dosage forms (depo-type products) and by devices and formulations suitable for transdermal delivery and nasal/inhalation administration. It is responsibly acknowledged that many factors may influence the overall pharmacokinetic profile of a drug product, for instance, the particle size distribution of the drug substance may markedly influence drug substance bioavailability. Hence, the optimum practice of this invention when employed for a specific drug product must account for the multitude of additional factors. The benefit of the current invention is a means to provide a dominating or controlling factor to prevent abuse while achieving efficacious and therapeutic patient dosages to which refinements, adjustments or modifications can be asserted to yield an optimal response.

The three primary mechanistic approaches to prohibiting abuse; antagonist, prodrug and formulation; attempt to address abuse potential by impacting the route of administration, or to differentiate the physiological environment in which the drug fulfills its intended purpose versus the drug's misuse. Each of these routes was shown to possess inherent limitations for mitigating drug abuse. For the purposes of additional clarity and completeness, the mineral acid salts, which are typically abused, do not exhibit a suitable means to prevent abuse. The dissolution properties of the mineral acid salts of the physiologically active and/or controlled substance amines consistently exhibit high dissolution rates and substantial achievable release rates (85-100%) over the entire physiological pH range.

In contrast, it is relevant to the present invention to note the importance of pH in controlling the release of a drug substance from its product formulation to achieve absorption and consequently, the medicinal effect. The pH of the gastrointestinal tract essentially remains highly acidic with the exception of the lower colon which reaches pH 8; vaginal pH is typically around 5.8 and the nasal cavity is approximately pH 4.5. More generally, each of the mucosal surfaces, particularly ocular, nasal, pulmonary, buccal, sublingual, gingival, rectal and vaginal are receptive to drug absorption if release can occur. A dominating feature of the present invention is the severely retarded release of the controlled substance, particularly amine-containing pamoate salt (or related salt family) in the pH range of about 4 to 9 which encompasses the physiological pH of the mucosa. These release properties were an unexpected finding recognized and observed after performing dissolution tests over a wide pH range on several unrelated compounds. The release properties and saturation solubility profiles are a means to evaluate a reasonable dosage application to the mucosa. The non-release of the drug in the 4 to 9 pH range negates absorption and prevents the physical act of abuse. For the amine-containing hydrochloride salts, an abuse mechanism remains operative since these salts do not exhibit the discriminating "on/off" switch of the present invention.

An experimental refinement of the dissolution tests was performed on several compounds to better represent the physiological conditions encountered during abuse attempts and to account for the saturation solubility factor. Further, control experiments were included in the experimental design to compare the organic acid addition salts of the current invention with the hydrochloride salts of identical amine-containing controlled substances. In some cases, model compounds were used to demonstrate the principles of the invention instead of using compounds legally designated as controlled substances. Side-by-side dissolution experiments on hydrochloride salts versus those of the present invention were conducted at three different pH conditions: a) a pH of about 1 to simulate gastric conditions, b) pH of about 4.5 to simulate mucosal surface pH, and c) a pH of about 7 to evaluate a potential pH range of mucosal surfaces and blood pH for purposes of simulating injection. In addition, the experimentation was designed to demonstrate the equivalence of the organic acid addition salts to the mineral acid salts if used by their intended route of oral administration route and hence the concentration effects were included in the study. For oral administration of a dosage form, the United States Pharmacopeia (USP) recommends the immediate release testing procedure on a unit dosage to be performed on a simulated stomach "solution" volume of 900 mL. For the mucosal membranes, the available mucous fluid may be better approximated at 10 mL. Hence, dissolution tests were conducted at different concentrations at the different pH levels. Besides temperature, pH and concentration, the time factor was also evaluated under the presumption that an individual abusing a drug will want to obtain their anticipated physiological response within an hour.

Also disclosed herein are processes for the preparation of drug substances and DEA controlled drug substances (APIs) using organic acid addition salts of the active pharmaceutical ingredient (API) which are optionally formulated with other non-therapeutic materials to aid in delivery, stability, efficacy, targeted release and to engineer a pharmacokinetic profile of the organic acid addition salts as compared to other salt forms, including inorganic (mineral) acid salt forms. The present invention provides for release of the API for its intended purpose and prevents availability of the drug substance for typical routes of abuse. The present invention describes a method for evaluating, and formulations for, the organic acid addition salts of appropriate APIs to provide an efficacious and therapeutic dosage to animals and humans.

A drug formulation which is selected for the prevention of drug abuse is specifically a drug which is bio-unavailable or not isolable if efforts to alter the intended or established route of administration are undertaken. In a preferred embodiment the drug formulation is not released under aqueous conditions at a pH of about 4 to about 9 and generates a solid of an organic acid at pH below about 4. At pH above about 9, the organic acid (as its inorganic salt) and the amine containing active pharmaceutical ingredient (as its free base) are sufficiently soluble as to prevent separation of the components and thus inhibiting direct isolation of the API (as its free base) without additional processing.

In the present invention a drug product can be prescribed and administered in a manner wherein proper administration provides a therapeutic effect and the function of the API is realized. With a different manner of administration, in other words, a non-therapeutic administration of the API does not enter the bloodstream in an amount sufficient to be active. To be effective the API must be bio-available. For the purposes of the present invention, one method of establishing a compound's bio-availability is by determining the percentage of weight API recovered from an aqueous solution at a pH representative of the method of administration described herein. For the purposes of the present invention a compound is considered to be effective when less than 85 wt % of the compound is recovered from an aqueous solution at a pH representative of the method of administration. If, by contrast for example, 85 weight percent or more of a drug compound is recovered from a solution at a pH of 4-9, pH 7 for example, the material is considered to be bio-unavailable at a mucosal membrane and is considered non-permeable at the mucosal membrane and the compound exhibits prophylactic properties. If, for example, less than 85 weight percent of a drug compound is recovered from a solution at a pH of less than 4, pH 1 for example, the material is considered to be bio-available under oral administration and is considered permeable in, for example, the gastrointestinal tract due to the release of the API at the pH of the gastrointestinal tract. For the purposes of the present invention therapeutic dose is characterized as immediate dose, slow dose and controlled dose. An immediate dose is defined as a formulation wherein at least 85 wt % of the active ingredient is bioavailable at 1 hour at a representative pH. For example, 1 N HCl. For the purposes of the present invention bioavailable is defined as the weight percent which is not recovered by filtration. Slow release is defined as a formulation wherein at least 50 wt % to less than 85 wt % of the active ingredient is bioavailable at 1 hour at a representative pH. Controlled release is defined as a formulation wherein no more than 50 wt % of the active ingredient is bioavailable at 1 hour at a representative pH. More preferably, with controlled release at least 12.5 wt % to no more than 42.5 wt % is bioavailable at 1 hour at a representative pH. In one embodiment the representative pH approximates the stomach pH which corresponds to 0.1 N HCl. It is particularly preferred that the representative pH be between 1.6 and 7.2.

A particularly preferred embodiment and method of administering the amine-containing pharmaceutically active compound is by oral dose. The oral dose is prepared by first preparing an organic acid salt of the active compound. The organic salt is then formulated into a carrier matrix to provide an oral dose drug product. The carrier matrix is composed of ingredients (excipients) optionally selected from the group, but not limited to binders, fillers, flow enhancers, surfactants, disintegrants, buffers, and the like, typically employed in the art and found in the "Handbook of Pharmaceutical Excipients", Rowe, Sheskey and Owen (Editors), Fifth Edition, 2006, Pharmaceutical Press (publishers). When the oral dose is ingested the organic salt dissociates under physiological conditions. The organic acid portion of the amine-containing organic acid addition salt forms the insoluble (organic) acid while the active compound is liberated and becomes bio-available. Efforts to directly isolate the active compound from the oral dose would be thwarted as described herein.

An "alkaloid" is an amine nitrogen containing natural product, or synthetically modified or derivatized natural product, or wholly synthesized analog of a natural product, or an amine containing compound that exhibits biological activity in animals or humans. The amine nitrogen can be present as a primary, secondary, tertiary or quaternary amine moiety and a given compound may contain more than one type of amine functionality. Examples of these materials are the US Drug Enforcement Agency's (DEA) Form 225 of Schedule I through V controlled substances, generally divided between narcotic and non-narcotic materials. There are also other compounds applicable to the present invention not found on the DEA list or which may be added to it in the future. Further, the compounds applicable to the present invention may arise from plant or animal origin, or may be totally obtained through human effort of design and synthesis. A reference to compound classes (pharmocophores) applicable to the invention are found within *Strategies for Organic Drug Synthesis*, by Daniel Lednicer, published by John Wiley and Sons, Inc.© 1998, Chapters 7 through 13 inclusive and individually, Chapter's 13 and 15. Classes of compounds subject to this invention include but are not limited to opiates, morphinoids, tropinoids, amphetamines, compounds containing a piperidine or substituted piperidine sub-structure within the molecule, benzodiazepines, benzazepines, and compounds containing a phenethyl amine or substituted phenethylamine sub-structure within the molecule. The common characteristic to each compound is the presence of an amine nitrogen whereby the amine nitrogen is either a primary, secondary or tertiary amine group and is capable of forming a salt with an inorganic or organic acid, or combinations thereof. Within the description of the invention, the term alkaloid or amine may be used interchangeably to identify a compound possessing, or suspected of possessing, biological activity in humans or animals, in its free base (non-salt form) or in a salt form. The differentiating factor defining the invention is the alkaloid's ability to form an organic acid salt that will retain the expected biological activity when used as intended for legitimate therapeutic purposes, but is not readily accessible for abuse by inhalation (smoking), mucosal application, nasal absorption (snorting) or by intravenous injection (shooting).

A "drug substance" is a molecular entity or compound, also known as an active pharmaceutical ingredient (API) that exhibits biological activity for the purpose of providing human or animal medication to treat disease, pain or any medically diagnosed condition. It is possible for a drug substance to be used in combination with one or more different drug substances to ultimately impart a biological response in humans or animals. A drug substance is typically formulated with other, non-biologically active compounds to provide a means of predictable and quantitative dosage delivery, or perhaps to impart acceptable stability features to the drug product. What is meant by a drug product is a formulation, mixture or admixture of the drug substance with combinations of excipients, processing aids, buffers and perhaps other inert ingredients that allow delivery of the drug substance by the selected delivery mechanism to the patient at a predictable dosage (the carrier matrix). Various delivery mechanisms include solid oral dosage, for example, pills, tablets, or capsules. Additional delivery systems can include solution or suspension injection dosage forms (including depo drug products), transdermal patches, and nasal or inhalation devices. The dosage is the actual concentration delivered to the patient, and depending upon many factors and the actual delivery system selected, the dosage may be available for essentially immediate release, release over time, or manipulated by additional means for stimulated release such as for example, by irradiation. Immediate release is defined as a drug substance wherein under simulated gastric conditions at least 85% is released within 1 hour.

It is a well-known chemical principle that an acid and a base will react to form a salt. It is sometimes possible to predict the physical and chemical properties of these compounds in generalized concepts such as which way a melting point will change compared to the un-reacted acid or base. Dissolution and dissociation rates of drug salts and their associated achievable solution concentrations are substantially less predictable when attempting to correlate this experimental data to some anticipated bio-availability of the drug. For instance, at a given pH, an observed dissolution rate and the associated solution concentration of the drug may be dissociation controlled (i.e. ionization) rather than governed strictly by solubility parameters. Indeed, different salts of the same amine-containing active ingredient are likely to display diverging mechanisms of bio-availability as a function of pH. As such, an evaluation of amine-containing active ingredients and their different salts would help elucidate their bio-availability mechanisms. This approach could be incorporated into a broader design feature to address drug abuse.

API salts and their polymorphs often exhibit different dissolution characteristics. For instance the rate of dissolution is pH dependent, and therefore yields a different pharmacokinetic profile and/or therapeutic efficacy. Sometimes, a given drug product formulation expertise or technology can dominate any biological effects the API salt and/or polymorph present. Conversely, drug product formulation and the resulting mechanical properties of a tablet, capsule or bead can be dominated by the physical behavior of the API salt and/or its particular crystal structure. It is not unusual that difficult trade-offs must be made between the ease of manufacture of the drug product and the pharmacokinetics desired.

Drug product formulation can impact the pharmacokinetics of an API salt candidate (and potential polymorph) by a host of technologies, including but not limited to, preparing formulated beads, different sized beads, coated beads, combinations of various bead technologies, formulated matrix systems, addition of hydrophobic layers to tablets, capsules or beads (for example, as a control mechanism to limit the dissolution rate of hydrophilic gelatin capsules), coated tablets and capsules, capsules filled with beads, and different mixtures of beads with different coatings. These formulation techniques make available a wide range of drug product properties including, but not limited to, slow release, controlled release, and extended release drug pharmacokinetics. These activities are dependent upon the API salt selected (and potential polymorph issues) because of the salt's dissolution profile at the pH where drug release is to occur (for liberation of the API from its salt form). In fact, different API salts and formulation techniques can be selected based on where the desired release is to occur in the gastrointestinal tract and the formulator can use the API salt's pKa, solubility, melting point, shape and particle size as primary factors to utilize, moderate or overcome localized insolubility through the use of formulation techniques.

The term "drug system" refers to a dosage wherein at least two doses are provided. The two doses can be concurrent, sequential, or overlapping and each dose, of the two doses, may be the same or different.

Throughout the specification the term organic acid is used generically to refer to the acid form or the salt form of a compound.

EXPERIMENTAL METHODS

Differential Scanning calorimetry (DSC)

Samples were evaluated using a Differential Scanning calorimeter from TA Instruments (DSC 2010). Prior to analysis of samples, a single-point calibration of the TA Instruments DSC 2010 Differential Scanning calorimeter (DSC 2010) with the element indium as calibration standard (156.6±0.25° C.) was completed.

Infrared Spectroscopy (FTIR)

IR Spectra were obtained in a KBr disc using a Perkin Elmer Spectrum BX Fourier Transform Infrared Spectrophotometer.

Powder X-Ray Diffraction (PXRD)

Powder X-Ray diffraction patterns were acquired on a Scintag XDS2000 powder diffractometer using a copper source and a germanium detector. A powder is defined herein as amorphous if the counts per second of the underlying broad (>20 Deg. 2Theta at half height) absorption exceeds the counts per second of narrow (<5 Deg. 2Theta at half height) peaks rising there above. A powder is defined herein as crystalline if the counts per second of the underlying broad (>20 Deg. 2Theta at half height) absorption is less than the counts per second of narrow (<5 Deg. 2Theta at half height) peaks rising there above. Crystalline and polycrystalline are not distinguished herein. Crystalline materials are defined as having a morphology even if the actual morphology is not elucidated. Polycrystalline materials are defined as being polymorphic.

HPLC

HPLC analyses were performed on a Waters 2695 HPLC system equipped with a Waters 2996 photo diode array detector.

$^1$H NMR Spectroscopy $^1$H NMR spectra were obtained on a 300 MHz Varian Gemini 2000 spectrometer. Spectra were referenced to solvent (DMSO-$d_6$).

Example 1

Preparation of Oxycodone Free Base

To a 150 mL beaker was charged 10.0 g oxycodone hydrochloride and 100 mL water. Concentrated ammonium hydroxide (2.6 grams) was then added to bring the pH to approximately 9. The product was collected by vacuum filtration, washed with cold water and dried for about 5 hours under vacuum to provide 8.3 g (93% yield) of a white solid consistent in structure with oxycodone free base. This procedure was used to prepare hydrocodone, hydromorphone and morphine free base as needed.

Example 2

Oxycodone Pamoate (Amorphous)

To a 100 mL one neck round bottom flask equipped with a magnetic stir bar, thermo-well and nitrogen inlet was charged oxycodone free base (3.0 g) as prepared in Example 1. DMF (50 mL, 99.9% HPLC grade) was then added which produced a clear colorless solution. Pamoic acid (1.85 g, 99%) was subsequently added over thirty seconds which produced a clear yellow solution. The solution was stirred under nitrogen for about 1.5 hours at ambient temperature and then subsequently filtered through a medium fritted glass filter to remove any particulates. The filtrate was transferred to a 1 L one-neck round bottom flask and about 750 mL iso-propanol was added over about one minute upon which a flocculent white precipitate formed. The mixture was stored in the refrigerator overnight and the off-white solids collected by vacuum filtration (Whatman #4 filter paper). The product was washed with about 200 mL iso-propanol and subsequently transferred to a 250 mL one-neck round bottom flask. To the flask was then added about 90 mL iso-propanol and the solvent removed from the slurry under reduced pressure at about 40° C. (rotary evaporator). This evaporation procedure was repeated twice and the resulting product dried overnight under vacuum at ambient temperature (to provide 3.8 g (79%) of an off-white solid which was analyzed by DSC (FIG. 1), HPLC (assay as 2:1 salt; amine: pamoate), FTIR (FIG. 2), KF (range 0.5-3% water; replicate synthetic preparations) and PXRD (FIG. 3). The PXRD diffractogram indicated the product was amorphous.

The original mother liquor from above reaction was cooled in a refrigerator overnight and the resulting product collected by filtration, washed with a small portion of iso-propanol and dried overnight under vacuum (ambient temperature) to provide an additional 0.4 g product (8% yield second crop, 87% total yield) with analytical results consistent with those reported above.

Example 3

Preparation of Oxycodone Pamoate (1st Polymorphic Form)

To a 50 mL one neck round bottom flask equipped with a magnetic stir bar, thermowell and nitrogen inlet was charged oxycodone free base (1.3 g, 99%) as prepared in Example 1. DMF (22 mL, HPLC grade) was then added which produced a clear colorless solution. Pamoic acid (0.80 g, 99%) was subsequently added over about thirty seconds which produced a clear yellow solution. The solution was stirred under nitrogen for about 1.5 hours at ambient temperature and then subsequently vacuum filtered through a medium fritted glass filter to remove any particulates. The filtrate was transferred to a 250 mL one-neck round bottom flask and 45g iso-propanol was added to make the solution slightly turbid. The mixture was allowed to stir at ambient temperature overnight upon which off-white solids formed. The product was collected by filtration (Whatman #4 filter paper) and washed with a small portion of iso-propanol. The product was dried overnight at ambient temperature and under reduced pressure to provide 1.8 g (86%) of an off-white solid which was analyzed by DSC (FIG. 4), HPLC (assay 2:1 salt, amine:pamoate), FTIR (FIG. 5), KF (range 2-5% water; replicate synthetic preparations) and PXRD (FIG. 6). The PXRD diffractogram confirmed the product was a polymorphic form of oxycodone pamoate.

The original mother liquor from above reaction later deposited more crystals which were collected by filtration, washed with a small portion of iso-propanol and dried overnight under reduced pressure (ambient temperature) to provide an additional 0.2 g (9.5% yield second crop, 95.5% total yield) of material analytically consistent with the first crystals isolated.

Example 4

Preparation of Oxycodone Pamoate in 2nd Polymorphic Form

Figure 101:
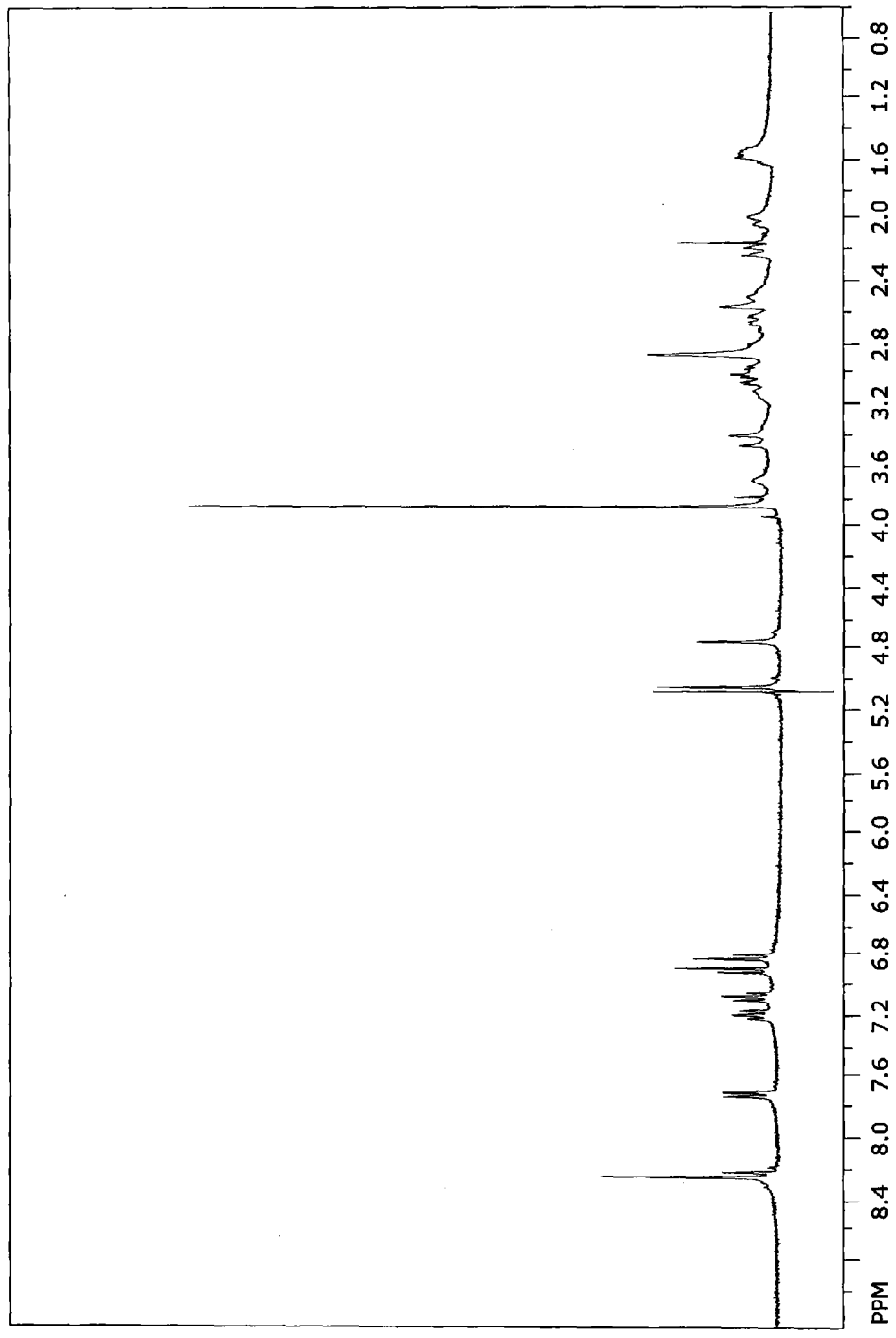
FIG. 101 is the Nuclear Magnetic Resonance (NMR) spectrum of oxycodone pamoate in a $2^{nd}$ polymorphic form.

To a 50 mL round bottom flask equipped with a magnetic stir bar, reflux condenser and nitrogen inlet was charged oxycodone pamoate (amorphous, 1.0 g, as prepared in Example 2) and acetone (14.9 g). The mixture was heated and maintained at reflux overnight under nitrogen upon which all the material dissolved. The flask was then allowed to cool to ambient temperature upon which a white solid formed. The solid was collected by filtration, washed with a small portion of acetone (~5 mL) and dried overnight under reduced pressure and at ambient temperature to provide 0.8 g of a white solid (80% recovery). The product was characterized by, DSC (FIG. 98), FTIR (FIG. 99), KF (range 2-5% water; replicate synthetic preparations), PXRD (FIG. 100) and $^1$H-NMR (FIG. 101). Accordingly, the FTIR and $^1$H-NMR spectra were absent evidence of acetone inclusion in the crystal; the PXRD diffractogram confirmed the material's polymorphic nature yet different from that described in Example 3.

Example 5

Preparation of Oxycodone Xinafoate

To a 50 mL one neck round bottom flask equipped with a magnetic stir bar, thermowell and nitrogen inlet was charged oxycodone free base (0.5 g) as prepared in Example 1. DMF (8 mL, HPLC grade) was then added which produced a clear colorless solution. BON acid (3-hydroxy-2-naphthoic acid, 0.298 g) was subsequently added over about thirty seconds which produced a clear yellow solution. The solution was stirred under nitrogen for about 2 hours at ambient temperature. To the clear solution was added MTBE (methyl t-butylether, 2 mL) and the solution placed in a freezer overnight. The product was subsequently collected by filtration (Whatman #4 filter paper) and washed with a small portion of MTBE and dried overnight under reduced pressure and at ambient temperature to provide 0.5 g (63%) of a light-orange solid which was analyzed by DSC (FIG. 7), HPLC, FTIR (FIG. 8), KF (range 0.5-3% water; replicate synthetic preparations) and PXRD (FIG. 9). PXRD confirmed the product was partially crystalline.

Example 6

Preparation of Amorphous Hydrocodone Pamoate

Figure 12:
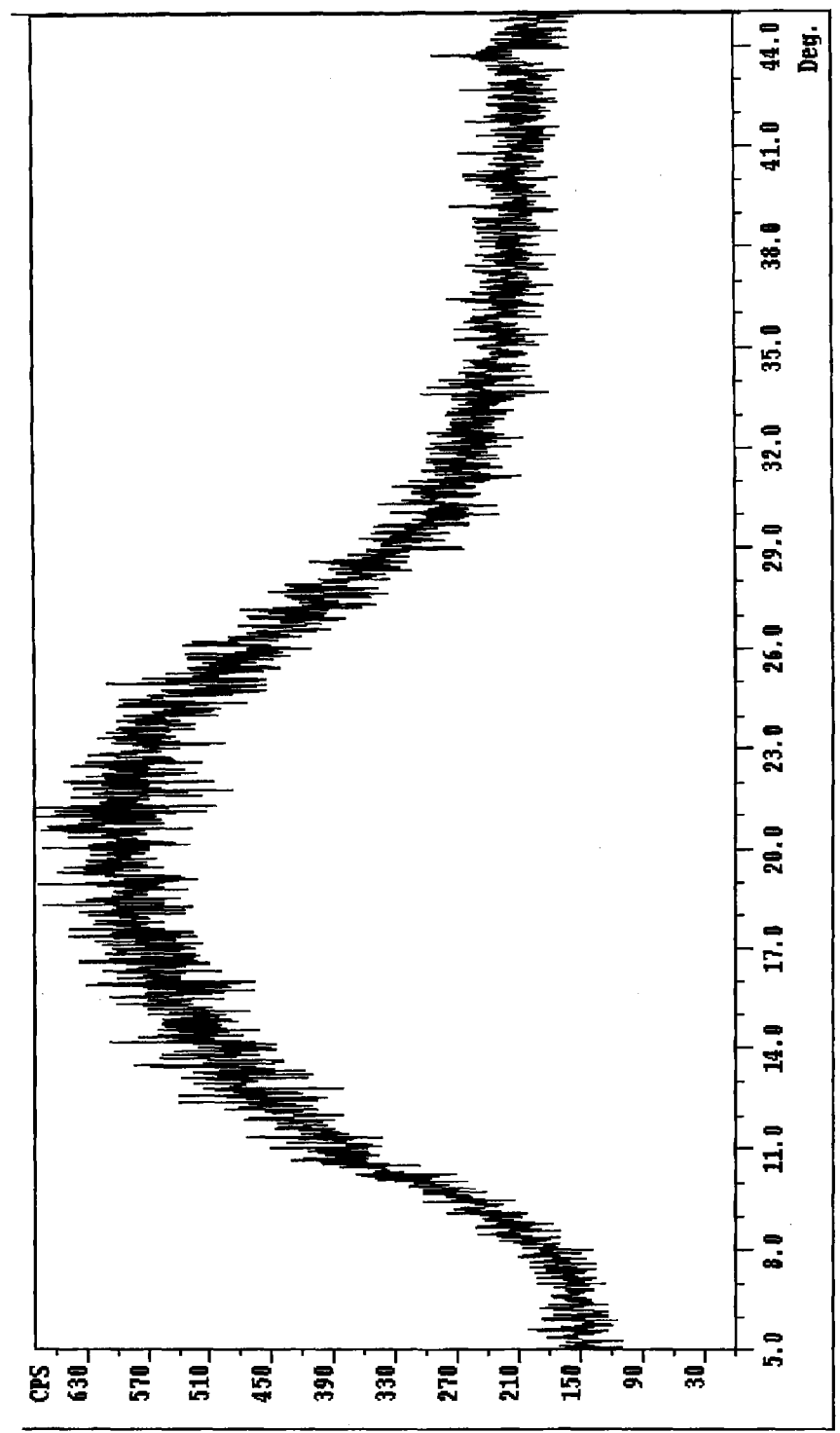
FIG. 12 is the powder X-ray diffraction (PXRD) diffractogram of amorphous hydrocodone pamoate.
Figure 13:
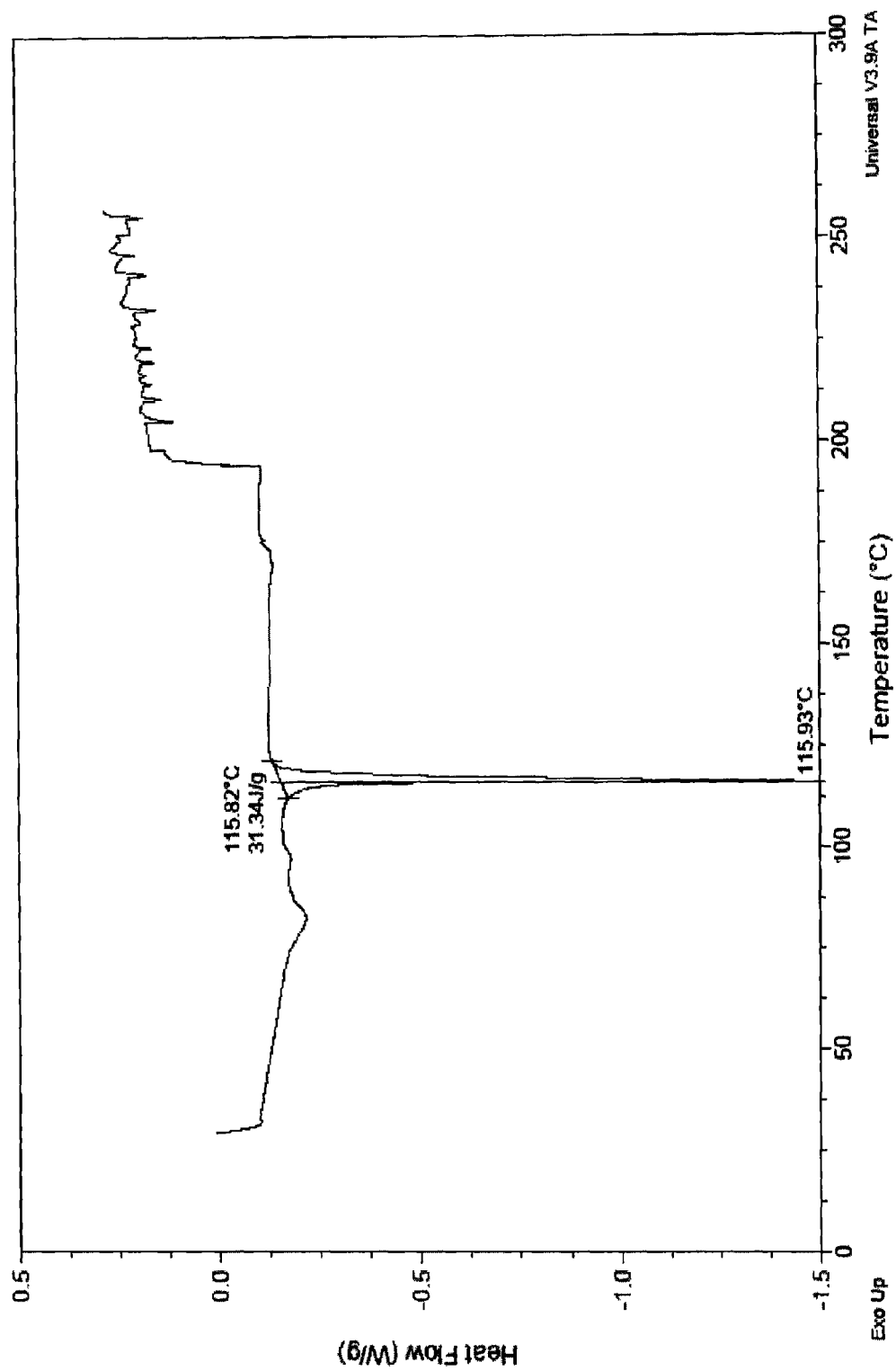
FIG. 13 is the differential scanning calorimetry (DSC) thermogram of polymorphic hydrocodone pamoate.
Figure 14:
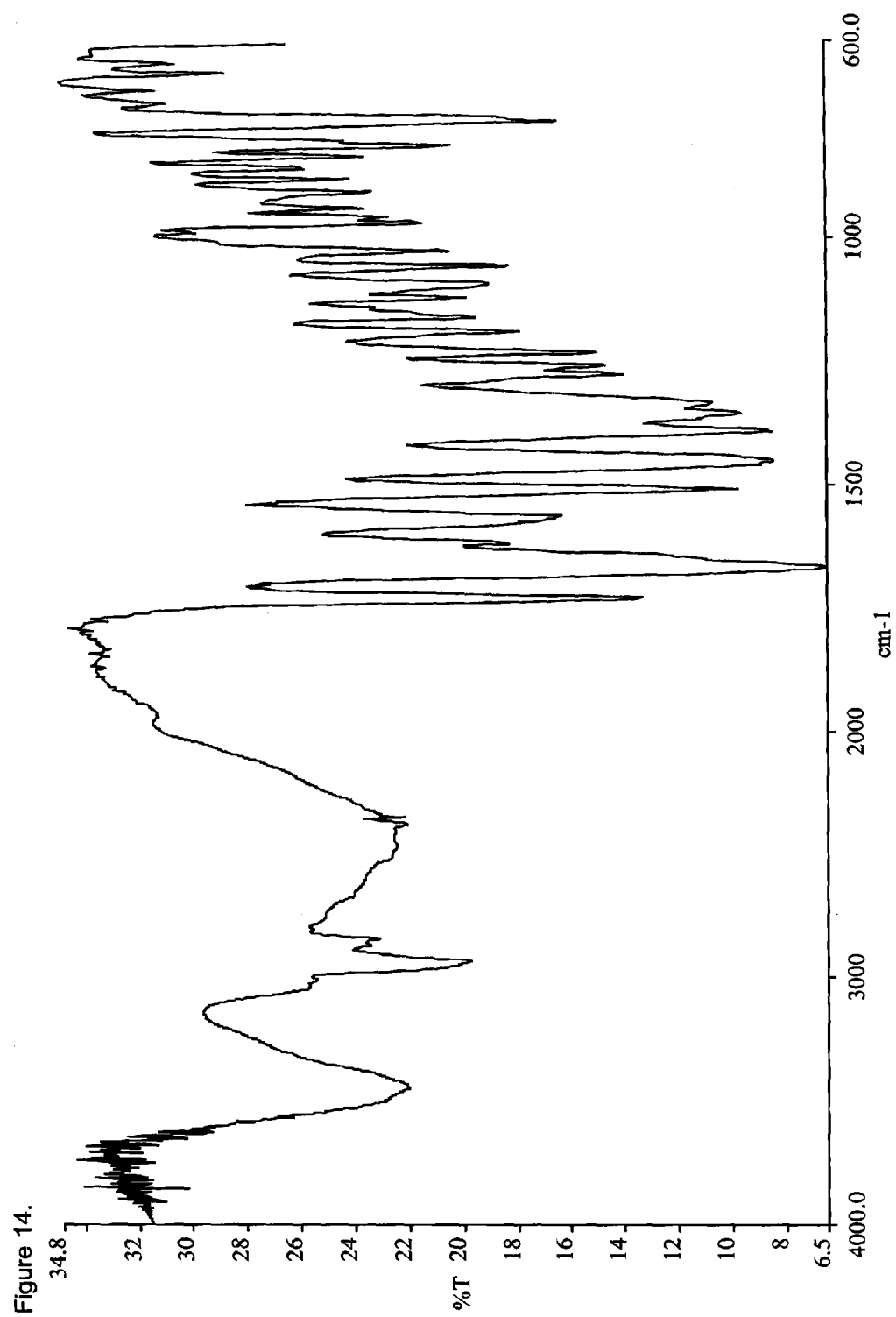
FIG. 14 is the Fourier Transform Infrared (FTIR) spectrum of polymorphic hydrocodone pamoate.

A solution of hydrocodone free base (4.8 g), prepared in an analogous manner as the procedure described in Example 1, in about 60 mL of DMF (HPLC grade) was treated with 3.1 g of pamoic acid with stirring at about 25° C. The resulting mixture became a clear yellow solution after about 5 minutes and was stirred for about an additional 45 minutes. The DMF solution was diluted with 600 mL of isopropyl alcohol and chilled to about 7° C. for overnight. A yellow-tan precipitate was formed which was isolated on a Buchner funnel and washed with fresh isopropyl alcohol. The material was re-slurried in isopropyl alcohol and the slurry was stripped to dryness under reduced pressure on a rotary evaporator. The re-slurry/stripping process was repeated twice whereupon the material was isolated yielding yield 6.6 g (84%) of a dry powder. The product was analyzed by DSC (FIG. 10), FTIR FIG. 11), HPLC (assay 2:1 salt; amine:pamoate), KF (range 1-5%; replicate synthetic preparations) and PXRD (FIG. 12). The PXRD diffractogram indicated the material was amorphous.

Example 7

Preparation of Amorphous Hydrocodone Pamoate Acetone Solvate

To a 50 mL round bottom flask equipped with a magnetic stir bar, reflux condenser and nitrogen inlet was charged hydrocodone pamoate (amorphous, 0.8 g, see Example 6) and acetone (~20 mL). The mixture was heated and maintained at reflux overnight under nitrogen upon which all the material dissolved. The flask was allowed to cool to ambient temperature and concentrated under reduced pressure (rotary evaporator) to provide an off-white solid. The product was dried overnight under vacuum at ambient temperature to provide 0.6 g (75% recovery) of a white solid. The material was characterized by DSC, FTIR, PXRD and $^1$H-NMR. The FTIR and $^1$H-NMR spectra confirmed the inclusion of acetone; the PXRD diffractogram indicated the product was amorphous.

Example 8

Preparation of Hydrocodone Pamoate (Polymorphic)

Figure 15:
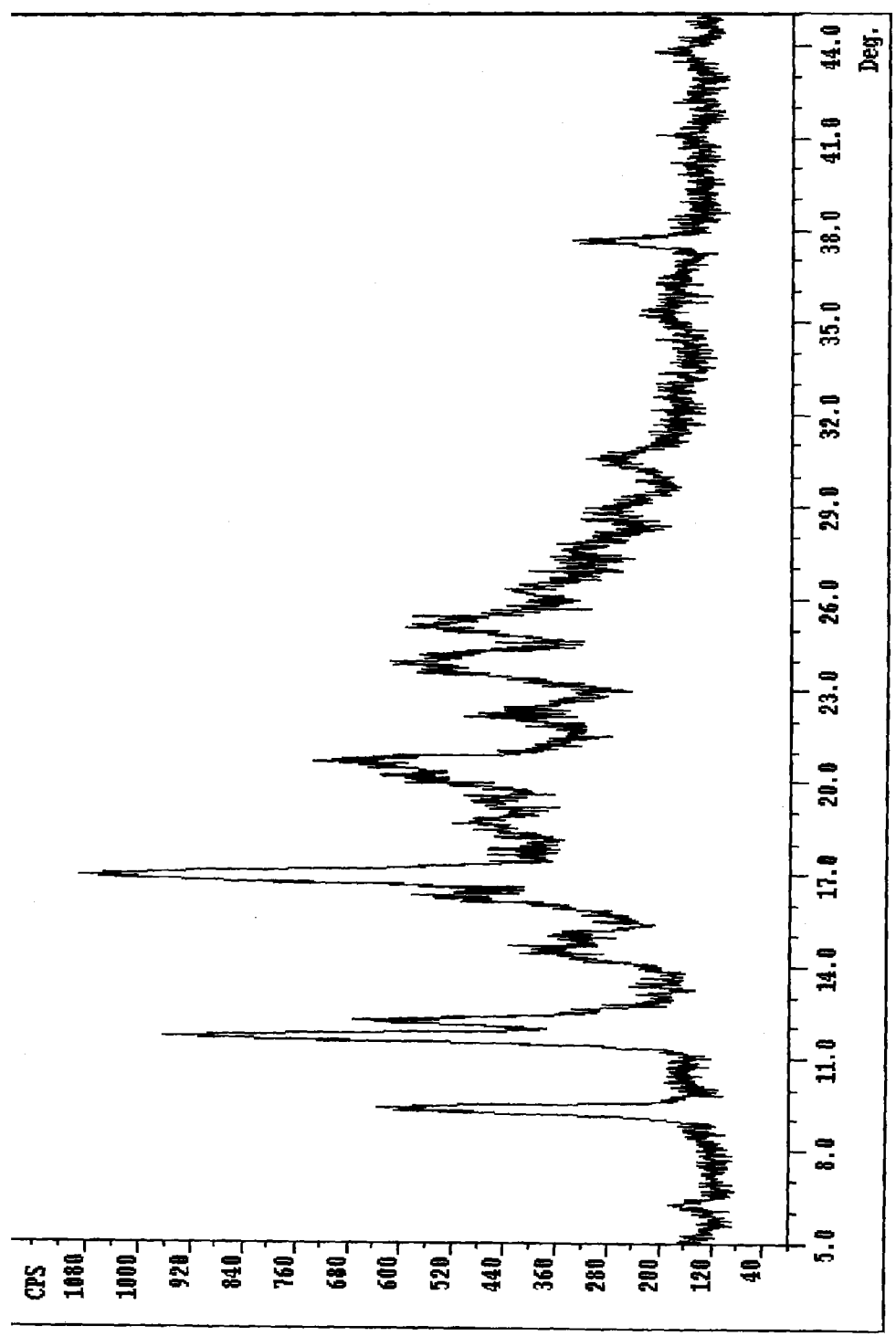
FIG. 15 is the powder X-ray diffraction (PXRD) diffractogram of polymorphic hydrocodone pamoate.
Figure 16:
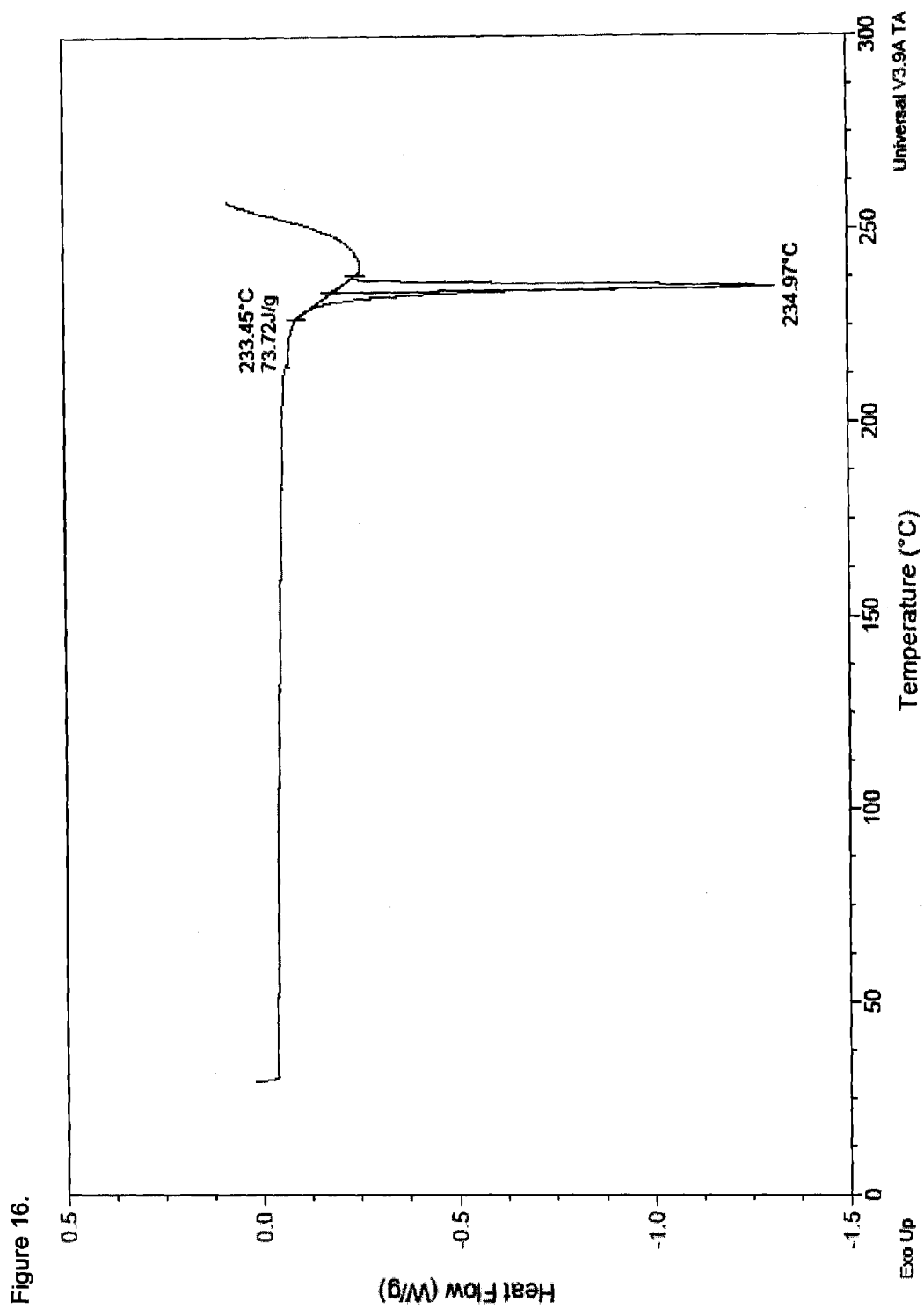
FIG. 16 is the differential scanning calorimetry (DSC) thermogram of hydrocodone xinafoate.
Figure 17:
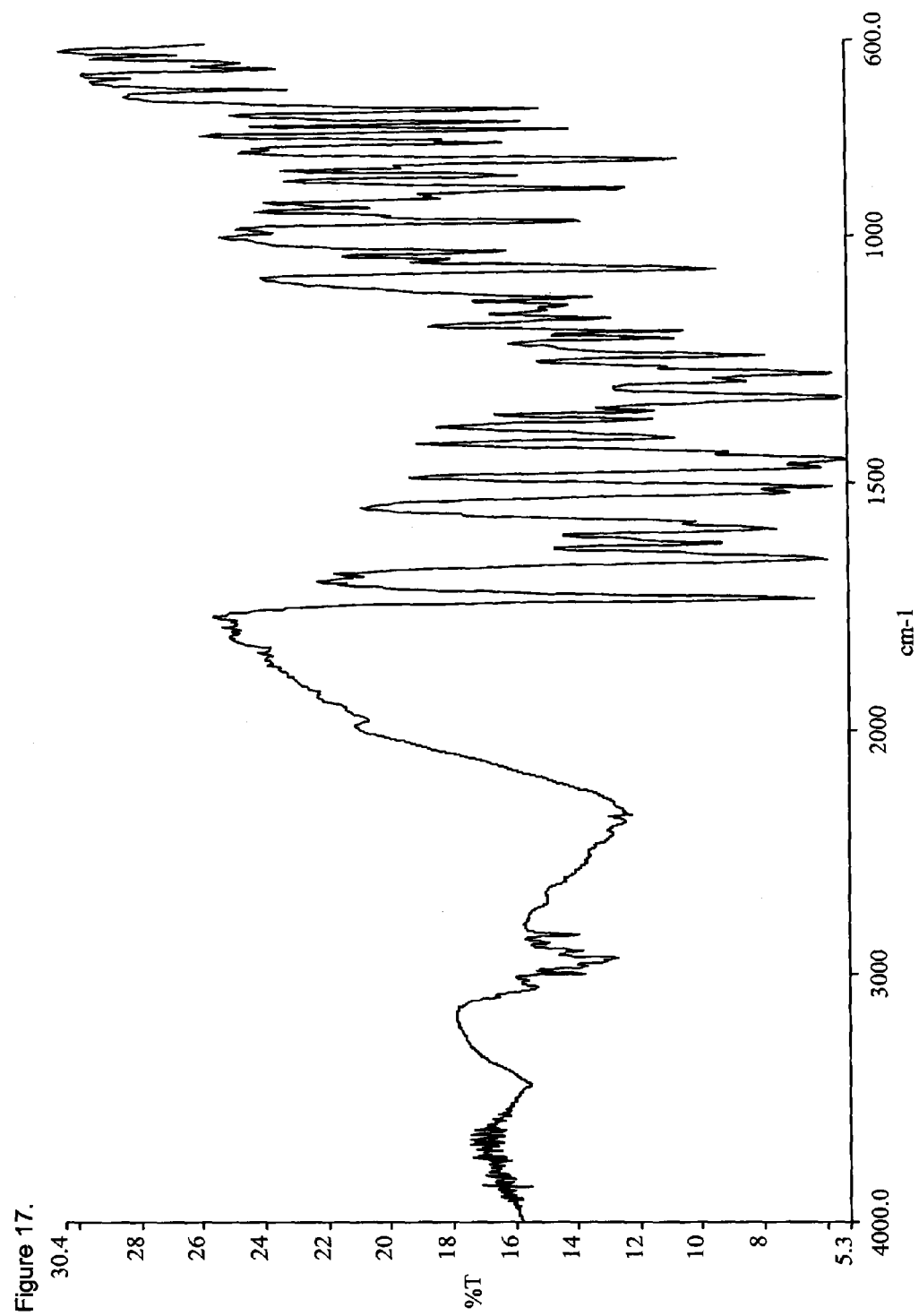
FIG. 17 is the Fourier Transform Infrared (FTIR) spectrum of hydrocodone xinafoate.

A solution of 6.5 g disodium pamoate in about 100 mL of USP water was treated with enough 1 N sodium hydroxide solution to adjust the pH to about 9.0-9.5. The resulting solution was treated with a second solution of hydrocodone hydrochloride prepared by slurrying 9.0 g of hydrocodone base in about 100 mL of USP water and adding enough 1 N hydrochloric acid to adjust the pH to 4.0-4.5. The hydrocodone solution was added in a dropwise manner to the disodium pamoate solution over a period of about 25 minutes at about 25° C. The resulting mixture was warmed to about 50° C. and samples were removed periodically for analysis by DSC. After approximately 120 hours the product was filtered and washed with water and dried. The resulting sample weighed 14.4 g and contained about 4 moles of water as analyzed by coulometric titration. The material was further characterized by DSC, HPLC, FTIR, and PXRD. The PXRD diffractogram indicated the material was amorphous and similar in character to that obtained in Example 6. A portion (1.0 g) was dissolved in DMF (8.0 g) to produce a yellow solution which was stirred under nitrogen at room temperature. Iso-propanol (~16.1 g) was then added and the solution stirred at ambient temperature for about 1 hour. The solids were then collected by filtration, washed with iso-propanol and dried under vacuum to provide 0.1 g. A second crop of crystals later formed in the mother liquor which were collected by filtration and washed with iso-propanol to provide an additional 0.6 g. The collected solids from the two crops were found to be identical as characterized by DSC (FIG. 13), HPLC (assay as 2:1 salt; amine:pamoate), FTIR (FIG. 14), KF (range 1-4% water; replicate synthetic preparations) and PXRD (FIG. 15). The PXRD diffractogram indicated the material was crystalline.

Example 9

Preparation of Hydrocodone Xinafoate

Figure 18:
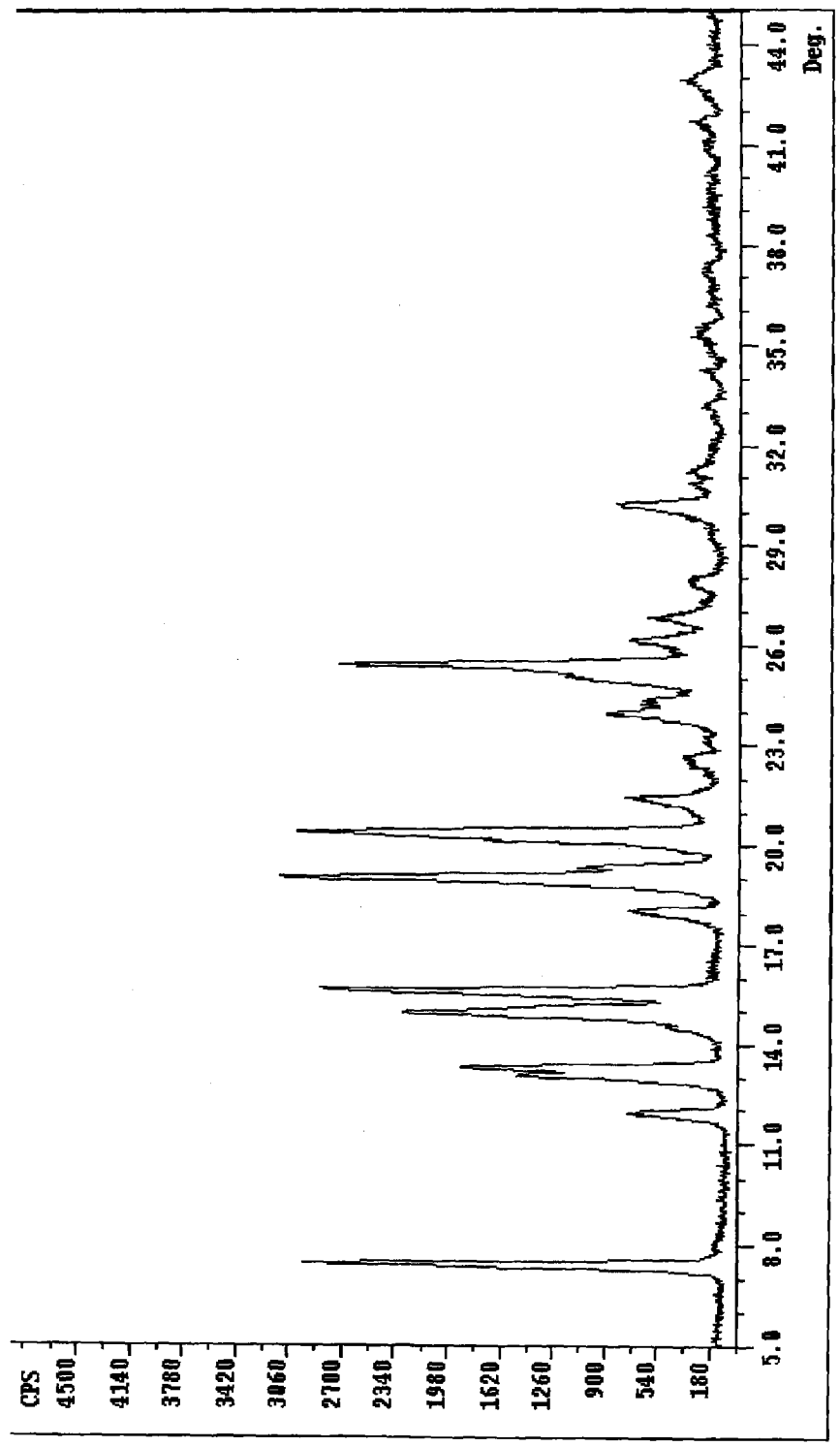
FIG. 18 is the powder X-ray diffraction (PXRD) diffractogram of hydrocodone xinafoate.

To a 100 mL one neck round bottom flask equipped with a magnetic stir bar, thermowell and nitrogen inlet was charged hydrocodone free base (1.0 g). DMF (~14 mL, HPLC grade) was then added and produced a clear colorless solution. To the solution was added BON acid (3-hydroxy-2-naphthoic acid, 0.629 g) over about thirty seconds which produced a clear yellow solution. The solution was stirred under nitrogen at ambient temperature for about 1 hour. To the clear solution was added about 184 g iso-propanol and the solution placed in a refrigerator (~5° C.) overnight. A precipitate was collected by filtration (Whatman #4 filter paper), washed with a small portion of iso-propanol and dried overnight under reduced pressure at ambient temperature to provide 1.3 g (80%) of an off-white solid characterized by DSC (FIG. 16), HPLC, FTIR (FIG. 17), KF (range 0-4% water; replicate synthetic preparations) and PXRD (FIG. 18). The PXRD diffractogram confirmed the material was crystalline.

Example 10

Preparation of Amorphous Hydromorphone Pamoate

A solution of 4.3 g of disodium pamoate in about 50 mL USP water was treated with enough 0.01 N sodium hydroxide solution to adjust the pH to about 9.0-9.5. The resulting solution was treated with a second solution of hydromorphone hydrochloride prepared by dissolving 3.2 g of hydromorphone hydrochloride in about 50 mL USP water and adding enough 0.1 N hydrochloric acid to adjust the pH to about 4.0-4.5. The hydromorphone solution was added in a dropwise manner to the disodium pamoate solution over a period of about 5 minutes at about 20° C. The resulting mixture was stirred at ambient temperature for about 2 hours during which time a precipitate formed. The product was filtered and washed with water and dried in vacuo. The material was characterized by HPLC, DSC (FIG. 19), FTIR (FIG. 20), KF (range 1-5% water, replicate synthetic preparations); HPLC (2:1 salt; amine:pamoate) and PXRD (FIG. 21). The PXRD diffractogram indicated the material was amorphous. The reagent molar equivalents had been combined in a ratio to prepare the 1:1 amine:pamoate salt yet the 2:1 salt was isolated. Similarly, the 2:1 salt was also isolated from material prepared analogous to the procedure described in Example 3 with the exception however, the reagent molar equivalents were charged in a 1:1 ratio.

Example 11

Preparation of Hydromorphone Pamoate
(Polymorphic Acetone Solvate)

To a 100 mL round bottom flask equipped with a magnetic stir bar, reflux condenser and nitrogen inlet was charged hydromorphone pamoate (amorphous, 500 mg) and acetone (~50 mL). The mixture was heated and maintained at reflux overnight under nitrogen. The white slurry formed was allowed to cool to ambient temperature, solids collected by filtration and dried overnight under vacuum and at ambient temperature to provide 0.5 g of an off-white solid. The product was characterized by DSC (FIG. 22), FTIR (FIG. 23), PXRD (FIG. 24), KF (~2% water) and $^1$H-NMR. The FTIR and $^1$H-NMR spectra indicated the material isolated contained acetone (about one equivalent); proton integration confirmed the salt form was the 2:1 ratio of amine:pamoate. The PXRD indicated the material was crystalline.

Example 12

Preparation of Hydromorphone Xinafoate

A slurry of 1.9 g of 3-hydroxy-2-naphthoic acid (BON acid) in about 50 mL USP water was treated with enough 1 N sodium hydroxide solution to adjust the pH to about 9.0-9.5. The resulting solution was treated with a second solution of 3.2 grams of hydromorphone hydrochloride in 50 mL USP water. The pH of the hydromorphone solution was adjusted to about 4.0-4.5 by addition of a small amount of dilute hydrochloric acid. The hydromorphone solution was added in a dropwise manner to the naphthoate solution over a period of several minutes at about 20° C. The resulting mixture was stirred at ambient temperature for about 1 hour and then heated briefly to 50° C. The reaction mixture was allowed to cool to ambient temperature and was left stirring under nitrogen for about 18 hours. The aqueous reaction liquor was decanted from the gummy product and the product was re-dissolved in about 200 mL acetone. After brief warming, the product crystallized, the precipitate collected by filtration, and air dried to give 3.1 g of crystalline material. The material was characterized by DSC (FIG. 25), FTIR (FIG. 26), HPLC and PXRD (FIG. 27).

Example 13

Preparation of Morphine Pamoate (Amorphous)

A solution of 3.03 g of morphine in about 30 mL DMF was treated with 3.88 g pamoic acid and the mixture stirred at about 25° C. The mixture became a clear yellow solution after about 5 minutes and was stirred for an additional 30 minutes. The DMF solution was diluted with isopropyl alcohol (IPA) until turbidity was observed and reaction mixture chilled overnight at about 7° C. A yellow-tan precipitate was collected on a Buchner funnel and washed with fresh isopropyl alcohol. The gummy material was re-slurried in isopropyl alcohol and the solvent removed under reduced pressure (rotary evaporator). The re-slurry/stripping process was repeated twice and the dry material was scraped from the flask to give 2.5 g of powder. The DMF/IPA filtrates were re-concentrated and re-diluted with 50 mL isopropyl alcohol to yield a second crop of material which was subjected three times to the isopropyl alcohol slurry/drying process as described for the first crop The isolation and crystallization process for the second crop yielded another 1.5 g of material which was characterized by $^1$H NMR (2:1 salt; amine:pamoate), DSC (FIG. 28), FT IR (FIG. 29), and PXRD (FIG. 30).

Example 14

Preparation of Morphine Pamoate (Polymorphic Acetone Solvate)

To a 100 mL round bottom flask equipped with a magnetic stir bar, reflux condenser and nitrogen inlet was charged morphine pamoate (amorphous, 400 mg; see Example 13) and acetone (~50 mL). The mixture was heated and maintained at refluxed overnight and under nitrogen whereupon almost all of the material dissolved. The flask was allowed to cool to ambient temperature and white solid formed. The solid was collected by filtration and dried overnight under vacuum to provide 0.3 g of an off-white solid. The product was characterized by DSC (FIG. 31, FTIR (FIG. 32), PXRD (FIG. 33) and $^1$H-NMR. The FTIR and $^1$H-NMR confirmed the product contained about one equivalent of acetone. The PXRD diffractogram indicated the product was crystalline.

Example 15

Preparation of Morphine Xinafoate

A slurry of 1.88 g of 3-hydroxy-2-naphthoic acid (BON acid) in about 25 mL USP water was treated with enough 1 N sodium hydroxide solution to adjust the pH to about 9.0-9.5. The resulting solution was treated with a second solution of morphine hydrochloride prepared by slurrying 3.0 g of morphine base in 25 mL USP water and adding enough 1 N hydrochloric acid to adjust the pH to about 4.0-4.5. The morphine solution was added in a dropwise manner to the naphthoate solution over a period of about 5 minutes at about 20° C. The resulting mixture was stirred at ambient temperature for about 1 hour and then heated briefly to 50° C. The reaction mixture was allowed to cool to ambient temperature and was left stirring under nitrogen for about 72 hours. The product was filtered, washed with water, and dried under vacuum. The resulting sample weighed 4.4 g and contained about 1 equivalent of water by coulometric titration. The material was further characterized by, DSC (FIG. 34), FTIR (FIG. 35) and PXRD (FIG. 36). The PXRD diffractogram indicated the material was crystalline.

Example 16

Dissolution Procedure

The opioid salts of the present invention were tested to determine their dissolution profile as a function of pH, and as a function of ethanol concentration in acidic media (dose dumping). To perform these experiments the buffered dissolution media and acidic ethanol solutions were prepared as identified herein, "Preparation of Solutions". The test procedure was derived from the procedures cited in the United States Pharmacopeia and National Formulary (USP), numbers <1087> and <711>. The dose dumping procedure was adopted from the United States Food and Drug Administration's guidance regarding the dose dumping of oxymorphone. The sampling interval and regimen was defined and each sample analyzed by HPLC. Results from the HPLC analyses were plotted as a function of time and dissolution condition (FIG. 37 through FIG. 97 inclusive, and FIGS. 102-105). This procedure was used to obtain the pH and dose dumping dissolution profiles disclosed herein. Verb tense within the procedure description does not indicate a prospective condition but was used to facilitate the method's description herein. All activities within the procedure were conducted and executed for each of the compounds reported herein. Unless otherwise stated HPLC measurements were done and reported at ambient temperature and dissolution testing was done nominally at 37° C.

Mean plasma concentration studies would be done in accordance with standard procedures as set forth in U.S. Pat. No. 5,549,912 which is incorporated herein by reference. Suitable test and control formulations would be prepared in accordance with the teachings herein. A predetermined number of appropriate subjects would be treated with test formulations and an appropriate number of subjects would be treated with control formulations. Control formulations may include placebos or actual pharmaceutical formulations. Pain could be monitored over a period of time and the relative pain between the groups compared. Alternatively, plasma concentrations could be determined, such as by high performance liquid chromatography, with subsequent determination of means and half-lives for comparison. One would expect the inventive samples to demonstrate no increase in blood plasma level due to ingested alcohol versus comparative samples.

Preparation of Solutions:

All reagents are ACS grade or equivalent. All solvents used are a minimum of HPLC grade. Water used in the preparations of all solutions was USP grade. These solution preparations are identical to those described in USP.

Preparation of 0.1 N HCl:

To prepare 4 L of solution, add 33.3 mL of concentrated HCl to 977.7 mL of water, then add an additional 3000 mL of water.

Preparation of pH 4.5 Acetate Buffer:

To prepare 1 L of solution add 2.99 g of sodium acetate tri-hydrate ($NaC_2H_3O_2.3H_2O$) to a 1000 mL volumetric flask, then add 14.0 mL of 2N acetic acid solution. Dissolve and dilute to volume with water.

Preparation of pH 6.8 Phosphate Buffer:

To prepare 200 mL of solution first prepare a 0.2 M potassium phosphate solution by adding 27.22 g of monobasic potassium phosphate ($KH_2PO_4$) to a 1000 mL volumetric flask, then dissolve and dilute to volume with water. Add 50 mL of this solution to a 200 mL volumetric flask, then add 22.4 mL of 0.2M NaOH and dilute to volume with water.

Preparation of 5% Ethanol Solution for Dose Dumping Dissolution Profiles:

To prepare 900 mL of media combine 45 mL of 200 proof ethanol with 855 mL of 0.1 N HCl (see preparation procedure above).

Preparation of 20% Ethanol Solution for Dose Dumping Dissolution Profiles:

To prepare 900 mL of media combine 180 mL of 200 proof ethanol with 720 mL of 0.1 N HCl (see preparation procedure above).

Preparation of 40% Ethanol Solution for Dose Dumping Dissolution Profiles:

To prepare 900 mL of media combine 360 mL of 200 proof ethanol with 540 mL of 0.1 N HCl (see preparation procedure above).

Preparation of Mobile Phase A (0.1% TFA in H2O):

To prepare 1 L of mobile phase, add 1.0 mL of TFA to 1000 mL of $H_2O$. Mix well and filter this solution through a 0.45 µM nylon filter.

Preparation of Mobile Phase B (0.1% TFA in Acetonitrile):

To prepare 1 L of mobile phase, add 1.0 mL of TFA to 1000 mL of acetonitrile. Mix well and filter this solution through a 0.45 µM nylon filter.

Preparation of Mobile Needle/Seal Wash solution:

To prepare 1 L of solution, add 500 mL of $H_2O$ to 500 mL of acetonitrile and mix well.

Procedures:

Intrinsic Dissolution Profiles:

The following procedures were derived from USP <1087> Intrinsic Dissolution and USP <711> Dissolution methods, as well as manufacturer recommended procedures for use of the International Crystals Laboratories intrinsic dissolution disks.

Preparation of API Pellet for Intrinsic Dissolution:

The material which is to be subjected to dissolution is weighed using an analytical balance. 45.00-55 mg of the analyte was weighed and transferred to an International Crystals Laboratories fixed/static disk 316 stainless die with a 0.8 cm diameter die cavity. A hardened steel punch was then inserted into the cavity and the material was compressed at 2000 psi for 4-5 minutes using a bench top hydraulic press. The punch is then removed to expose the 0.5 $cm^2$ pellet surface. A Viton gasket is then placed around the threaded shoulder of the die and a polypropylene cap is threaded onto the die. This process can be repeated to generate as many pellets as is necessary for the experiment.

Setup of Intrinsic Dissolution Apparatus:

A Distek Dissolution System equipped with a model number TCS0200C temperature control system was filled with water and set to a temperature of 37.3° C. The vessel cavities were then equipped with four 1 L flat-bottomed Distek dissolution vessels. Four vessels were then filled with 500 mL of the following media: 0.1 N HCl, pH 4.5 acetate buffer, pH 6.8 phosphate buffer, and USP grade water. The solutions were allowed to warm in the water bath for approximately 1 hour, but not exceeding 3 hours, or until the temperature of the media matched that of the water bath. Paddles were then mounted to the Distek stirring apparatus above the four dissolution vessels such that the distance between the paddle and the die face is 1 inch. The paddle speed is then set to 50 RPM.

Intrinsic Dissolution Dose Dumping Profiles:

The following procedures were derived from the FDA Draft Guidance for Oxymorphone Hydrochloride (recommended in November, 2007).

Preparation of API Pellet for Intrinsic Dissolution Dose Dumping Profile:

The material which is to be subjected to dissolution is weighed using an analytical balance. 85.00-95.00 mg of the analyte was weighed and transferred to an International Crystals Laboratories fixed/static disk 316 stainless die with a 0.8 cm diameter die cavity. A hardened steel punch was then inserted into the cavity and the material was compressed at 2000 psi for 4-5 minutes using a bench top hydraulic press. The punch is then removed to expose the 0.5 $cm^2$ pellet surface. A Viton gasket is then placed around the threaded shoulder of the die and a polypropylene cap is threaded onto the die. This process can be repeated to generate as many pellets as is necessary for the experiment.

Setup of Intrinsic Dissolution Apparatus for Dose Dumping Profile:

A Distek Dissolution System equipped with a model number TCS0200C temperature control system, was filled with water and set to a temperature of 37.3° C. The vessel cavities were then equipped with four 1 L flat-bottomed Distek dissolution vessels. The vessels were then filled with 900 mL of the following media: 0.1 N HCl, 5% ethanol solution, 20% ethanol solution, and 40% ethanol solution. The solutions were allowed to warm in the water bath for approximately 1 hour, but not exceeding 3 hours, or until the temperature of the media matched that of the water bath. Paddles were then mounted to the Distek stirring apparatus above the four dissolution vessels such that the distance between the paddle and the die face is 1 inch. The paddle speed is then set to 75 RPM.

Performing an Intrinsic Dissolution Experiment (Dose Dumping or pH Media):

The pellet prepared as described above was submerged into a vessel prepared as described above, with the pellet surface facing up (metal die up, polypropylene cap facing down). Forceps are used to aid this process so that the pellet apparatus can be gently placed into the bottom of the vessel. A timer is used to track the sampling intervals, and is started when the pellet is dropped into the solution. The lid to the dissolution apparatus is then lowered and the stirring apparatus is activated. Some planning is required in spacing out pellet drops such that each vessel can be sampled at the desired time intervals. Sampling is done by aspirating 10 mL of the solution using a Popper® Micro-Mate® Interchangeable Hypodermic Syringe equipped with a Vortex Pharma Group 10 micron cannula porous filter. This filter should be replaced after each use. Although sampling intervals can change from experiment to experiment, the following has been heavily utilized for the experiments described herein. Sampling occurring at t=0, 5, 10, 15, 30, 45, 60, 90, 120, 150, 180 (minutes).

HPLC Methodology

HPLC Procedure for Analyzing Opioid Salts:

All samples should be analyzed with bracketing standard injections. The standard used should be from a qualified vendor with a known purity. Standard solutions should be prepared to have a concentration that is reasonably close to that of the samples being analyzed. All samples were run on a Waters Alliance 2695 Separations Module model number WAT270008 equipped with an Alliance 996 Photodiode Array Detector model number 186000869. The instrument was equipped with an Agilent 300 Extend-C18 5 µm 4.6×250 mm Zorbax column (PN 770995-902). The instrument was then plumbed with the proper solutions mentioned above in the section titled "Preparation of Solutions". The instrument is then set to initial column conditions (see gradient table below):

| Time (minutes) | % A | % B |
| --- | --- | --- |
| 0.00 | 90 | 10 |
| 2.00 | 90 | 10 |
| 8.00 | 25 | 75 |
| 8.01 | 0 | 100 |
| 13.00 | 0 | 100 |
| 13.01 | 90 | 10 |
| 17.00 | 90 | 10 |

This method can be used to analyze samples to plot a dissolution profile or to determine the ratio of drug to organic salt. Due to the differences in response factors when dealing with an opioid salt (pamoate or xinafoate), a dilution is required to quantify the salt portion of the mixture.

The sample diluent that is utilized also has an impact on the chromatography when implementing this method. The following sample diluents were used when analyzing opioid salts for ratio analysis, as well as dissolution profiles.

| Opioid | Diluent (H₂O:ACN) |
|---|---|
| Oxycodone HCl | 62:38 |
| Hydrocodone Bitartrate | 62:38 |
| Morphine Sulfate Pentahydrate | 100:0 |
| Hydromorphone HCl | 100:0 |
| Oxycodone Pamoate or Xinafoate | 62:38 |
| Hydrocodone Pamoate or Xinafoate | 62:38 |
| Morphine Pamoate or Xinafoate | 90:10* |
| Hydromorphone Pamoate or Xinafoate | 90:10* |

*More acetonitrile (ACN) may be added if a solution cannot be obtained with this diluent The invention has been described with particular focus on the preferred embodiments without limit thereto. One of skill in the art would realize additional embodiments and alterations which are not specifically stated but which are within the mete and bounds as set forth in the claims appended hereto.

Claimed is

1. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping and wherein one of said first opioid or said second opioid is a material selected from the group consisting of:
   amorphous hydrocodone pamoate characterized by at least one method selected from the group consisting of:
      a differential scanning calorimeter thermogram of FIG. 10;
      an FTIR of FIG. 11; and
      an X-ray diffraction diffractogram of FIG. 12;
   polymorphic hydrocodone pamoate characterized by at least one method selected from the group consisting of:
      a differential scanning calorimeter thermogram of FIG. 13;
      an FTIR of FIG. 14; and
      an X-ray diffraction diffractogram of FIG. 15;
   amorphous oxycodone pamoate characterized by at least one method selected from the group consisting of:
      a differential scanning calorimetery thermogram of FIG. 1;
      an FTIR of FIG. 2; and
      an X-ray diffraction diffractogram of FIG. 3;
   polymorphic oxycodone pamoate characterized by at least one method selected from the group consisting of:
      a differential scanning calorimetery thermogram of FIG. 4;
      an FTIR of FIG. 5; and
      an X-ray diffraction diffractogram of FIG. 6;
   oxycodone xinafoate characterized by at least one method selected from the group consisting of:
      a differential scanning calorimetery thermogram of FIG. 7;
      an FTIR of FIG. 8; and
      an X-ray diffraction diffractogram of FIG. 9;
   amorphous morphine pamoate characterized by at least one method selected from the group consisting of:
      a differential scanning calorimetery thermogram of FIG. 28;
      an FTIR of FIG. 29; and
      an X-ray diffraction diffractogram of FIG. 30;
   polymorphic morphine pamoate characterized by at least one method selected from the group consisting of:
      a differential scanning calorimetery thermogram of FIG. 31;
      an FTIR of FIG. 32; and
      an X-ray diffraction diffractogram of FIG. 32; and
   morphine xinafoate characterized by at least one method selected from the group consisting of:
      a differential scanning calorimetery thermogram of FIG. 34;
      an FTIR of FIG. 35;
      an X-ray diffraction diffractogram of FIG. 36;
   hydrocodone xinafoate characterized by at least one method selected from the group consisting of:
      a differential scanning calorimetery thermogram of FIG. 16;
      an FTIR of FIG. 17; and
      X-ray diffraction diffractogram of FIG. 18;
   amorphous hydromorphone pamoate characterized by at least one method selected from the group consisting of:
      a differential scanning calorimetery thermogram of FIG. 19;
      an FTIR of FIG. 20; and
      X-ray diffraction diffractogram of FIG. 21;
   polymorphic hydromorphone pamoate characterized by at least one method selected from the group consisting of:
      a differential scanning calorimetery thermogram of FIG. 22;
      an FTIR of FIG. 23; and
      X-ray diffraction diffractogram of FIG. 24; and
   hydromorphone xinafoate characterized by at least one method selected from the group consisting of:
      a differential scanning calorimetery thermogram of FIG. 25;
      an FTIR of FIG. 26; and
      X-ray diffraction diffractogram of FIG. 27.

2. The drug system of claim 1 wherein said first drug substance and said second drug substance are in a common drug product.

3. The drug system of claim 1 comprising a first drug product comprising said first drug substance and a second drug product comprising said second drug substance.

4. The drug system of claim 1 wherein said first opioid is said material and said second opioid is selected from the group consisting of oxycodone, hydrocodone, morphine, apomorphine, hydromorphone, oxymorphone, codeine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, levorphanol, nalbuphine, nalmefene, naloxone, naltrexone, noscapine, opium and oripavine.

5. The drug system of claim 4 wherein said second opioid is selected from oxycodone pamoate, oxycodone xinafoate, hydrocodone pamoate, hydrocodone xinafoate, hydromorphone pamoate, hydromorphone xinafoate, morphine pamoate and morphine xinafoate.

6. The drug system of claim 5 wherein said second opioid is amorphous oxycodone pamoate.

7. The drug system of claim 6 wherein said oxycodone pamoate is characterized by a differential scanning calorimetery thermogram of FIG. 1.

8. The drug system of claim 6 wherein said oxycodone pamoate is characterized by an FTIR of FIG. 2.

9. The drug system of claim 6 wherein said oxycodone pamoate is characterized by an X-ray diffraction diffractogram of FIG. 3.

10. The drug system of claim 5 wherein said second opioid is polymorphic oxycodone pamoate.

11. The drug system of claim 10 wherein said oxycodone pamoate is characterized by a differential scanning calorimetery thermogram of FIG. 4.

12. The drug system of claim 10 wherein said oxycodone pamoate is characterized by an FTIR of FIG. 5.

13. The drug system of claim 10 wherein said oxycodone pamoate is characterized by an X-ray diffraction diffractogram of FIG. 6.

14. The drug system of claim 5 wherein said second opioid is oxycodone xinafoate is characterized by a differential scanning calorimetery thermogram of FIG. 7.

15. The drug system of claim 5 wherein said second opioid is oxycodone xinafoate is characterized by an FTIR of FIG. 8.

16. The drug system of claim 5 wherein said second opioid is oxycodone xinafoate characterized by an X-ray diffraction diffractogram of FIG. 9.

17. The drug system of claim 5 wherein said second opioid is morphine pamoate with less than 3 waters of hydration.

18. The drug system of claim 5 wherein said second opioid is amorphous morphine pamoate.

19. The drug system of claim 18 wherein said morphine pamoate is characterized by a differential scanning calorimetery thermogram of FIG. 28.

20. The drug system of claim 18 wherein said morphine pamoate is characterized by an FTIR of FIG. 29.

21. The drug system of claim 18 wherein said morphine pamoate is characterized by an X-ray diffraction diffractogram of FIG. 30.

22. The drug system of claim 5 wherein said second opioid is polymorphic morphine pamoate.

23. The drug system of claim 22 wherein said morphine pamoate is characterized by a differential scanning calorimetery thermogram of FIG. 31.

24. The drug system of claim 22 wherein said morphine pamoate is characterized by an FTIR of FIG. 32.

25. The drug system of claim 22 wherein said morphine pamoate is characterized by an X-ray diffraction diffractogram of FIG. 33.

26. The drug system of claim 5 wherein said second opioid is morphine xinafoate characterized by a differential scanning calorimetery thermogram of FIG. 34.

27. The drug system of claim 5 wherein said second opioid is morphine xinafoate characterized by an FTIR of FIG. 35.

28. The drug system of claim 5 wherein said second opioid is morphine xinafoate characterized by an X-ray diffraction diffractogram of FIG. 36.

29. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping wherein one of said first opioid or said second opioid is amorphous hydrocodone pamoate and wherein said hydrocodone pamoate is characterized by a differential scanning calorimetery thermogram of FIG. 10.

30. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping wherein one of said first opioid of said second opioid is amorphous hydrocodone pamoate and wherein said hydrocodone pamoate is characterized by an FTIR of FIG. 11.

31. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping wherein one of said first opioid or said second opioid is amorphous hydrocodone pamoate and wherein said hydrocodone pamoate is characterized by an X-ray diffraction diffractogram of FIG. 12.

32. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping wherein one of said first opioid or said second opioid is polymorphic hydrocodone pamoate and said hydrocodone pamoate is characterized by a differential scanning calorimetery thermogram of FIG. 13.

33. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping wherein one of said first opioid or said second opioid is polymorphic hydrocodone pamoate and wherein said hydrocodone pamoate is characterized by an FTIR of FIG. 14.

34. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping wherein one of said first opioid or said second opioid is polymorphic hydrocodone pamoate and wherein said hydrocodone pamoate is characterized by an X-ray diffraction diffractogram of FIG. 15.

35. The drug system of claim 5 wherein said material is hydrocodone xinafoate characterized by a differential scanning calorimetery thermogram of FIG. 16.

36. The drug system of claim 5 wherein said material is hydrocodone xinafoate characterized by an FTIR of FIG. 17.

37. The drug system of claim 5 wherein said material is hydrocodone xinafoate characterized by an X-ray diffraction diffractogram of FIG. 18.

38. The drug system of claim 5 wherein said material is amorphous hydromorphone pamoate.

39. The drug system of claim 38 wherein said hydromorphone pamoate is characterized by a differential scanning calorimetery thermogram of FIG. 19.

40. The drug system of claim 38 wherein said hydromorphone pamoate is characterized by an FTIR of FIG. 20.

41. The drug system of claim 38 wherein said hydromorphone pamoate is characterized by an X-ray diffraction diffractogram of FIG. 21.

42. The drug system of claim 5 wherein said material is polymorphic hydromorphone pamoate.

43. The drug system of claim 42 wherein said hydromorphone pamoate is characterized by a differential scanning calorimetery thermogram of FIG. 22.

44. The drug system of claim 42 wherein said hydromorphone pamoate is characterized by an FTIR of FIG. 23.

45. The drug system of claim 42 wherein said hydromorphone pamoate is characterized by an X-ray diffraction diffractogram of FIG. 24.

46. The drug system of claim 5 wherein said material is hydromorphone xinafoate characterized by a differential scanning calorimetery thermogram of FIG. 25.

47. The drug system of claim 5 wherein said material is hydromorphone xinafoate is characterized by an FTIR of FIG. 26.

48. The drug system of claim 5 wherein said material is hydromorphone xinafoate characterized by an X-ray diffraction diffractogram of FIG. 27.

49. The drug system of claim 1 wherein said first drug substance is said material and said second drug substance is an organic acid addition salt of said second opioid.

50. The drug system of claim 49 wherein said organic acid is defined by Structure A

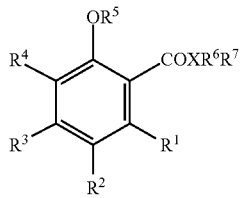

Structure A wherein $R^1$-$R^4$ are independently selected from H, alkyl or substituted alkyl of 1-6 carbons, adjacent groups may be taken together to form a cyclic alkyl, cyclic alkyl-aryl, or cyclic aryl moiety;
$R^5$ is selected from H, or an alkali earth cation;
$R^6$ and $R^7$ are independently selected from H, alkyl of 1-6 carbons, an alkali earth cation, and aryl of 6 to 12 carbons, in a number sufficient to complete the valence bonding of X, and
wherein X is selected from nitrogen, oxygen or sulfur.

51. The drug system of claim 50 wherein said organic acid is selected from the group consisting of:

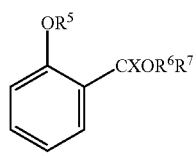

Structure B wherein $R^5$, $R^6$, $R^7$ and X remain as defined above for Structure A;

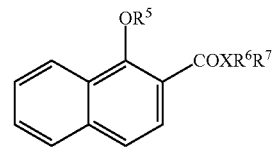

Structure C wherein X, $R^5$, $R^6$ and $R^7$ remain as defined above for Structure A;

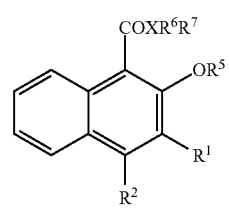

Structure D wherein X, $R^1$, $R^2$, $R^5$, $R^6$ and $R^7$ remain as defined above for Structure A;

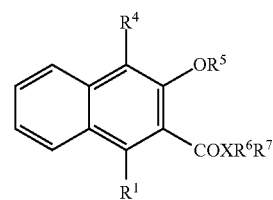

Structure E wherein X, $R^1$, $R^4$, $R^5$, $R^6$ and $R^7$ remain as defined above for Structure A;

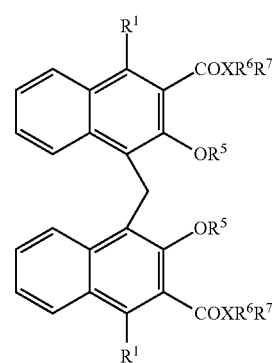

Structure F wherein X, $R^1$, $R^5$, $R^6$ and $R^7$ are independently defined as above for Structure A; and

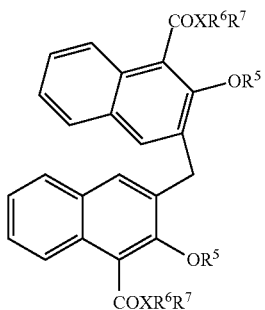

Structure G wherein X, $R^5$, $R^6$ and $R^7$ are independently defined as above for Structure A.

52. The drug system of claim 51 wherein for Structure B X is O.

53. The drug system of claim 51 wherein for Structure D X is O; $R^1$ and $R^2$ are hydrogen.

54. The drug system of claim 51 wherein for Structure E X is O, $R^1$ and $R^4$ are hydrogen.

55. The drug system of claim 51 wherein for Structure F at least one X is O and at least one $R^1$ is hydrogen.

56. The drug system of claim 51 wherein for Structure G X is O and $R^5$ is hydrogen.

57. The drug system of claim 51 wherein said organic acid comprises a material selected from the group consisting of pamoic acid, disodium pamoate, di-ammonium pamoate, di-potassium pamoate, lower molecular weight di-alkyl amine pamoate, lower molecular weight di-aryl amine pamoate, lower molecular weight di-alkyl esters of pamoic acid, lower molecular weight di-aryl esters of pamoic acid, lower molecular weight di-alkylacyl O-esters of pamoic acid, lower molecular weight di-arylacyl O-esters of pamoic acid and monoalkali pamoate.

58. The drug system of claim 51 wherein said organic acid comprises a material selected from the group consisting of ortho isomers of hydroxy naphthoic acid, sodium hydroxy naphthoic acid, ammonium hydroxy naphthoate, potassium hydroxy naphthoate, lower molecular weight alkyl amine salts of hydroxy naphthoic acid, lower molecular weight aryl amine salts of hydroxy naphthoic acid, lower molecular weight alkyl esters of hydroxy naphthoic acid, lower molecular weight aryl esters of hydroxy naphthoic acid, lower molecular weight alkylacyl O-esters of hydroxyl naphthoic acid, lower molecular weight di-arylacyl O-esters of pamoic acid and monoalkali pamoate.

59. The drug system of claim 51 wherein said organic acid is selected from the group consisting of salicylic acid, sodium salicylate, ammonium salicylate, potassium salicylate, lower molecular weight alkyl amine salts of salicylic acid, lower molecular weight aryl amine salts of salicylic acid, lower molecular weight alkyl esters of salicylic acid, lower molecular weight aryl esters of salicylic acid, lower molecular weight alkylacyl O-esters of salicylic acid and lower molecular weight arylacyl O-esters of salicylic acid.

60. The drug system of claim 51 wherein said organic acid salt comprises an acid selected from pamoic acid or a synthetic equivalent thereof; salicylic acid or a synthetic equivalent thereof and hydroxy naphthoic acid or a synthetic equivalent thereof.

61. The drug system of claim 1 wherein at least one of said first drug substance and said second drug substance is incorporated in a form selected from the group consisting of a tablet, a capsule, a caplet, and an oral suspension.

62. The drug system of claim 1 wherein at least one of said first drug substance and said second drug substance comprises an additive.

63. The drug system of claim 62 wherein said additive comprises a third opioid.

64. The drug system of claim 63 wherein said third opioid is selected from the group consisting of oxycodone, hydrocodone, morphine, apomorphine, hydromorphone, oxymorphone, codeine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, levorphanol, nalbuphine, nalmefene, naloxone, naltrexone, noscapine, opium and oripavine.

65. The drug system of claim 62 wherein said additive is defined by Structure H:

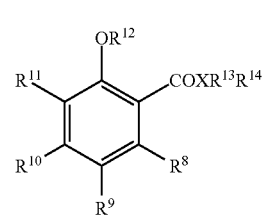

Structure H wherein $R^8$-$R^{11}$ are independently selected from H, alkyl or substituted alkyl of 1-6 carbons, adjacent groups may be taken together to form a cyclic alkyl, cyclic alkyl-aryl, or cyclic aryl moiety;

$R^{12}$ is selected from H, or an alkali earth cation;

$R^{13}$ and $R^{14}$ are independently selected from H, alkyl of 1-6 carbons, an alkali earth cation, and aryl of 6 to 12 carbons, in a number sufficient to complete the valence bonding of X; and wherein X is selected from nitrogen, oxygen or sulfur.

66. The drug system of claim 65 wherein at least one of $R^{12}$ and $R^{13}$ is an alkali earth cation.

67. The drug system of claim 65 wherein said additive is selected from the group consisting of pamoic acid, an alkali earth salt of pamoate, bon acid and an alkali earth salt of bon acid.

68. The drug system of claim 67 comprising disodium pamoate and at least one drug substance selected from oxycodone pamoate, hydrocodone pamoate, morphine pamoate, hydromorphone pamoate, morphine, hydromorphone, oxycodone and hydrocodone.

69. The drug system of claim 65 wherein said additive and one of said first opioid or said second opioid are present in a ratio of between 0.5:1 and 1:1.

70. The drug system of claim 62 wherein said additive is selected from the group consisting of binder, colorant, flow agent, disintegrants, release agent, surfactant, buffer, wetting agent and particle coating.

Figure 2:
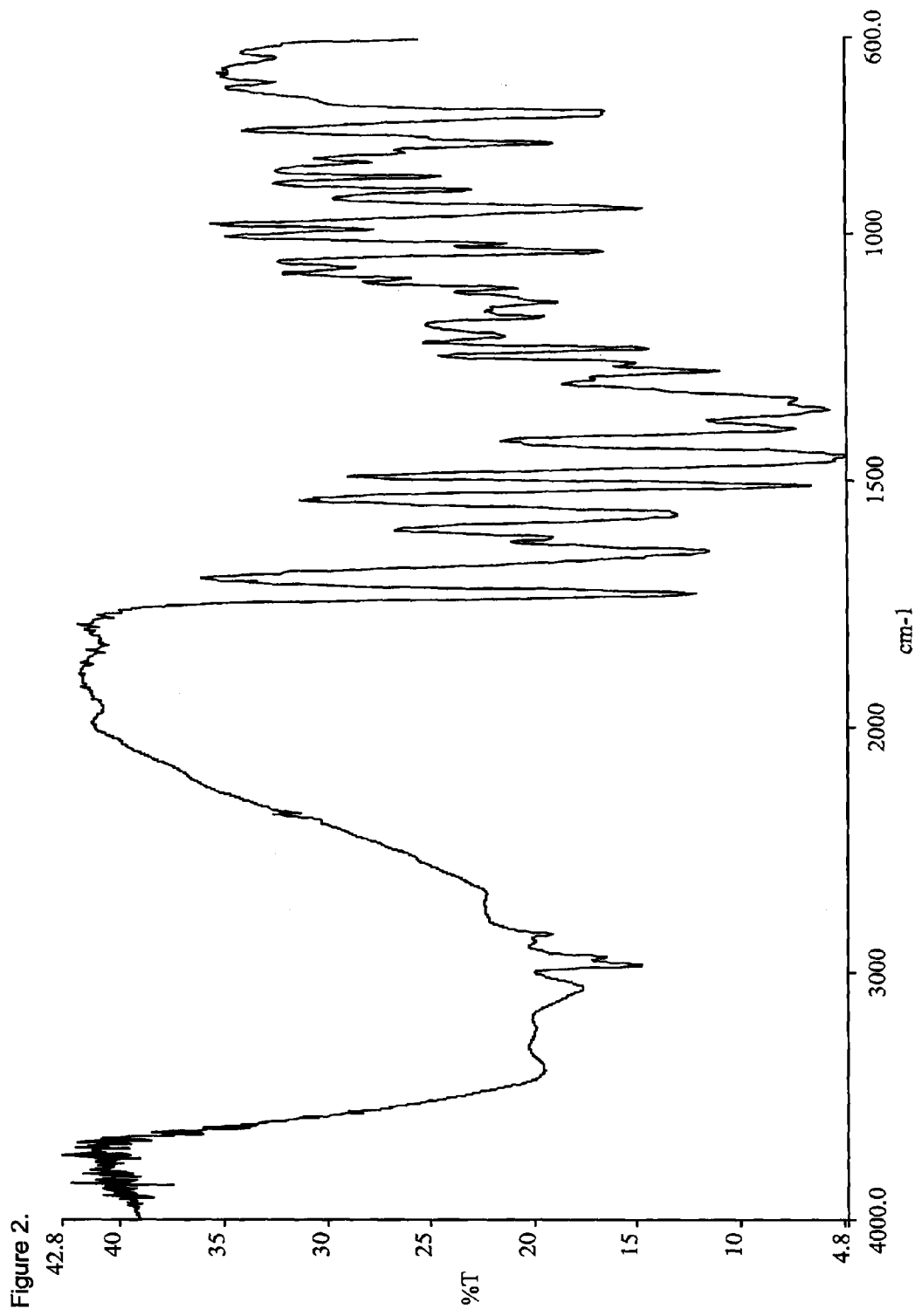
FIG. 2 is the Fourier Transform Infrared (FTIR) spectrum of amorphous oxycodone pamoate.
Figure 3:
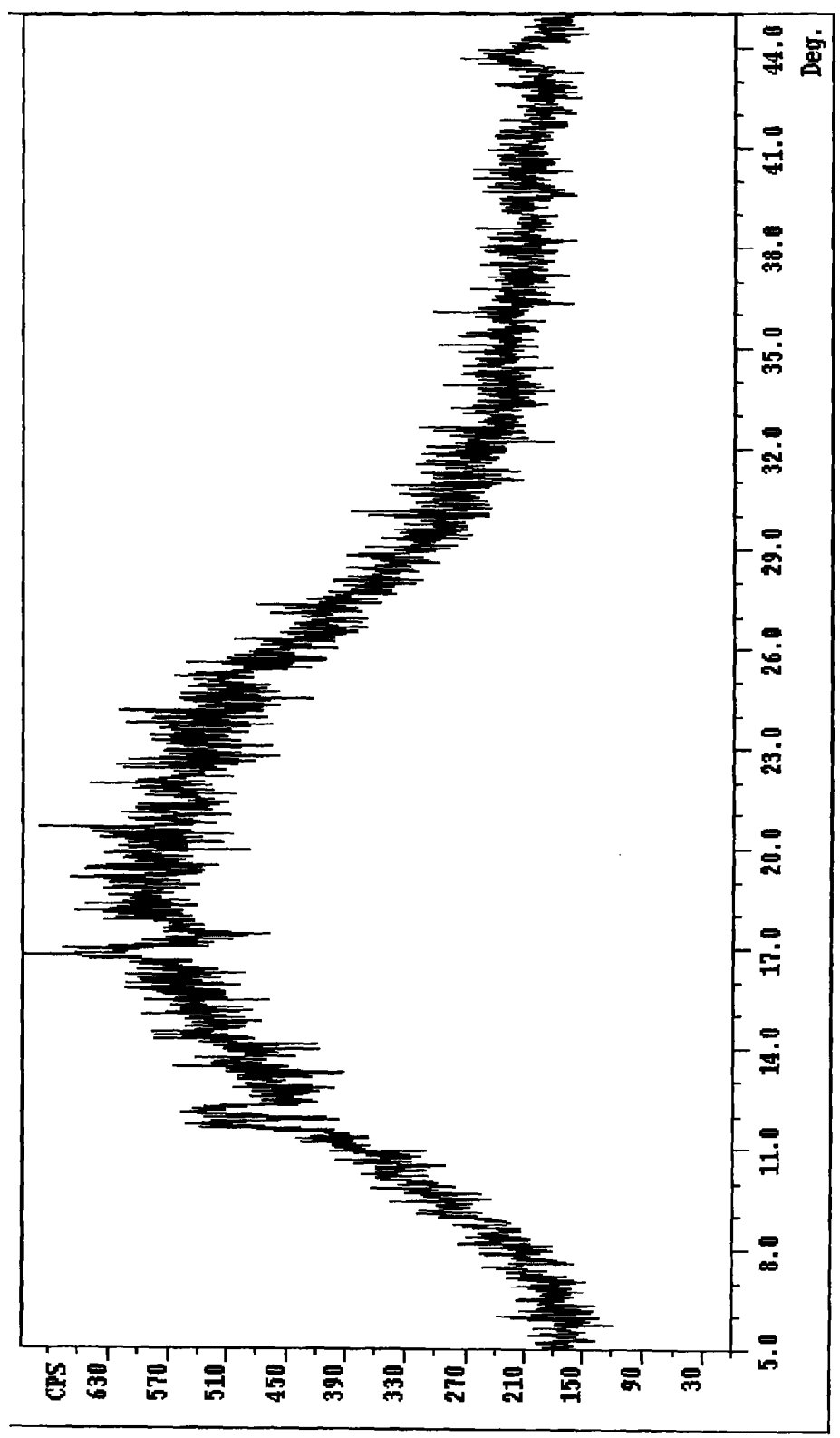
FIG. 3 is the powder X-ray diffraction (PXRD) diffractogram of amorphous oxycodone pamoate.
Figure 4:
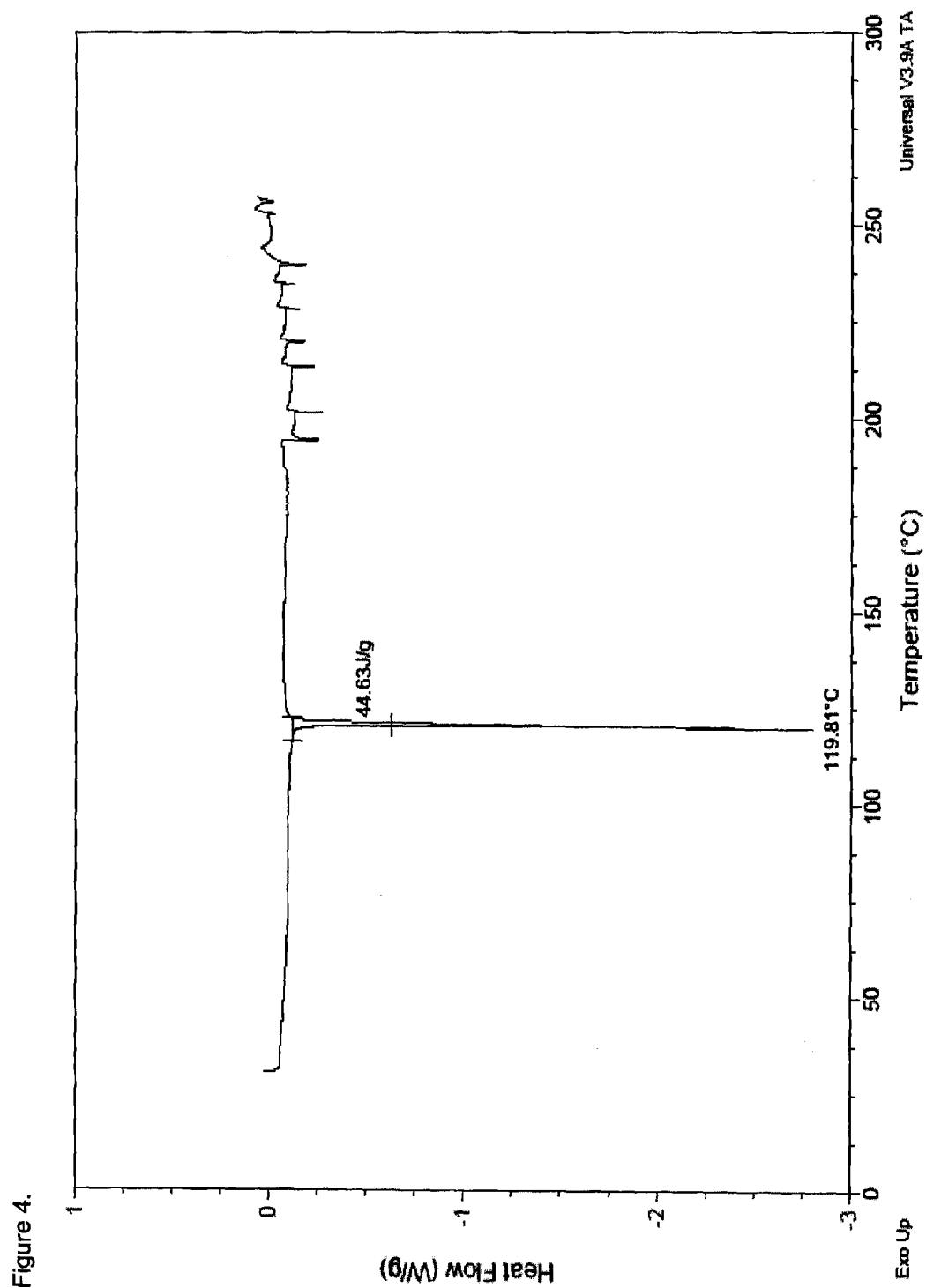
FIG. 4 is the differential scanning calorimetry (DSC) thermogram of polymorphic oxycodone pamoate.
Figure 5:
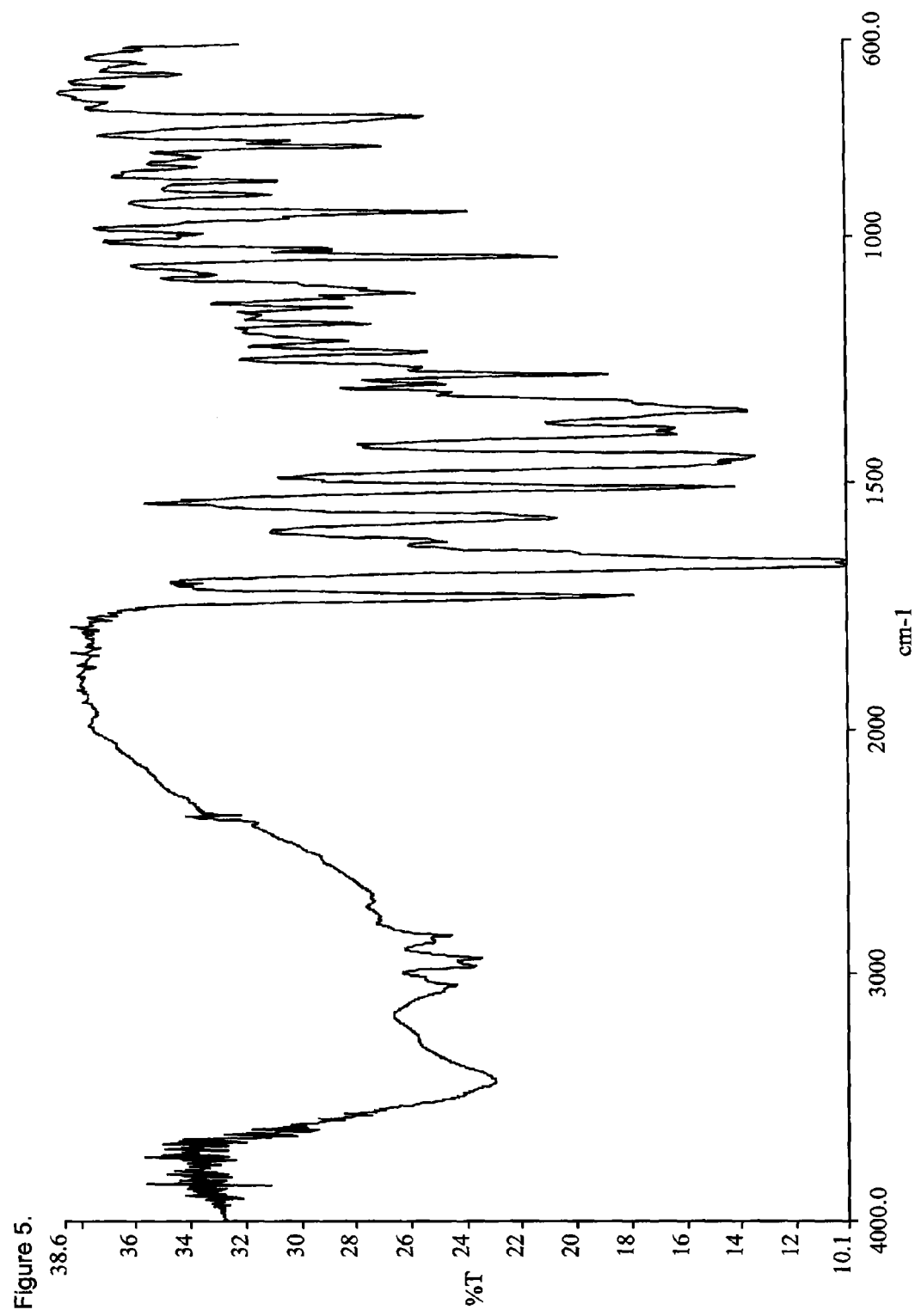
FIG. 5 is the Fourier Transform Infrared (FTIR) spectrum of polymorphic oxycodone pamoate.
Figure 6:
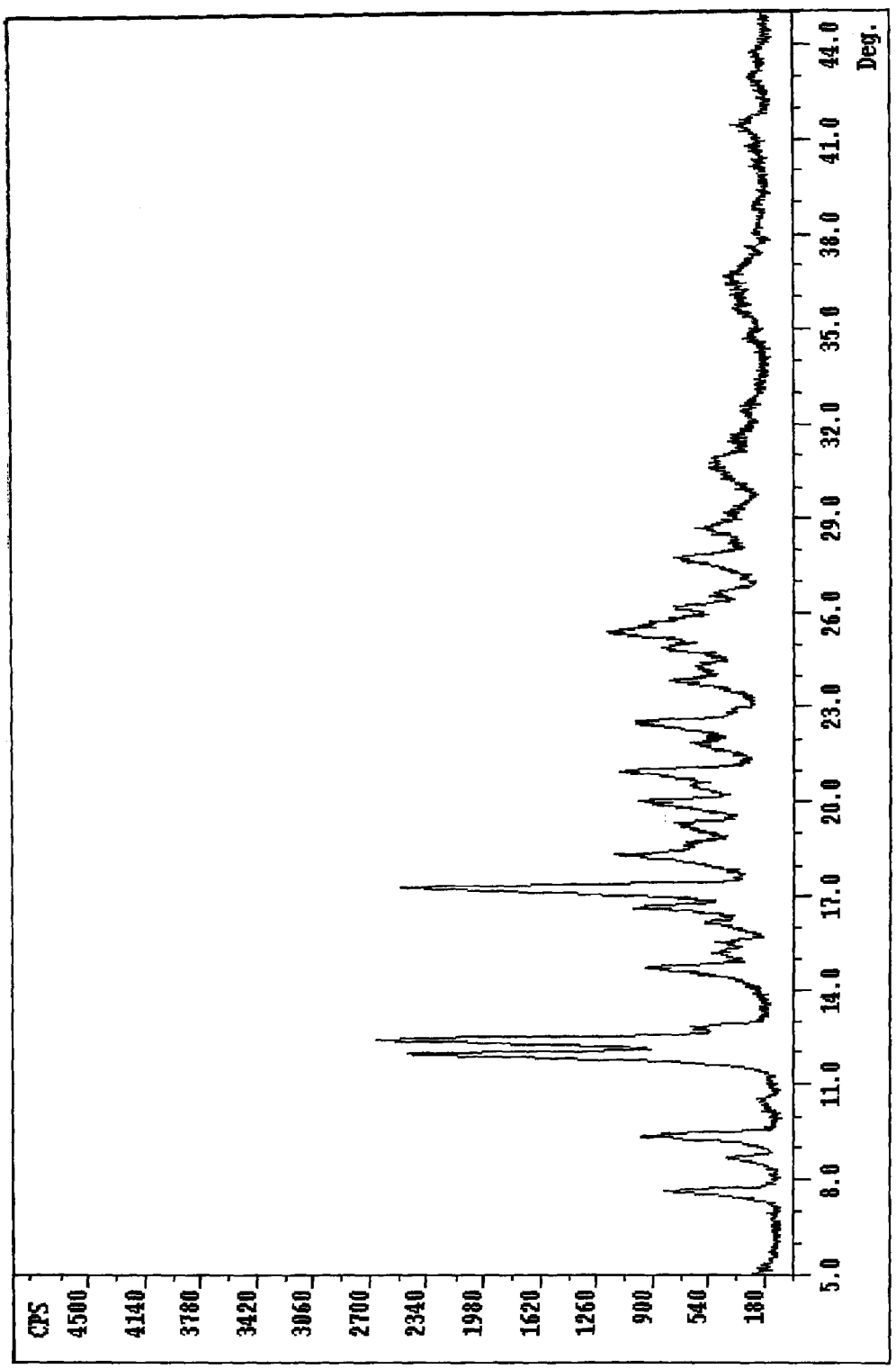
FIG. 6 is the powder X-ray diffraction (PXRD) diffractogram of polymorphic oxycodone pamoate.
Figure 7:
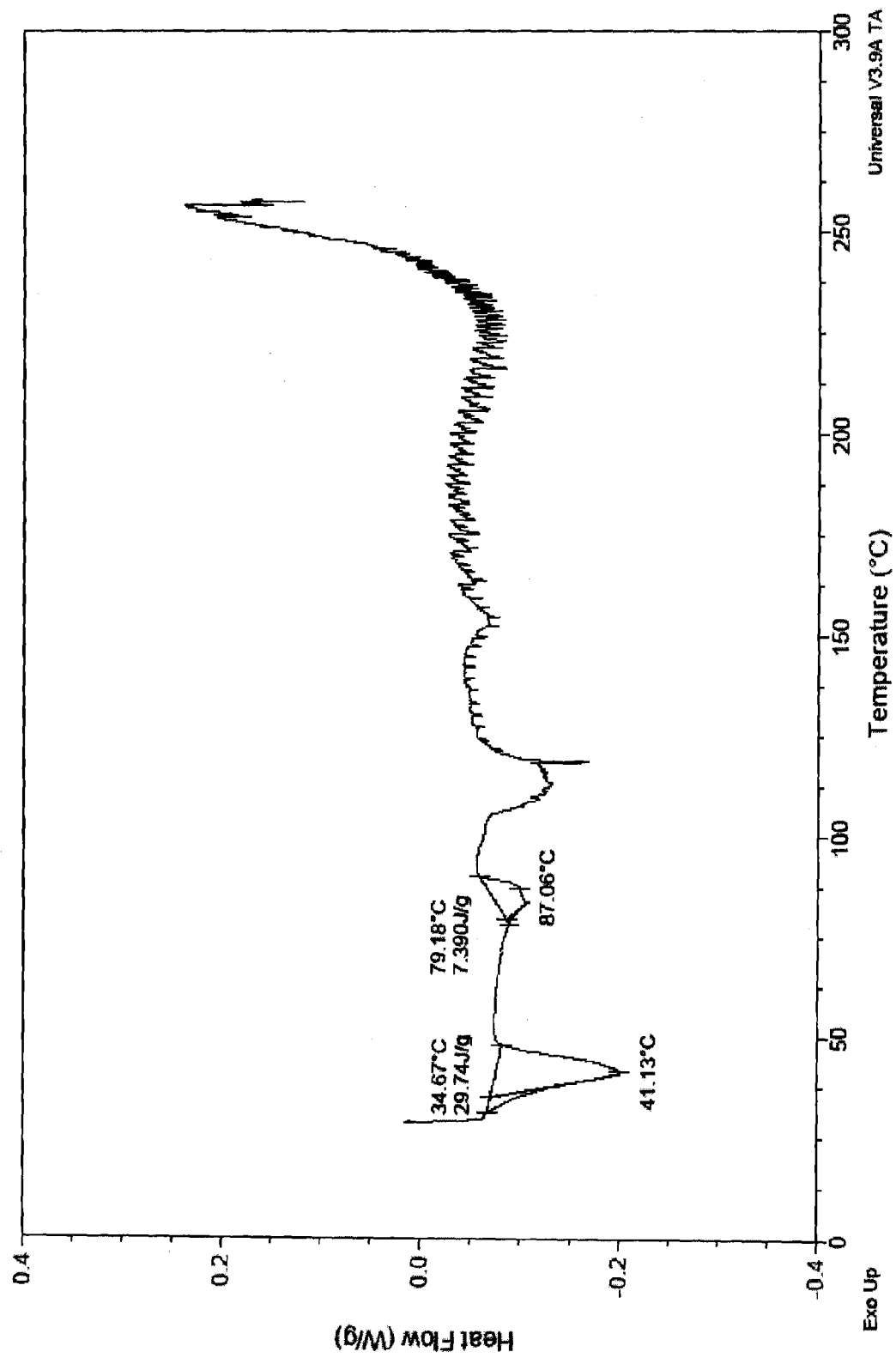
FIG. 7 is the differential scanning calorimetry (DSC) thermogram of oxycodone xinafoate.
Figure 8:
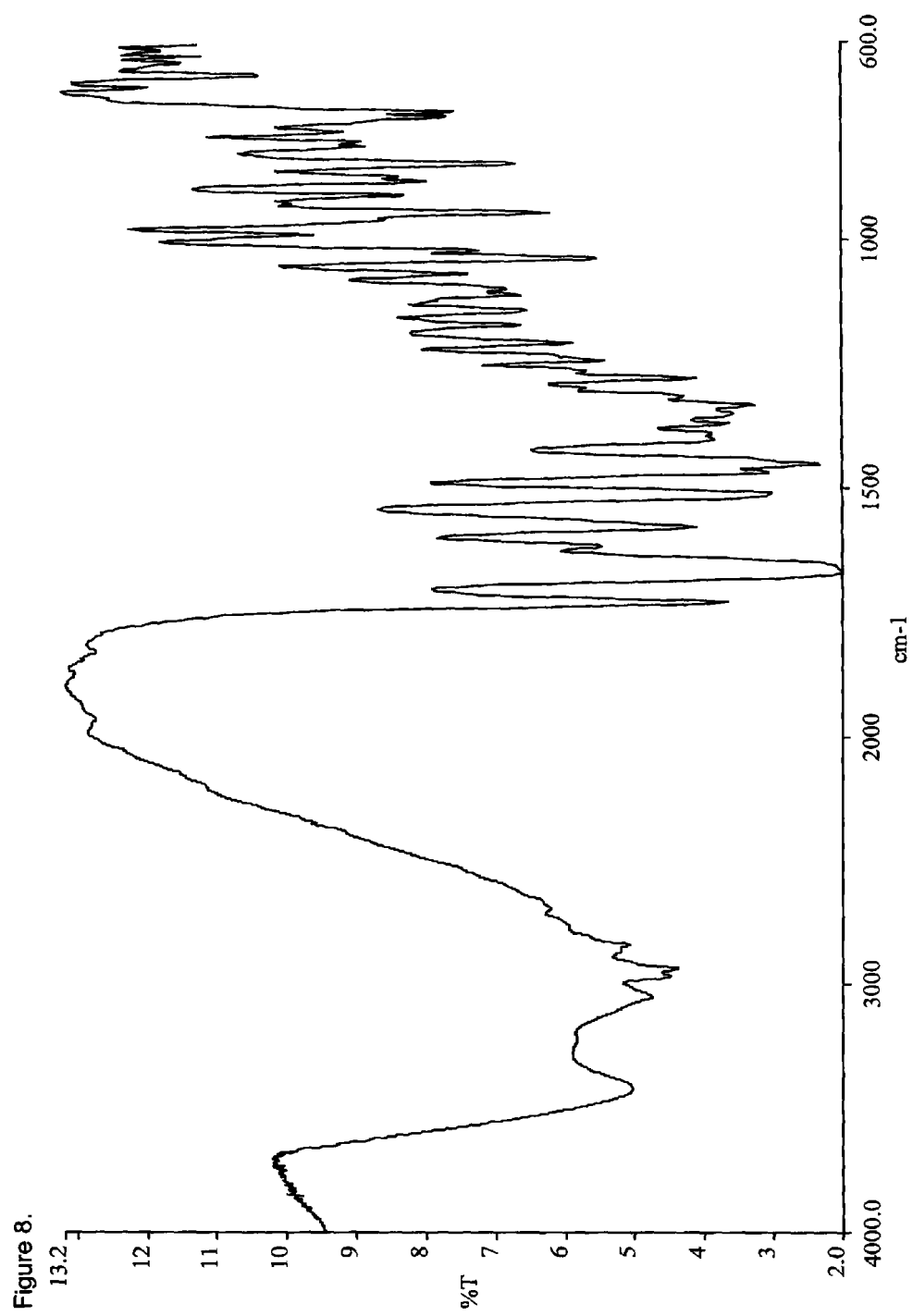
FIG. 8 is the Fourier Transform Infrared (FTIR) spectrum of oxycodone xinafoate.
Figure 9:
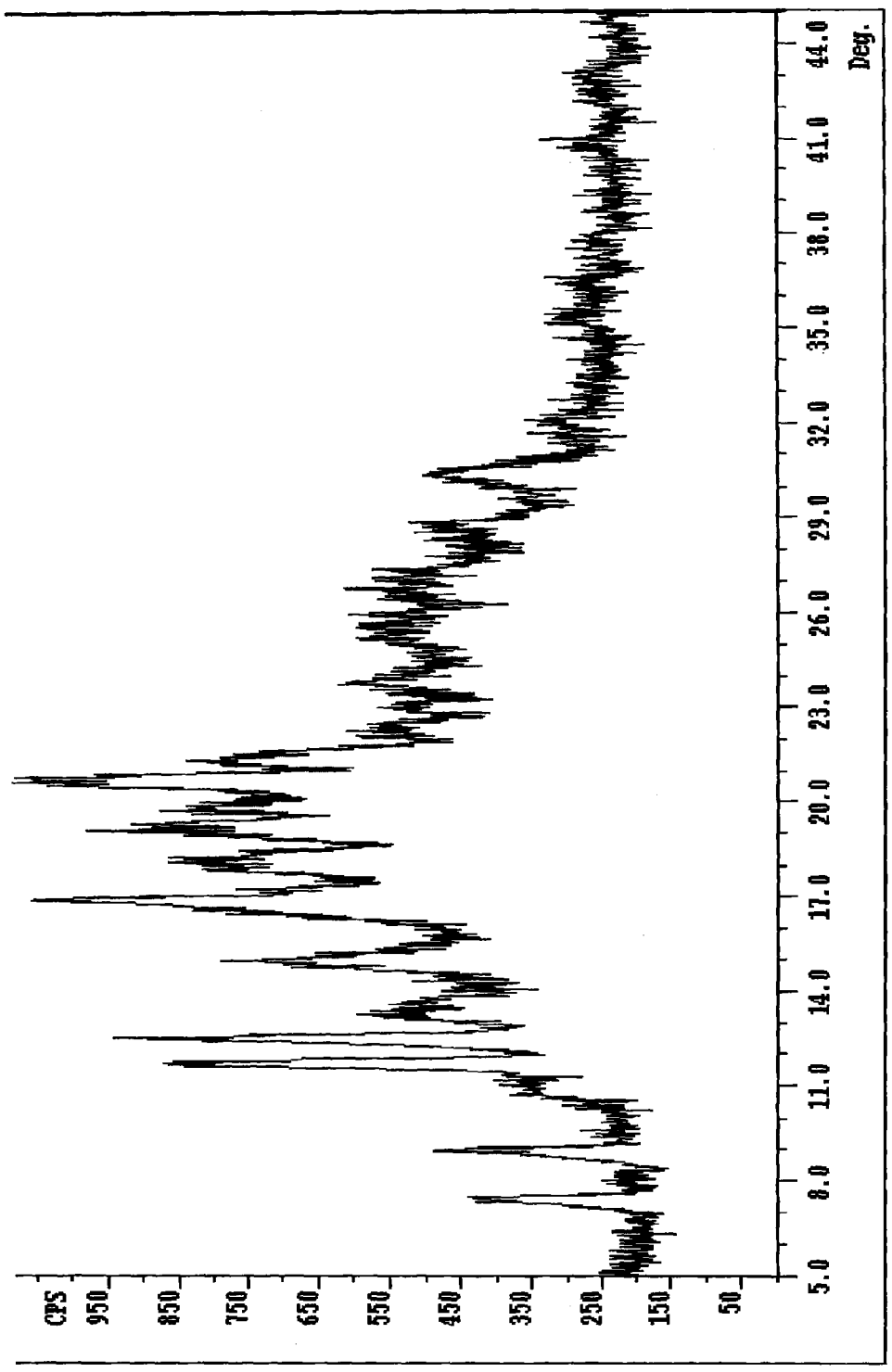
FIG. 9 is the powder X-ray diffraction (PXRD) diffractogram of oxycodone xinafoate.
Figure 10:
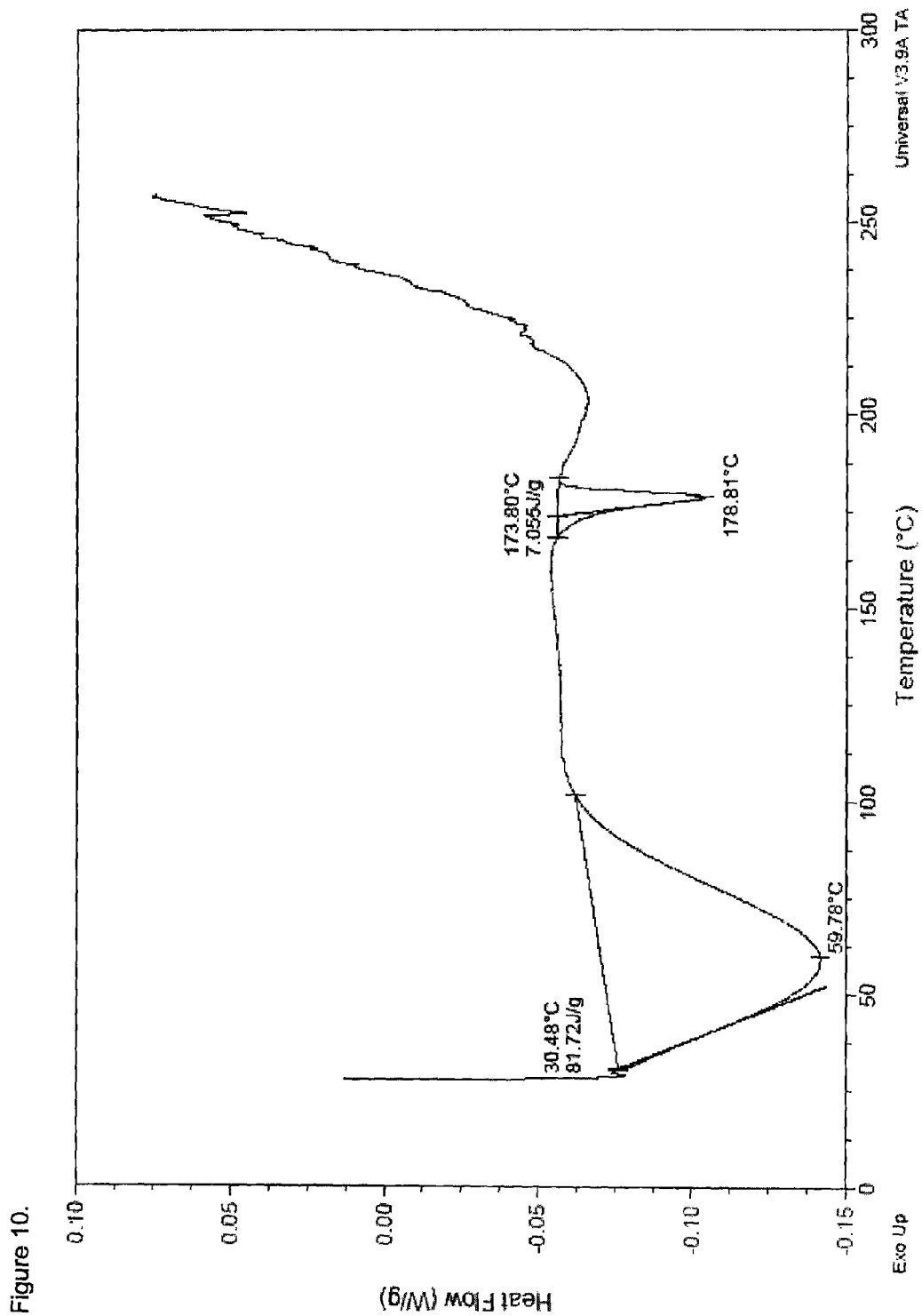
FIG. 10 is the differential scanning calorimetry (DSC) thermogram of amorphous hydrocodone pamoate.
Figure 11:
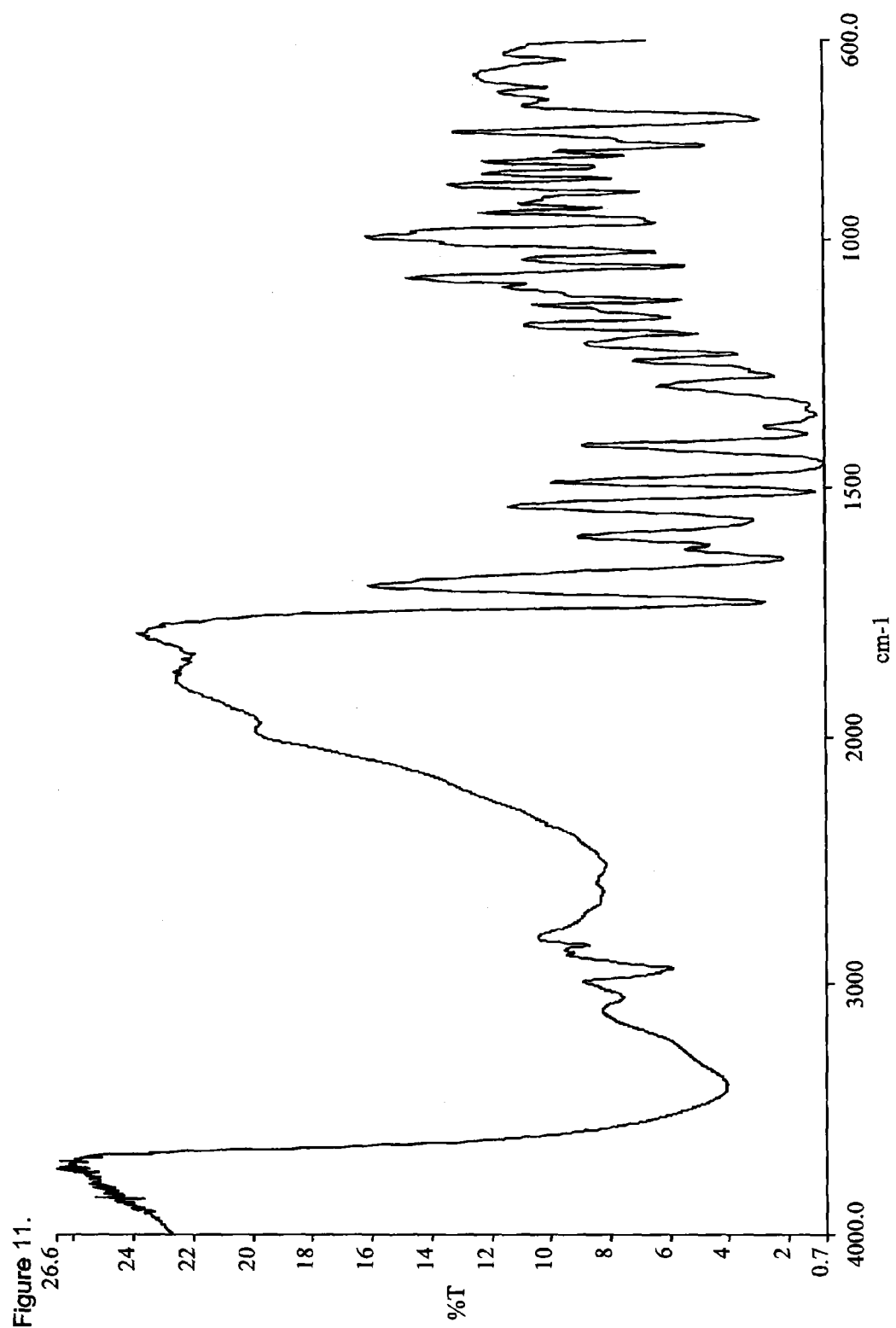
FIG. 11 is the Fourier Transform Infrared (FTIR) spectrum of amorphous hydrocodone pamoate.
Figure 19:
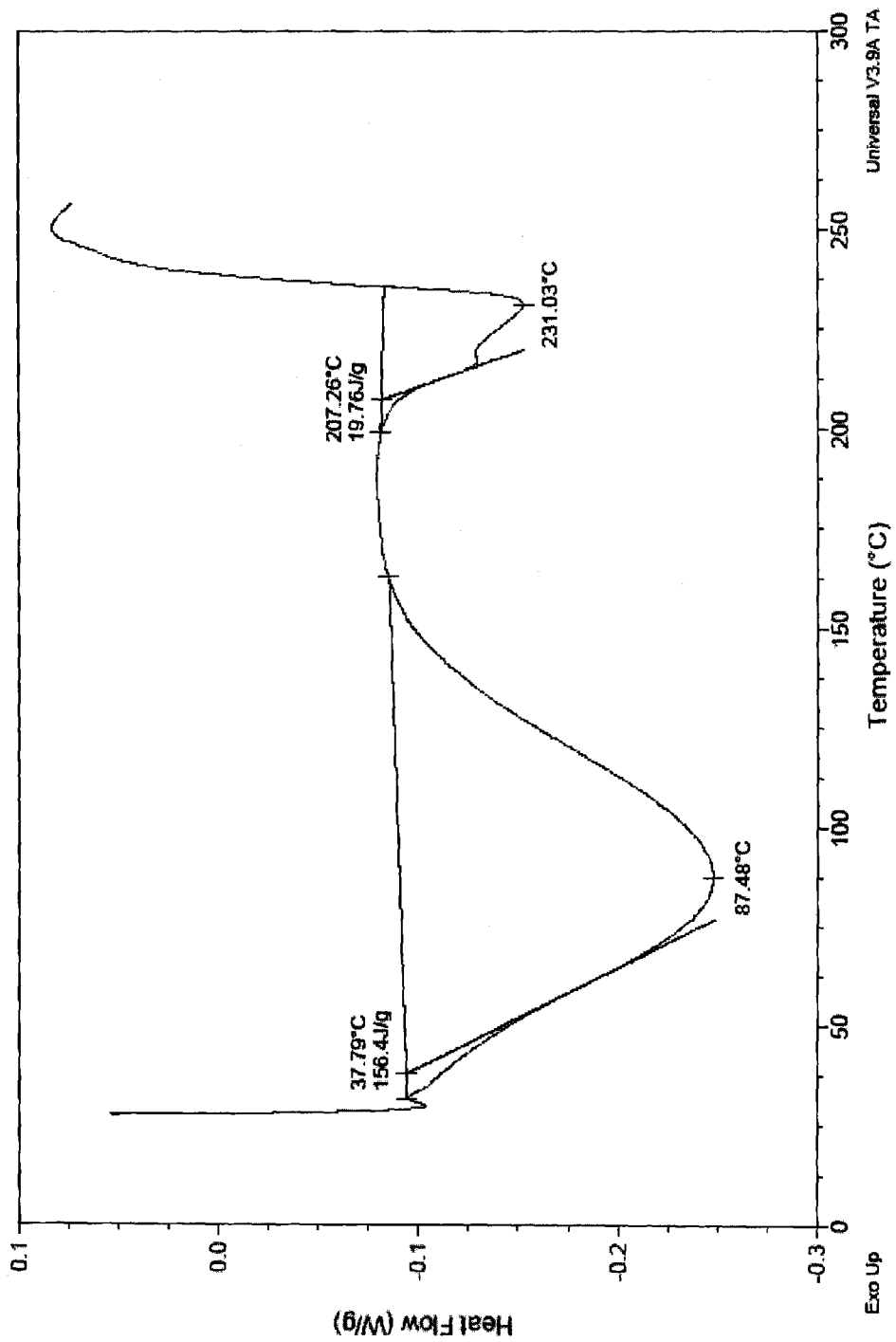
FIG. 19 is the differential scanning calorimetry (DSC) thermogram of amorphous hydromorphone pamoate.
Figure 20:
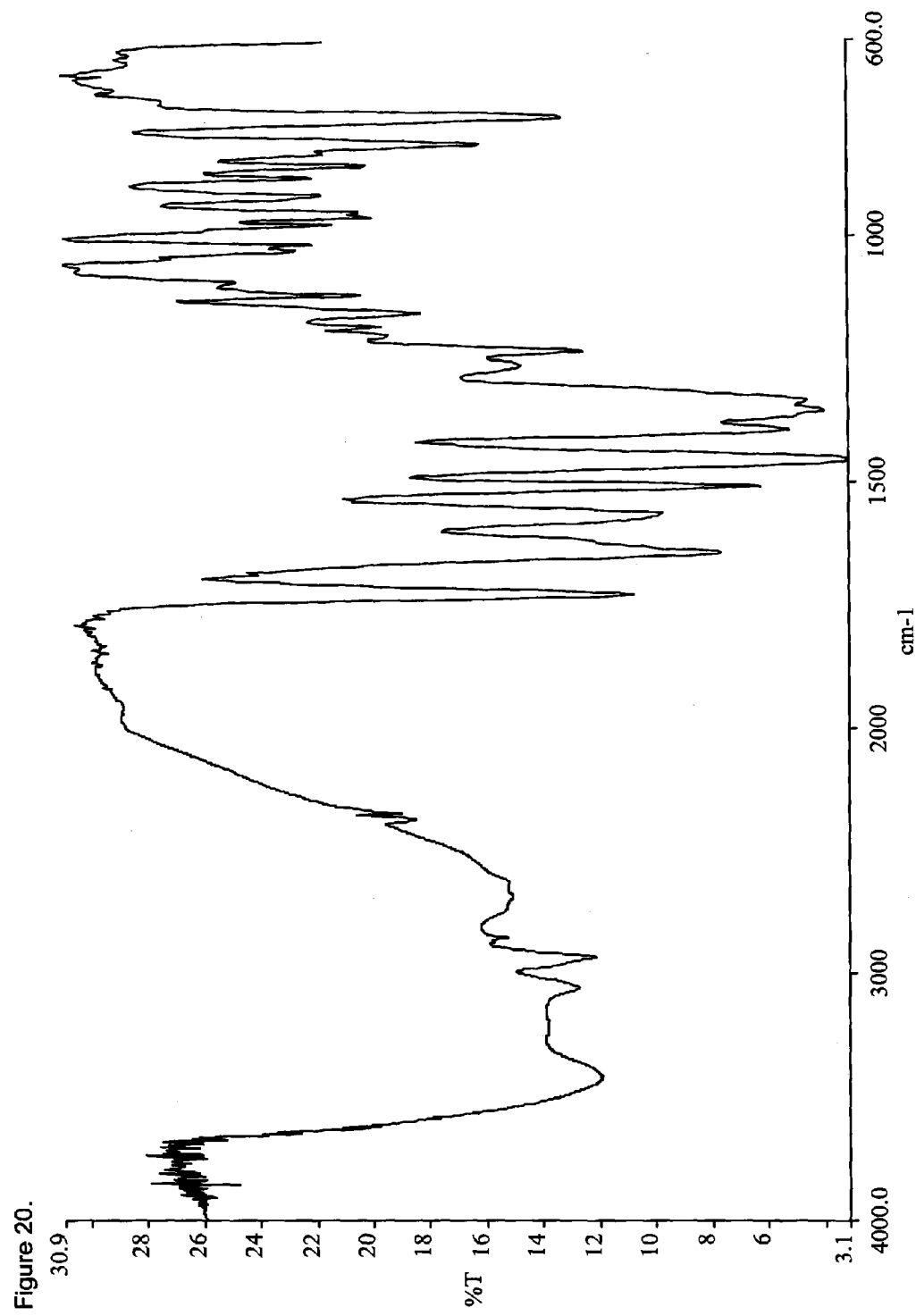
FIG. 20 is the Fourier Transform Infrared (FTIR) spectrum of amorphous hydromorphone pamoate.
Figure 21:
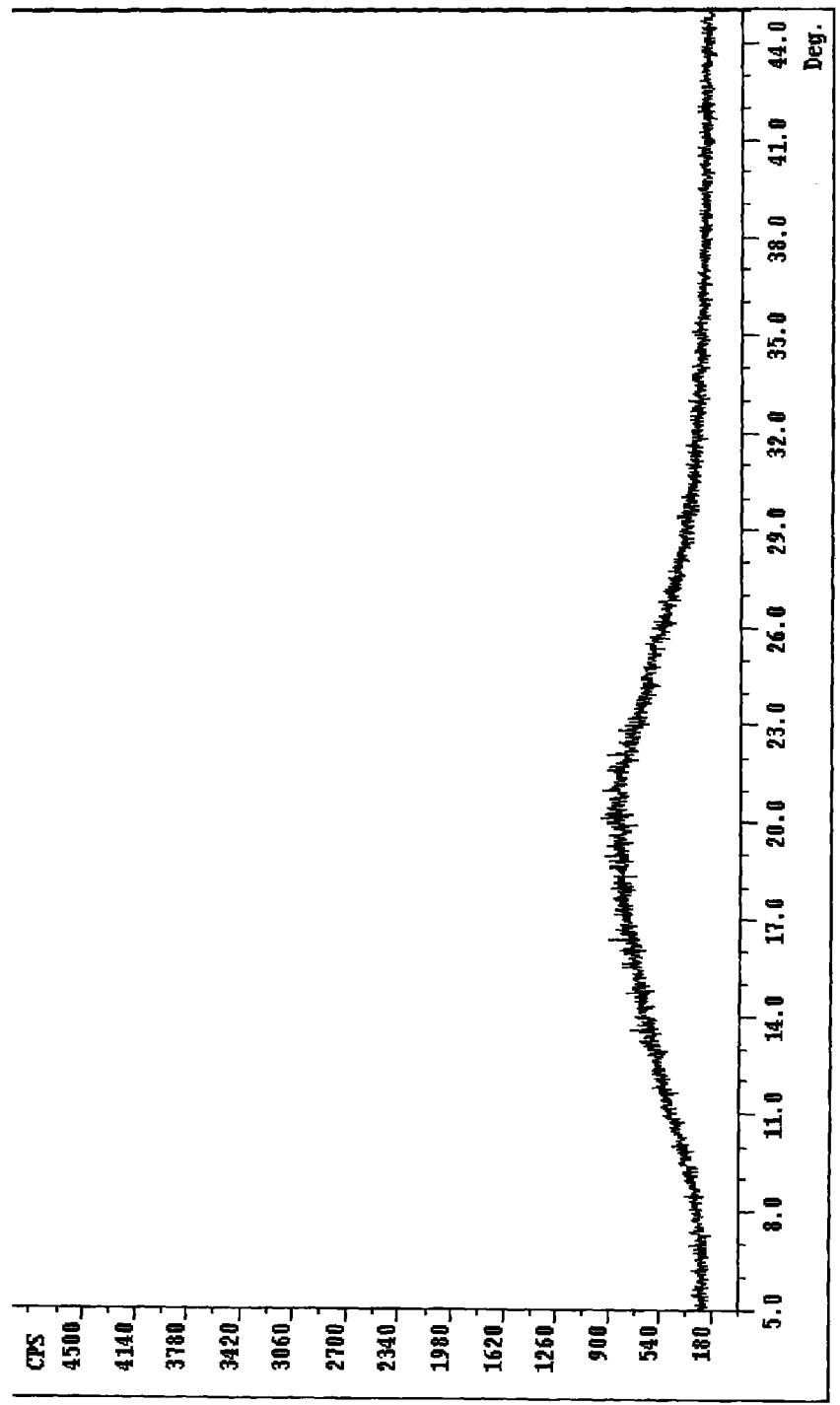
FIG. 21 is the powder X-ray diffraction (PXRD) diffractogram of amorphous hydromorphone pamoate.
Figure 22:
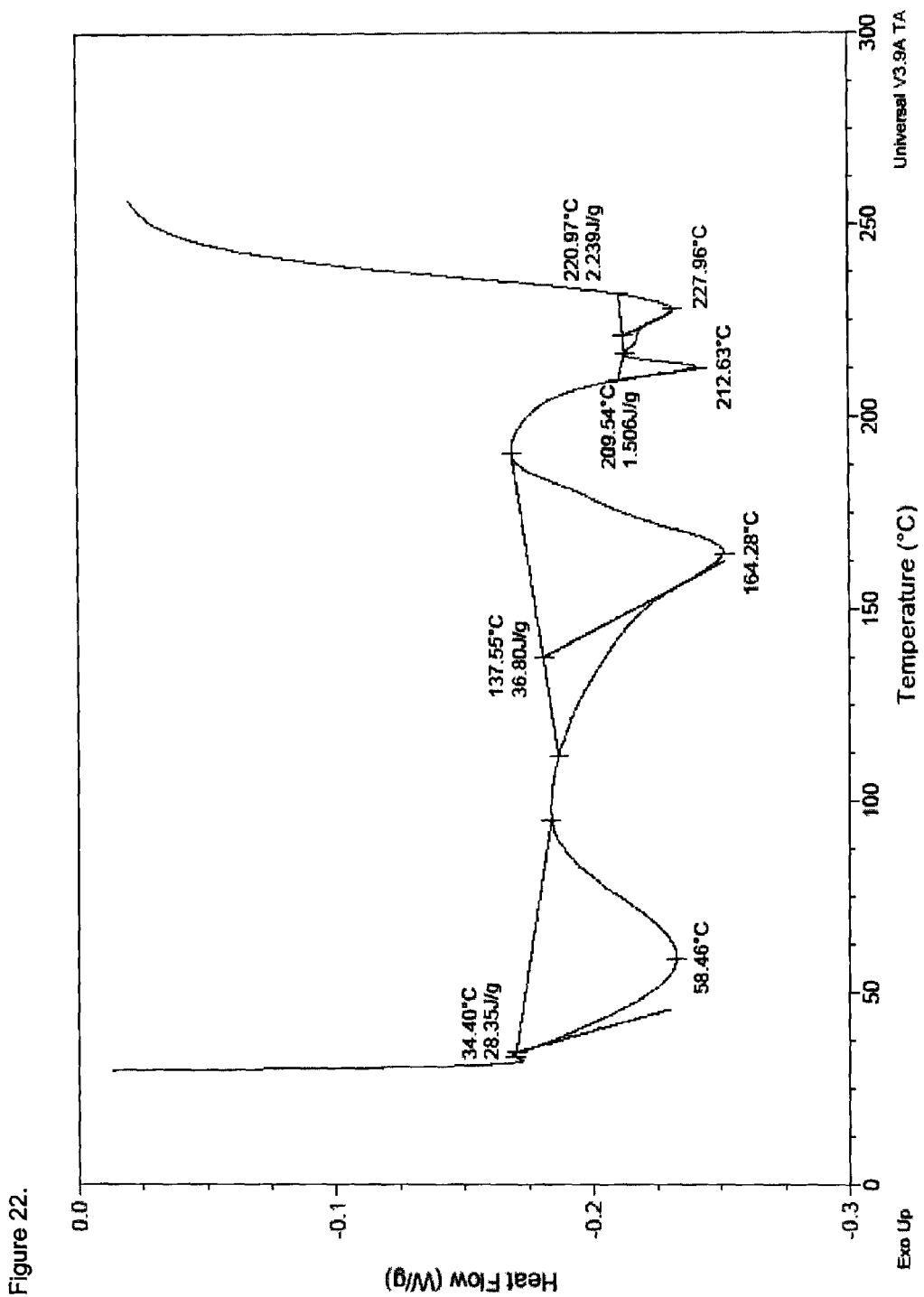
FIG. 22 is the differential scanning calorimetry (DSC) thermogram of polymorphic hydromorphone pamoate.
Figure 23:
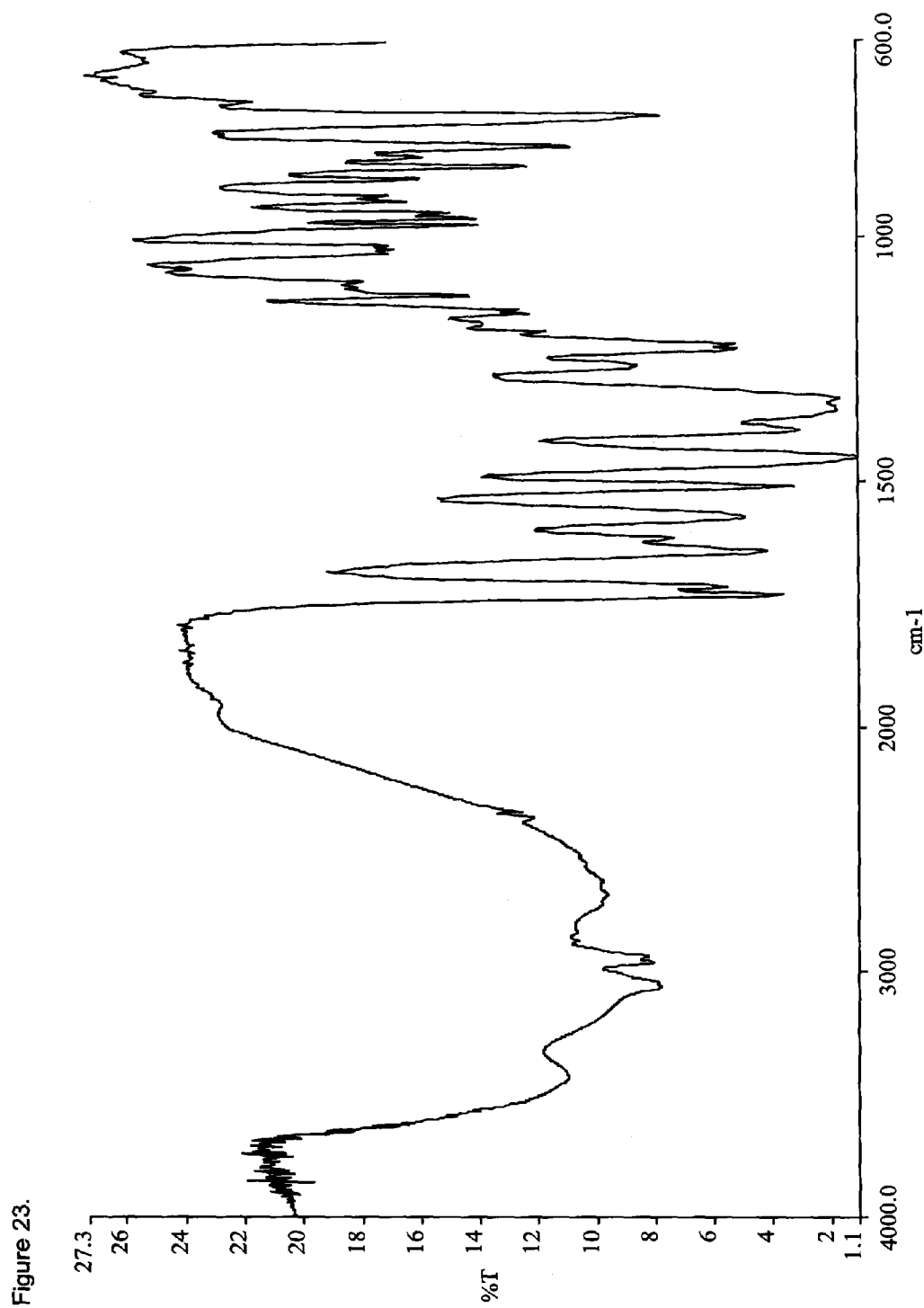
FIG. 23 is the Fourier Transform Infrared (FTIR) spectrum of polymorphic hydromorphone pamoate.
Figure 24:
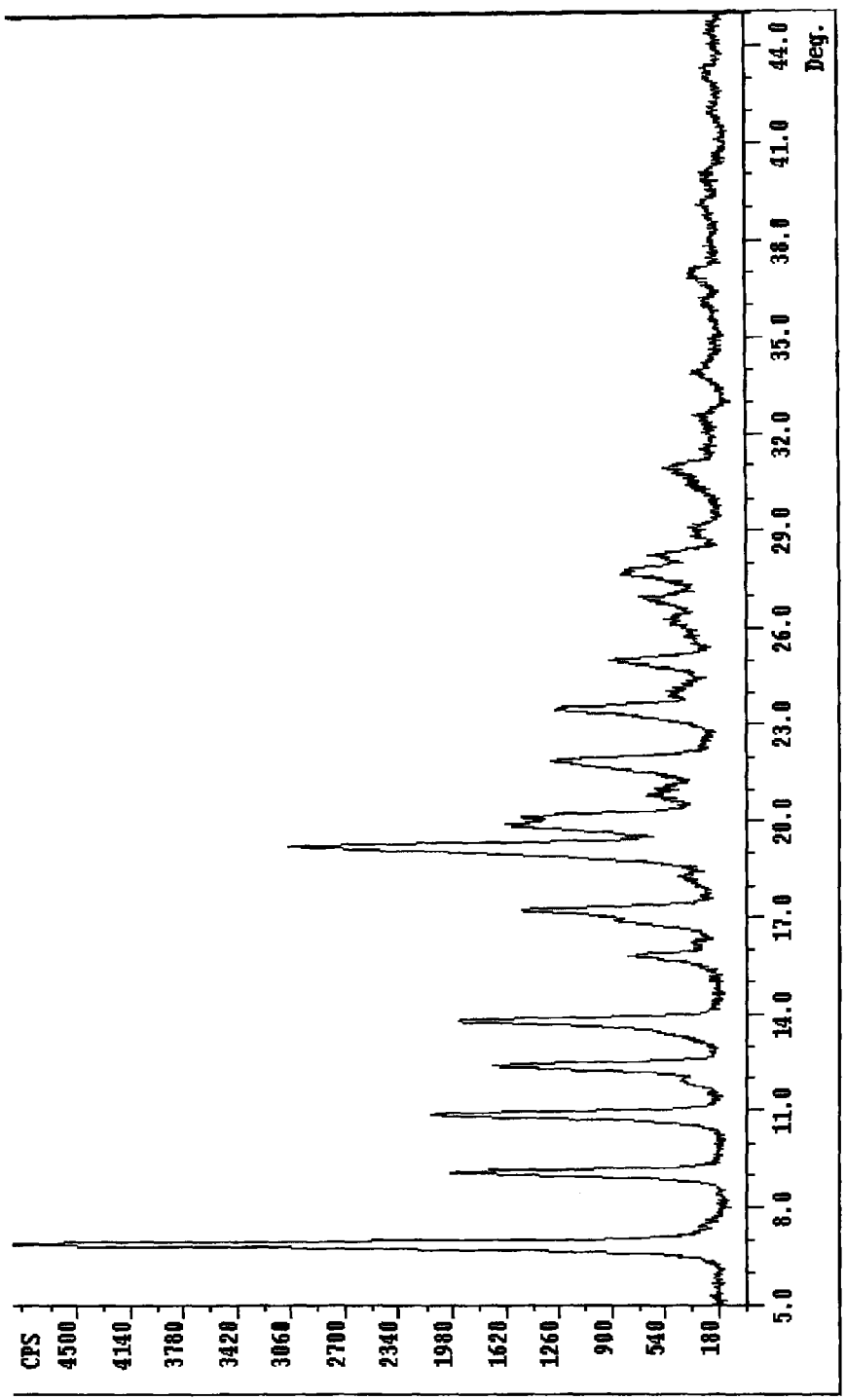
FIG. 24 is the powder X-ray diffraction (PXRD) diffractogram of polymorphic hydromorphone pamoate.
Figure 25:
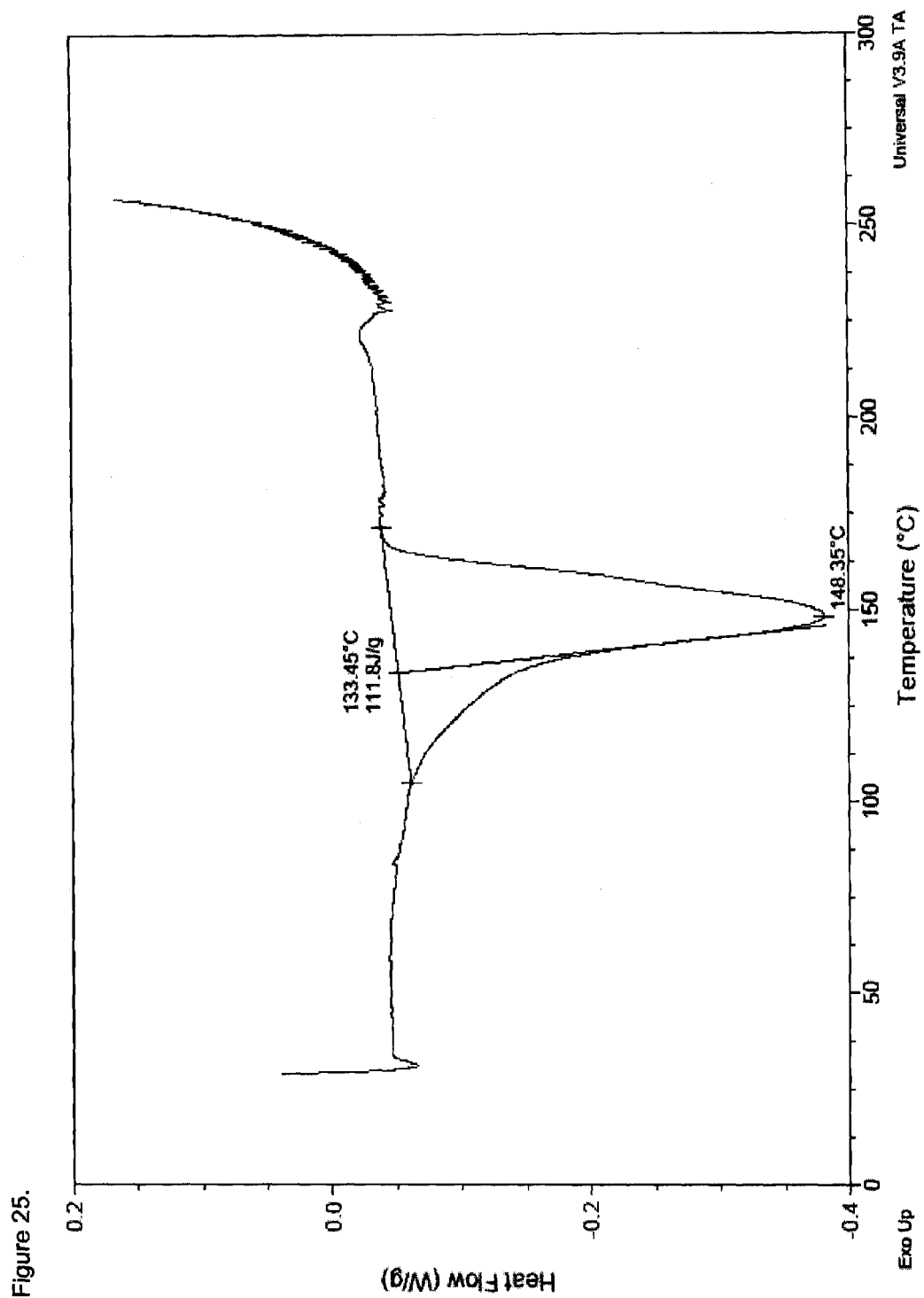
FIG. 25 is the differential scanning calorimetry (DSC) thermogram of hydromorphone xinafoate.
Figure 26:
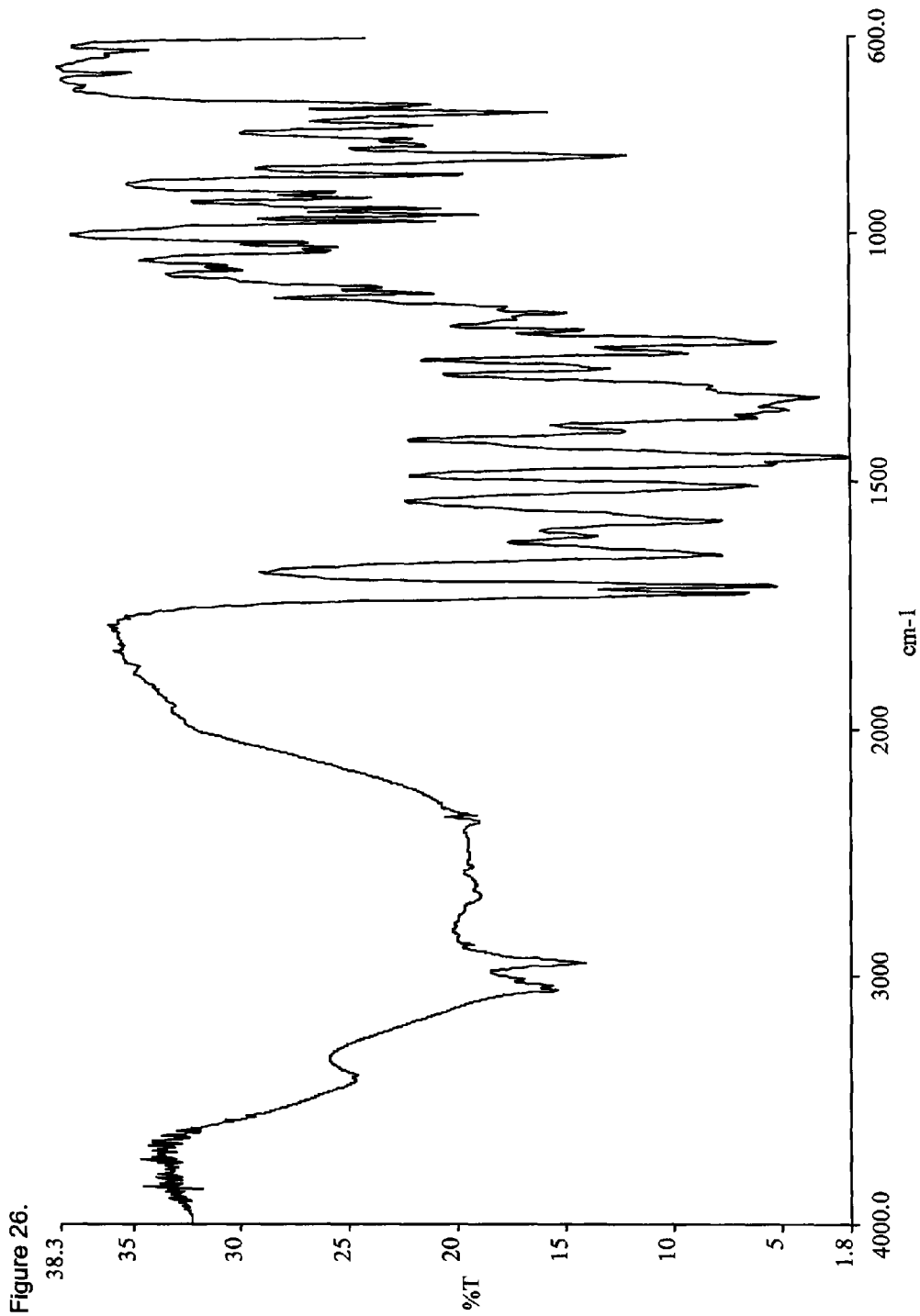
FIG. 26 is the Fourier Transform Infrared (FTIR) spectrum of hydromorphone xinafoate.
Figure 27:
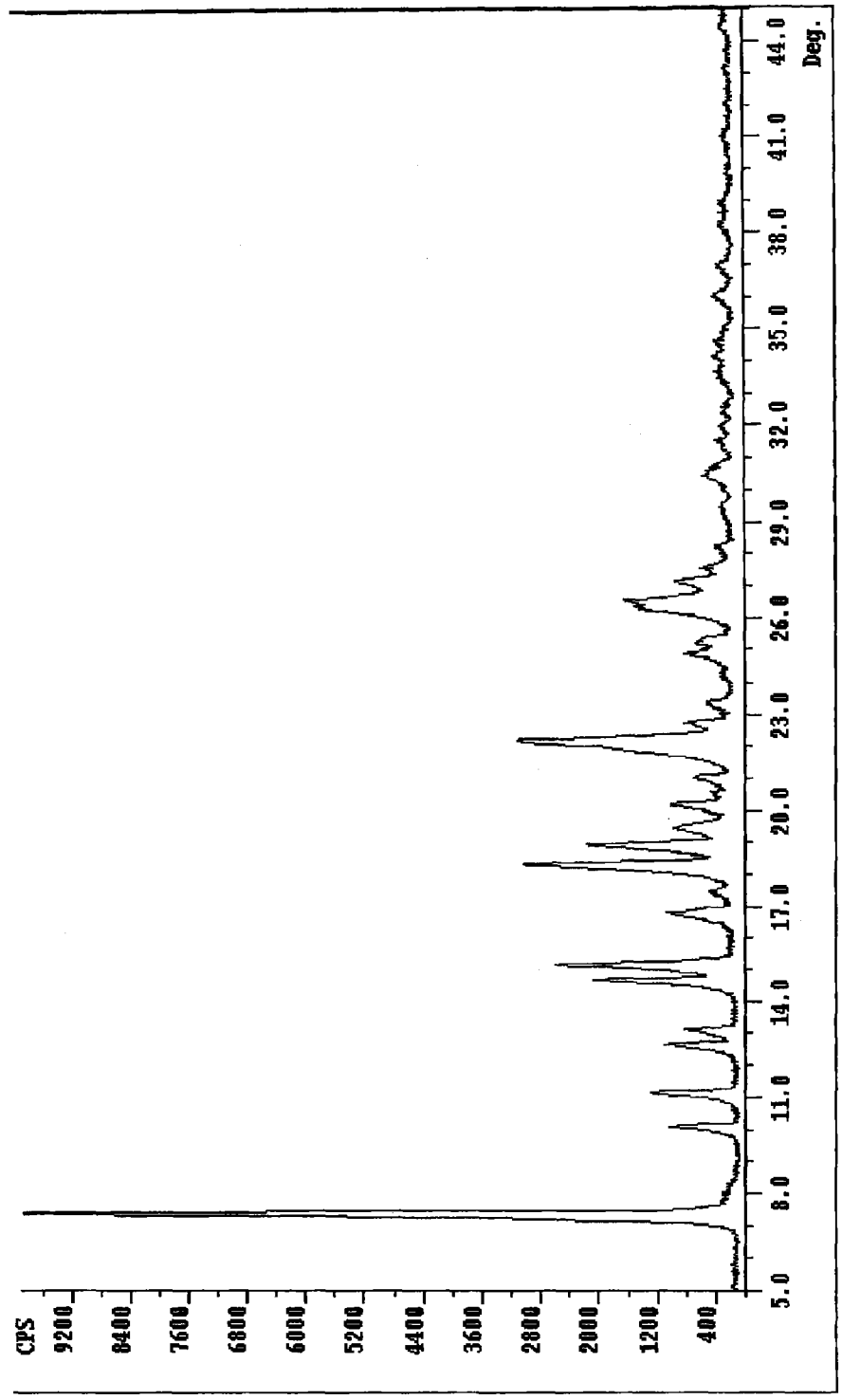
FIG. 27 is the powder X-ray diffraction (PXRD) diffractogram of hydromorphone xinafoate.
Figure 28:
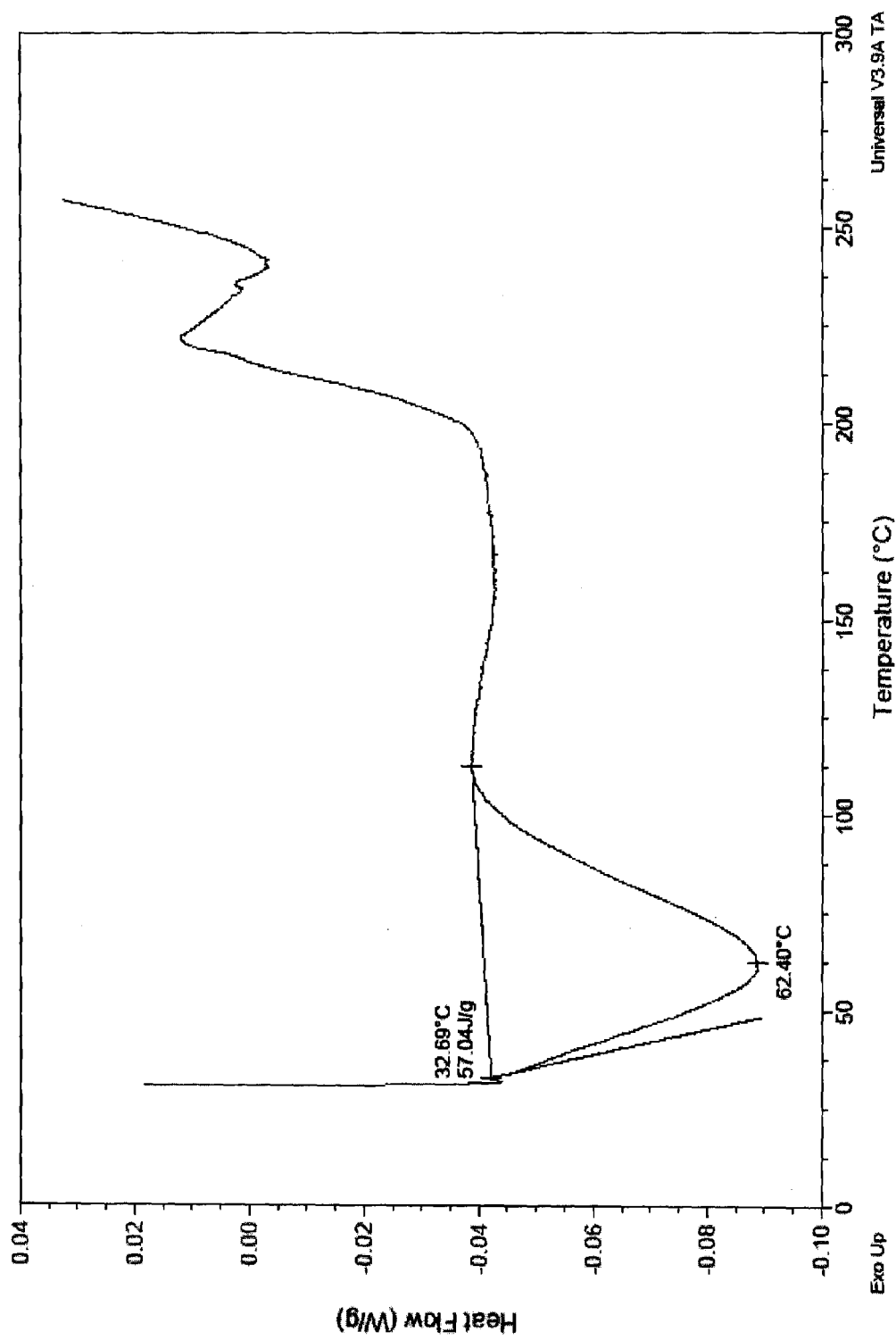
FIG. 28 is the differential scanning calorimetry (DSC) thermogram of amorphous morphine pamoate.
Figure 29:
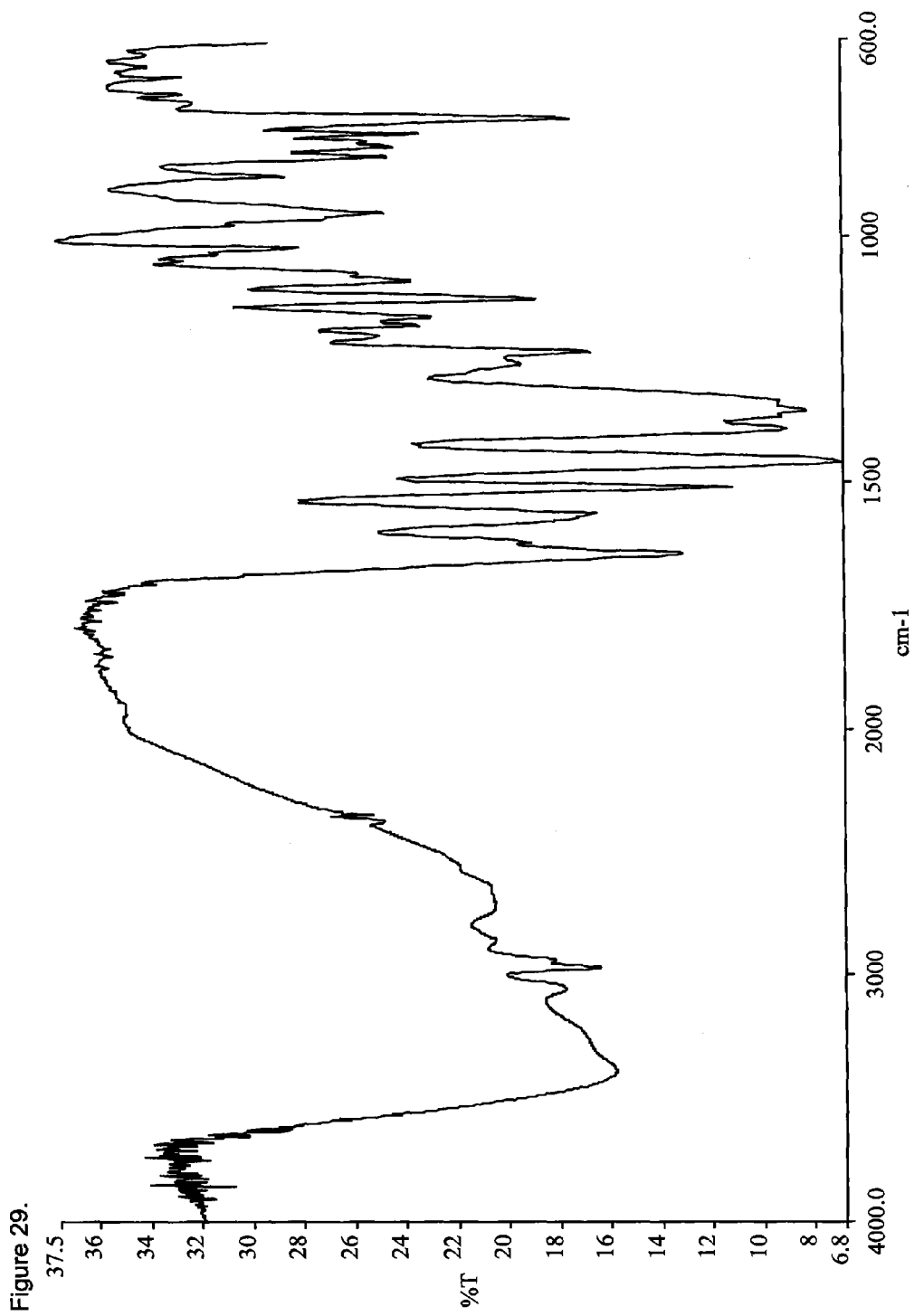
FIG. 29 is the Fourier Transform Infrared (FTIR) spectrum of amorphous morphine pamoate.
Figure 30:
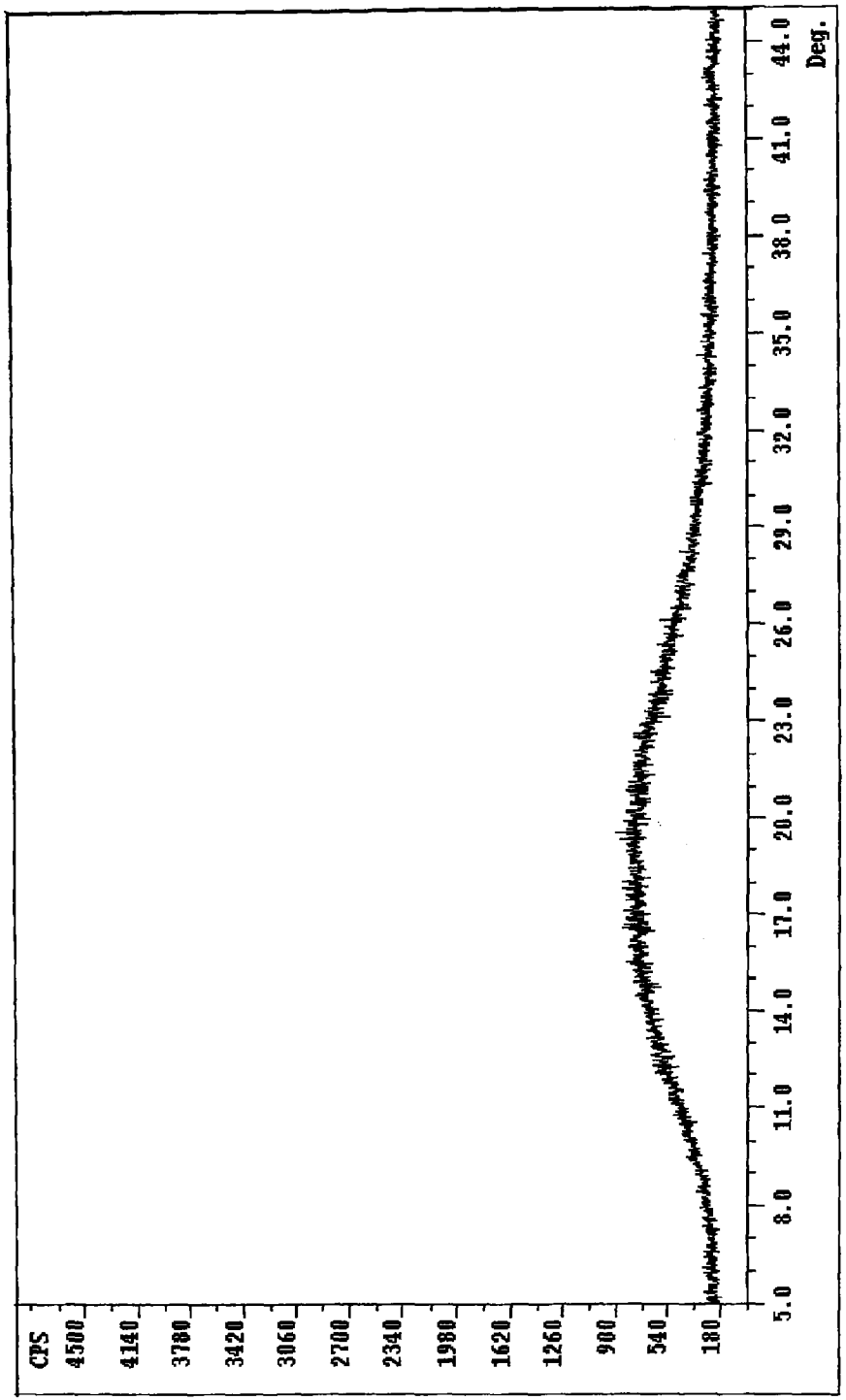
FIG. 30 is the powder X-ray diffraction (PXRD) diffractogram of amorphous morphine pamoate.
Figure 31:
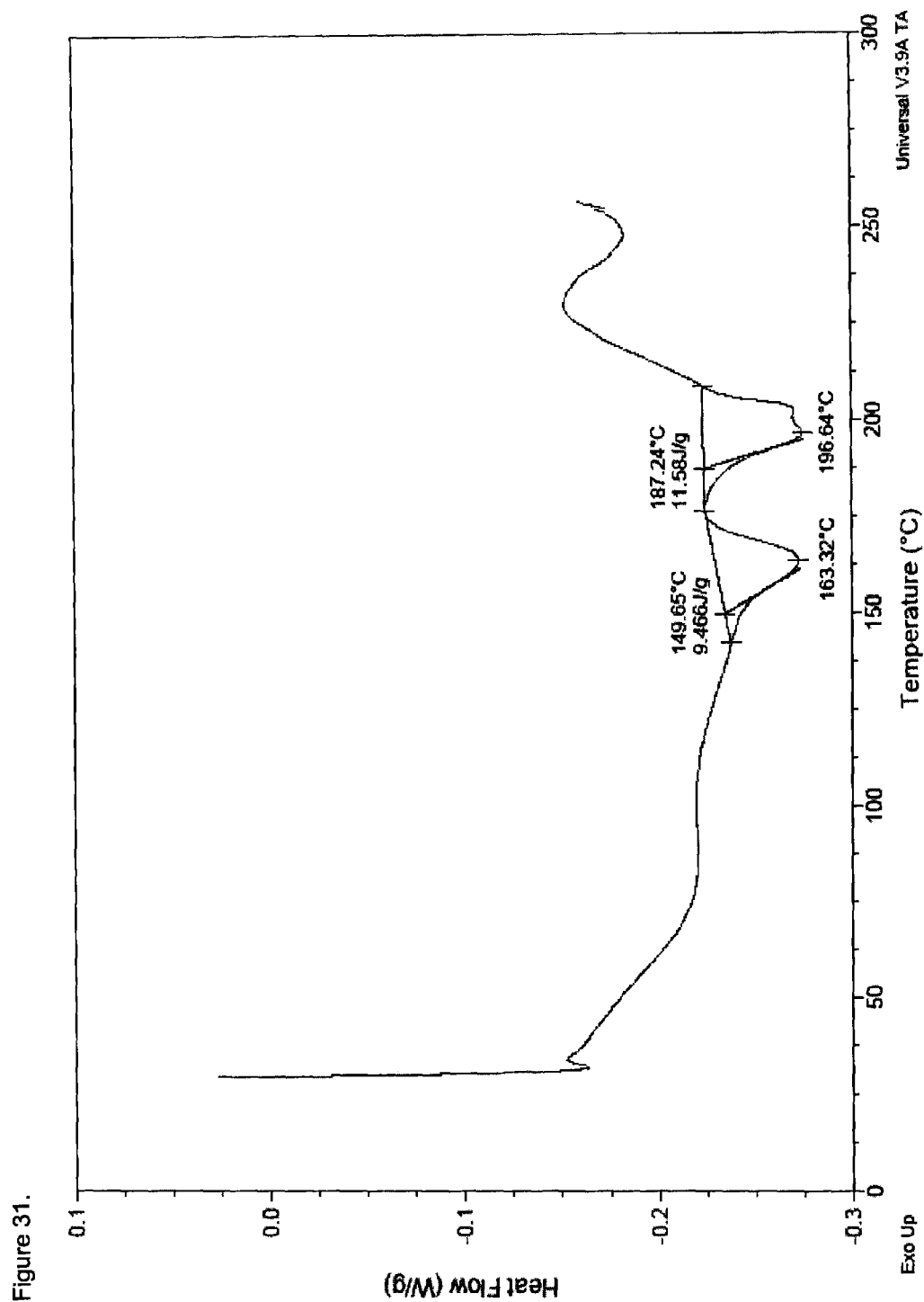
FIG. 31 is the differential scanning calorimetry (DSC) thermogram of polymorphic morphine pamoate.
Figure 32:
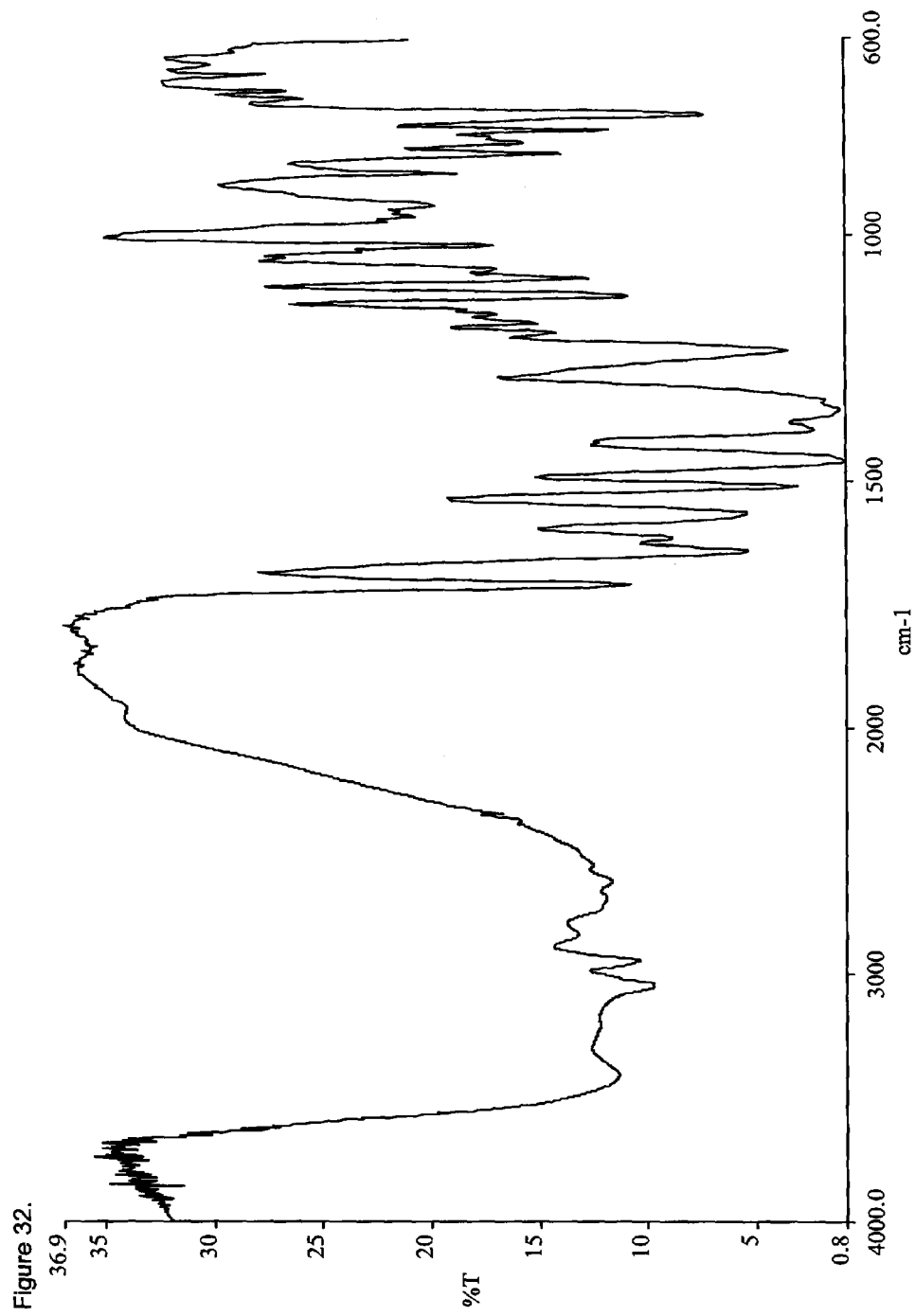
FIG. 32 is the Fourier Transform Infrared (FTIR) spectrum of polymorphic morphine pamoate.
Figure 33:
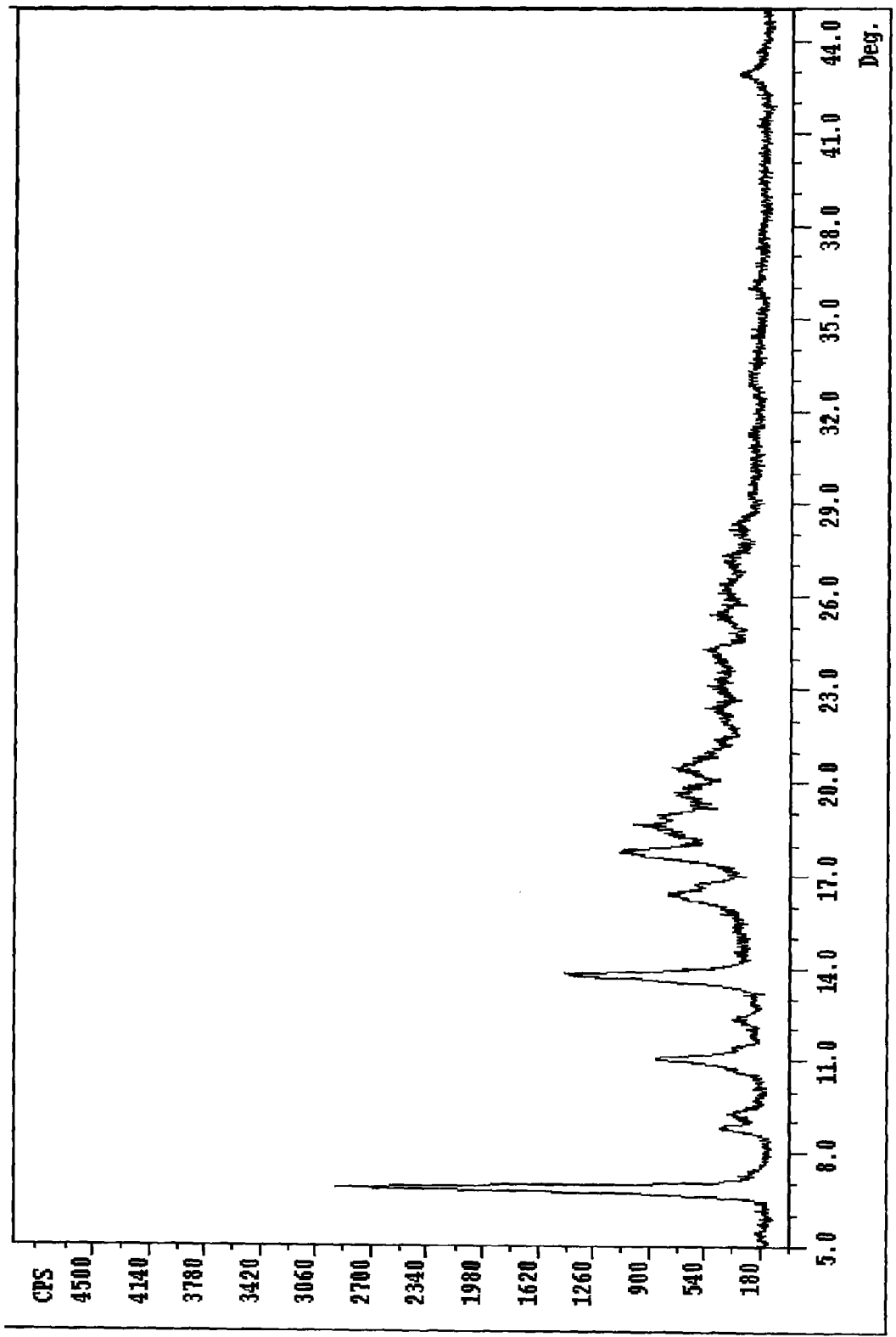
FIG. 33 is the powder X-ray diffraction (PXRD) diffractogram of polymorphic morphine pamoate.
Figure 34:
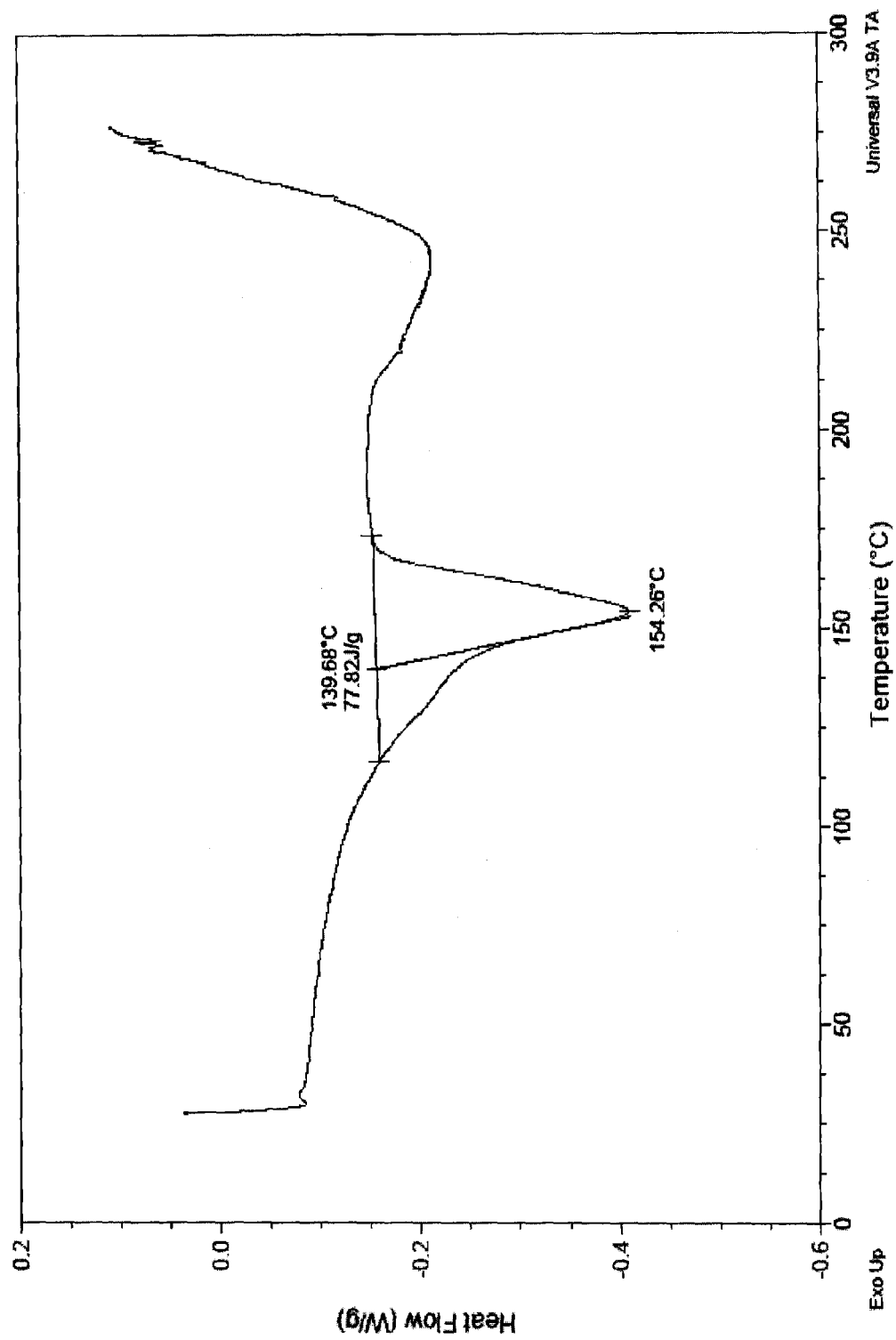
FIG. 34 is the differential scanning calorimetry (DSC) thermogram of morphine xinafoate.
Figure 35:
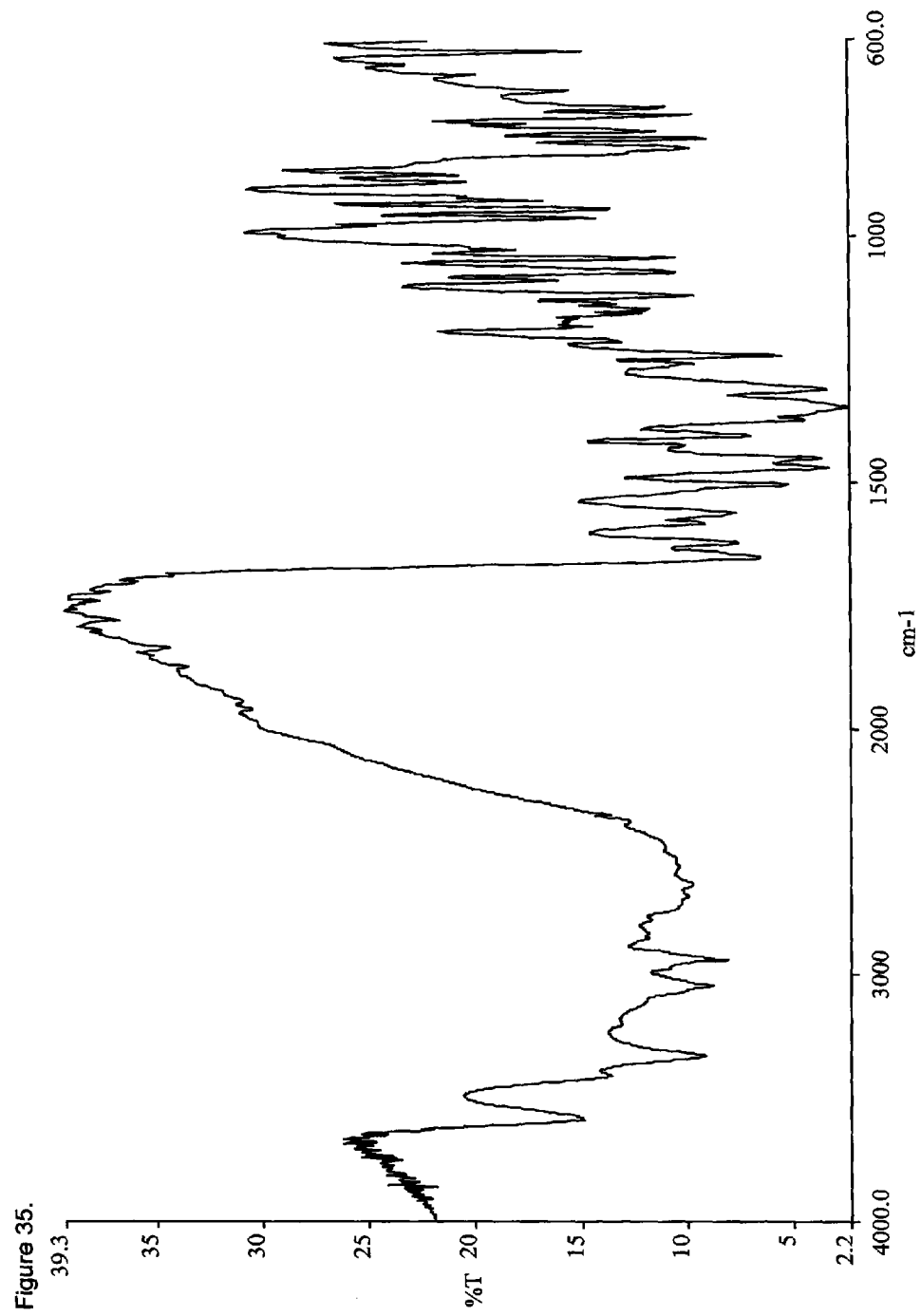
FIG. 35 is the Fourier Transform Infrared (FTIR) spectrum of morphine xinafoate.
Figure 36:
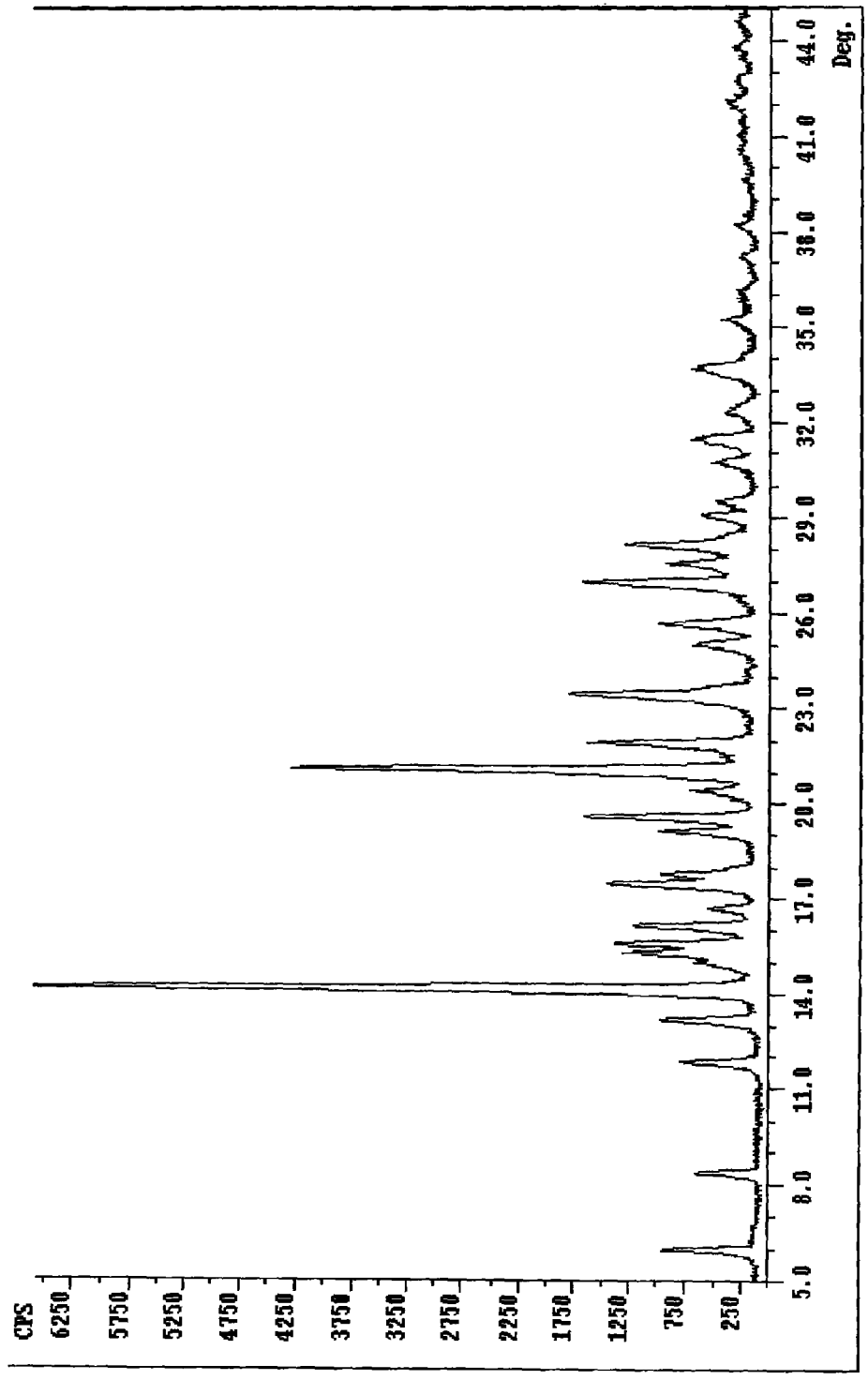
FIG. 36 is the powder X-ray diffraction (PXRD) diffractogram of morphine xinafoate.

71. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping and wherein one of said first opioid or said second opioid is a material selected from the group consisting of:

amorphous oxycodone pamoate characterized by at least one method selected from the group consisting of:
a differential scanning calorimetery thermogram of FIG. 1;
an FTIR of FIG. 2; and
an X-ray diffraction diffractogram of FIG. 3;
polymorphic oxycodone pamoate characterized by at least one method selected from the group consisting of:
a differential scanning calorimetery thermogram of FIG. 4;
an FTIR of FIG. 5; and
an X-ray diffraction diffractogram of FIG. 6;
oxycodone xinafoate characterized by at least one method selected from the group consisting of:
a differential scanning calorimetery thermogram of FIG. 7;
an FTIR of FIG. 8; and
an X-ray diffraction diffractogram of FIG. 9;
amorphous morphine pamoate characterized by at least one method selected from the group consisting of:
a differential scanning calorimetery thermogram of FIG. 28;
an FTIR of FIG. 29; and
an X-ray diffraction diffractogram of FIG. 30;
polymorphic morphine pamoate characterized by at least one method selected from the group consisting of:
a differential scanning calorimetery thermogram of FIG. 31;
an FTIR of FIG. 32; and
an X-ray diffraction diffractogram of FIG. 32; and
morphine xinafoate characterized by at least one method selected from the group consisting of:
a differential scanning calorimetery thermogram of FIG. 34;
an FTIR of FIG. 35;
an X-ray diffraction diffractogram of FIG. 36;
amorphous hydromorphone pamoate characterized by at least one method selected from the group consisting of:
a differential scanning calorimetery thermogram of FIG. 19;
an FTIR of FIG. 20; and
X-ray diffraction diffractogram of FIG. 21;
polymorphic hydromorphone pamoate characterized by at least one method selected from the group consisting of:
a differential scanning calorimetery thermogram of FIG. 22;
an FTIR of FIG. 23; and
X-ray diffraction diffractogram of FIG. 24; and
hydromorphone xinafoate characterized by at least one method selected from the group consisting of:
a differential scanning calorimetery thermogram of FIG. 25;
an FTIR of FIG. 26; and
X-ray diffraction diffractogram of FIG. 27.

72. A drug system comprising a first drug substance comprising a first opioid with an immediate release profile to reach a therapeutic level and a second drug substance comprising a second opioid with a slower release profile suitable for maintaining said therapeutic level wherein at least one drug substance selected from said first drug substance and said second drug substance is not susceptible to dose dumping and wherein one of said first opioid or said second opioid is
hydrocodone xinafoate characterized by at least one method selected from the group consisting of:
a differential scanning calorimetery thermogram of FIG. 16;
an FTIR of FIG. 17; and
X-ray diffraction diffractogram of FIG. 18.

73. The drug system of claim 1 wherein said second opioid is said material and said first opioid is selected from the group consisting of oxycodone, hydrocodone, morphine, apomorphine, hydromorphone, oxymorphone, codeine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, levorphanol, nalbuphine, nalmefene, naloxone, naltrexone, noscapine, opium and oripavine.

74. The drug system of claim 73 wherein said first opioid is selected from oxycodone pamoate, oxycodone xinafoate, hydrocodone pamoate, hydrocodone xinafoate, hydromorphone pamoate, hydromorphone xinafoate, morphine pamoate and morphine xinafoate.

75. The drug system of claim 74 wherein said first opioid is amorphous oxycodone pamoate.

76. The drug system of claim 75 wherein said oxycodone pamoate is characterized by a differential scanning calorimetery thermogram of FIG. 1.

77. The drug system of claim 75 wherein said oxycodone pamoate is characterized by an FTIR of FIG. 2.

78. The drug system of claim 75 wherein said oxycodone pamoate is characterized by an X-ray diffraction diffractogram of FIG. 3.

79. The drug system of claim 74 wherein said first opioid is polymorphic oxycodone pamoate.

80. The drug system of claim 79 wherein said oxycodone pamoate is characterized by a differential scanning calorimetery thermogram of FIG. 4.

81. The drug system of claim 79 wherein said oxycodone pamoate is characterized by an FTIR of FIG. 5.

82. The drug system of claim 79 wherein said oxycodone pamoate is characterized by an X-ray diffraction diffractogram of FIG. 6.

83. The drug system of claim 74 wherein said first opioid is oxycodone xinafoate characterized by a differential scanning calorimetery thermogram of FIG. 7.

84. The drug system of claim 74 wherein said first opioid is oxycodone xinafoate characterized by an FTIR of FIG. 8.

85. The drug system of claim 74 wherein said first opioid is oxycodone xinafoate characterized by an X-ray diffraction diffractogram of FIG. 9.

86. The drug system of claim 74 wherein said first opioid is morphine pamoate with less than 3 waters of hydration.

87. The drug system of claim 74 wherein said first opioid is amorphous morphine pamoate.

88. The drug system of claim 87 wherein said morphine pamoate is characterized by a differential scanning calorimetery thermogram of FIG. 28.

89. The drug system of claim 87 wherein said morphine pamoate is characterized by an FTIR of FIG. 29.

90. The drug system of claim 87 wherein said morphine pamoate is characterized by an X-ray diffraction diffractogram of FIG. 30.

91. The drug system of claim 74 wherein said first opioid is polymorphic morphine pamoate.

92. The drug system of claim 91 wherein said morphine pamoate is characterized by a differential scanning calorimetery thermogram of FIG. 31.

93. The drug system of claim 91 wherein said morphine pamoate is characterized by an FTIR of FIG. 32.

94. The drug system of claim 91 wherein said morphine pamoate is characterized by an X-ray diffraction diffractogram of FIG. 33.

95. The drug system of claim 74 wherein said first opioid is morphine xinafoate characterized by a differential scanning calorimetery thermogram of FIG. 34.

96. The drug system of claim 74 wherein said first opioid is morphine xinafoate characterized by an FTIR of FIG. 35.

97. The drug system of claim 74 wherein said first opioid is morphine xinafoate characterized by an X-ray diffraction diffractogram of FIG. 36.

98. The drug system of claim 74 wherein said material is hydrocodone xinafoate characterized by a differential scanning calorimetery thermogram of FIG. 16.

99. The drug system of claim 74 wherein said material is hydrocodone xinafoate characterized by an FTIR of FIG. 17.

100. The drug system of claim 74 wherein said material is hydrocodone xinafoate characterized by an X-ray diffraction diffractogram of FIG. 18.

101. The drug system of claim 74 wherein said material is amorphous hydromorphone pamoate.

102. The drug system of claim 101 wherein said hydromorphone pamoate is characterized by a differential scanning calorimetery thermogram of FIG. 19.

103. The drug system of claim 101 wherein said hydromorphone pamoate is characterized by an FTIR of FIG. 20.

104. The drug system of claim 101 wherein said hydromorphone pamoate is characterized by an X-ray diffraction diffractogram of FIG. 21.

105. The drug system of claim 74 wherein said material is polymorphic hydromorphone pamoate.

106. The drug system of claim 105 wherein said hydromorphone pamoate is characterized by a differential scanning calorimetery thermogram of FIG. 22.

107. The drug system of claim 105 wherein said hydromorphone pamoate is characterized by an FTIR of FIG. 23.

108. The drug system of claim 105 wherein said hydromorphone pamoate is characterized by an X-ray diffraction diffractogram of FIG. 24.

109. The drug system of claim 74 wherein said material is hydromorphone xinafoate characterized by a differential scanning calorimetery thermogram of FIG. 25.

110. The drug system of claim 74 wherein said material is hydromorphone xinafoate characterized by an FTIR of FIG. 26.

111. The drug system of claim 74 wherein said material is hydromorphone xinafoate characterized by an X-ray diffraction diffractogram of FIG. 27.

112. The drug system of claim 1 wherein said second drug substance is said material and said first drug substance is an organic acid addition salt of said first opioid.

113. The drug system of claim 112 wherein said organic acid is defined by Structure A

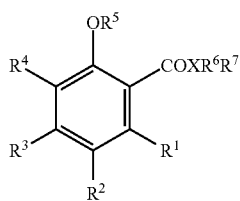

Structure A wherein $R^1$-$R^4$ are independently selected from H, alkyl or substituted alkyl of 1-6 carbons, adjacent groups may be taken together to form a cyclic alkyl, cyclic alkyl-aryl, or cyclic aryl moiety;

$R^5$ is selected from H, or an alkali earth cation;

$R^6$ and $R^7$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur.

114. The drug system of claim 113 wherein said organic acid is selected from the group consisting of:

Structure B wherein $R^5$, $R^6$, $R^7$ and X remain as defined above for Structure A;

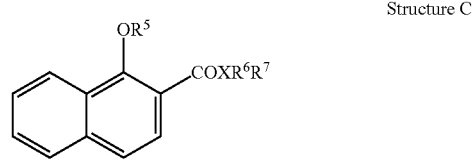

Structure C wherein X, $R^5$, $R^6$ and $R^7$ remain as defined above for Structure A;

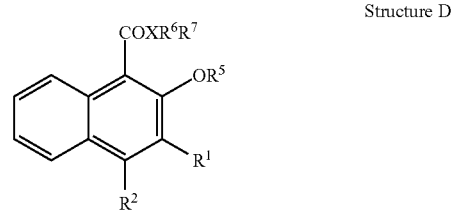

Structure D wherein X, $R^1$, $R^2$, $R^5$, $R^6$ and $R^7$ remain as defined above for Structure A;

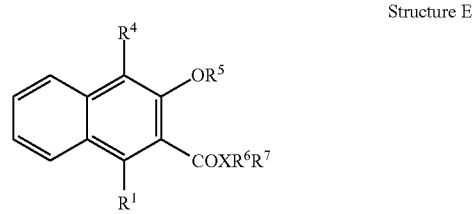

Structure E wherein X, $R^1$, $R^4$, $R^5$, $R^6$ and $R^7$ remain as defined above for Structure A;

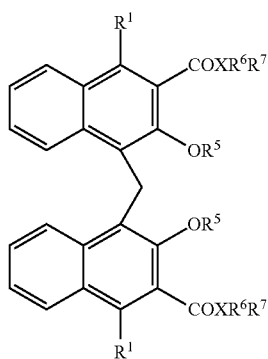

Structure F wherein X, R$^1$, R$^5$, R$^6$ and R$^7$ are independently defined as above for Structure A; and

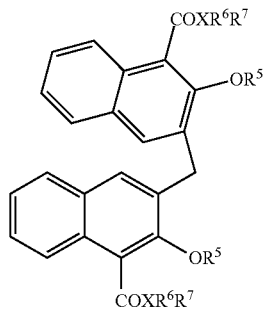

Structure G wherein X, R$^5$, R$^6$ and R$^7$ are independently defined as above for Structure A.

115. The drug system of claim 114 wherein for Structure B X is O.

116. The drug system of claim 114 wherein for Structure D X is O; R$^1$ and R$^2$ are hydrogen.

117. The drug system of claim 114 wherein for Structure E X is O, R$^1$ and R$^4$ are hydrogen.

118. The drug system of claim 114 wherein for Structure F at least one X is O and at least one R$^1$ is hydrogen.

119. The drug system of claim 114 wherein for Structure G X is O and R$^5$ is hydrogen.

120. The drug system of claim 114 wherein said organic acid comprises a material selected from the group consisting of pamoic acid, disodium pamoate, di-ammonium pamoate, di-potassium pamoate, lower molecular weight di-alkyl amine pamoate, lower molecular weight di-aryl amine pamoate, lower molecular weight di-alkyl esters of pamoic acid, lower molecular weight di-aryl esters of pamoic acid, lower molecular weight di-alkylacyl O-esters of pamoic acid, lower molecular weight di-arylacyl O-esters of pamoic acid and monoalkali pamoate.

121. The drug system of claim 114 wherein said organic acid comprises a material selected from the group consisting of ortho isomers of hydroxy naphthoic acid, sodium hydroxy naphthoic acid, ammonium hydroxy naphthoate, potassium hydroxy naphthoate, lower molecular weight alkyl amine salts of hydroxy naphthoic acid, lower molecular weight aryl amine salts of hydroxy naphthoic acid, lower molecular weight alkyl esters of hydroxy naphthoic acid, lower molecular weight aryl esters of hydroxy naphthoic acid, lower molecular weight alkylacyl O-esters of hydroxyl naphthoic acid, lower molecular weight di-arylacyl O-esters of pamoic acid and monoalkali pamoate.

122. The drug system of claim 114 wherein said organic acid is selected from the group consisting of salicylic acid, sodium salicylate, ammonium salicylate, potassium salicylate, lower molecular weight alkyl amine salts of salicylic acid, lower molecular weight aryl amine salts of salicylic acid, lower molecular weight alkyl esters of salicylic acid, lower molecular weight aryl esters of salicylic acid, lower molecular weight alkylacyl O-esters of salicylic acid and lower molecular weight arylacyl O-esters of salicylic acid.

123. The drug system of claim 114 wherein said organic acid salt comprises an acid selected from pamoic acid or a synthetic equivalent thereof; salicylic acid or a synthetic equivalent thereof and hydroxy naphthoic acid or a synthetic equivalent thereof.

124. The drug system of claim 3 wherein at least one of said first drug product or said second drug product comprises an additive.

125. The drug system of claim 124 wherein said additive comprises a third opioid.

126. The drug system of claim 125 wherein said third opioid is selected from the group consisting of oxycodone, hydrocodone, morphine, apomorphine, hydromorphone, oxymorphone, codeine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, levorphanol, nalbuphine, nalmefene, naloxone, naltrexone, noscapine, opium and oripavine.

127. The drug system of claim 124 wherein said additive is defined by Structure H:

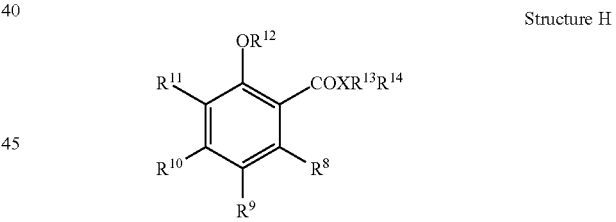

Structure H wherein R$^8$-R$^{11}$ are independently selected from H, alkyl or substituted alkyl of 1-6 carbons, adjacent groups may be taken together to form a cyclic alkyl, cyclic alkyl-aryl, or cyclic aryl moiety;
R$^{12}$ is selected from H, or an alkali earth cation;
R$^{13}$ and R$^{14}$ are independently selected from H, alkyl of 1-6 carbons, an alkali earth cation, and aryl of 6 to 12 carbons, in a number sufficient to complete the valence bonding of X; and
wherein X is selected from nitrogen, oxygen or sulfur.

128. The drug system of claim 127 wherein at least one of R$^{12}$ and R$^{13}$ is an alkali earth cation.

129. The drug system of claim 127 wherein said additive is selected from the group consisting of pamoic acid, an alkali earth salt of pamoate, bon acid and an alkali earth salt of bon acid.

130. The drug system of claim 129 comprising disodium pamoate and at least one drug substance selected from oxycodone pamoate, hydrocodone pamoate, morphine pamoate, hydromorphone pamoate, morphine, hydromorphone, oxycodone and hydrocodone.

131. The drug system of claim 127 wherein said additive and one of said first opioid or said second opioid are present in a ratio of between 0.5:1 and 1:1.

132. The drug system of claim 124 wherein said additive is selected from the group consisting of binder, colorant, flow agent, disintegrants, release agent, surfactant, buffer, wetting agent and particle coating.

* * * * *